(12) United States Patent
Marx et al.

(10) Patent No.: US 11,932,633 B2
(45) Date of Patent: Mar. 19, 2024

(54) KRAS G12C INHIBITORS

(71) Applicants: Mirati Therapeutics, Inc., San Diego, CA (US); Array BioPharma, Inc., Boulder, CO (US)

(72) Inventors: Matthew Arnold Marx, San Diego, CA (US); Matthew Randolph Lee, Del Mar, CA (US); James F. Blake, Boulder, CO (US); Mark Joseph Chicarelli, Boulder, CO (US); Jay Bradford Fell, Boulder, CO (US); John P. Fischer, Boulder, CO (US); Erik James Hicken, Boulder, CO (US); Pavel Savechenkov, Boulder, CO (US); Tony Tang, Boulder, CO (US); Guy P. A. Vigers, Boulder, CO (US); Henry J. Zecca, Boulder, CO (US)

(73) Assignees: Mirati Therapeutics, Inc., San Diego, CA (US); Array Biopharma Inc., Boulder, CO (US)

( * ) Notice: Subject to any disclaimer, the term of this patent is extended or adjusted under 35 U.S.C. 154(b) by 805 days.

(21) Appl. No.: 17/053,273

(22) PCT Filed: May 6, 2019

(86) PCT No.: PCT/US2019/030896
§ 371 (c)(1),
(2) Date: Nov. 5, 2020

(87) PCT Pub. No.: WO2019/217307
PCT Pub. Date: Nov. 14, 2019

(65) Prior Publication Data
US 2021/0380570 A1 Dec. 9, 2021

Related U.S. Application Data

(60) Provisional application No. 62/667,695, filed on May 7, 2018.

(51) Int. Cl.
| | | |
|---|---|---|
| C07D 413/06 | (2006.01) | |
| A61P 35/00 | (2006.01) | |
| C07D 413/04 | (2006.01) | |
| C07D 413/14 | (2006.01) | |
| C07D 417/14 | (2006.01) | |

(52) U.S. Cl.
CPC ............ *C07D 413/14* (2013.01); *A61P 35/00* (2018.01); *C07D 413/06* (2013.01)

(58) Field of Classification Search
CPC .... C07D 413/06; C07D 41/14; C07D 417/14; A61P 35/00
See application file for complete search history.

(56) References Cited

U.S. PATENT DOCUMENTS

| | | | |
|---|---|---|---|
| 8,163,763 | B2 | 4/2012 | Bergeron et al. |
| 8,426,401 | B2 | 4/2013 | Bian et al. |
| 9,562,019 | B2 | 2/2017 | Djaballah et al. |
| 9,840,516 | B2 | 12/2017 | Li et al. |
| 10,125,134 | B2 | 11/2018 | Blake et al. |
| 2003/0191143 | A1 | 10/2003 | Pitts et al. |
| 2009/0239900 | A1 | 10/2009 | Kolton et al. |
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2018/0015087 | A1 | 1/2018 | Liu et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |

(Continued)

FOREIGN PATENT DOCUMENTS

| | | |
|---|---|---|
| WO | 02/053558 A1 | 7/2002 |
| WO | 02/087513 A2 | 11/2002 |

(Continued)

OTHER PUBLICATIONS

International Search Report for corresponding PCT Application No. PCT/US2019/030896 dated Jul. 15, 2019.
Rajitha et al. 'Synthesis and pharmacological evaluations of novel 2H-benzo[b][1,4]oxazin-3(4H)-one derivatives as a new class of anti-cancer agents', European Journal of Medicinal Chemistry, 2011, vol. 46, pp. 4887-4896. p. 4896, Table 1.
Sung, Y. et al., "Mutagenesis of the H-ras p21 at Glycine-60 Residue Disrupts GTP-Induced Conformational Change", Biochemistry 1995, 34, 3470-3477, American Chemical Society.
Tape, C. et al., "Oncogenic KRAS Regulates Tumor Cell Signaling via Stromal Reciprocation", Cell 165, 1-11 May 5, 2016.

(Continued)

Primary Examiner — Samira J Jean-Louis
(74) Attorney, Agent, or Firm — Wood, Phillips, Katz, Clark & Mortimer

(57) ABSTRACT

The present invention relates to compounds that inhibit KRas G12C. In particular, the present invention relates to compounds that irreversibly inhibit the activity of KRas G12C, pharmaceutical compositions comprising the compounds and methods of use therefor.

41 Claims, No Drawings

(56) References Cited

U.S. PATENT DOCUMENTS

| | | |
|---|---|---|
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | Mccormick et al. |
| 2020/0262837 A1 | 8/2020 | Marx et al. |
| 2020/0399297 A1 | 12/2020 | Campbell et al. |

FOREIGN PATENT DOCUMENTS

| | | |
|---|---|---|
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |

(56) References Cited

FOREIGN PATENT DOCUMENTS

| | | |
|---|---|---|
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |

OTHER PUBLICATIONS

Thierry, A. et al., "Clinical validation of the detection of KRAS and BRAF mutations from circulating tumor DNA", Nature Medicine, vol. 20, No. 4, pp. 430-436, Apr. 2014.
Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.
Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.
Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.
Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.
Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.
Wood, K. et al., "Reply" Comments & Response, Letters JAMA Oncology Published online Jul. 21, 2016, American Medical Association.
Xiong, Y. et al., "Development of covalent guanosine mimetic inhibitors of G12C KRAS", ACS Med. Chem. Lett., Just Accepted Manuscript. DOI: 10.1021/acsmedchemlett.6b00373 • Publication Date (Web): Nov. 30, 2016 Downloaded from http://pubs.acs.org on Dec. 1, 2016.
Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.
Janes et al., "Targeting KRAS Mutant Cancers with a Covalent G12C-Specific Inhibitor", Cell 172, 578-589, Jan. 25, 2018.
Singh et al., "A Gene Expression Signature Associated with K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Serafimova et al., "Reversible targeting of noncatalytic cysteines with chemically tuned electrophiles", Nat Chem Biol.; 8(5):471-476. doi:10.1038/nchembio.925.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLOS One, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.

(56) References Cited

OTHER PUBLICATIONS

Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 dated Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
International Search Report and Written Opinion for PCT Application No. PCT/US2019/030896 dated Jul. 15, 2019.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS One | DOI:10.1371/journal.pone.0149099 Feb. 16, 2016.

Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et alll., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.

(56) References Cited

OTHER PUBLICATIONS

Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi: 10.1038/nrd.2016.139.
Ostrem, J. et al., "K-Ras(G12C) inhibitors allosterically control GTP affinity and effector interactions", Nature, vol. 603: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Rudoni, S. et al., "Role of guanine nucleotides in the regulation of the Ras/cAMP pathway in *Saccharomyces cerevisiae*", Biochimica et Biophysica Acta 1538 (2001) 181△189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag Gmbh & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
Nabet, B. et al., "It Takes Two To Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432. CCR-18-1640, Downloaded from clincancerres.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review," JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Calles, et al., "Immunohistochemical Loss of LKB1 Is a Biomarker for More Aggressive Biology in KRAS-Mutant Lung Adenocarcinoma", Clin Cancer Res. 2015. 21(12).
Torralvo et al., "The Activity of Immune Checkpoint Inhibition in KRAS Mutated Non-small Cell Lung Cancer: A Single Centre Experience", Cancer Genomics & Proteomics, 2019. 16: 577-582.

KRAS G12C INHIBITORS

FIELD OF THE INVENTION

The present invention relates to compounds that inhibit KRas G12C. In particular, the present invention relates to compounds that irreversibly inhibit the activity of KRas G12C, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRAs in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Despite many failed efforts to target KRas, compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well as target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

Thus, there is a need to develop new KRas G12C inhibitors that demonstrate sufficient efficacy, stability and/or safety for treating KRas G12C-mediated cancer. The compounds and compositions of the present invention advantageously overcome one or more of the previous shortcomings by providing selective KRas G12C inhibitors.

SUMMARY OF THE INVENTION

In one aspect of the invention, compounds are provided that inhibit KRas G12C activity. In certain embodiments, the compounds are represented by Formula I:

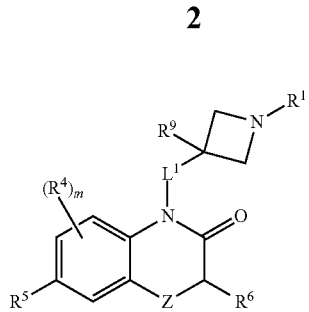

Formula I or a pharmaceutically acceptable salt or solvate thereof;
wherein:
$R^1$ is —C(O)C($R^A$)═══C($R^B$)$_p$ or —SO$_2$C($R^A$)═══C($R^B$)$_p$;
$L^1$ is a bond or —(CH$_2$)$_q$CR$^2$R$^3$(CH$_2$)$_t$—, wherein q and t are each independently 0, 1, 2, or 3 and q+t is equal to or less than 3;
$R^2$ and $R^3$ are each independently hydrogen, cyano, —OR$^{10}$, C3-C4 cycloalkyl, or C1-C3 alkyl, wherein the C1-C3 alkyl may be optionally substituted with cyano or —OR$^{10}$; or $R^2$ and $R^3$ together with the carbon atom to which they are attached form a C3-C4 cycloalkyl;
each $R^4$ is independently cyano, C1-C3 alkyl, C1-C3 alkoxy, halogen, haloalkyl, aryl, or heteroaryl, wherein the aryl and heteroaryl may be optionally substituted with one or more $R^7$;
$R^5$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^7$;
Z is O or S;
$R^6$ is hydrogen, alkyl, hydroxyalkyl, dihydroxyalkyl, alkylaminylalkyl, dialkylaminylalkyl, —W—NR$^{10}$R$^{11}$, —W—C(═O)NR$^{10}$R$^{11}$, heterocyclyl, heterocyclylalkyl, aryl, heteroaryl, or heteroarylalkyl, wherein each of the heterocyclyl, heterocyclylalkyl, aryl, heteroaryl, and heteroarylalkyl may be optionally substituted with one or more $R^8$;
W is C1-C5 alkylene;
each $R^7$ is independently halogen, hydroxyl, alkyl, cycloalkyl, alkoxy, haloalkyl, haloalkyloxy, amino, alkylaminyl, cyano or hydroxyalkyl;
each $R^8$ is independently acyl, hydroxyl, hydroxyalkyl, cyano, halogen, alkyl, cycloalkyl, alkoxy, heteroalkyl, or dialkylaminyl;
$R^9$ is hydrogen, hydroxyl, cyano, halogen, haloalkyl, or alkyl;
each $R^{10}$ is independently hydrogen or C1-C3 alkyl;
each $R^{11}$ is independently hydrogen, acyl, alkyl, heteroalkyl or hydroxyalkyl;
m is 0, 1, 2, or 3;
$R^A$ is absent, hydrogen, or C1-C3 alkyl;
each $R^B$ is independently hydrogen, C1-C3 alkyl, alkylaminylalkyl or dialkylaminylalkyl;
p is one or two; and wherein,
when ═══ is a triple bond then $R^A$ is absent, $R^B$ is present and p equals one,
or when ═══ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

Also included are compounds of Formula I having the Formula I-A:

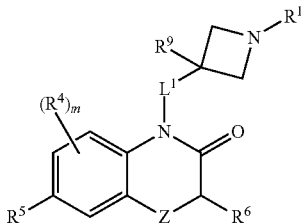

Formula I-A where $R^1$, $R^4$, $R^5$, $R^6$, $R^9$, Z, $L^1$ and m are as defined for Formula I.

In another aspect, provided herein are compounds of Formula I having Formula I-B:

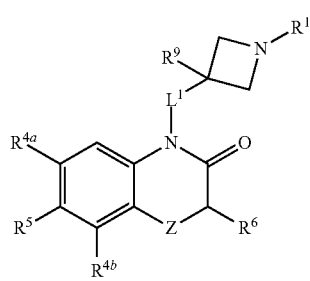

I-B wherein:
$R^1$ is —C(O)C($R^A$)=C($R^B$)$_p$;
$L^1$ is —(CH$_2$)$_q$CR$^2$R$^3$(CH$_2$)$_t$—, wherein q and t are each 0;
$R^2$ and $R^3$ are each independently hydrogen or C1-C3 alkyl;
$R^{4a}$ and $R^{4b}$ are independently hydrogen, cyano, C1-C3 alkyl or halogen;
$R^5$ is aryl or heteroaryl, each of which is optionally independently substituted with one or more $R^7$;
Z is O or S;
$R^6$ is hydrogen, C1-C4 alkyl, alkylaminylalkyl, heterocyclyl or heterocyclylalkyl, wherein each of the heterocyclyl and heterocyclylalkyl may be optionally substituted with one or more $R^8$;
each $R^7$ is independently hydroxyl, C1-C3 alkyl, haloalkyl, or haloalkoyloxy;
each $R^8$ is independently C1-C3 alkyl, alkoxy or dialkylaminyl;
$R^9$ is hydrogen, halogen or C1-C3 alkyl;
$R^A$ is hydrogen;
each $R^B$ is hydrogen;
p is 2; and
===== is a double bond.

In another aspect of the invention, pharmaceutical compositions are provided comprising a therapeutically effective amount of a compound of the present invention or a pharmaceutically acceptable salt or solvate thereof and a pharmaceutically acceptable excipient.

In yet another aspect of the invention, provided herein are methods for inhibiting KRas G12C activity in a in a cell, comprising contacting the cell with a compound of Formula I, Formula I-A or Formula I-B, or a pharmaceutically acceptable salt or solvate thereof. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula I, Formula I-A or Formula I-B, or a pharmaceutically acceptable salt or solvate thereof, or a pharmaceutical composition thereof as defined herein.

Also provided are methods for treating cancer in a patient in need thereof, comprising administering a therapeutically effective amount of a compound of the present invention or a pharmaceutically acceptable salt or solvate thereof, or a or pharmaceutical composition thereof.

Also provided herein is a method of treating a KRas G12C-associated disease or disorder in a patient in need of such treatment, the method comprising administering to the patient a therapeutically effective amount of a compound of Formula I, Formula I-A or Formula I-B, or a pharmaceutically acceptable salt or solvate thereof, or a pharmaceutical composition thereof as defined herein.

Also provided herein is a compound of Formula I, Formula I-A or Formula I-B, or a pharmaceutically acceptable salt or solvate thereof, or a pharmaceutical composition thereof as defined herein for use in therapy.

Also provided herein is a compound of Formula I, Formula I-A or Formula I-B, or a pharmaceutically acceptable salt or solvate thereof or a pharmaceutical composition thereof as defined herein for use in the treatment of cancer.

Also provided herein is a compound of Formula I, Formula I-A or Formula I-B, or a pharmaceutically acceptable salt or solvate thereof for use in the inhibition of KRas G12C.

Also provided herein is a compound of Formula I, Formula I-A or Formula I-B, or a pharmaceutically acceptable salt or solvate thereof or a pharmaceutical composition thereof as defined herein, for use in the treatment of a KRas G12C-associated disease or disorder.

Also provided herein is the use of a compound of Formula I, Formula I-A or Formula I-B, or a pharmaceutically acceptable salt or solvate thereof, as defined herein in the manufacture of a medicament for the treatment of cancer.

Also provided herein is a use of a compound of Formula I, Formula I-A or Formula I-B, or a pharmaceutically acceptable salt or solvate thereof, as defined herein in the manufacture of a medicament for the inhibition of activity of KRas G12C.

Also provided herein is the use of a compound of Formula I, Formula I-A or Formula I-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining if the cancer is associated with a KRas G12C mutation (e.g., a KRas G12C-associated cancer); and (b) if the cancer is determined to be associated with a KRas G12C mutation (e.g., a KRas G12C-associated cancer), administering to the patient a therapeutically effective amount of a compound of Formula I, Formula I-A or Formula I-B, or a pharmaceutically acceptable salt or solvate thereof, or a pharmaceutical composition thereof.

Also provided herein is a process for preparing a compound of Formula I or Formula I-A, or a pharmaceutically acceptable salt or solvate thereof.

Also provided herein is a compound of Formula I, Formula I-A or Formula I-B, or a pharmaceutically acceptable salt or solvate thereof obtained by a process of preparing the compound as defined herein.

DETAILED DESCRIPTION OF THE INVENTION

The present invention relates to inhibitors of KRas G12C. In particular, the present invention relates to compounds that irreversibly inhibit the activity of KRas G12C, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by formulae (I) as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

In some embodiments of any of the methods or uses described herein, an assay is used to determine whether the patient has KRas G12C mutation using a sample (e.g., a biological sample or a biopsy sample (e.g., a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to —NH$_2$;

The term "acyl" refers to —C(O)CH$_3$.

The term "alkyl" as employed herein refers to straight and branched chain aliphatic groups having from 1 to 12 carbon atoms, 1-8 carbon atoms 1-6 carbon atoms, or 1-3 carbon atoms, each of which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain in which one or more hydrogen has been replaced by a halogen. Examples of haloalkyls are trifluoromethyl, difluoromethyl and fluoromethyl.

The term "haloalkyloxy" refers to —O-haloalkyl.

An "alkylene," group is an alkyl group that is positioned between and serves to connect two other chemical groups. Exemplary alkylene groups are C1-C5 alkylene groups including, without limitation, methylene, ethylene, propylene, butylene and pentylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted.

Examples of cycloalkyl groups include, without limitation, cyclopropyl, cyclobutyl, cyclopentyl, cyclopentenyl, cyclohexyl, cyclohexenyl, cycloheptyl, and cyclooctyl.

As used herein, the term "hydroxyalkyl" refers to -alkyl-OH.

The term "dihydroxyalkyl" refers to an alkyl group as defined herein wherein two carbon atoms are each substituted with a hydroxyl group.

The term "alkylaminyl" refers to —NR$^x$-alkyl, wherein R$^x$ is hydrogen.

The term "dialkylaminyl" refers to —N(R$^y$)$_2$, wherein each R$^y$ is independently C1-C3 alkyl, wherein the alkyl of the -alkyl-N(R$^y$)$_2$ may be optionally substituted with hydroxy or hydroxyalkyl.

The term "alkylaminylalkyl" refers to -alkyl-NR$^x$-C1-C4 alkyl, wherein R$^x$ is hydrogen.

The term "dialkylaminylalkyl" refers to -alkyl-N(R$^y$)$_2$, wherein each R$^y$ is independently C1-C4 alkyl, wherein the alkyl of the alkyl-N(R$^y$)$_2$ may be optionally substituted with hydroxy or hydroxyalkyl.

An "aryl" group is a C6-C14 aromatic moiety comprising one to three aromatic rings, which is optionally substituted. As one embodiment, the aryl group is a C$_6$-C$_{10}$ aryl group. Examples of aryl groups include, without limitation, phenyl, naphthyl, anthracenyl, and fluorenyl.

An "aralkyl" or "arylalkyl" group comprises an aryl group covalently linked to an alkyl group, either of which may independently be optionally substituted or unsubstituted, and wherein the radical is on the alkyl portion. An example of an aralkyl group is —(C$_1$-C$_6$)alkyl(C$_6$-C$_{10}$)aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a saturated ring structure having from about 3 to about 12 ring atoms, for example 4 to 8 ring atoms, wherein one or more ring atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with R$^7$ on carbon or nitrogen at one or more positions, wherein R$^7$ is as defined for Formula I. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, thiomorpholinyl, thiomorpholinyl 1,1 dioxide, morpholinyl, oxazepanyl, azabicycloheptanes and oxa azabicycloheptanes. Specifically excluded from the scope of this term are compounds having adjacent annular O and/or S atoms.

The term "heterocyclylalkyl" refers to a heterocyclyl group as defined herein linked to the remaining portion of the molecule via an alkyl linker, wherein the alkyl linker of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuaranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1, 2,5-thiadiazinyl, 1,2,3-thiadiazolyl, 1,2,4-thiadiazolyl, 1,2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein, "an effective amount" of a compound is an amount that is sufficient to negatively modulate or inhibit the activity of KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

In one aspect of the invention, compounds are provided represented by Formula I:

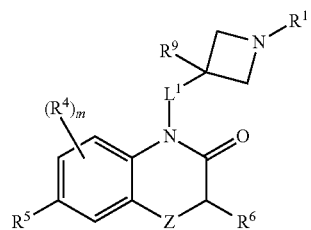

Formula I or a pharmaceutically acceptable salt or solvate thereof, wherein
R$^1$ is —C(O)C(R$^A$)═══C(R$^B$)$_p$ or —SO$_2$C(R$^A$)═══(R$^B$)$_p$;

$L^1$ is a bond or $-(CH_2)_q CR^2R^3(CH_2)_t-$, wherein q and t are each independently 0, 1, 2, or 3 and q+t is equal to or less than 3;

$R^2$ and $R^3$ are each independently hydrogen, cyano, $-OR^{10}$, C3-C4 cycloalkyl, or C1-C3 alkyl, wherein the C1-C3 alkyl may be optionally substituted with cyano or $-OR^{10}$; or $R^2$ and $R^3$ together with the carbon atom to which they are attached form a C3-C4 cycloalkyl;

each $R^4$ is independently cyano, C1-C3 alkyl, C1-C3 alkoxy, halogen, haloalkyl, aryl, or heteroaryl, wherein the aryl and heteroaryl may be optionally substituted with one or more $R^7$;

$R^5$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^7$;

Z is O or S;

$R^6$ is hydrogen, alkyl, hydroxyalkyl, dihydroxyalkyl, alkylaminylalkyl, dialkylaminylalkyl, $-W-NR^{10}R^{11}$, $-W-C(=O)NR^{10}R^{11}$, heterocyclyl, heterocyclylalkyl, aryl, heteroaryl, or heteroarylalkyl, wherein each of the heterocyclyl, heterocyclylalkyl, aryl, heteroaryl, and heteroarylalkyl may be optionally substituted with one or more $R^8$;

W is C1-C5 alkylene;

each $R^7$ is independently halogen, hydroxyl, alkyl, cycloalkyl, alkoxy, haloalkyl, haloalkyloxy, amino, alkylaminyl, cyano or hydroxyalkyl;

each $R^8$ is independently acyl, hydroxyl, hydroxyalkyl, cyano, halogen, alkyl, cycloalkyl, alkoxy, heteroalkyl, or dialkylaminyl;

$R^9$ is hydrogen, hydroxyl, cyano, halogen, haloalkyl, or alkyl;

each $R^{10}$ is independently hydrogen or alkyl;

each $R^{11}$ is independently hydrogen, acyl, alkyl, heteroalkyl or hydroxyalkyl;

m is 0, 1, 2, or 3;

$R^A$ is absent, hydrogen, or C1-C3 alkyl;

each $R^B$ is independently hydrogen, C1-C3 alkyl, alkylaminylalkyl or dialkylaminylalkyl;

p is one or two; and wherein, when ===== is a triple bond then $R^A$ is absent, $R^B$ is present and p equals one, or when ===== is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

In particular embodiments, $R^1$ is $-C(O)C(R^A)===C(R^B)_p$ where $R^A$, $R^B$ and p are as defined for Formula I. In one embodiment, $R^1$ is $-C(O)CH=CH_2$.

In one embodiment, $L^1$ is $-(CH_2)_q CR^2R^3(CH_2)_t-$, wherein q and t are as defined in Formula I. In certain embodiments, q and t are each zero, $R^2$ is hydrogen or methyl and $R^3$ is hydrogen. In one embodiment, $R^2$ and $R^3$ are each hydrogen. In another embodiment, $R^2$ is methyl and $R^3$ is hydrogen.

In particular embodiments, Z is S. In other embodiments, Z is O.

In one embodiment, m is zero. In other embodiments, m is 1 or 2, and each $R^4$ is independently C1-C3 alkyl, halogen or cyano. In one embodiment, m is one and $R^4$ is halogen. In certain embodiments, the halogen is chlorine or fluorine. In one embodiment, m is one and $R^4$ is C1-C3 alkyl. In certain embodiments, $R^4$ is methyl. In one embodiment, m is one and $R^4$ is cyano. In one embodiment, m is two and each $R^4$ is independently selected from a halogen. In certain embodiments, each $R^4$ is independently selected from chlorine, bromine or fluorine. In one embodiment, m is two and each $R^4$ is independently selected from chlorine and fluorine.

In one embodiment, $R^5$ is aryl optionally substituted with one or more $R^7$. In certain embodiments, the aryl is phenyl or naphthyl, each optionally substituted with one or more $R^7$. In certain embodiments, the aryl is phenyl or naphthyl, each optionally substituted with one $R^7$. In one embodiment, $R^7$ is independently selected from halogen, hydroxyl, C1-C3 alkyl, haloalkyl, haloalkyloxy, and alkoxy. In one embodiment, $R^7$ is independently selected from hydroxyl, haloalkyl, and haloalkyloxy. In another embodiment, $R^7$ is halogen or hydroxyl. In one embodiment, $R^7$ is hydroxyl, trifluoromethyl or trifluoromethoxy.

In one embodiment, $R^5$ is heteroaryl optionally substituted with one or more $R^7$. In certain embodiments, the heteroaryl is indazolyl, benzisoxazolyl, benzimidazolyl or pyrazolyl, each substituted with one or more $R^7$. In one embodiment, each $R^7$ is independently selected from C1-C6 alkyl. In one embodiment, the indazolyl, benzimidazolyl and pyrazolyl are each substituted with 1-2 independently selected C1-C6 alkyl. In one embodiment, $R^5$ is indazolyl, benzimidazolyl and pyrazolyl, each of which is substituted with 1-2 methyl groups.

In particular embodiments, $R^6$ is hydrogen, C1-C4 alkyl, hydroxyalkyl, dialkylaminylalkyl, $-W-NR^{10}R^{11}$, heterocyclyl or heterocyclylalkyl, wherein each of the heterocyclyl or heterocyclylalkyl are independently optionally substituted with $R^8$. In one embodiment, $R^6$ is hydrogen, C1-C4 alkyl, dialkylaminylalkyl, heterocyclyl or heterocyclylalkyl, wherein each of the heterocyclyl or heterocyclylalkyl are independently optionally substituted with $R^8$. In one embodiment, $R^6$ is hydrogen. In one embodiment, $R^6$ is C1-C4 alkyl. In one embodiment, $R^6$ is isobutyl. In another embodiment, $R^6$ is dialkylaminylalkyl. In one embodiment, $R^6$ is dimethylaminylethyl or dimethylaminylmethyl. In one embodiment, $R^6$ is heterocyclyl or heterocyclylalkyl, wherein each of the heterocyclyl or heterocyclylalkyl are independently optionally substituted with one or more $R^8$. In one embodiment, $R^8$ is selected from C1-C3 alkyl, alkoxy and dialkylaminyl. In one embodiment, the heterocyclyl and the heterocyclyl portion of the heterocylcylalkyl are independently selected from pyrrolidinyl, piperidinyl and piperazinyl, each of which is optionally independently substituted with $R^8$. In one embodiment, the heterocyclyl and the heterocyclyl portion of the heterocylcylalkyl are independently selected from pyrrolidinyl, piperidinyl and piperazinyl, each of which is optionally independently substituted with $R^8$, wherein $R^8$ is selected from C1-C3 alkyl, alkoxy and dialkylaminyl. In one embodiment, the heterocyclyl and the heterocyclyl portion of the heterocylcylalkyl are independently pyrrolidinyl, 1-methyl-pyrrolinidinyl, 3-methoxy-pyrrolidinyl, piperdinyl, 1-methyl-piperdinyl, 4-dimethylaminyl-piperdinyl, piperazinyl, 4-methyl-piperazinyl or morpholinyl.

In one embodiment, $R^9$ is hydrogen. In one embodiment, $R^9$ is C1-C3 alkyl or halogen. In certain embodiments, the halogen is fluorine. In certain embodiments, $R^9$ is methyl.

In one embodiment, Formula I includes compounds having the Formula I-A:

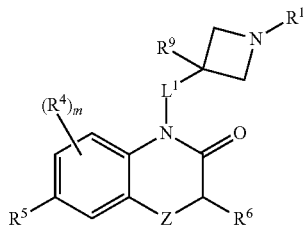

Formula I-A where $R^1$, $R^4$, $R^5$, $R^6$, $R^9$, Z, $L^1$ and m are as defined for Formula I. In one embodiment of Formula I-A, $R^4$ is C1 C3 alkyl, cyano or halogen. In one embodiment of Formula I-A, Z is O. In one embodiment of Formula I-A, $L^1$ is —($CH_2$)$_q$$CR^2R^3$($CH_2$)$_t$—, wherein q and t are as defined in Formula I. In one embodiment of Formula I-A, q and t are each zero, $R^2$ is hydrogen or methyl and $R^3$ is hydrogen. In one embodiment of Formula I-A, $R^2$ and $R^3$ are each hydrogen. In one embodiment of Formula I-A, $R^2$ is methyl and $R^3$ is hydrogen. In one embodiment of Formula I-A, $R^5$ is aryl optionally substituted with one or more $R^7$. In one embodiment of Formula I-A, $R^5$ is phenyl or naphthyl, each optionally substituted with one or more $R^7$. In one embodiment of Formula I-A, $R^5$ is phenyl or naphthyl, each optionally substituted with one or more $R^7$, wherein $R^7$ is independently halogen, hydroxyl, C1-C3 alkyl, haloalkyl, haloalkyloxy, and alkoxy. In one embodiment of Formula I-A, $R^5$ is phenyl or naphthyl, each optionally substituted with one or more $R^7$, wherein $R^7$ is halogen or hydroxyl. In one embodiment of Formula I-A, $R^5$ is heteroaryl optionally substituted with one or more independently selected $R^7$. In one embodiment of Formula I-A, $R^5$ is indazolyl, benzisoxazolyl, benzimidazolyl, or pyrazolyl, each independently optionally substituted with one or more $R^7$. In one embodiment of Formula I-A, $R^5$ is indazolyl, benzisoxazolyl, benzimidazolyl, or pyrazolyl, each independently optionally substituted with one or more $R^7$, wherein each $R^7$ is independently selected from C1-C6 alkyl. In one embodiment of Formula I-A, $R^5$ is indazolyl, benzimidazolyl or pyrazolyl optionally substituted with one or two independently selected C1-C6 alkyl. In one embodiment of Formula I-A, $R^6$ is hydrogen, C1-C4 alkyl, hydroxyalkyl, dialkylaminylalkyl, —W—$NR^{10}R^{11}$, heterocyclyl or heterocyclylalkyl, wherein each of the heterocyclyl or heterocyclylalkyl are independently optionally substituted with $R^8$. In one embodiment of Formula I-A, $R^6$ is hydrogen, C1-C4 alkyl, dialkylaminylalkyl, heterocyclyl or heterocyclylalkyl, wherein each of the heterocyclyl or heterocyclylalkyl are independently optionally substituted with $R^8$. In one embodiment, $R^1$ is selected from C1-C3 alkyl, alkoxy and dialkylaminyl. In one embodiment of Formula I-A, $R^6$ is hydrogen. In one embodiment of Formula I-A, $R^6$ is C1-C4 alkyl. In one embodiment of Formula I-A, $R^6$ is isobutyl. In one embodiment of Formula I-A, $R^6$ is dialkylaminylalkyl. In one embodiment of Formula I-A, $R^6$ is dimethylaminoethyl or dimethylaminomethyl. In one embodiment of Formula I-A, $R^6$ is heterocyclyl or heterocyclylalkyl, wherein each of the heterocyclyl or heterocyclylalkyl are independently optionally substituted with one or more $R^8$. In one embodiment, $R^8$ is selected from C1-C3 alkyl, alkoxy and dialkylaminyl. In one embodiment, the heterocyclyl and the heterocyclyl portion of the heterocylcylalkyl are independently selected from pyrrolidinyl, piperidinyl and piperazinyl, each of which is optionally independently substituted with $R^8$. In one embodiment, the heterocyclyl and the heterocyclyl portion of the heterocylcylalkyl are independently selected from pyrrolidinyl, piperidinyl and piperazinyl, each of which is optionally independently substituted with $R^8$, wherein $R^8$ is selected from C1-C3 alkyl, alkoxy and dialkylaminyl. In one embodiment of Formula I-A, $R^6$ is heterocyclyl or heterocyclylalkyl, wherein the heterocyclyl and the heterocyclyl portion of the heterocylcylalkyl are independently pyrrolidinyl, 1-methyl-pyrrolinidinyl, 3-methoxypyrrolidinyl, piperdinyl, 1-methyl-piperdinyl, 4-dimethylaminyl-piperdinyl, piperazinyl, 4-methyl-piperazinyl or morpholinyl. In one embodiment of Formula I-A, $R^9$ is hydrogen. In one embodiment of Formula I-A, $R^9$ is C1-C3 alkyl or halogen. In one embodiment of Formula I-A, $R^9$ is fluorine. In one embodiment of Formula I-A, $R^9$ is methyl.

In one embodiment, Formula I includes compounds having the Formula I-B:
wherein:
$R^1$ is —C(O)C($R^A$)=C($R^B$)$_p$;
$L^1$ is —($CH_2$)$_q$$CR^2R^3$($CH_2$)$_t$—, wherein q and t are each 0;
$R^2$ and $R^3$ are each independently hydrogen or C1-C3 alkyl;
$R^{4a}$ and $R^{4b}$ are independently hydrogen, cyano, C1-C3 alkyl or halogen;
$R^5$ is aryl or heteroaryl, each of which is optionally independently substituted with one or more $R^7$;
Z is O or S;
$R^6$ is hydrogen, C1-C4 alkyl, alkylaminylalkyl, heterocyclyl or heterocyclylalkyl, wherein each of the heterocyclyl and heterocyclylalkyl may be optionally substituted with one or more $R^8$;
each $R^7$ is independently hydroxyl, C1-C3 alkyl, haloalkyl, or haloalkoyloxy;
each $R^8$ is independently C1-C3 alkyl, alkoxy or dialkylaminyl;
$R^9$ is hydrogen, halogen or C1-C3 alkyl;
$R^a$ is hydrogen;
each $R^B$ is hydrogen;
p is 2; and
===== is a double bond.

In one embodiment of Formula I-B, $R^{4a}$ is hydrogen, cyano, C1-C3 alkyl or halogen. In one embodiment of Formula I-B, $R^{4a}$ is hydrogen, cyano, methyl, fluoro or chloro.

In one embodiment of Formula I-B, $R^{4b}$ is hydrogen or halogen. In one embodiment of Formula I-B, $R^{4b}$ is hydrogen or fluoro. In one embodiment of Formula I-B, $R^{4b}$ is hydrogen. In one embodiment of Formula I-B, $R^{4b}$ is fluoro.

In one embodiment of Formula I-B, $R^{4a}$ is hydrogen, cyano, methyl, fluoro or chloro, and $R^{4b}$ is hydrogen or fluoro.

In one embodiment of Formula I-B, $R^5$ is aryl optionally substituted with one or more $R^7$. In one embodiment of Formula I-B, $R^5$ is phenyl or naphthyl, each optionally substituted with one or more $R^7$. In one embodiment of Formula I-B, $R^5$ is phenyl or naphthyl, each optionally substituted with one or more $R^7$, wherein $R^7$ is independently halogen, hydroxyl, C1-C3 alkyl, haloalkyl, haloalkyloxy, and alkoxy. In one embodiment of Formula I-B, $R^5$ is phenyl or naphthyl, each optionally substituted with one or more $R^7$, wherein $R^7$ is halogen or hydroxyl.

In one embodiment of Formula I-B, $R^{4a}$ is hydrogen, cyano, methyl, fluoro or chloro; $R^{4b}$ is hydrogen or fluoro;

and $R^5$ is phenyl or naphthyl, each optionally substituted with one or more $R^7$, wherein $R^7$ is halogen or hydroxyl.

In one embodiment of Formula I-B, $R^5$ is heteroaryl optionally substituted with one or more independently selected $R^7$. In one embodiment of Formula I-B, $R^5$ is indazolyl, benzisoxazolyl, benzimidazolyl, or pyrazolyl, each of which is independently optionally substituted with one or more $R^7$. In one embodiment of Formula I-B, $R^5$ is indazolyl, benzisoxazolyl, benzimidazolyl, or pyrazolyl, each of which is independently optionally substituted with one or more $R^7$, wherein each $R^7$ is independently selected from C1-C6 alkyl. In one embodiment of Formula I-B, $R^5$ is indazolyl, benzisoxazolyl, benzimidazolyl, or pyrazolyl optionally substituted with one or two independently selected C1-C6 alkyl.

In one embodiment of Formula I-B, $R^{4a}$ is hydrogen, cyano, methyl, fluoro or chloro; $R^{4b}$ is hydrogen or fluoro; and $R^5$ is indazolyl, benzisoxazolyl, benzimidazolyl, or pyrazolyl, each of which is optionally substituted with one or two independently selected C1-C6 alkyl.

In one embodiment of Formula I-B, $R^6$ is hydrogen.

In one embodiment of Formula I-B, $R^6$ is C1-C4 alkyl.

In one embodiment of Formula I-B, $R^6$ is dialkylaminylalkyl.

In one embodiment of Formula I-B, $R^6$ is heterocyclyl or heterocyclylalkyl, wherein each of the heterocyclyl or heterocyclylalkyl is independently optionally substituted with $R^8$, wherein $R^8$ is selected from C1-C3 alkyl, alkoxy and dialkylaminyl.

In one embodiment of Formula I-B $R^9$ is hydrogen.

In one embodiment of Formula I-B, $R^9$ is halogen.

In one embodiment of Formula I-B $R^9$ is C1-C3 alkyl.

Non-limiting examples of compounds of Formula I include:

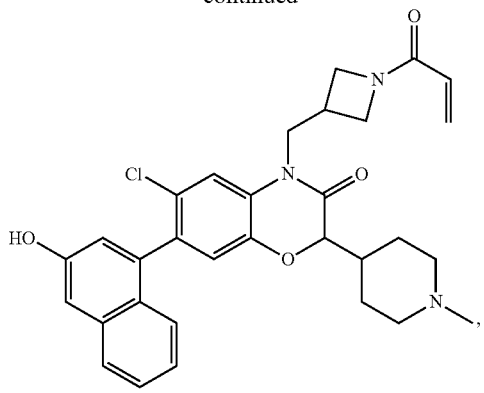

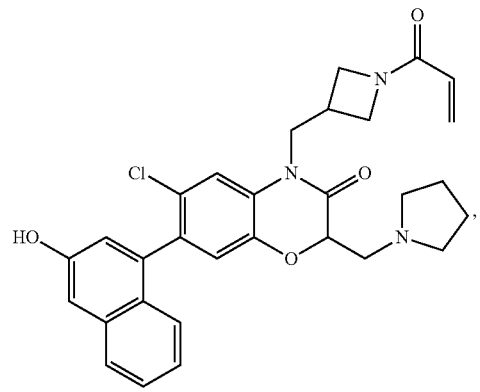

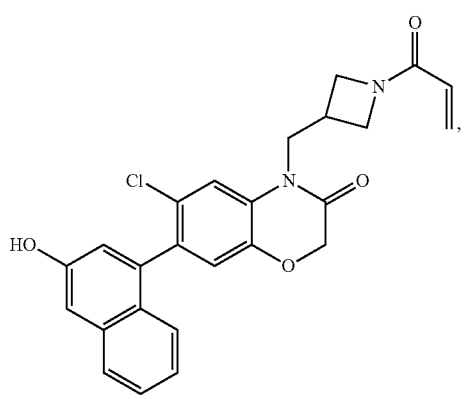

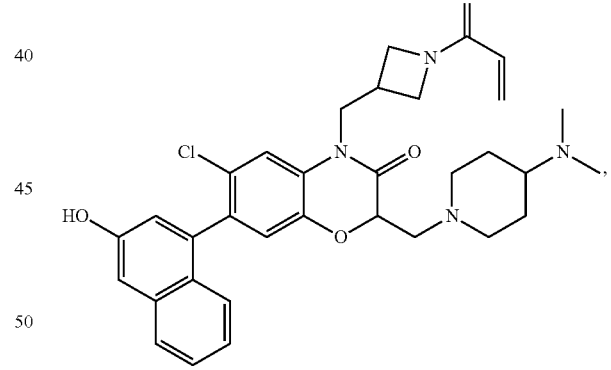

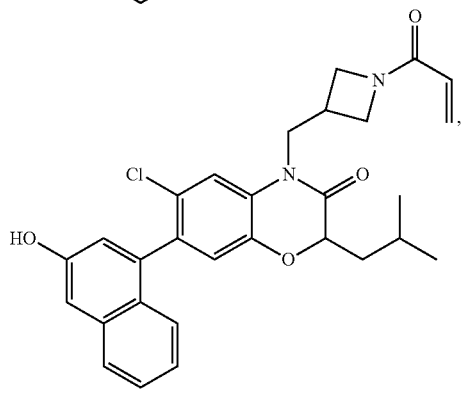

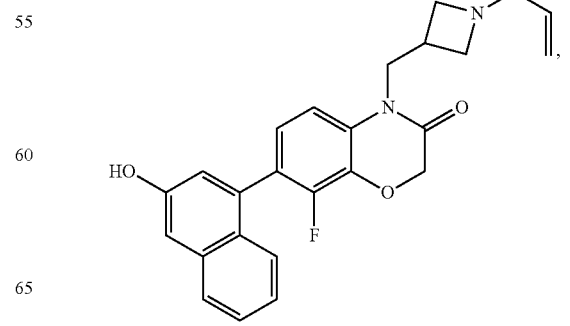

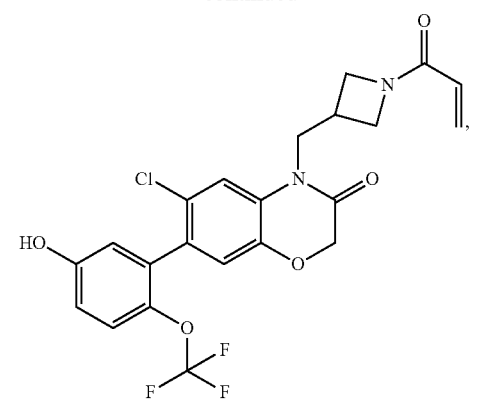
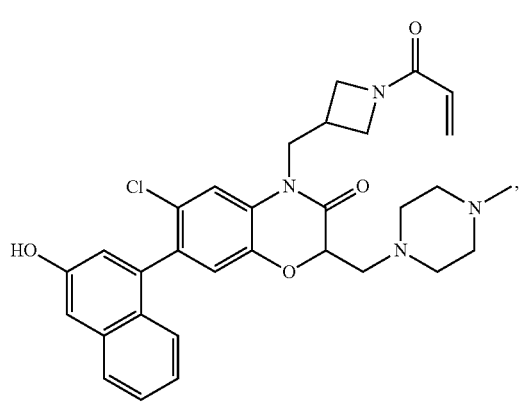
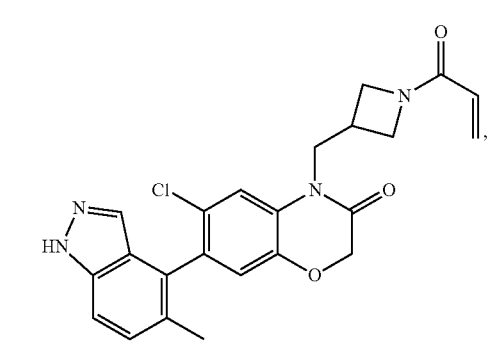
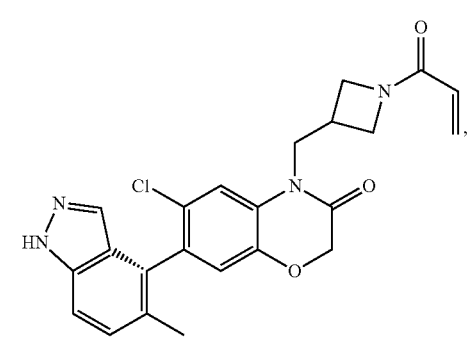
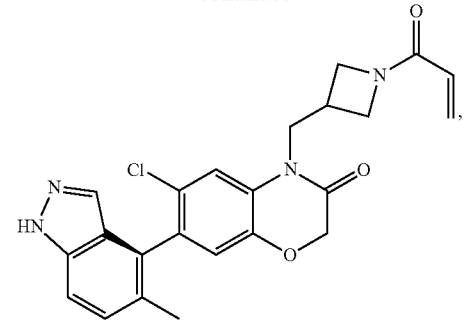
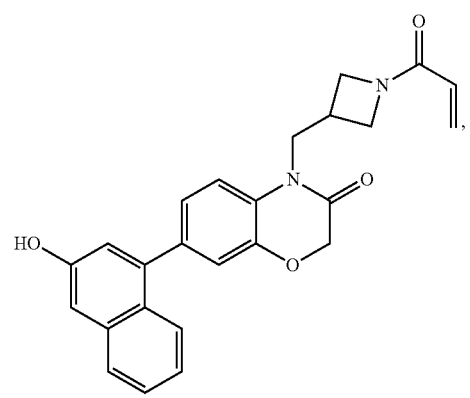
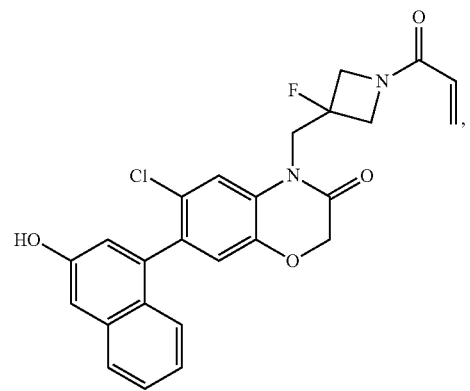
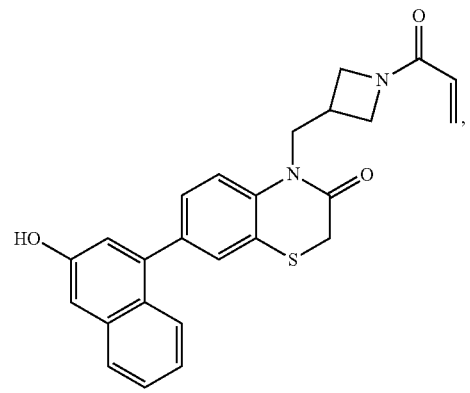

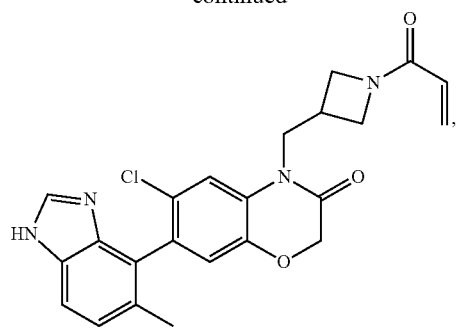
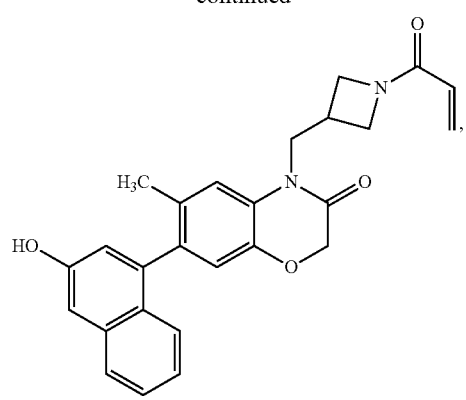
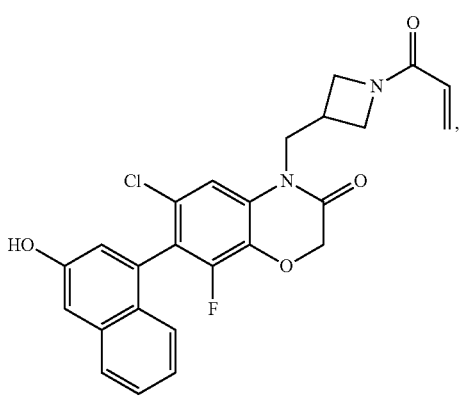
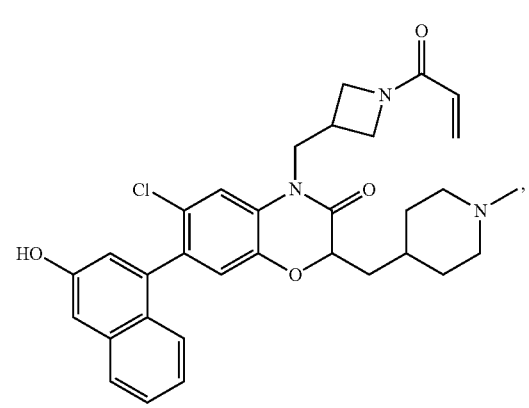
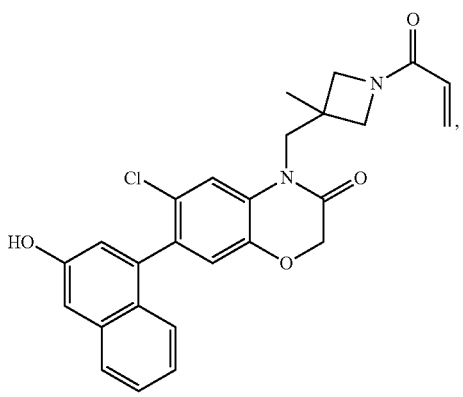
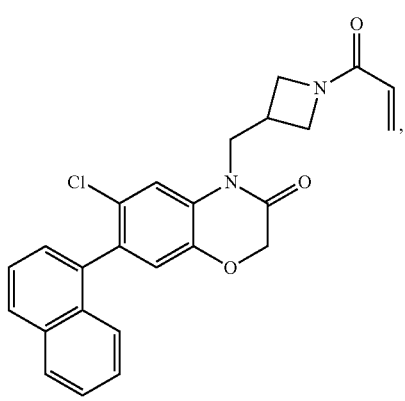
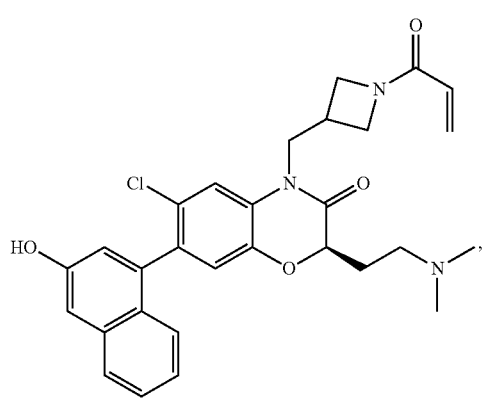
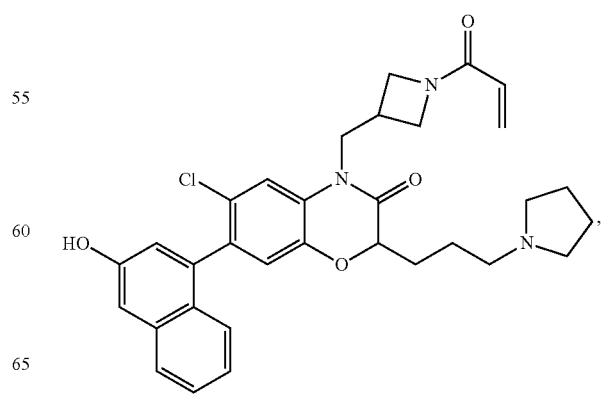

19
-continued
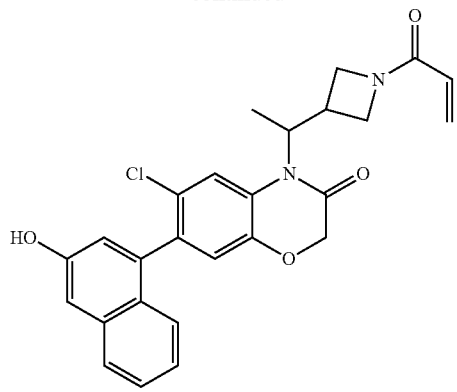
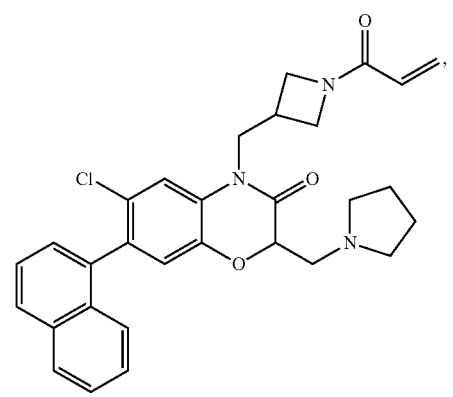
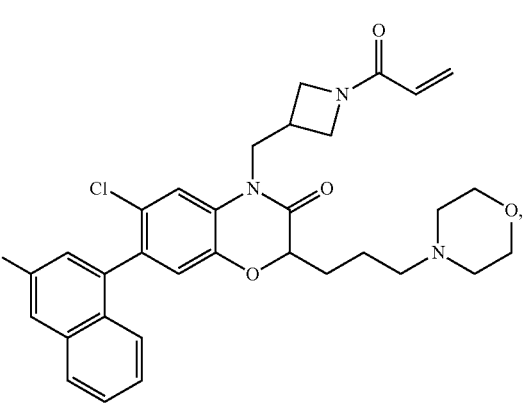
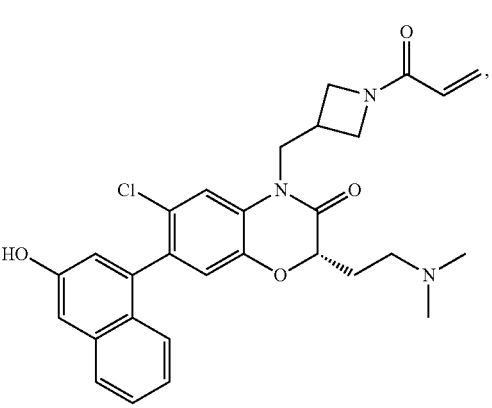
20
-continued
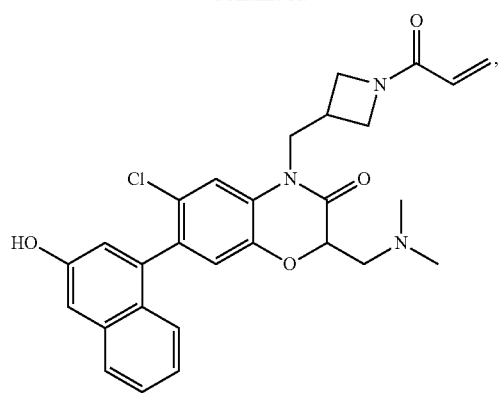
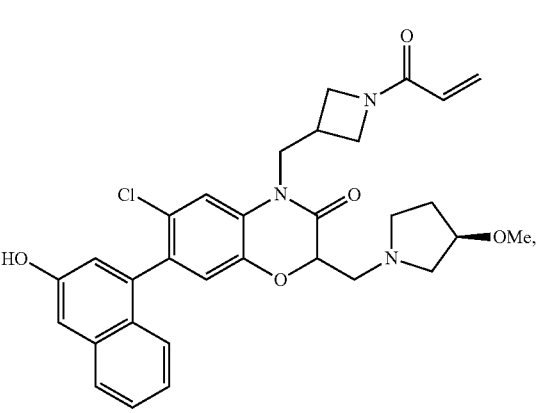
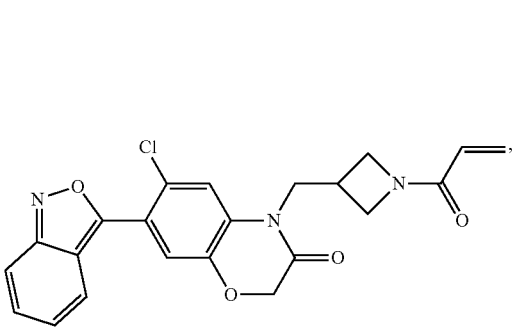
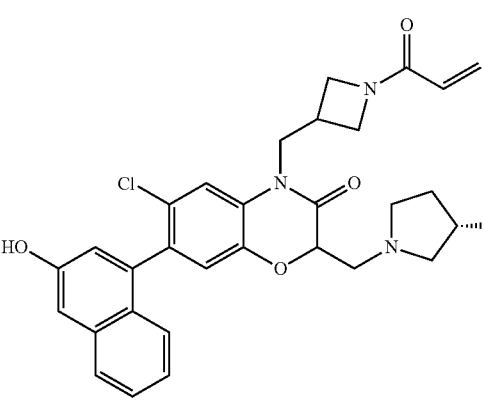

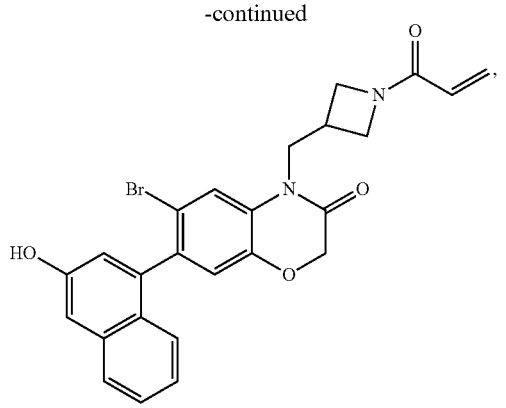

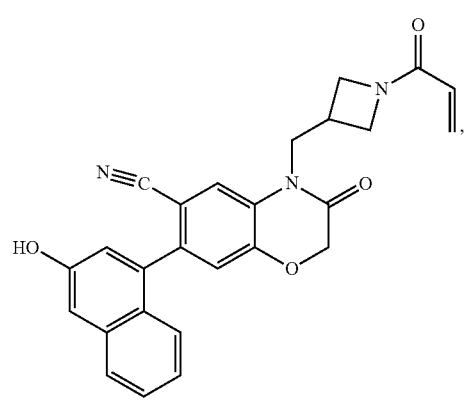

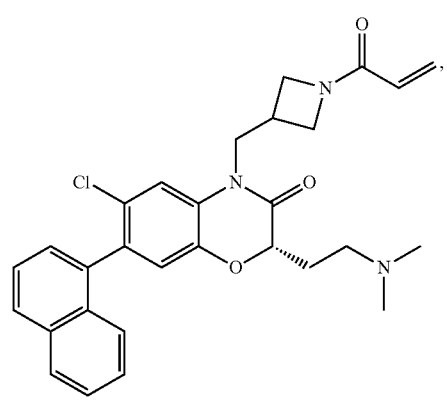

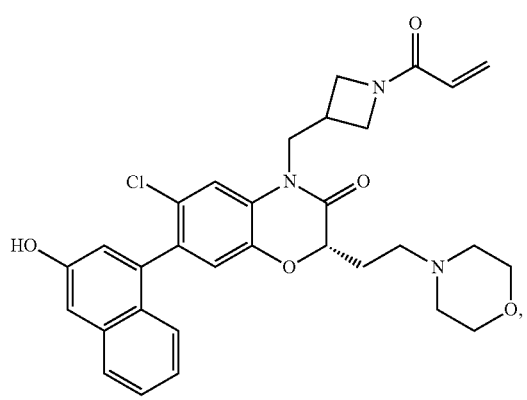

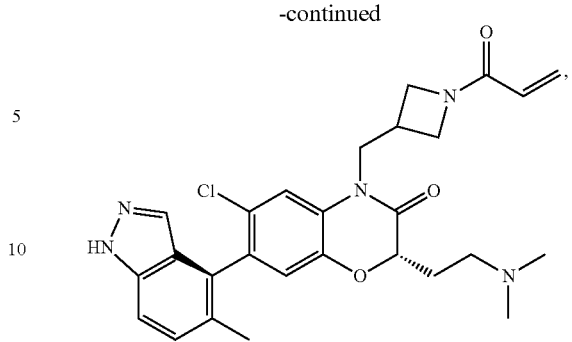

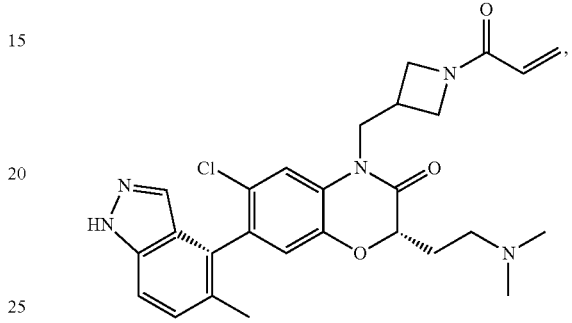

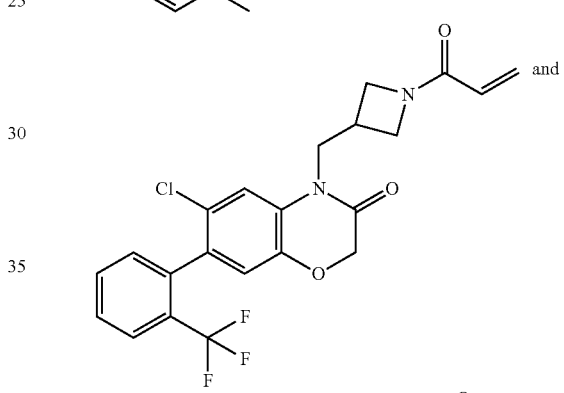

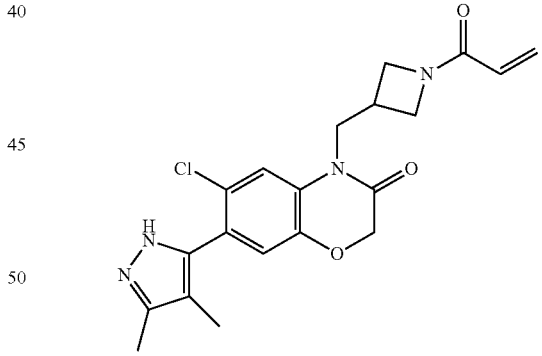

and pharmaceutical acceptable salts thereof. In one embodiment, the compounds are in the form of a free base. In one embodiment, the compounds are in the form of a salt. In one embodiment, the compounds are trifluoroacetate salts.

The compounds of Formula I, Formula I-A and Formula I-B may be formulated into pharmaceutical compositions.

Pharmaceutical Compositions

In another aspect, the invention provides pharmaceutical compositions comprising a KRas G12C inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route. In one embodiment, the pharmaceutical compositions are formulated as tablets or capsules for oral administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salt" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the conditions disclosed herein is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12C activity in a cell, comprising contacting the cell in which inhibition of KRas G12C activity is desired with an effective amount of a compound of Formula I, Formula I-A and Formula I-B, or a pharmaceutically acceptable salt or solvate thereof or a pharmaceutical composition containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12C with a compound provided herein includes the administration of a compound provided herein to an individual or patient, such as a human, having KRas G12C, as well as, for example, introducing a compound provided herein into a sample containing a cellular or purified preparation containing the KRas G12C.

In one embodiment, a cell in which inhibition of KRas G12C activity is desired is contacted with an effective amount of a compound of Formula I, Formula I-A and Formula I-B, to negatively modulate the activity of KRas G12C. In other embodiments, a therapeutically effective amount of pharmaceutically acceptable salt or solvate thereof or pharmaceutical compositions containing the compound of formula (I) may be used.

By negatively modulating the activity of KRas G12C, the methods described herein are designed to inhibit undesired cellular proliferation resulting from enhanced KRas G12C activity within the cell. The cells may be contacted in a single dose or multiple doses in accordance with a particular treatment regimen to effect the desired negative modulation of KRas G12C. The degree of covalent modification of KRas G12C may be monitored in vitro using well known methods, including those described in Example A below. In addition, the inhibitory activity of exemplary compounds in cells may be monitored, for example, by measuring the inhibition of KRas G12C activity of the amount of phosphylated ERK, including those described in Example B below, to assess the effectiveness of treatment and dosages may be adjusted accordingly by the attending medical practitioner.

In another aspect, also provided are methods of treating cancer in a patient in need thereof, comprising administering to said patient a therapeutically effective amount of a compound of Formula I, Formula I-A and Formula I-B, or a pharmaceutically acceptable salt or solvate thereof or pharmaceutical compositions comprising the compound or pharmaceutically acceptable salt or solvate thereof.

The compositions and methods provided herein may be used for the treatment of a KRas G12C-associated cancer in a patient in need thereof, comprising administering to said patient a therapeutically effective amount of a compound of Formula I, Formula I-A and Formula I-B, or a pharmaceutically acceptable salt thereof or solvate thereof, or a pharmaceutical composition comprising the compound or pharmaceutically acceptable salt or solvate thereof. In one embodiment, the KRas G12C-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer. In certain embodiment, the lung cancer has a KRas G12C mutation.

The concentration and route of administration to the patient will vary depending on the cancer to be treated. The compounds, pharmaceutically acceptable salts or solvates thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula I, Formula I-A and Formula I-B, or a pharmaceutically acceptable salt or solvate thereof, or a pharmaceutical composition thereof as defined herein for use in therapy.

Also provided herein is a compound of Formula I, Formula I-A and Formula I-B, or a pharmaceutically acceptable salt or solvate thereof or a pharmaceutical composition thereof as defined herein for use in the treatment of cancer.

Also provided herein is a compound of Formula I, Formula I-A and Formula I-B, or a pharmaceutically acceptable salt or solvate thereof for use in the inhibition of KRas G12C.

Also provided herein is a compound of Formula I, Formula I-A and Formula I-B, or a pharmaceutically acceptable salt or solvate thereof or a pharmaceutical composition thereof as defined herein, for use in the treatment of a KRas G12C-associated disease or disorder.

Also provided herein is the use of a compound of Formula I, Formula I-A and Formula I-B, or a pharmaceutically acceptable salt or solvate thereof, as defined herein in the manufacture of a medicament for the treatment of cancer.

Also provided herein is a use of a compound of Formula I, Formula I-A and Formula I-B, or a pharmaceutically acceptable salt or solvate thereof, as defined herein in the manufacture of a medicament for the inhibition of activity of KRas G12C.

Also provided herein is the use of a compound of Formula I, Formula I-A and Formula I-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining if the cancer is associated with a KRas G12C mutation (e.g., a KRas G12C-associated cancer) (e.g., as determined using a regulatory agency-approved, e.g., FDA-approved, assay or kit); and (b) if the cancer is determined to be associated with a KRas G12C mutation (e.g., a KRas G12C-associated cancer), administering to the patient a therapeutically effective amount of a compound of Formula I, Formula I-A and Formula I-B, or a pharmaceutically acceptable salt or solvate thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Reaction Schemes and Examples

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I and II.

General Reaction Schemes

SCHEME 1

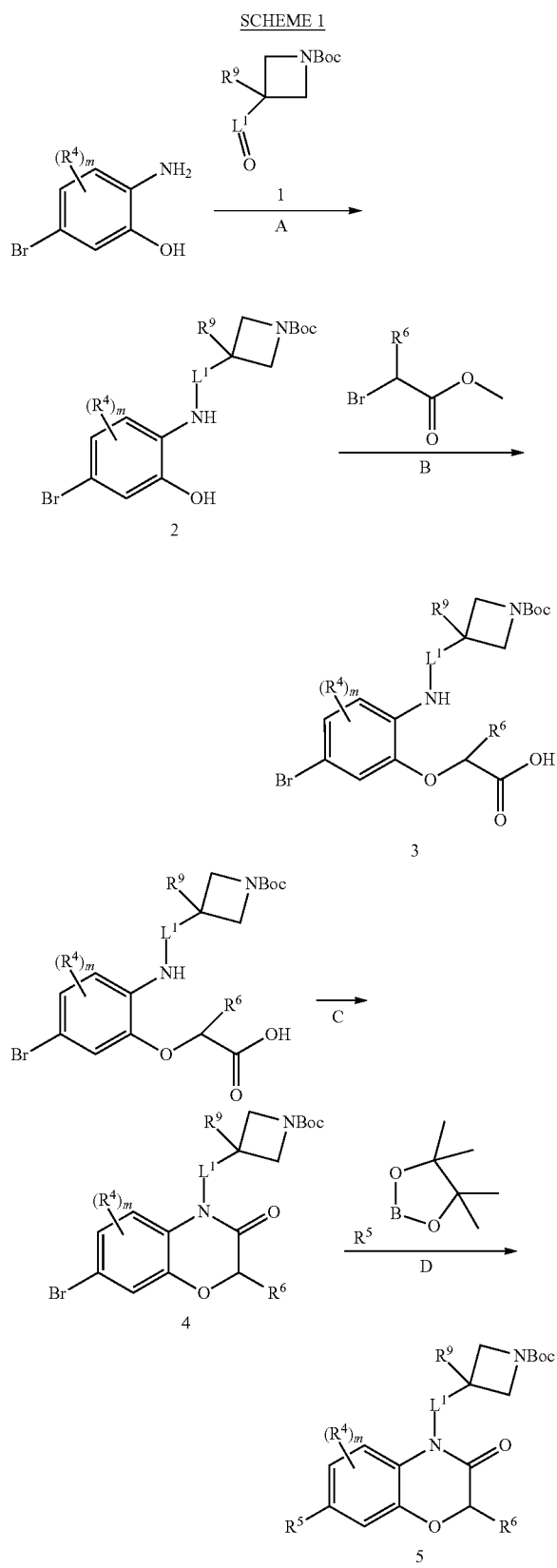

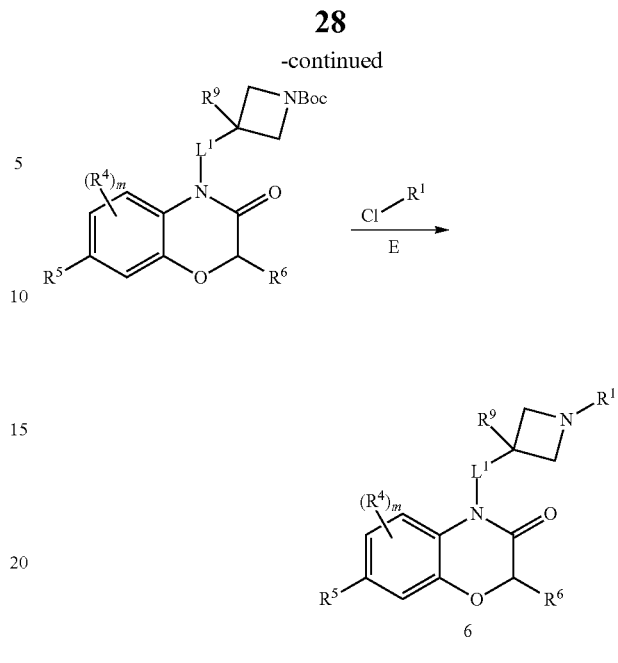

Compounds of Formula I wherein Z is O, $R^5$ is an optionally substituted aryl or heteroaryl and $R^1$, $L^1$, $R^4$, $R^5$ $R^6$ and m are as defined for Formula I can be prepared according to Scheme 1. In step A, an appropriately protected azetidinyl—$L^1$ aldehyde (1) is coupled to an aniline containing zero to three $R^4$ substituents to provide compound (2). This reductive amination proceeds in the presence of a reducing agent such as sodium triacetoxyborhydride. In step B, the substituent $R^6$ is introduced by reaction of an alpha-halo ester with (2) using a suitable base such as potassium carbonate in DMF to provide an intermediate ester, and the ester is hydrolyzed using a suitable base such as NaOH in a solvent such as ethanol, to give compound (3). In step C, the bicycle is prepared by amidation with appropriate reagents, such as EDC with HOBt in DMF to give compound (4). In step D, the substituent $R^5$ is introduced with a palladium coupling, using a suitable functionalized aryl or heteroaryl system, for example an aryl boronate, in the presence of a palladium catalyst such as $Pd_2DBA_3$/Xantphos in a solvent such as toluene with a base such as sodium tert-butoxide to provide compound (5). In step, E, the protecting group of azetidinyl ring compound (5) is removed by treating with a suitable acid such as TFA in a solvent such as methylene chloride, and $R^1$ is introduced to provide a compound of Formula I, for example by treating with an acid chloride having the formula Cl—C(O)C($R^A$)═C($R^B$)$_p$ or Cl—SO$_2$C($R^A$)═C($R^B$)$_p$, where $R^A$, $R^B$ and p are as defined for Formula I. For example, in the case where $R^1$ is an acryloyl group, this reaction proceeds, for example, in a solvent such as methylene chloride in the presence of acryloyl chloride and a base such as Hunig's base. In some cases, the $R^5$ substituent will also contain a protecting group, which can be removed at a subsequent step in the synthetic sequence.

Compounds (2), (3), (4) and (5) as shown and described above for Scheme I are useful as intermediates for preparing compounds of Formula I and are provided as further aspects of the invention.

SCHEME II

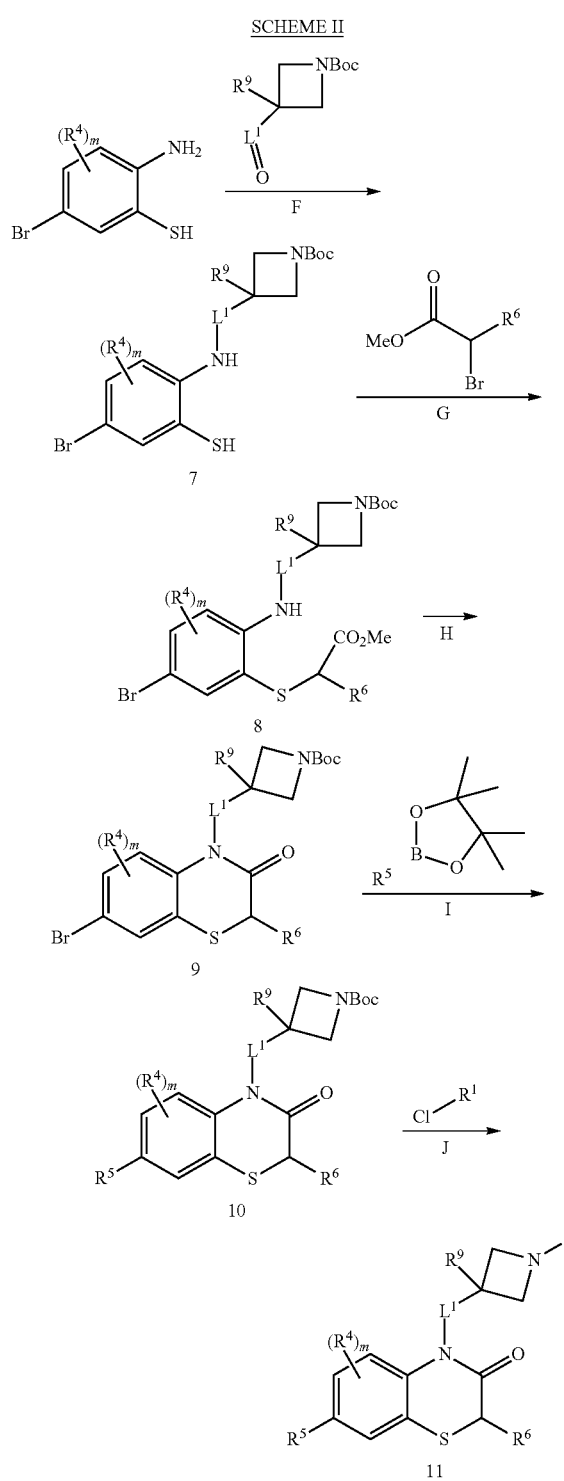

Compounds of Formula I wherein Z is S, R⁵ is an optionally substituted aryl or heteroaryl and $R^1$, $L^1$, $R^4$, $R^5$ $R^6$ and m are as defined for Formula I can be prepared according to Scheme II. In step F, an appropriately protected azetidine—$L^1$ aldehyde is coupled to an aniline to provide compound (7). In step G, the substituent $R^6$ is introduced by reaction of an alpha-halo ester with (7) using a suitable base such as potassium carbonate in DMF to provide an intermediate ester (8), and the ester is hydrolyzed using a suitable base such as NaOH in a solvent such as ethanol, followed by formation of the lactam using reagents for amide bond formation such as EDC and HOBt in a solvent such as DMF affords compound (9) in step H. In step I, the substituent $R^5$ is introduced with a palladium coupling, using a suitable functionalized aryl or heteroaryl system, for example an aryl boronate, in the presence of a palladium catalyst such as Pd₂DBA₃/Xantphos in a solvent such as toluene with a base such as sodium tert-butoxide to provide compound (10). In step J, the protecting group of the azetidine ring in compound (11) is removed by treating with a suitable acid such as TFA in a solvent such as methylene chloride, and $R^1$ is introduced to provide a compound of Formula I, for example by treating with an acid chloride having the formula Cl—C(O)C($R^A$)═C($R^B$)$_p$ or Cl—SO₂C($R^A$)═C($R^B$)$_p$, where $R^A$, $R^B$ and p are as defined for Formula I. For example, in the case where $R^1$ is an acryloyl group, this reaction proceeds, for example, in a solvent such as methylene chloride in the presence of acryloyl chloride and a base such as Hunig's base. In some cases, the species $R^5$ will also contain a protecting group, which can be removed at a subsequent step in the synthetic sequence.

Compounds (7), (8), (9) and (10) as shown and described above for Scheme II are useful as intermediates for preparing compounds of Formula I and are provided as further aspects of the invention.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention.

The following Examples are intended to illustrate further certain embodiments of the invention and are not intended to limit the scope of the invention.

Example 1

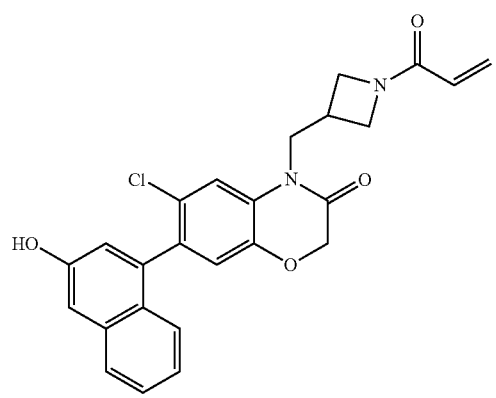 [SMILES: C=CC(=O)N1CC(CN2C(=O)COc3cc(-c4cc(O)cc5ccccc45)c(Cl)cc32)C1]

Preparation of 4-((1-acryloylazetidin-3-yl)methyl)-6-chloro-7-(3-hydroxynaphthalen-1-yl)-2H-benzo[b][1,4]oxazin-3(4H)-one

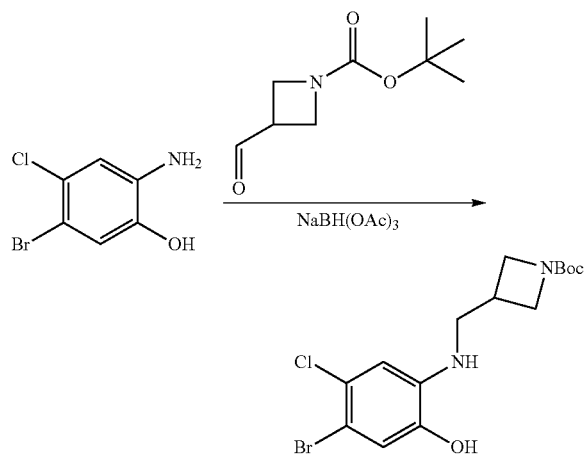

Step A: tert-butyl 3-(((4-bromo-5-chloro-2-hydroxyphenyl)amino)methyl)azetidine-1-carboxylate. To a round bottom flask was added 2-amino-5-bromo-4-chlorophenol (1.0 g, 4.50 mmol) and 1-Boc-3-azetidinecarboxaldehyde (0.916 g, 4.94 mmol) followed by $CH_2Cl_2$ (12.8 mL). To the resulting suspension was added sodium triacetoxyborohydride (1.24 g, 5.84 mmol) in one portion and then acetic acid (0.257 mL, 4.50 mmol) was added and the mixture was stirred at ambient temperature overnight (16 h). A saturated aqueous $NaHCO_3$ solution was added and the mixture was extracted with 5% IPA/$CHCl_3$ (3×25 mL) and the combined organic extracts were dried over $Na_2SO_4$, filtered and concentrated to dryness. The crude product was purified via column chromatography (2% MeOH/DCM) to afford the product as a red/brown solid (1.35 g, 76%). ES+APCI MS m/z 391.0 [M–H]$^-$.

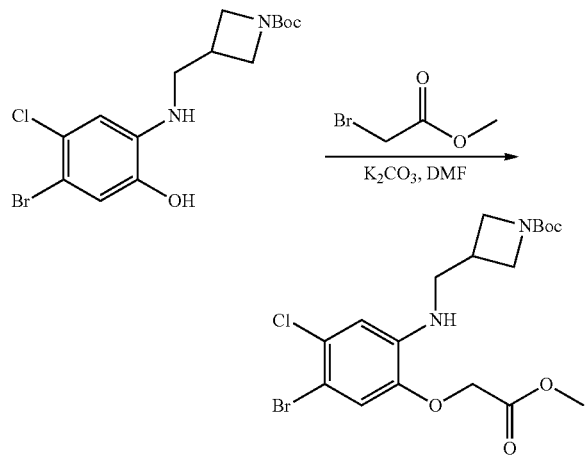

Step B: tert-butyl 3-(((4-bromo-5-chloro-2-(2-methoxy-2-oxoethoxy)phenyl)amino) methyl)azetidine-1-carboxylate. To a solution of tert-butyl 3-(((4-bromo-5-chloro-2-hydroxyphenyl)amino)methyl)azetidine-1-carboxylate (0.200 g, 0.5106 mmol) in DMF (5.10 mL) was added $K_2CO_3$ (0.212 g, 1.53 mmol) followed by methyl 2-bromoacetate (0.141 mL, 1.532 mmol). The mixture was stirred at ambient temperature for 4 hours. The mixture was diluted with $H_2O$ (20 mL) and the mixture was stirred for 30 minutes. The resulting sticky orange solid was removed by vacuum filtration and washed with water. The solid was dissolved in EtOAc (20 mL) and the solution was dried over $Na_2SO_4$, filtered and concentrated in vacuo to afford the crude product as a red/tan solid (0.226 g, 95%). ES+APCI MS m/z 365.0 [M–Boc]$^+$.

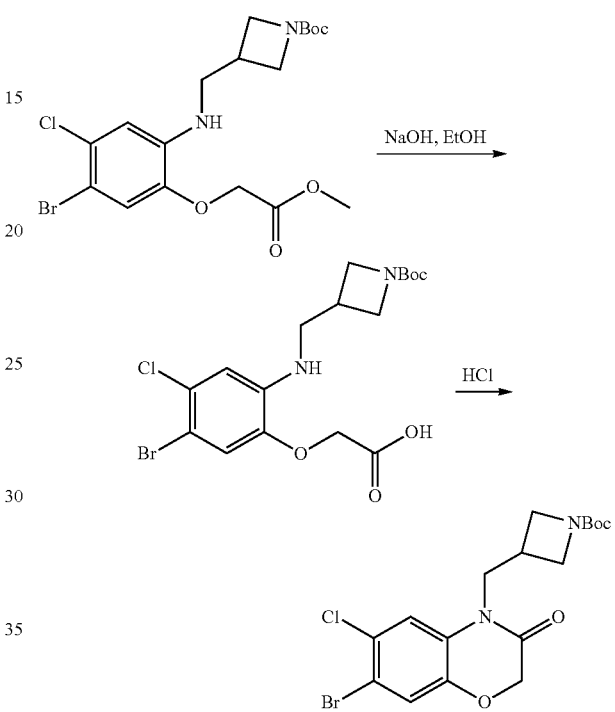

Step C: tert-butyl 3-((7-bromo-6-chloro-3-oxo-2,3-dihydro-4H-benzo[b][1,4]oxazin-4-yl)methyl)azetidine-1-carboxylate. To a suspension of tert-butyl 3-(((4-bromo-5-chloro-2-(2-methoxy-2-oxoethoxy)phenyl)amino)methyl)azetidine-1-carboxylate (0.226 g, 0.487 mmol) in EtOH (4.87 mL) was added NaOH (1.46 mL, 1.46 mmol, 1.0M Aq). The mixture was stirred overnight at 50° C. The mixture was cooled to 0° C. and the mixture was treated with 1.5 mL of 1M HCl and stirred for 5 minutes. The mixture was extracted with $CHCl_3$ (3×10 mL) and the combined organic layers were dried over $Na_2SO_4$, filtered and concentrated. The crude product was purified via column chromatography (5-10% EtOAc/DCM) to afford the title compound as a white solid (0.145 g, 68%). ES+APCI MS m/z 331.0 [M–Boc]$^+$.

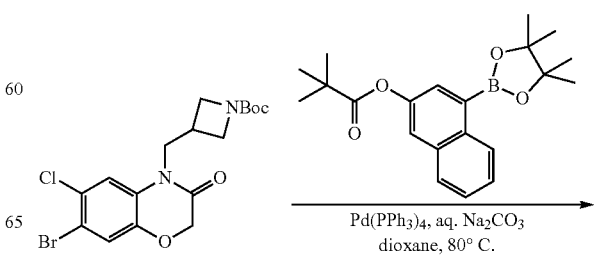

-continued

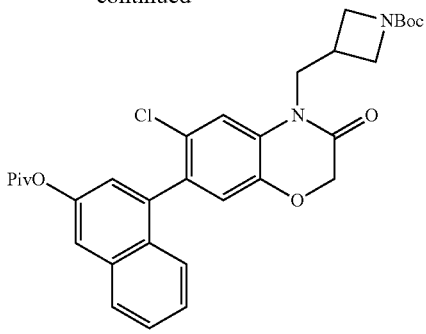

Step D: tert-butyl 3-((6-chloro-3-oxo-7-(3-(pivaloyloxy) naphthalen-1-yl)-2,3-dihydro-4H-benzo[b][1,4]oxazin-4-yl) methyl)azetidine-1-carboxylate. To a vial was added tert-butyl 3-((7-bromo-6-chloro-3-oxo-2,3-dihydro-4H-benzo [b][1,4]oxazin-4-yl)methyl)azetidine-1-carboxylate (0.135 g, 0.313 mmol), 4-(4,4,5,5-tetramethyl-1,3,2-dioxaborolan-2-yl)naphthalen-2-yl pivalate (0.144 g, 0.407 mmol) and dioxane (2.61 mL). To this was added tetrakis(triphenylphosphine)palladium (0) (0.036 g, 0.031 mmol) and $Na_2CO_3$ (0.469 mL, 0.938 mmol, 2.0M Aq). The mixture was purged with Ar, then heated to 80° C. under an Ar atmosphere and stirred for 2.5 hours. The mixture was cooled to ambient temperature diluted with $CH_2Cl_2$ and filtered. The filtrate was dried over $Na_2SO_4$, filtered and concentrated. The crude product was purified via column chromatography (1-2% MeOH/DCM) to afford the product as a tan foam (0.165 g, 72%). ES+APCI MS m/z 579.2 [M+H]⁺.

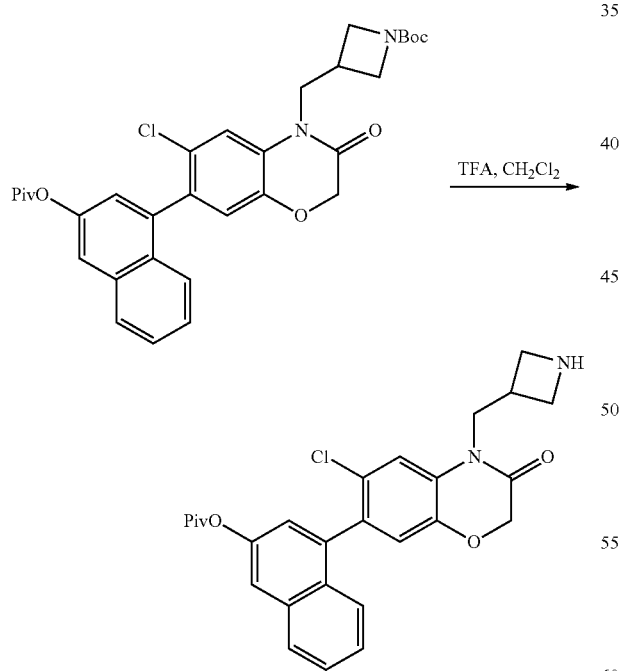

Step E: 4-(4-(azetidin-3-ylmethyl)-6-chloro-3-oxo-3,4-dihydro-2H-benzo[b][1,4]oxazin-7-yl)naphthalen-2-yl pivalate. To a solution of tert-butyl 3-((6-chloro-3-oxo-7-(3-(pivaloyloxy)naphthalen-1-yl)-2,3-dihydro-4H-benzo[b][1, 4]oxazin-4-yl)methyl)azetidine-1-carboxylate (0.100 g, 0.1727 mmol) in $CH_2Cl_2$ (1.73 mL) at 0° C. was added trifluoroacetic acid (0.265 mL, 3.454 mmol) and the mixture was warmed to ambient temperature where it stirred for 1 hour. The mixture was concentrated in vacuo to afford the crude product as a viscous oil. The mixture was dissolved in minimal DCM and added to a solution of saturated aqueous $NaHCO_3$. The mixture was extracted with 10% $IPA/CHCl_3$ (3×10 mL). The combined organic extracts were dried over $Na_2SO_4$, filtered and concentrated to afford an orange foam. The crude product was used directly in the subsequent step.

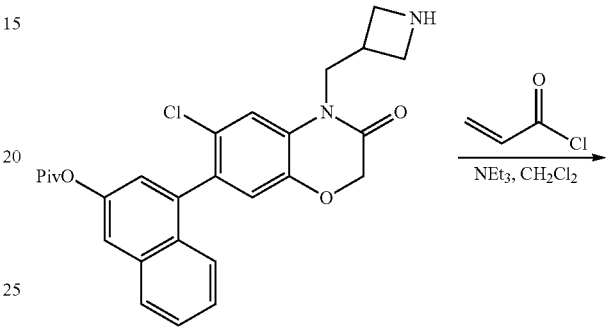

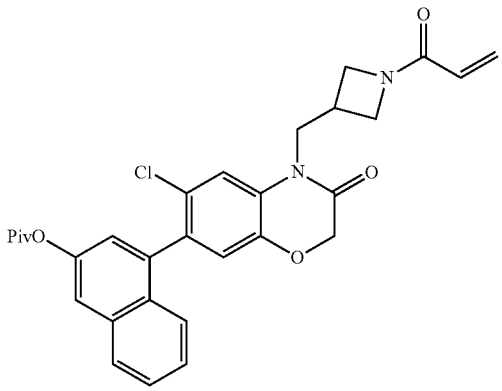

Step F: 4-(4-((1-acryloylazetidin-3-yl)methyl)-6-chloro-3-oxo-3,4-dihydro-2H-benzo[b][1,4]oxazin-7-yl)naphthalen-2-yl pivalate. To a solution of 4-(4-(azetidin-3-ylmethyl)-6-chloro-3-oxo-3,4-dihydro-2H-benzo[b][1,4] oxazin-7-yl)naphthalen-2-yl pivalate (0.082 g, 0.17 mmol) in $CH_2Cl_2$ (1.7 mL) at −78° C. was added Triethylamine (0.048 mL, 0.34 mmol). Then Acryloyl chloride (0.015 mL, 0.19 mmol) was added and the reaction was stirred for 0.5 h. The mixture was diluted with $CHCl_3$ and a saturated aqueous $NH_4Cl$ solution. The layers were separated and the aqueous layer was extracted with $CHCl_3$ (2×10 mL). The combined extracts were dried over $Na_2SO_4$, filtered and concentrated. The crude product was purified via column chromatography (10-20% EtOAc/DCM) to afford the impure product as a white foam. ES+APCI MS m/z 533.1 [M+H]+.

35

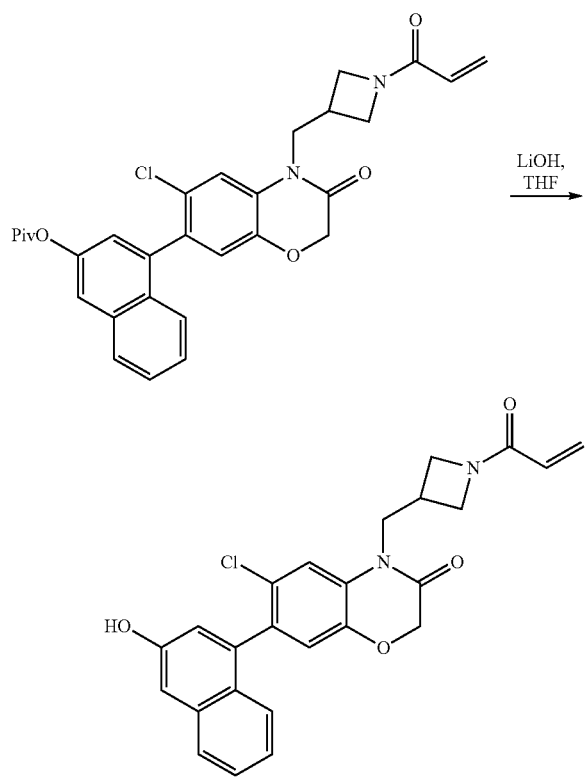

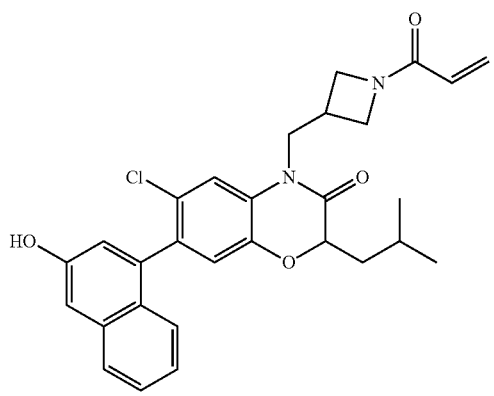 [SMILES: C=CC(=O)N1CC(CN2C(=O)C(CC(C)C)Oc3cc(-c4cc(O)cc5ccccc45)c(Cl)cc32)C1]

Step G: 4-((1-acryloylazetidin-3-yl)methyl)-6-chloro-7-(3-hydroxynaphthalen-1-yl)-2H-benzo[b][1,4]oxazin-3(4H)-one. Impure 4-(4-((1-acryloylazetidin-3-yl)methyl)-6-chloro-3-oxo-3,4-dihydro-2H-benzo[b][1,4]oxazin-7-yl) naphthalen-2-yl pivalate (0.022 g, 0.041 mmol) was dissolved in THF (0.825 mL) and the solution was treated with LiOH (0.206 mL, 0.413 mmol, 2M aq) and the mixture was stirred vigorously at ambient temperature for 3 hours. The reaction mixture was purified directly via column chromatography (2-5% MeOH/DCM with 0.1% NH₄OH) to afford the title compound (0.0049 g) as a white foam. ES+APCI MS m/z 449.2 [M+H]⁺.

Example 2

36

Preparation of 4-((1-acryloylazetidin-3-yl)methyl)-6-chloro-7-(3-hydroxynaphthalen-1-yl)-2-isobutyl-2H-benzo[b][1,4]oxazin-3(4H)-one

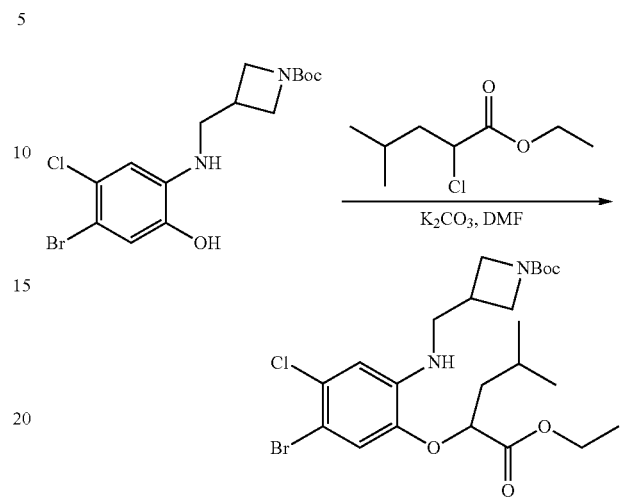

Step A: tert-butyl 3-(((4-bromo-5-chloro-2-((1-ethoxy-4-methyl-1-oxopentan-2-yl)oxy)phenyl)amino)methyl)azetidine-1-carboxylate. To a solution of tert-butyl 3-(((4-bromo-5-chloro-2-hydroxyphenyl)amino)methyl)azetidine-1-carboxylate (0.200 g, 0.511 mmol) in DMF (5.11 mL) was added K₂CO₃ (0.212 g, 1.53 mmol) followed by ethyl 2-chloro-4-methylpentanoate (0.274 g, 1.53 mmol). The mixture was stirred at ambient temperature for 20 hours. The mixture was diluted with H₂O (20 mL) and was extracted with EtOAc (2×10 mL). The combined extracts were washed with brine, dried over Na₂SO₄, filtered and concentrated in vacuo to afford the crude product as a dark thick oil (0.290 g). ES+APCI MS m/z 433.0[M−Boc]⁺.

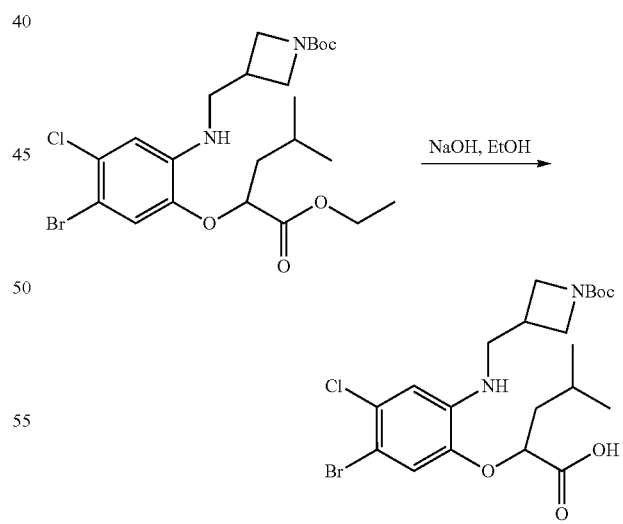

Step B: 2-(5-bromo-2-(((1-(tert-butoxycarbonyl)azetidin-3-yl)methyl)amino)-4-chlorophenoxy)-4-methylpentanoic acid. To a suspension of tert-butyl 3-(((4-bromo-5-chloro-2-((1-ethoxy-4-methyl-1-oxopentan-2-yl)oxy)phenyl) amino)methyl)azetidine-1-carboxylate (0.273 g, 0.511 mmol) in EtOH (5.11 mL) was added NaOH (1.53 ml, 1.53 mmol, 1.0M Aq). The mixture was stirred overnight at 50°

C. The mixture was cooled to 0° C. and it was treated with HCl (1.59 mL, 1.59 mmol, 1.0M HCl). The mixture was extracted with CHCl₃ (3×10 mL) and the combined organic layers were dried over Na₂SO₄, filtered and concentrated. The crude product (0.252 g) was taken directly to the next step. ES+APCI MS m/z 505.2 [M−H]⁻.

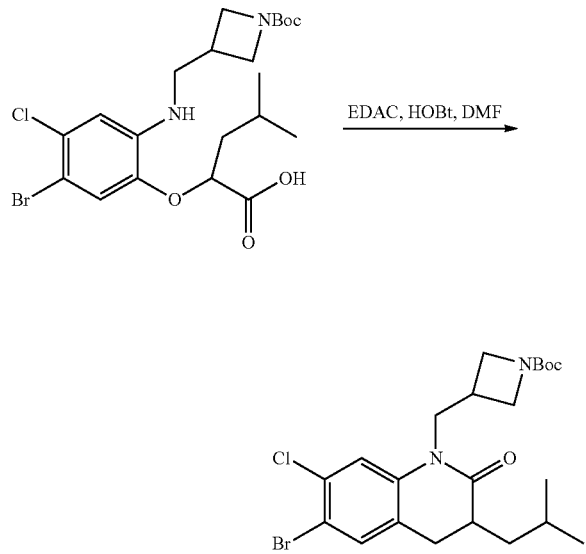 [SMILES: CC(C)CC(Oc1cc(Br)c(Cl)cc1NCC1CN(C(=O)OC(C)(C)C)C1)C(=O)O ; CC(C)CC1Cc2cc(Br)c(Cl)cc2N(CC2CN(C(=O)OC(C)(C)C)C2)C1=O]

Step C: tert-butyl 3-((7-bromo-6-chloro-2-isobutyl-3-oxo-2,3-dihydro-4H-benzo[b][1,4]oxazin-4-yl)methyl)azetidine-1-carboxylate. To a solution of crude 2-(5-bromo-2-(((1-(tert-butoxycarbonyl)azetidin-3-yl)methyl)amino)-4-chlorophenoxy)-4-methylpentanoic acid (0.252 g, 0.498 mmol) in DMF (4.98 mL) was added 1-(3-dimethylaminopropyl)-3-ethylcarbodiimide hydrochloride (0.143 g, 0.747 mmol) followed by 1-Hydroxybenzotriazole hydrate (0.114 g, 0.747 mmol). The mixture was stirred at ambient temperature for 22 h. H₂O was added followed by a saturated aqueous NH₄Cl solution and the mixture was extracted with EtOAc (3×10 mL). The combined organic extracts were washed with brine and dried over Na₂SO₄, filtered and concentrated. The crude product was purified via column chromatography (5-10% EtOAc/DCM) to afford the product as a pale yellow oil that became a foam under high vac (0.159 g, 65% for three steps). ES+APCI MS m/z 490.1[M+H]⁺.

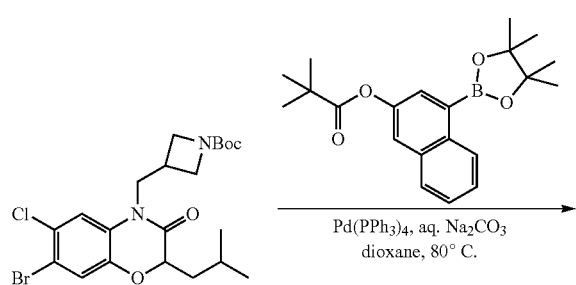

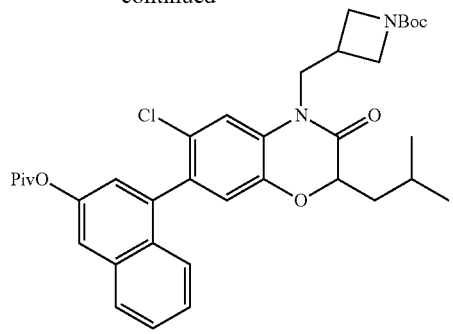

Step D: tert-butyl 3-((6-chloro-2-isobutyl-3-oxo-7-(3-(pivaloyloxy)naphthalen-1-yl)-2,3-dihydro-4H-benzo[b][1,4]oxazin-4-yl)methyl)azetidine-1-carboxylate. To a vial was added tert-butyl 3-((7-bromo-6-chloro-2-isobutyl-3-oxo-2,3-dihydro-4H-benzo[b][1,4]oxazin-4-yl)methyl)azetidine-1-carboxylate (0.148 g, 0.303 mmol), 4-(4,4,5,5-tetramethyl-1,3,2-dioxaborolan-2-yl)naphthalen-2-yl pivalate (0.140 g, 0.394 mmol) and dioxane (2.53 mL). To this was added Tetrakis(triphenylphosphine)palladium (0) (0.035 g, 0.030 mmol) and Na₂CO₃ (0.455 mL, 0.910 mmol, 2.0M Aq). The mixture was purged with Ar and then heated to 80° C. under an Ar atmosphere and stirred for 6.5 hours. The mixture was cooled to ambient temperature diluted with CH₂Cl₂ and was filtered. The filtrate was dried over Na₂SO₄, filtered and concentrated. The crude product was purified via column chromatography (2-10% EtOAc/DCM) to afford the product as a yellow foam (0.176 g, 91%). ES+APCI MS m/z 636.3[M+H]⁺.

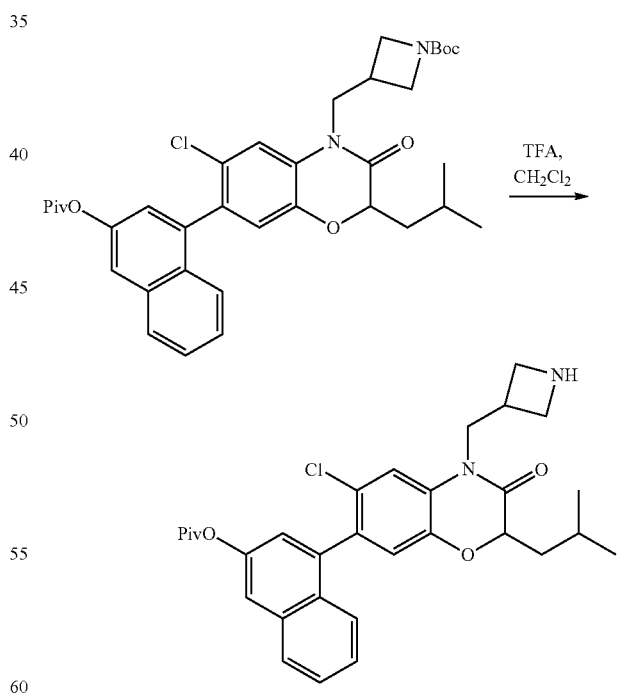

Step E: 4-(4-(azetidin-3-ylmethyl)-6-chloro-2-isobutyl-3-oxo-3,4-dihydro-2H-benzo[b][1,4]oxazin-7-yl)naphthalen-2-yl pivalate. To a solution of tert-butyl 3-((6-chloro-2-isobutyl-3-oxo-7-(3-(pivaloyloxy)naphthalen-1-yl)-2,3-dihydro-4H-benzo[b][1,4]oxazin-4-yl)methyl)azetidine-1-carboxylate (0.176 g, 0.2771 mmol) in ClH₂Cl₂ (2.77 mL) at 0° C. was added trifluoroacetic acid (0.424 mL, 5.542 mmol) and the mixture was stirred at 0° C. for 1.5 hours. The mixture was carefully added to a solution of saturated aqueous NaHCO₃. The mixture was extracted with DCM (3×10 mL). The combined organic extracts were dried over Na₂SO₄, filtered and concentrated to afford an orange foam. The crude product was used directly in the subsequent step. ES+APCI MS m/z 535.2[M+H]⁺.

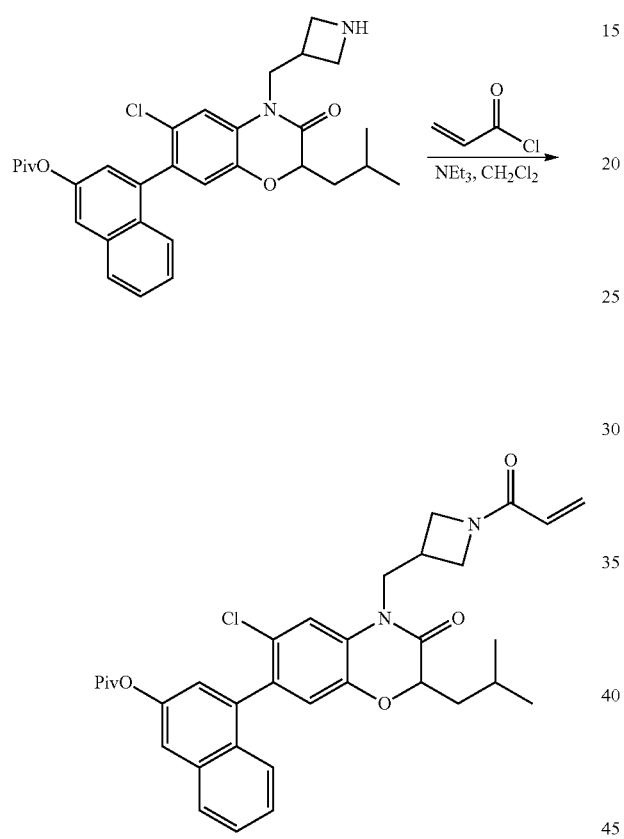

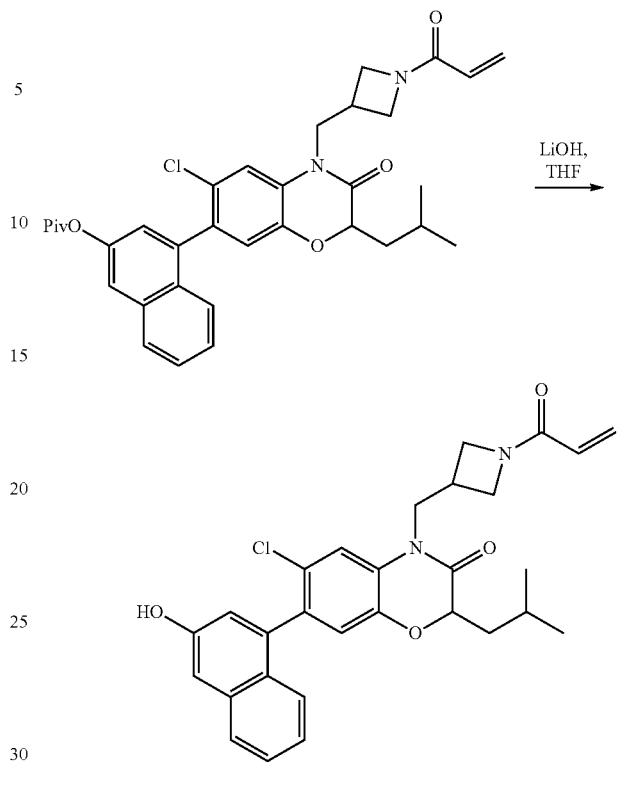

Step G: 4-((1-acryloylazetidin-3-yl)methyl)-6-chloro-7-(3-hydroxynaphthalen-1-yl)-2-isobutyl-2H-benzo[b][1,4]oxazin-3(4H)-one. 4-(4-((1-acryloylazetidin-3-yl)methyl)-6-chloro-2-isobutyl-3-oxo-3,4-dihydro-2H-benzo[b][1,4]oxazin-7-yl)naphthalen-2-yl pivalate (0.067 g, 0.114 mmol) was dissolved in THF (1.14 mL) and the solution was treated with LiOH (0.569 mL, 1.14 mmol, 2M aq) and the mixture was stirred vigorously at ambient temperature for 7 hours. The reaction mixture was purified directly via column chromatography (5-30% EtOAc/DCM) to afford the product as a white solid (0.038 g, 62% for three steps). ES+APCI MS m/z 505.2[M+H]⁺.

Example 3

Step F: 4-(4-((1-acryloylazetidin-3-yl)methyl)-6-chloro-2-isobutyl-3-oxo-3,4-dihydro-2H-benzo[b][1,4]oxazin-7-yl)naphthalen-2-yl pivalate. To a solution of 4-(4-(azetidin-3-ylmethyl)-6-chloro-2-isobutyl-3-oxo-3,4-dihydro-2H-benzo[b][1,4]oxazin-7-yl)naphthalen-2-yl pivalate (0.148 g, 0.277 mmol) in CH₂Cl₂ (2.77 mL) at −78° C. was added Triethylamine (0.058 mL, 0.4149 mmol). Acryloyl chloride (0.025 ml, 0.304 mmol) was added and the reaction was stirred for 0.5 h. The mixture was diluted with CHCl₃ and a saturated aqueous NH₄Cl solution. The layers were separated and the aqueous layer was extracted with CHCl₃ (2×10 mL). The combined extracts were dried over Na₂SO₄, filtered and concentrated. The crude product was purified via column chromatography (10-25% EtOAc/DCM) to afford the product (0.077 g) as a pale yellow foam. ES+APCI MS m/z 589.3 [M+H]⁺.

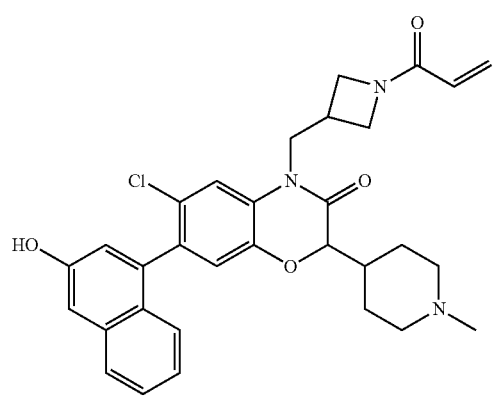 [SMILES: C=CC(=O)N1CC(CN2C(=O)C(C3CCN(C)CC3)Oc3cc(-c4cc(O)cc5ccccc45)c(Cl)cc32)C1]

Preparation of 4-((1-acryloylazetidin-3-yl)methyl)-6-chloro-7-(3-hydroxynaphthalen-1-yl)-2-(1-methylpiperidin-4-yl)-2H-benzo[b][1,4]oxazin-3(41H)-one

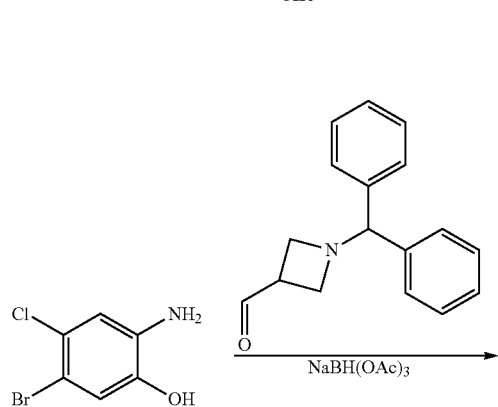

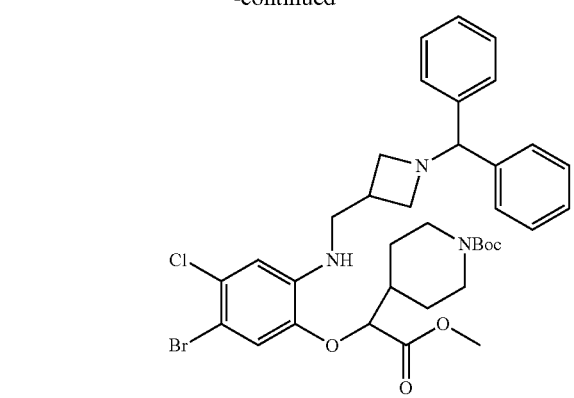

Step B: tert-butyl 4-(1-(2-(((1-benzhydrylazetidin-3-yl)methyl)amino)-5-bromo-4-chlorophenoxy)-2-methoxy-2-oxoethyl)piperidine-1-carboxylate. To a solution of 2-(((1-benzhydrylazetidin-3-yl)methyl)amino)-5-bromo-4-chlorophenol (0.195 g, 0.426 mmol) in DMF (4.26 mL) was added K$_2$CO$_3$ (0.177 g, 1.28 mmol) followed by 1-Boc-4-(bromo-methoxycarbonyl-methyl)-piperidine (0.430 g, 1.28 mmol). The mixture was stirred at 35° C. for 19 hours. The mixture was diluted with H$_2$O (20 mL) and the mixture was extracted with EtOAc (2×10 mL). The combined extracts were washed with brine, dried over Na$_2$SO$_4$, filtered and concentrated in vacuo to afford the crude product as a dark thick oil. The crude product was taken directly to the next step. ES+APCI MS m/z 712.1[M+H]$^+$.

Step A: 2-(((1-benzhydrylazetidin-3-yl)methyl)amino)-5-bromo-4-chlorophenol. To a round bottom flask was added 2-amino-5-bromo-4-chlorophenol (0.885 g, 3.98 mmol) and 1-benzhydrylazetidine-3-carbaldehyde (1.0 g, 3.98 mmol) followed by CH$_2$Cl$_2$ (11.4 mL). To the resulting suspension was added Sodium triacetoxyborohydride (1.10 g, 5.17 mmol) in one portion and then acetic acid (0.228 mL, 3.98 mmol) was added and the mixture was stirred at ambient temperature for 3 hours. A saturated aqueous NaHCO$_3$ solution was added and the mixture was extracted with 5% IPA/CHCl$_3$ (3×25 mL) and the combined organic extracts were dried over Na$_2$SO$_4$, filtered and concentrated to dryness in vacuo (1.73 g, 95%) and was used directly in the subsequent step. ES+APCI MS m/z 459.1[M+H]$^+$.

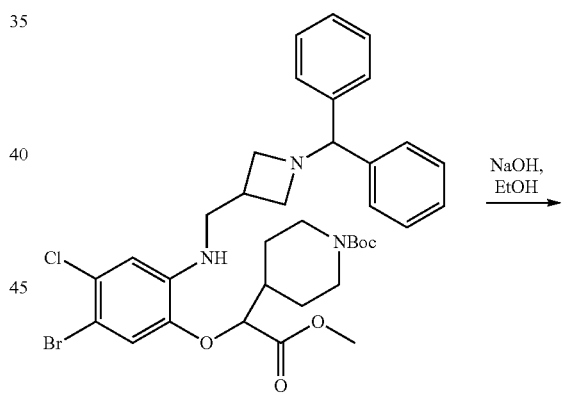

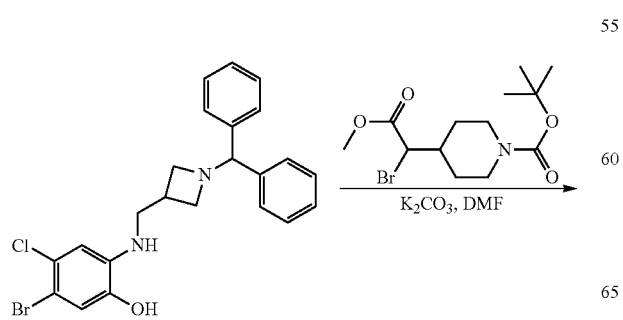

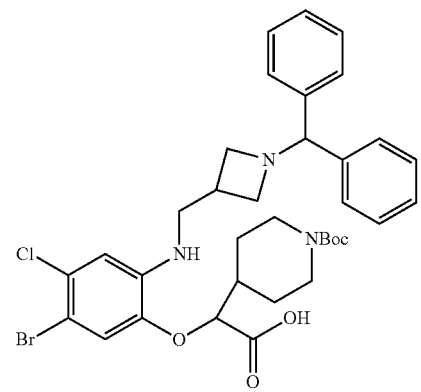

Step C: 2-(2-(((1-benzhydrylazetidin-3-yl)methyl)amino)-5-bromo-4-chlorophenoxy)-2-(1-(tert-butoxycarbonyl)piperidin-4-yl)acetic acid. To a solution of tert-butyl 4-(1-(2-(((1-benzhydrylazetidin-3-yl)methyl)amino)-5-bromo-4-chlorophenoxy)-2-methoxy-2-oxoethyl)piperidine-1-carboxylate (0.304 g, 0.426 mmol) in EtOH (4.26 mL) was added NaOH (1.28 mL, 1.28 mmol, 1.0M Aq). The mixture was stirred for 2 hours at 50° C. and then overnight at RT. The mixture was cooled to 0° C. and was treated with KHSO$_4$ (1.3 mL, 1.0M Aq). The mixture was extracted with CHCl$_3$ (3×10 mL) and the combined organic layers were dried over Na$_2$SO$_4$, filtered and concentrated. The crude product was taken directly to the next step. ES+APCI MS m/z 700.2[M+H]$^+$.

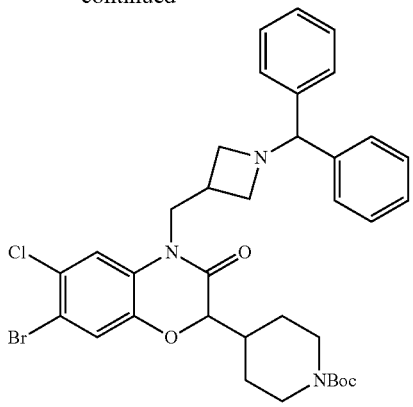

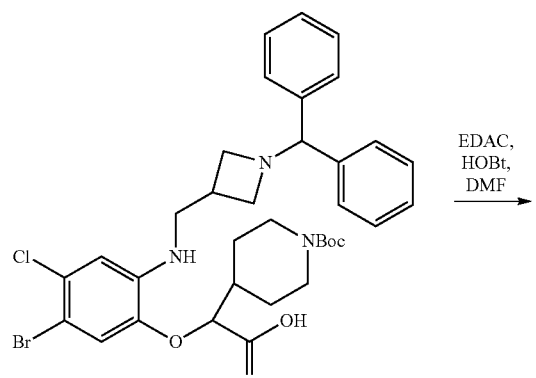

Step D: tert-butyl 4-(4-((1-benzhydrylazetidin-3-yl)methyl)-7-bromo-6-chloro-3-oxo-3,4-dihydro-2H-benzo[b][1,4]oxazin-2-yl)piperidine-1-carboxylate. To a solution of crude 2-(2-(((1-benzhydrylazetidin-3-yl)methyl)amino)-5-bromo-4-chlorophenoxy)-2-(1-(tert-butoxycarbonyl)piperidin-4-yl)acetic acid (0.298 g, 0.426 mmol) in DMF (4.26 mL) was added 1-(3-dimethylaminopropyl)-3-ethylcarbodiimide hydrochloride (0.123 g, 0.639 mmol) followed by 1-Hydroxybenzotriazole hydrate (0.0979 g, 0.639 mmol). The mixture was stirred at ambient temperature for 4 hours. Water (20 mL) was added followed by saturated aqueous NH$_4$Cl (10 mL) and the mixture was stirred and the resulting tan precipitate was isolated by vacuum filtration. The isolated solid was washed with water and dissolved in EtOAc. The organic solution was dried over Na$_2$SO$_4$, filtered and concentrated. The crude product was purified via column chromatography (5-25% EtOAc/DCM) to afford the product as a pale yellow oil that became a foam under high vac (0.278 g, 95% for three steps). ES+APCI MS m/z 680.1 [M+H]$^+$.

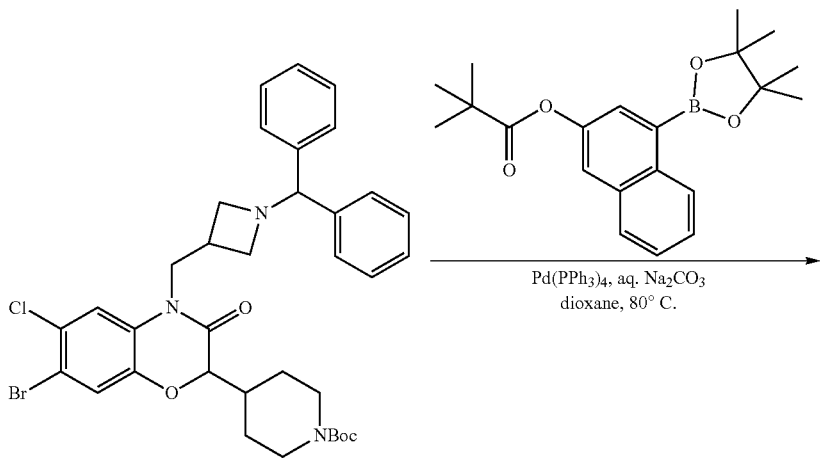

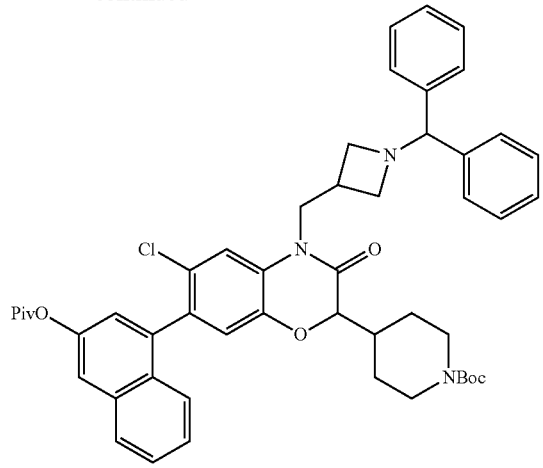

Step E: tert-butyl 4-(4-((1-benzhydrylazetidin-3-yl)methyl)-6-chloro-3-oxo-7-(3-(pivaloyloxy)naphthalen-1-yl)-3,4-dihydro-2H-benzo[b][1,4]oxazin-2-yl)piperidine-1-carboxylate. To a vial was added tert-butyl 4-(4-((1-benzhydrylazetidin-3-yl)methyl)-7-bromo-6-chloro-3-oxo-3,4-dihydro-2H-benzo[b][1,4]oxazin-2-yl)piperidine-1-carboxylate (0.274 g, 0.402 mmol), 4-(4,4,5,5-tetramethyl-1,3,2-dioxaborolan-2-yl)naphthalen-2-yl pivalate (0.185 g, 0.523 mmol) and dioxane (4.02 mL). To this was added Tetrakis(triphenylphosphine)palladium (0) (0.046 g, 0.040 mmol) and Na₂CO₃ (0.603 mL, 1.21 mmol, 2.0M Aq). The mixture was purged with Ar then heated to 80° C. under an Ar atmosphere where it stirred for 15 hours. The mixture was cooled to ambient temperature, diluted with CH₂Cl₂ and was filtered. The filtrate was dried over Na₂SO₄, filtered and concentrated. The crude product was purified via column chromatography (5-20% EtOAc/DCM) to afford the product as a pale yellow foam (0.200 g, 60%). ES+APCI MS m/z 828.3 [M+H]⁺.

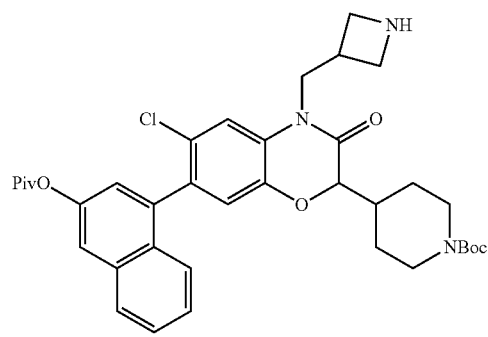

Step F: tert-butyl 4-(4-(azetidin-3-ylmethyl)-6-chloro-3-oxo-7-(3-(pivaloyloxy)naphthalen-1-yl)-3,4-dihydro-2H-benzo[b][1,4]oxazin-2-yl)piperidine-1-carboxylate. 1-chloroethyl chloroformate (0.017 mL, 0.155 mmol) was added to a solution of tert-butyl 4-(4-((1-benzhydrylazetidin-3-yl)methyl)-6-chloro-3-oxo-7-(3-(pivaloyloxy)naphthalen-1-yl)-3,4-dihydro-2H-benzo[b][1,4]oxazin-2-yl)piperidine-1-carboxylate (0.064 g, 0.077 mmol) in dry acetonitrile (1.55 mL) and the mixture was warmed to 60° C. for 2 hours after which the mixture was concentrated in vacuo. The residue was dissolved in MeOH (3.1 mL) and the mixture was stirred at ambient temperature for 2 hours. The solvent was evaporated by blowing N₂ and the residue dried in vacuo. The crude material was used directly in the subsequent step. ES+APCI MS m/z 662.3[M+H]⁺.

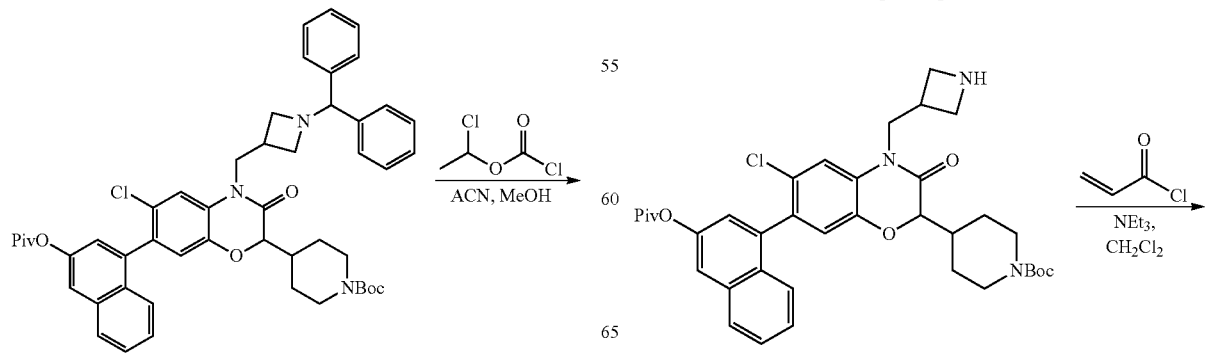

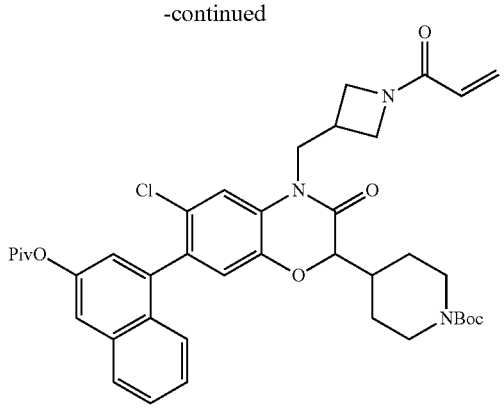

Step G: tert-butyl 4-(4-((1-acryloylazetidin-3-yl)methyl)-6-chloro-3-oxo-7-(3-(pivaloyloxy)naphthalen-1-yl)-3,4-dihydro-2H-benzo[b][1,4]oxazin-2-yl)piperidine-1-carboxylate. To a solution of tert-butyl 4-(4-(azetidin-3-ylmethyl)-6-chloro-3-oxo-7-(3-pivaloyloxy)naphthalen-1-yl)-3,4-dihydro-2H-benzo[b][1,4]oxazin-2-yl)piperidine-1-carboxylate (0.051 g, 0.077 mmol) in CH$_2$Cl$_2$ (1.5 mL) at −78° C. was added Triethylamine (0.064 ml, 0.46 mmol). Acryloyl chloride (0.77 ml, 0.23 mmol, 0.3M DCM) was added and the reaction was stirred for 0.5 hours. The mixture was diluted with CHCl$_3$ and a saturated aqueous NH$_4$Cl solution. The layers were separated and the aqueous layer was extracted with CHCl$_3$ (2×10 mL). The combined extracts were dried over Na$_2$SO$_4$, filtered and concentrated. The crude product was purified via column chromatography (20-80% EtOAc/DCM) to afford the title compound as an off-white foam (0.027 g, 49% for two steps). ES+APCI MS m/z 616.2[M+H]$^+$.

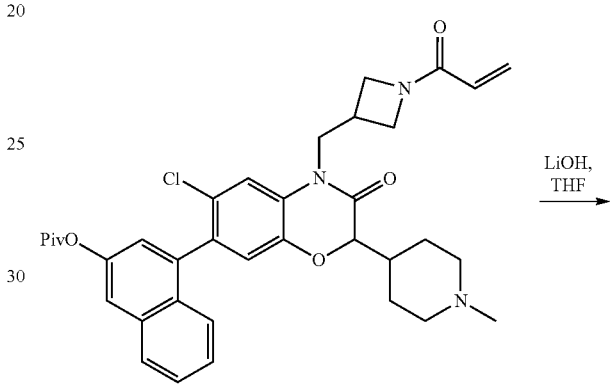

Step H: 4-(4-((1-acryloylazetidin-3-yl)methyl)-6-chloro-2-(1-methylpiperidin-4-yl)-3-oxo-3,4-dihydro-2H-benzo[b][1,4]oxazin-7-yl)naphthalen-2-yl pivalate. To a vial was added tert-butyl 4-(4-((1-acryloylazetidin-3-yl)methyl)-6-chloro-3-oxo-7-(3-(pivaloyloxy)naphthalen-1-yl)-3,4-dihydro-2H-benzo[b][1,4]oxazin-2-yl)piperidine-1-carboxylate (0.027 g, 0.038 mmol) which was dissolved in Formic acid (0.284 mL, 7.54 mmol). Formaldehyde (0.057 mL, 0.754 mmol, 37% aqueous) was added. The mixture was heated to 85° C. where it stirred for 2 hours. The mixture was cooled to ambient temperature and added to a saturated aqueous NaHCO$_3$ solution (10 mL). The mixture was transferred to a separatory funnel and the mixture was extracted with 5% IPA/CHCl$_3$ (3×10 mL) and the combined organic phases were dried over Na$_2$SO$_4$, filtered and concentrated. The crude product was purified by column chromatography (5-15% MeOH/DCM with 0.25% NH$_4$OH) to afford the product as a colorless glass (0.013 g, 50%). ES+APCI MS m/z 630.3[M+H]$^+$.

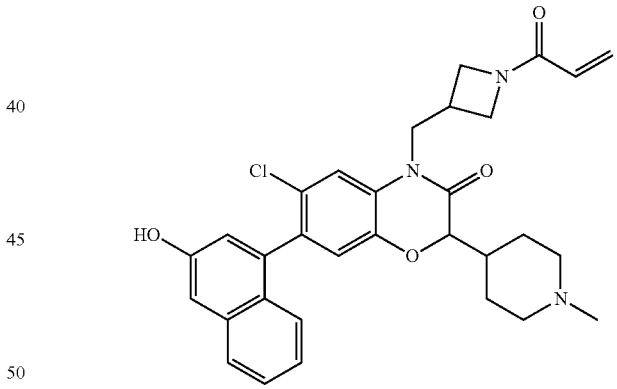

Step I: 4-((1-acryloylazetidin-3-yl)methyl)-6-chloro-7-(3-hydroxynaphthalen-1-yl)-2-(1-methylpiperidin-4-yl)-2H-benzo[b][1,4]oxazin-3(4H)-one. 4-(4-((1-acryloylazetidin-3-yl)methyl)-6-chloro-2-(1-methylpiperidin-4-yl)-3-oxo-3,4-dihydro-2H-benzo[b][1,4]oxazin-7-yl)naphthalen-2-yl pivalate (0.013 g, 0.021 mmol) was dissolved in THF (0.413 mL) and the solution was treated with LiOH (0.103 mL, 0.206 mmol, 2M aq) and the mixture was stirred vigorously at ambient temperature for 3 hours. The reaction was treated with additional LiOH (0.103 ml, 0.206 mmol, 2.0M Aq) at 3 hours and at 5 hours at which point the starting material was consumed. The reaction mixture was purified directly via column chromatography (5-12% MeOH/DCM with 0.25% NH$_4$OH) to afford the product as an off-white solid (0.0057 g, 45%). ES+APCI MS m/z 546.2[M+H]$^+$.

Example 4

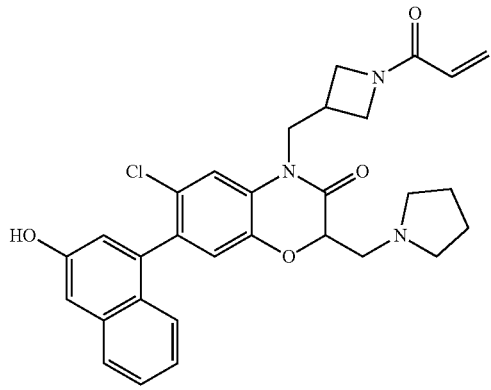 [SMILES: C=CC(=O)N1CC(CN2C(=O)C(CN3CCCC3)Oc3cc(-c4cc(O)cc5ccccc45)c(Cl)cc32)C1]

Preparation of 4-((1-acryloylazetidin-3-yl)methyl)-6-chloro-7-(3-hydroxynaphthalen-1-yl)-2-(pyrrolidin-1-ylmethyl)-2H-benzo[b][1,4]oxazin-3(4H)-one

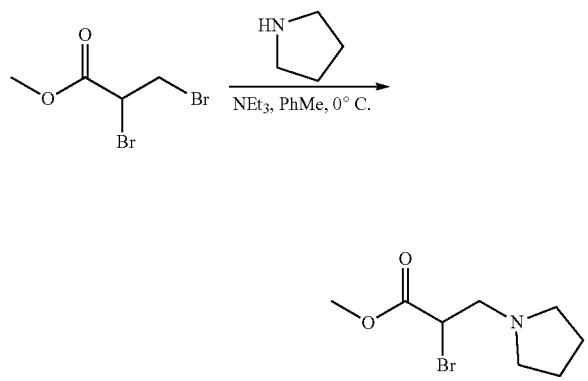

Step A: methyl 2-bromo-3-(pyrrolidin-1-yl)propanoate. A solution of methyl 2,3-dibromopropionate (1.76 g, 7.17 mmol) in toluene (117 mL) was cooled to 0° C. and Pyrrolidine (0.587 mL, 7.03 mmol) and Triethylamine (1.0 mL, 7.17 mmol) were added. After stirring at 0° C. for 1 hour, the resulting suspension was filtered, the filtrate was washed with H₂O (25 mL), dried over Na₂SO₄ and concentrated. The resulting crude yellow oil was used immediately in the next step. (Theoretical yield is 1.66 g)

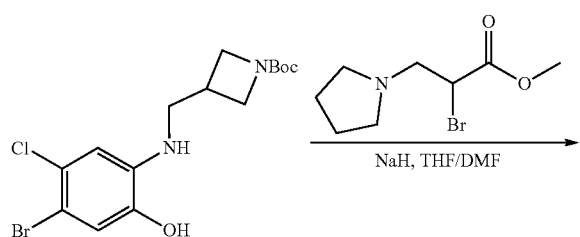

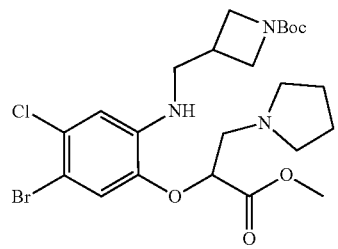

Step B: tert-butyl 3-(((4-bromo-5-chloro-2-((1-methoxy-1-oxo-3-(pyrrolidin-1-yl)propan-2-yl)oxy)phenyl)amino)methyl)azetidine-1-carboxylate. A solution of tert-butyl 3-(((4-bromo-5-chloro-2-hydroxyphenyl)amino)methyl)azetidine-1-carboxylate (0.250 g, 0.638 mmol) in THF (6.38 mL) and DMF (6.38 mL) was cooled to 0° C. NaH (0.0511 g, 1.28 mmol, 60% in mineral oil) was added and the mixture was warmed to ambient temperature where it stirred for 1 hour producing a dark homogeneous solution. Then freshly prepared methyl 2-bromo-3-(pyrrolidin-1-yl)propanoate (1.51 g, 6.38 mmol) was added and the reaction was stirred at ambient temperature for 2 hours. The mixture was diluted with H₂O (40 mL) and the mixture was extracted with EtOAc (2×40 mL). The combined extracts were washed with brine, dried over Na₂SO₄, filtered and concentrated in vacuo to afford the crude product as a dark thick oil. The crude product was taken directly to the next step. ES+APCI MS m/z 548.2[M+H]⁺.

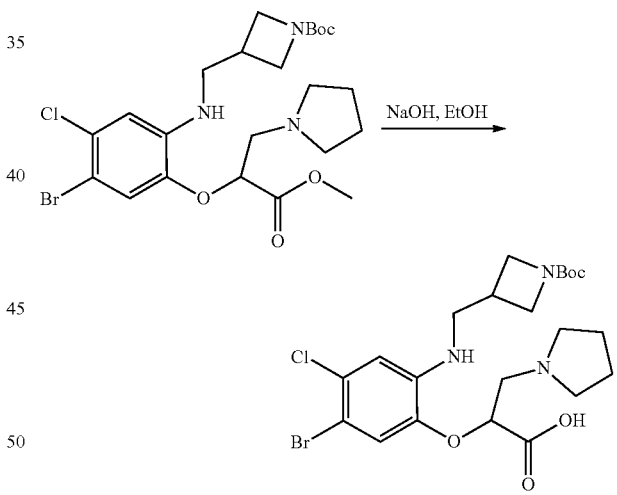

Step C: 2-(5-bromo-2-(((1-(tert-butoxycarbonyl)azetidin-3-yl)methyl)amino)-4-chlorophenoxy)-3-(pyrrolidin-1-yl)propanoic acid. To a suspension of crude tert-butyl 3-(((4-bromo-5-chloro-2-((1-methoxy-1-oxo-3-(pyrrolidin-1-yl)propan-2-yl)oxy)phenyl)amino)methyl)azetidine-1-carboxylate (0.349 g, 0.638 mmol) in EtOH (6.38 mL) was added NaOH (1.91 ml, 1.91 mmol, 1.0M Aq). The mixture was stirred for 2.5 hours at 45° C. The mixture was cooled to 0° C. and was treated with KHSO₄ (2.0 mL, 1.0M Aq). The mixture was extracted with CHCl₃ (3×10 mL) and the combined organic layers were dried over Na₂SO₄, filtered and concentrated. The dark, crude product was taken directly to the next step. ES+APCI MS m/z 534.1[M+H]⁺.

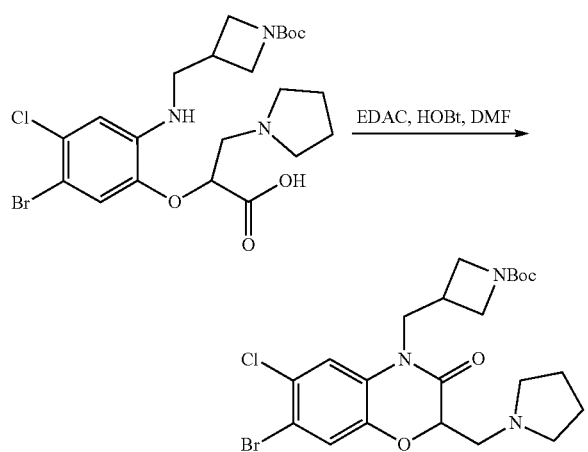

Step D: tert-butyl 3-((7-bromo-6-chloro-3-oxo-2-(pyrrolidin-1-ylmethyl)-2,3-dihydro-4H-benzo[b][1,4]oxazin-4-yl)methyl)azetidine-1-carboxylate. To a solution of crude 2-(5-bromo-2-(((1-(tert-butoxycarbonyl)azetidin-3-yl)methyl)amino)-4-chlorophenoxy)-3-(pyrrolidin-1-yl)propanoic acid (0.340 g, 0.638 mmol) in DMF (6.38 mL) was added 1-(3-dimethylaminopropyl)-3-ethylcarbodiimide hydrochloride (0.183 g, 0.957 mmol) followed by 1-Hydroxybenzotriazole hydrate (0.147 g, 0.957 mmol). The mixture was stirred at ambient temperature for 18 hours. H$_2$O was added followed by saturated aqueous NH$_4$Cl and the mixture was extracted with EtOAc (3×20 mL). The combined organic extracts were then washed with brine and then dried over Na$_2$SO$_4$, filtered and concentrated. The crude product was purified via column chromatography (2-5% MeOH/DCM) to afford the product as a dark solid foam (0.260 g, ~63% for three steps). ES+APCI MS m/z 516.1 [M+H]$^+$.

Step E: tert-butyl 3-((6-chloro-3-oxo-7-(3-(pivaloyloxy)naphthalen-1-yl)-2-(pyrrolidin-1-ylmethyl)-2,3-dihydro-4H-benzo[b][1,4]oxazin-4-yl)methyl)azetidine-1-carboxylate. To a vial was added tert-butyl 3-((7-bromo-6-chloro-3-oxo-2-(pyrrolidin-1-ylmethyl)-2,3-dihydro-4H-benzo[b][1,4]oxazin-4-yl)methyl)azetidine-1-carboxylate (0.221 g, 0.429 mmol), 4-(4,4,5,5-tetramethyl-1,3,2-dioxaborolan-2-yl)naphthalen-2-yl pivalate (0.198 g, 0.558 mmol) and dioxane (4.29 mL). To this was added Tetrakis(triphenylphosphine)palladium (0) (0.050 g, 0.043 mmol) and Na$_2$CO$_3$ (0.644 mL, 1.29 mmol, 2.0M Aq). The mixture was purged with Ar then heated to 80° C. under an Ar atmosphere where it stirred for 6 hours. The mixture was cooled to ambient temperature, diluted with CH$_2$Cl$_2$ and was filtered. The filtrate was dried over Na$_2$SO$_4$, filtered and concentrated. The crude product was purified via column chromatography (2-5% MeOH/DCM) to afford the title compound (0.200 g, 70%) as a yellow/tan foam. ES+APCI MS m/z 662.3[M+H]$^+$.

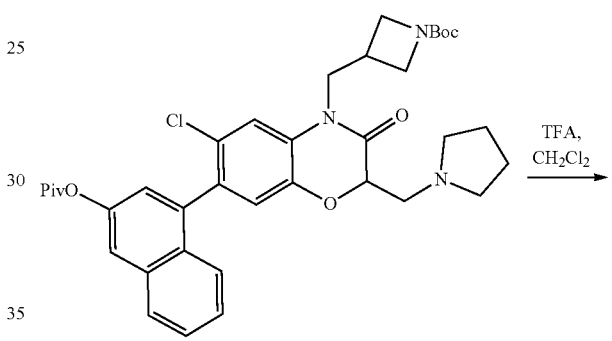

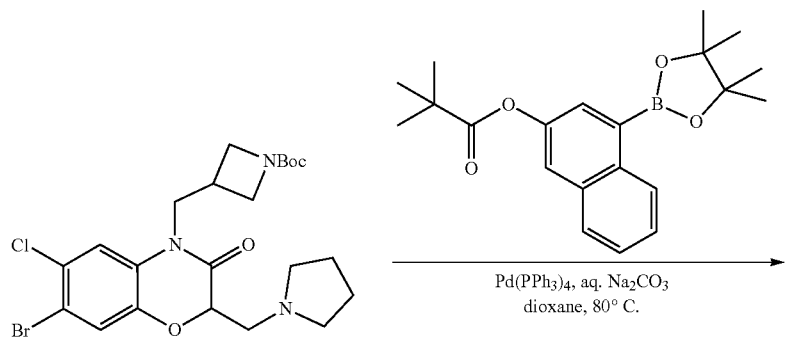

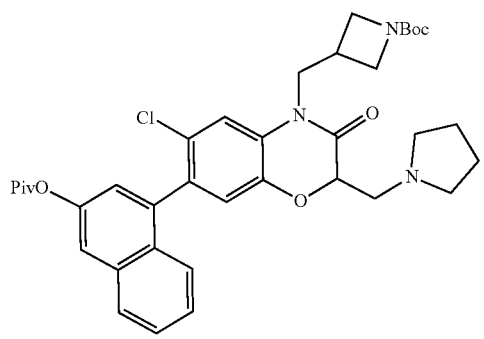

-continued

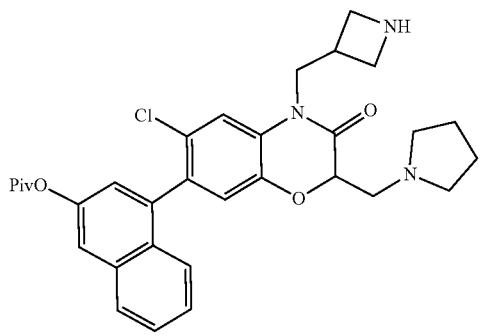

Step F: 4-(4-(azetidin-3-ylmethyl)-6-chloro-3-oxo-2-(pyrrolidin-1-ylmethyl)-3,4-dihydro-2H-benzo[b][1,4]oxazin-7-yl)naphthalen-2-yl pivalate. To a solution of tert-butyl 3-((6-chloro-3-oxo-7-(3-(pivaloyloxy)naphthalen-1-yl)-2-(pyrrolidin-1-ylmethyl)-2,3-dihydro-4H-benzo[b][1,4]oxazin-4-yl)methyl)azetidine-1-carboxylate (0.200 g, 0.302 mmol) in CH$_2$Cl$_2$ (3.02 mL) at 0° C. was added trifluoroacetic acid (0.463 mL, 6.040 mmol) and the mixture was stirred at 0° C. for 2.5 hours. The mixture was carefully added to a solution of saturated aqueous NaHCO$_3$. The mixture was extracted with DCM (3×10 mL). The combined organic extracts were then dried over Na$_2$SO$_4$, filtered and concentrated to afford an orange foam. The crude product was used directly in the subsequent step. ES+APCI MS m/z 562.2[M+H]$^+$.

Step G: 4-(4-((1-acryloylazetidin-3-yl)methyl)-6-chloro-3-oxo-2-(pyrrolidin-1-ylmethyl)-3,4-dihydro-2H-benzo[b][1,4]oxazin-7-yl)naphthalen-2-yl pivalate. To a solution of crude 4-(4-(azetidin-3-ylmethyl)-6-chloro-3-oxo-2-(pyrrolidin-1-ylmethyl)-3,4-dihydro-2H-benzo[b][1,4]oxazin-7-yl)naphthalen-2-yl pivalate (0.169 g, 0.301 mmol) in CH$_2$Cl$_2$ (3.01 mL) at −78° C. was added Triethylamine (0.063 ml, 0.451 mmol). Acryloyl chloride (0.027 mL, 0.331 mmol) was added and the reaction was stirred for 0.5 hour. The mixture was diluted with CHCl$_3$ and a saturated aqueous NH$_4$Cl solution. The layers were separated and the aqueous layer was extracted with CHCl$_3$ (2×10 mL). The combined extracts were dried over Na$_2$SO$_4$, filtered and concentrated. The crude product was purified via column chromatography (2-5% MeOH/DCM) to afford the product as an off-white foam. ES+APCI MS m/z 616.3[M+H]$^+$.

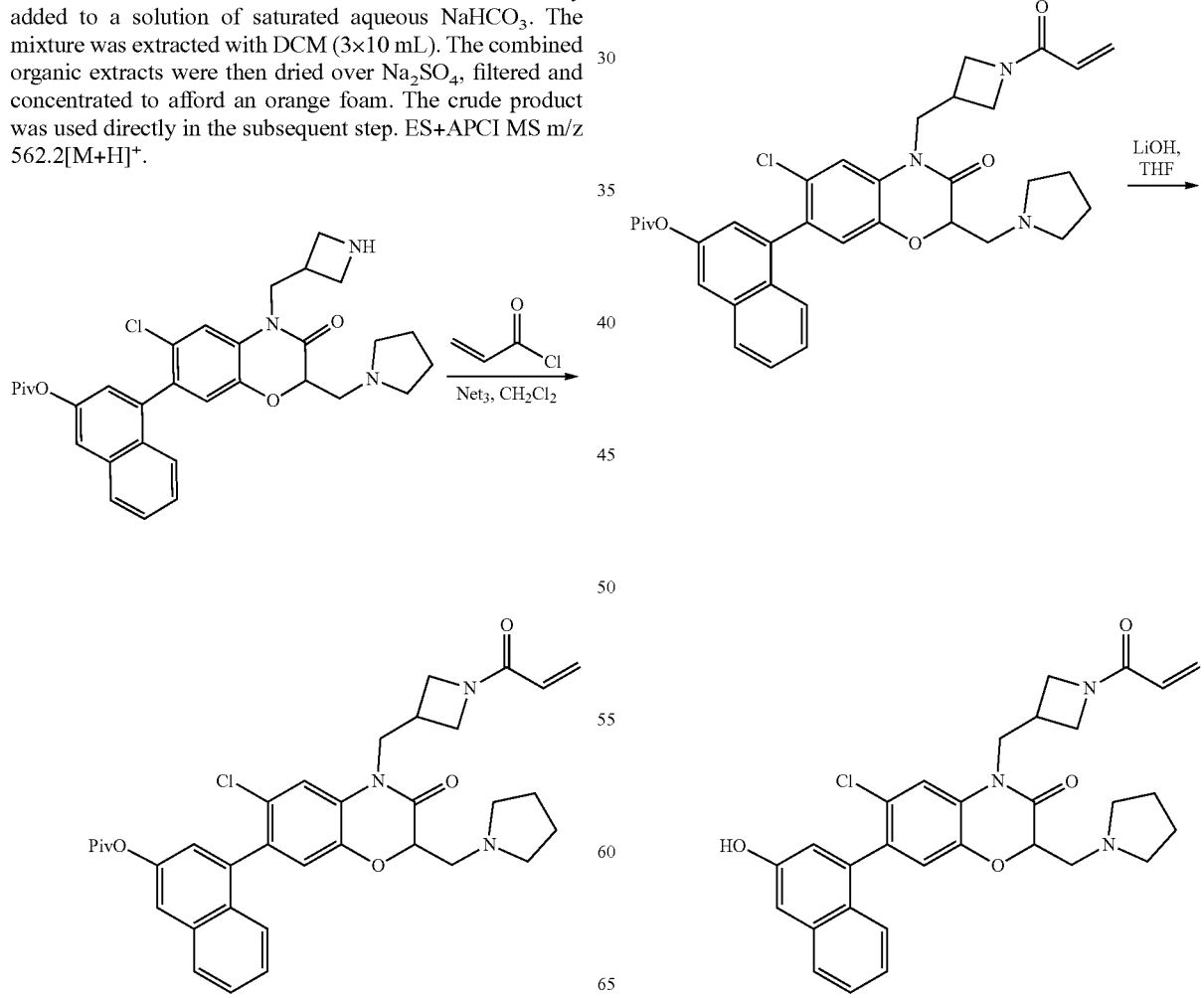

Step H: 4-((1-acryloylazetidin-3-yl)methyl)-6-chloro-7-(3-hydroxynaphthalen-1-yl)-2-(pyrrolidin-1-ylmethyl)-2H-benzo[b][1,4]oxazin-3(4H)-one. 4-(4-((1-acryloylazetidin-3-yl)methyl)-6-chloro-3-oxo-2-(pyrrolidin-1-ylmethyl)-3,4-dihydro-2H-benzo[b][1,4]oxazin-7-yl)naphthalen-2-yl pivalate (0.069 g, 0.112 mmol) was dissolved in THF (1.12 mL) and the solution was treated with LiOH (0.560 mL, 1.12 mmol, 2M aq) and the mixture was stirred vigorously at ambient temperature for 6 hours. The reaction mixture was purified directly via column chromatography (2-5% MeOH/DCM with 0.25% NH$_4$OH) to afford the product as a white solid (0.044 g). ES+APCI MS m/z 532.2[M+H]$^+$.

Example 5

Preparation of 4-((1-acryloylazetidin-3-yl)methyl)-6-chloro-2-((4-(dimethylamino)piperidin-1-yl)methyl)-7-(3-hydroxynaphthalen-1-yl)-2H-benzo[b][1,4]oxazin-3(4H)-one

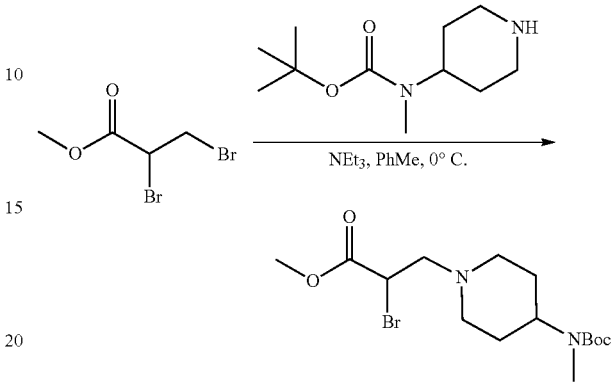

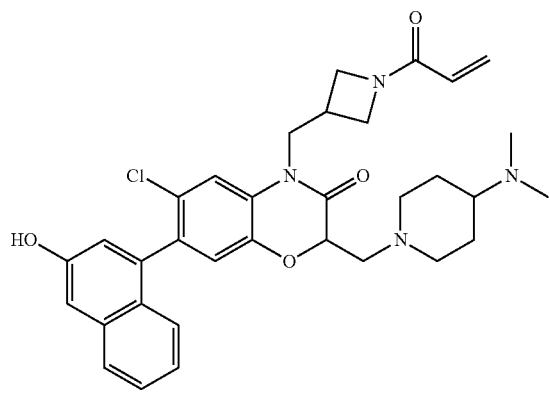 [SMILES: C=CC(=O)N1CC(CN2C(=O)C(CN3CCC(N(C)C)CC3)Oc3cc(-c4cc(O)cc5ccccc45)c(Cl)cc32)C1]

Step A: methyl 2-bromo-3-(4-((tert-butoxycarbonyl)(methyl)amino)piperidin-1-yl)propanoate. A solution of methyl 2,3-dibromopropionate (1.76 g, 7.14 mmol) in toluene (117 mL) was cooled to 0° C. and Methyl-piperidin-4-yl-carbamic acid tert-butyl ester (1.5 g, 7.00 mmol) (added as a toluene solution, 5 mL) and Triethylamine (0.995 ml, 7.14 mmol) were added. After stirring at 0° C. for 2 hours, the resulting suspension was filtered and the filtrate was washed with H$_2$O (2×15 mL), dried over Na$_2$SO$_4$ and concentrated. The resulting crude, thick yellow oil was used immediately in the next step. (Theoretical yield=2.65 g)

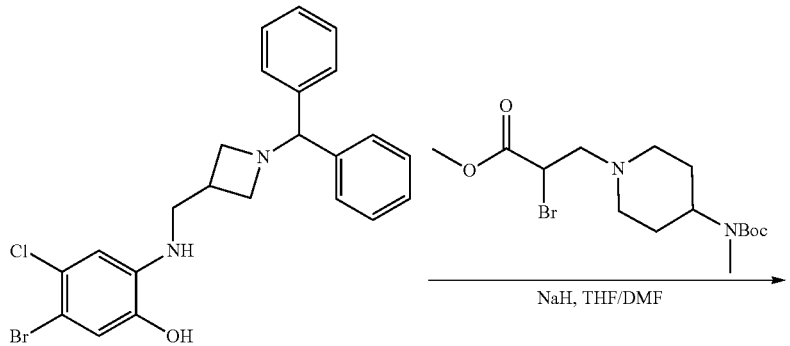

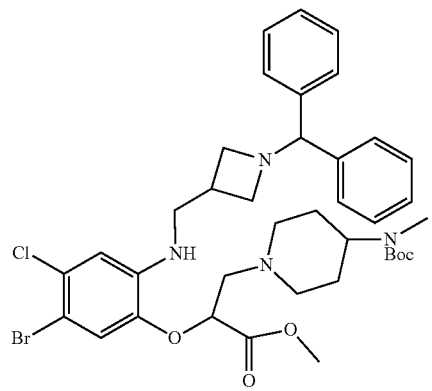

Step B: methyl 2-(2-(((1-benzhydrylazetidin-3-yl)methyl)amino)-5-bromo-4-chlorophenoxy)-3-(4-((tert-butoxycarbonyl)(methyl)amino)piperidin-1-yl)propanoate. A solution of 2-(((1-benzhydrylazetidin-3-yl)methyl)amino)-5-bromo-4-chlorophenol (0.300 g, 0.6553 mmol) in THF (6.55 mL) and DMF (6.55 mL) was cooled to 0° C. NaH (0.05242 g, 1.311 mmol, 60% in mineral oil) was added and the mixture was warmed to ambient temperature where it stirred for 1.25 hours producing a dark homogeneous solution. Then freshly prepared methyl 2-bromo-3-(4-((tert-butoxycarbonyl)(methyl)amino)piperidin-1-yl)propanoate (2.486 g, 6.553 mmol) was added and the reaction was stirred at ambient temperature for 2 hours. The mixture was diluted with H$_2$O (40 mL) and the mixture was extracted with EtOAc (2×40 mL). The combined extracts were washed with brine, dried over Na$_2$SO$_4$, filtered and concentrated in vacuo to afford the crude product as a dark thick oil. The crude product was taken directly to the next step. ES+APCI MS m/z 757.2[M+H]$^+$.

(1.97 ml, 1.97 mmol, 1.0M Aq). The mixture was stirred for 2.5 hours at 45° C. then at ambient temperature overnight. The mixture was cooled to 0° C. and was treated with KHSO$_4$ (2.0 mL, 1.0M Aq). The mixture was extracted with CHCl$_3$ (3×10 mL) and the combined organic layers were dried over Na$_2$SO$_4$, filtered and concentrated. The dark, crude product was taken directly to the next step. ES+APCI MS m/z 743.2[M+H]$^+$.

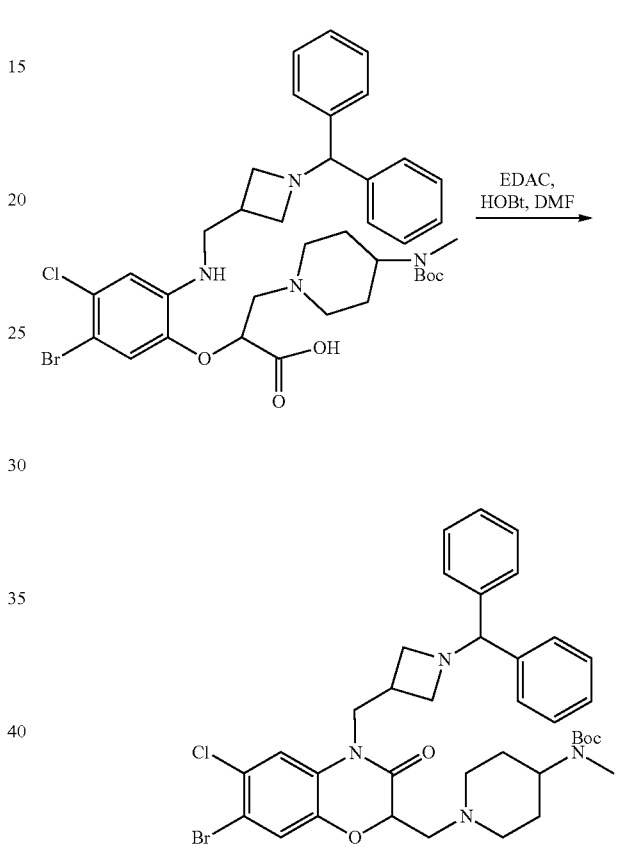

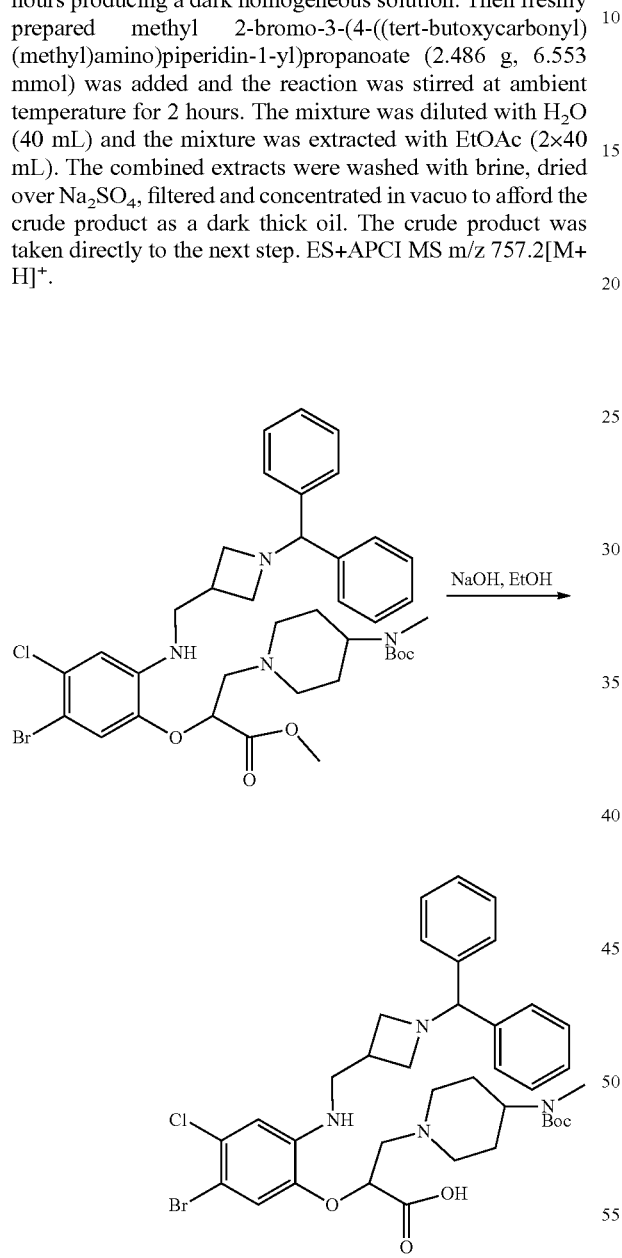

Step C: 2-(2-(((1-benzhydrylazetidin-3-yl)methyl)amino)-5-bromo-4-chlorophenoxy)-3-(4-((tert-butoxycarbonyl)(methyl)amino)piperidin-1-yl)propanoic acid. To a suspension of crude methyl 2-(2-(((1-benzhydrylazetidin-3-yl)methyl)amino)-5-bromo-4-chlorophenoxy)-3-(4-((tert-butoxycarbonyl)(methyl)amino)piperidin-1-yl)propanoate (0.496 g, 0.656 mmol) in EtOH (6.56 mL) was added NaOH Step D: tert-butyl (1-((4-((1-benzhydrylazetidin-3-yl)methyl)-7-bromo-6-chloro-3-oxo-3,4-dihydro-2H-benzo[b][1,4]oxazin-2-yl)methyl)piperidin-4-yl)(methyl)carbamate. To a solution of crude 2-(2-(((1-benzhydrylazetidin-3-yl)methyl)amino)-5-bromo-4-chlorophenoxy)-3-(4-((tert-butoxycarbonyl)(methyl)amino)piperidin-1-yl)propanoic acid (0.487 g, 0.656 mmol) in DMF (6.56 mL) was added 1-(3-dimethylaminopropyl)-3-ethylcarbodiimide hydrochloride (0.189 g, 0.984 mmol) followed by 1-Hydroxybenzotriazole hydrate (0.151 g, 0.984 mmol). The mixture was stirred at ambient temperature overnight. H$_2$O was added followed by saturated aqueous NH$_4$Cl and the mixture was extracted with EtOAc (3×20 mL). The combined organic extracts were washed with brine and then dried over Na$_2$SO$_4$, filtered and concentrated. The crude product was purified via column chromatography (2-5% MeOH/DCM) to afford the product as a pale yellow solid foam (0.232 g, 48% for three steps). ES+APCI MS m/z 725.2 [M+H]$^+$.

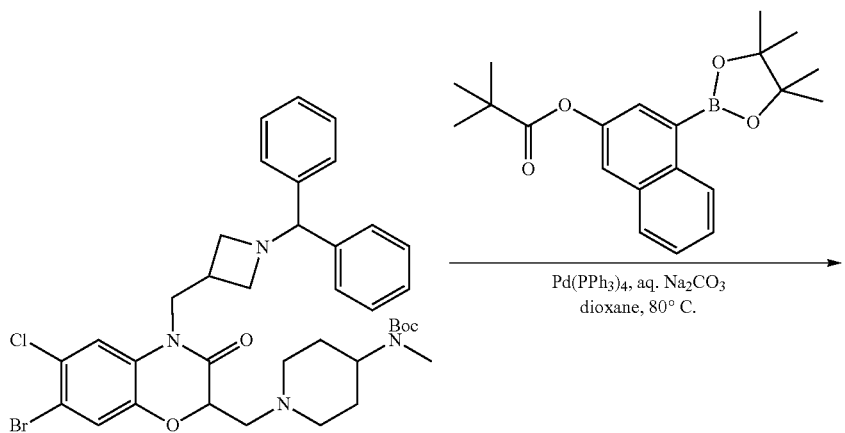

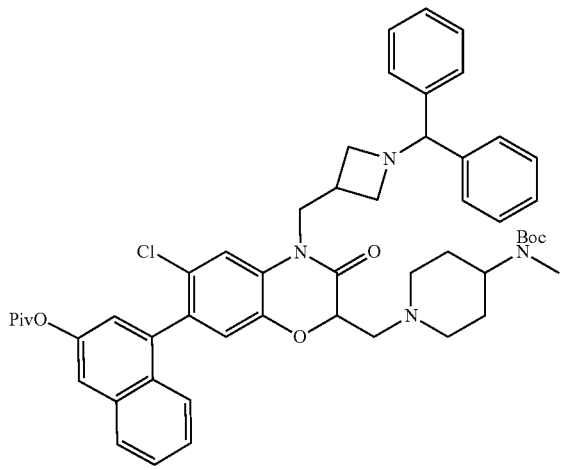

Step E: 4-(4-((1-benzhydrylazetidin-3-yl)methyl)-2-((4-((tert-butoxycarbonyl) (methyl)amino)piperidin-1-yl)methy)-6-chloro-3-oxo-3,4-dihydro-2H-benzo[b][1,4]oxazin-7-yl)naphthalen-2-yl pivalate. To a vial was added tert-butyl (1-((4-((1-benzhydrylazetidin-3-yl)methyl)-7-bromo-6-chloro-3-oxo-3,4-dihydro-2H-benzo[b][1,4]oxazin-2-yl)methyl)piperidin-4-yl)(methyl)carbamate (0.232 g, 0.320 mmol), 4-(4,4,5,5-tetramethyl-1,3,2-dioxaborolan-2-yl)naphthalen-2-yl pivalate (0.148 g, 0.416 mmol) and dioxane (3.20 mL). To this was added Tetrakis (triphenylphosphine)palladium (0) (0.037 g, 0.032 mmol) and $Na_2CO_3$ (0.481 mL, 0.961 mmol, 2.0M Aq). The mixture was purged with Ar then heated to 80° C. under an Ar atmosphere where it stirred for 16 hours. The mixture was cooled to ambient temperature diluted with $CH_2Cl_2$ and was filtered. The filtrate was dried over $Na_2SO_4$, filtered and concentrated. The crude product was purified via column chromatography (2-5% MeOH/DCM) to afford the product as a pale yellow foam (0.164 g, 58%). ES+APCI MS m/z 871.4[M+H]$^+$.

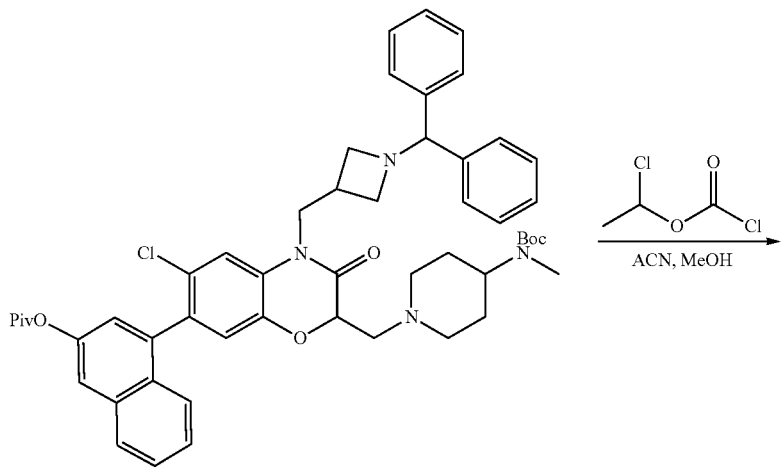

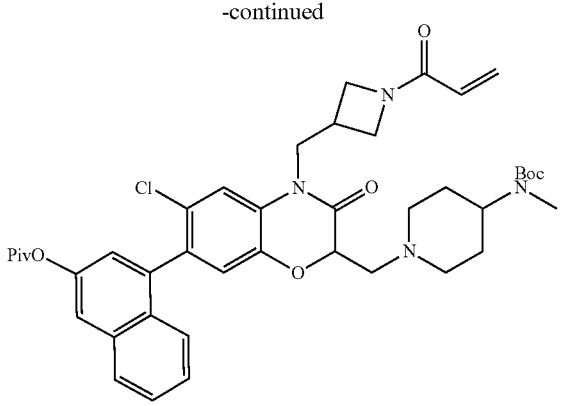

Step F: 4-(4-(azetidin-3-ylmethyl)-2-((4-((tert-butoxycarbonyl)(methyl)amino) piperidin-1-yl)methyl)-6-chloro-3-oxo-3,4-dihydro-2H-benzo[b][1,4]oxazin-7-yl)naphthalen-2-yl pivalate. 1-chloroethyl chloroformate (0.011 mL, 0.103 mmol) was added to a solution of 4-(4-((1-benzhydrylazetidin-3-yl)methyl)-2-((4-((tert-butoxycarbonyl(methyl)amino)piperidin-1-yl)methyl)-6-chloro-3-oxo-3,4-dihydro-2H-benzo[b][1,4]oxazin-7-yl)naphthalen-2-yl pivalate (0.060 g, 0.069 mmol) in dry acetonitrile (1.38 mL) and the mixture was warmed to 60° C. where it stirred for 2 hours, after which the mixture was concentrated in vacuo. The residue was dissolved in MeOH (2.75 mL) and the mixture was stirred at ambient temperature for 2 hours. The solvent was evaporated using a stream of $N_2$ and the residue dried in vacuo for 1 hour under high vacuum. The crude material was used directly in the subsequent step. ES+APCI MS m/z 705.3[M+H]+.

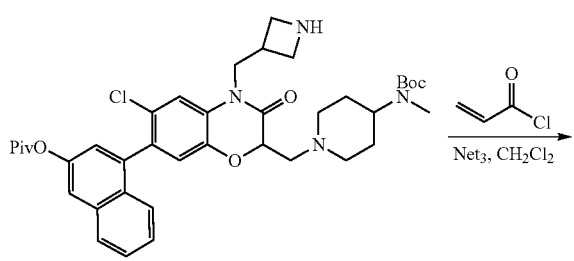

-continued

Step G: 4-(4-((1-acryloylazetidin-3-yl)methyl)-2-((4-((tert-butoxycarbonyl)(methyl)amino)piperidin-1-yl)methyl)-6-chloro-3-oxo-3,4-dihydro-2H-benzo[b][1,4]oxazin-7-yl)naphthalen-2-yl pivalate. To a solution of 4-(4-(azetidin-3-ylmethyl)-2-((4-((tert-butoxycarbonyl)(methyl)amino)piperidin-1-yl)methyl)-6-chloro-3-oxo-3,4-dihydro-2H-benzo[b][1,4]oxazin-7-yl)naphthalen-2-yl pivalate (0.048 g, 0.068 mmol) in $CH_2Cl_2$ (1.36 mL) at −78° C. was added Triethylamine (0.057 mL, 0.408 mmol). Acryloyl chloride (0.017 mL, 0.205 mmol) was added and the reaction was stirred for 0.5 hours. The mixture was diluted with $CHCl_3$ and a saturated aqueous $NH_4Cl$ solution. The layers were separated and the aqueous layer was extracted with $CHCl_3$ (2×10 mL). The combined extracts were dried over $Na_2SO_4$, filtered and concentrated. The crude product was purified via column chromatography (2-4% MeOH/DCM)

to afford the title compound (0.023 g, 44% for two steps) as an off-white foam. ES+APCI MS m/z 759.3[M+H]+.

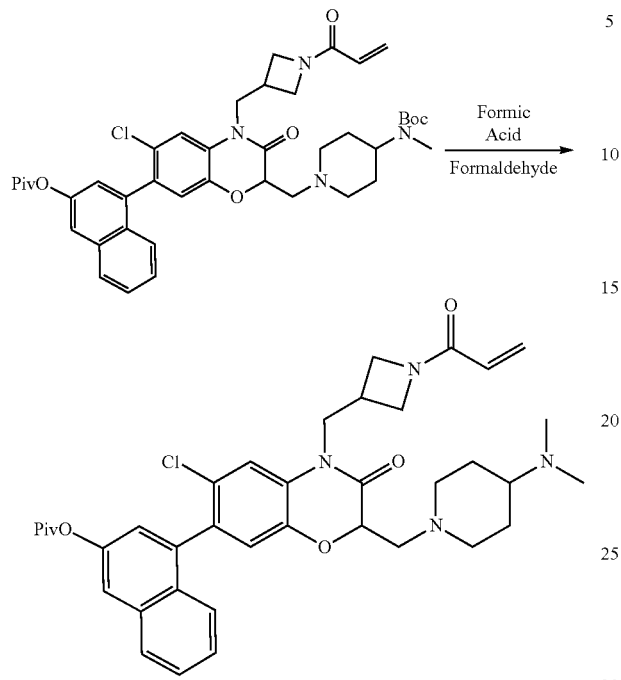

Step H: 4-(4-((1-acryloylazetidin-3-yl)methyl)-6-chloro-2-((4-(dimethylamino) piperidin-1-yl)methyl)-3-oxo-3,4-dihydro-2H-benzo[b][1,4]oxazin-7-yl)naphthalen-2-yl pivalate. To a vial was added 4-(4-((1-acryloylazetidin-3-yl) methyl)-2-((4-((tert-butoxycarbonyl)(methyl)amino) piperidin-1-yl)methyl)-6-chloro-3-oxo-3,4-dihydro-2H-benzo[b][1,4]oxazin-7-yl)naphthalen-2-yl pivalate (0.023 g, 0.030 mmol) which was dissolved in formic acid (0.229 mL, 6.06 mmol). Then formaldehyde (0.046 mL, 0.606 mmol, 37% aqueous) was added. The mixture was heated to 85° C. where it stirred for 1.25 hours. The mixture was cooled to ambient temperature and added to a saturated aqueous NaHCO3 solution (10 mL). The mixture was transferred to a separatory funnel and the mixture was extracted with 5% IPA/CHCl3 (3×10 mL) and the combined organic phases were dried over Na2SO4, filtered and concentrated. The crude product was purified by column chromatography (5-15% MeOH/DCM with 0.25% NH4OH) to afford the product as a white solid (0.017 g, 83%). ES+APCI MS m/z 673.3[M+H]+.

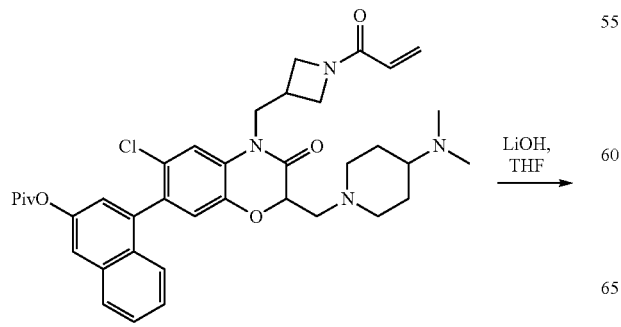

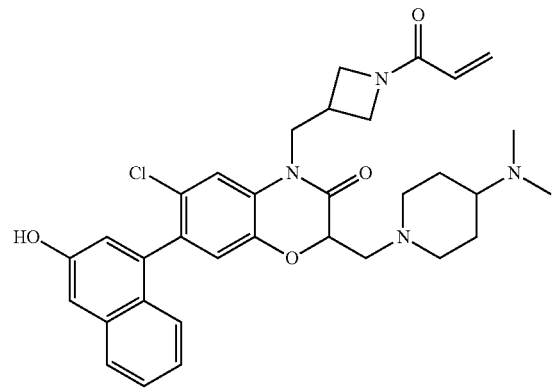

Step 1: 4-((1-acryloylazetidin-3-yl)methyl)-6-chloro-2-((4-(dimethylamino)piperidin-1-yl)methyl)-7-(3-hydroxynaphthalen-1-yl)-2H-benzo[b][1,4]oxazin-3(4H)-one. 4-(4-((1-acryloylazetidin-3-yl)methyl)-6-chloro-2-((4-(dimethylamino)piperidin-1-yl)methyl)-3-oxo-3,4-dihydro-2H-benzo[b][1,4]oxazin-7-yl)naphthalen-2-yl pivalate (0.017 g, 0.025 mmol) was dissolved in THF (0.500 ml) and the solution was treated with LiOH (0.126 mL, 0.253 mmol, 2M aq) and the mixture was stirred vigorously at ambient temperature for 6 hours. The reaction mixture was purified directly via column chromatography (4-16% MeOH/DCM with 0.25% NH4OH) to afford the desired product as a white solid (0.011 g, 71%). ES+APCI MS m/z 589.2[M+H]+.

Example 6

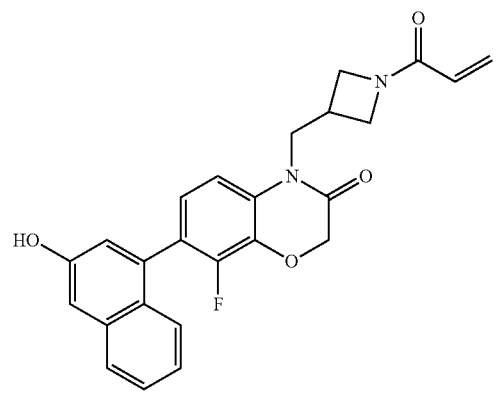

Preparation of 4-((1-acryloylazetidin-3-yl)methyl)-8-fluoro-7-(3-hydroxynaphthalen-1-yl)-2H-benzo[b][1,4]oxazin-3(4H)-one

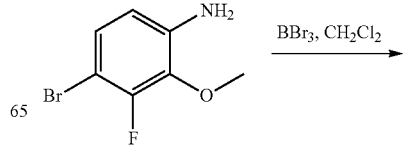

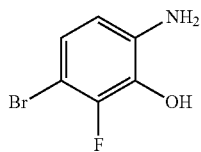

Step A: 6-amino-3-bromo-2-fluorophenol. To a solution of 4-bromo-3-fluoro-2-methoxyaniline (1.0 g, 4.54 mmol) in CH$_2$Cl$_2$ (11.4 ml, 4.54 mmol) at 0° C. was added boron tribromide (9.09 ml, 9.09 mmol) (1.0M CH$_2$Cl$_2$). The ice bath was removed and the mixture stirred at ambient temperature for 2 hours, during which time the reaction mixture turned to a light brown suspension. The reaction mixture was carefully quenched by the addition of a saturated aqueous NaHCO$_3$ solution. Once bubbling has ceased the layers were separated and the aqueous phase was extracted with EtOAc (3×50 mL). The combined organic extracts were washed with brine, dried over Na$_2$SO$_4$, filtered and concentrated providing the crude product which was used as is.

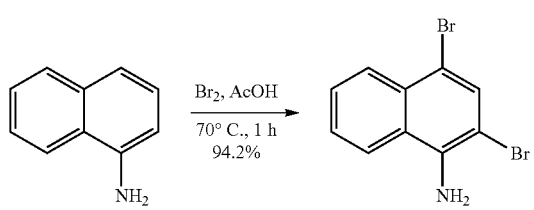 [SMILES: Nc1cccc2ccccc12 ; Nc1c(Br)cc(Br)c2ccccc12]

Step B: 2,4-dibromonaphthalen-1-amine. To a solution of Br$_2$ (246 g, 1.54 mol, 79.3 mL, 2.18 eq) in AcOH (750 mL) was added a solution of naphthalen-1-amine (101 g, 705 mmol, 99.0 mL, 1.00 eq) in AcOH (500 mL) at room temperature and the reaction stirred at 70° C. for 1 hour. The reaction mixture was cooled at room temperature and filtered. The filter cake was washed with AcOH (300 mL). The solid was suspended in 20% aqueous of NaOH (1.2 L). The mixture was stirred for 20 minutes and filtered. The solid was washed with water (1 L) and dried under vacuum to give 2,4-dibromonaphthalen-1-amine (200 g, 664 mmol, 94.2% yield) as gray solid. ES+APCI MS m/z 301.9 [M+H]$^+$.

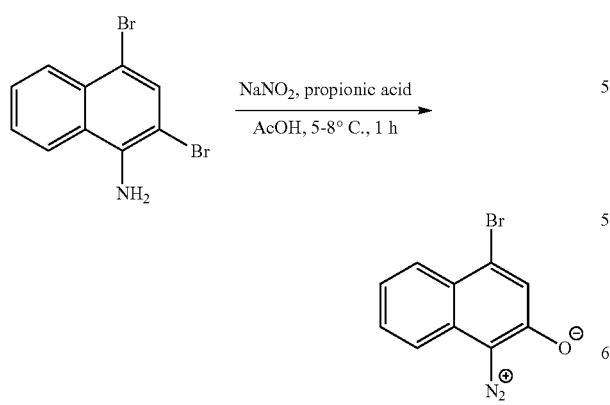

Step C: 4-bromo-1-diazonio-naphthalen-2-olate. To a solution of 2,4-dibromonaphthalen-1-amine (60.0 g, 199 mmol, 1.00 eq) in AcOH (900 mL) and propionic acid (150 mL) was added NaNO$_2$ (16.5 g, 239 mmol, 13.0 mL, 1.20 eq) portionwise at 5-8° C. over 30 minutes and the reaction mixture stirred at 5-8° C. for 30 minutes. The reaction mixture was poured into ice-water (4000 mL). The slurry was filtered and the collected solid was washed with water (2×50 mL) to give 4-bromo-1-diazonio-naphthalen-2-olate (150 g, wet crude) which was used directly in the next step without purification. $^1$H NMR (400 MHz, CDCl$_3$) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

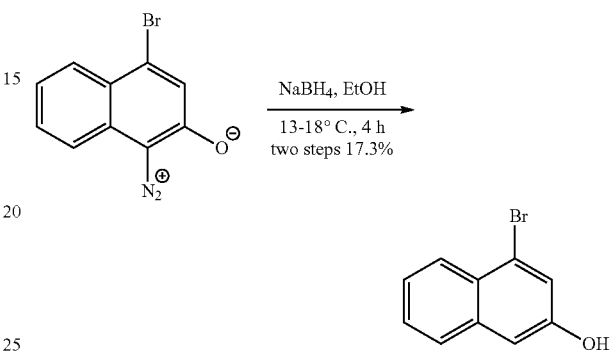

Step D: 4-bromonaphthalen-2-ol. To a solution of 4-bromo-1-diazonio-naphthalen-2-olate (100 g, 402 mmol, 1.00 eq) in EtOH (2.00 L) was added portion-wise NaBH$_4$ (30.4 g, 803 mmol, 2.00 eq) at 13-15° C. over 1 hour and the reaction stirred at 15-18° C. for 3 hours. The reaction was filtered and concentrated to dryness. The residue was dissolved in DCM (1000 mL) and washed with water (500 mL×2). The organics were dried over Na$_2$SO$_4$ and concentrated to dryness. The residue was purified by chromatography, eluting with petroleum ether/EtOAc (60/1→10/1). The isolated desired material was further purified by reversed phase HPLC to give 4-bromonaphthalen-2-ol (40.0 g, 139 mmol, 17.3% yield, 77.4% purity) as a gray solid. $^1$H NMR (400 MHz, CDCl$_3$) δ 8.07-8.05 (d, J=8.0 Hz, 1H), 7.60-7.58 (d, J=7.6 Hz, 1H), 7.41-7.36 (m, 3H), 7.07 (s, 1H).

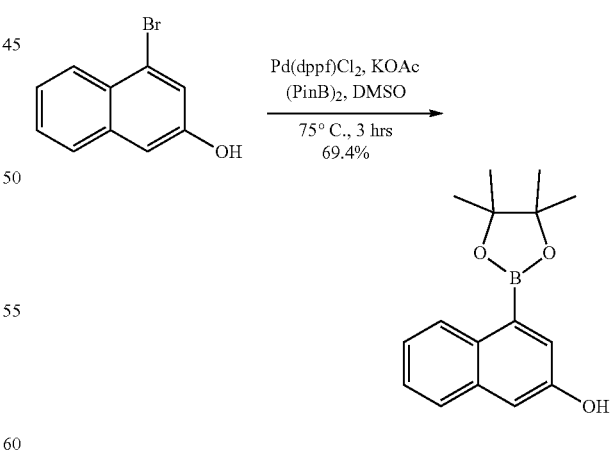

Step E: 4-(4,4,5,5-tetramethyl-1,3,2-dioxaborolan-2-yl)naphthalen-2-ol. To a solution of 4-bromonaphthalen-2-ol (5.00 g, 22.4 mmol, 1.00 eq) and 4,4,5,5-tetramethyl-2-(4,4,5,5-tetramethyl-1,3,2-dioxaborolan-2-yl)-1,3,2-dioxaborolane (11.4 g, 44.8 mmol, 2.00 eq) in DMSO (125 mL) was added KOAc (6.60 g, 67.2 mmol, 3.00 eq) and Pd(dppf)Cl$_2$ (1.64 g, 2.24 mmol, 0.10 eq). The reaction mixture was stirred at 75° C. for 3 hours under N₂. The reaction was diluted with water (100 ml) and extracted with EtOAc (3×100 mL). The combined organics were washed with brine (80 ml), dried over Na₂SO₄ and concentrated under vacuum. The residue was purified by silica gel chromatography using 1→10% petroleum ether/EtOAc as eluent to give 4-(4,4,5,5-tetramethyl-1,3,2-dioxaborolan-2-yl)naphthalen-2-ol (4.67 g, 15.6 mmol, 69.4% yield, 90.0% purity) as a brown solid. ¹H NMR (400 MHz, chloroform-d) δ=8.59-8.55 (d, J=8.0 Hz, 1H), 7.60-7.58 (m, 2H), 7.34-7.29 (m, 2H), 7.18 (d, J=1.6 Hz, 1H), 5.04 (s, 1H), 1.34 (s, 12H).

Steps D-F substituting (5-hydroxy-2-(trifluoromethoxy)phenyl)boronic acid for 4-(4,4,5,5-tetramethyl-1,3,2-dioxaborolan-2-yl)naphthalen-2-yl pivalate in Step D to provide desired product. ES+APCI MS m/z 483.1 [M+H]⁺.

Example 8

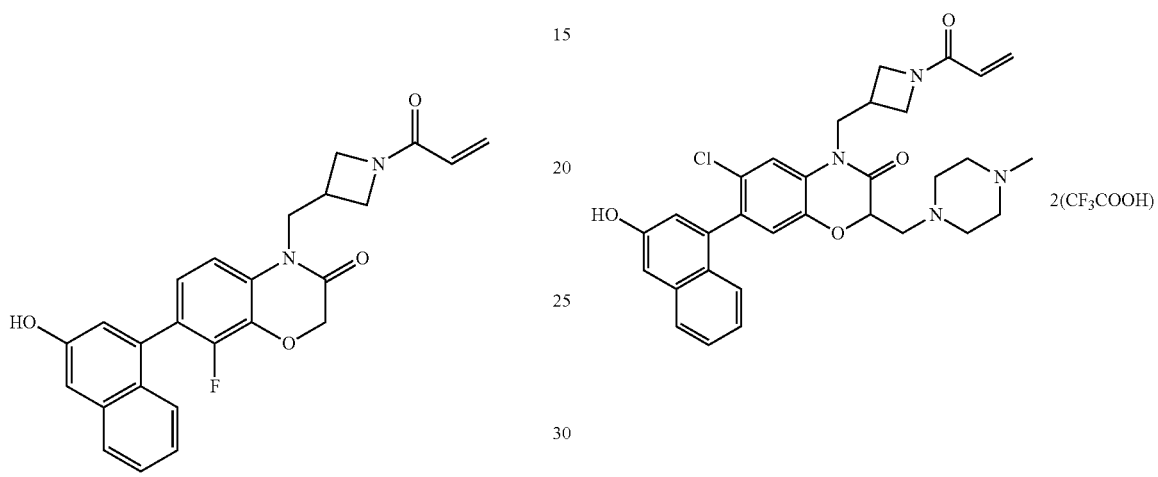

Step F: 4-((1-acryloylazetidin-3-yl)methyl)-8-fluoro-7-(3-hydroxynaphthalen-1-yl)-2H-benzo[b][1,4]oxazin-3(4H)-one. was prepared according to Example 1, substituting 6-amino-3-bromo-2-fluorophenol for 2-amino-5-bromo-4-chlorophenol in Step A and 4-(4,4,5,5-tetramethyl-1,3,2-dioxaborolan-2-yl)naphthalen-2-ol for 4-(4,4,5,5-tetramethyl-1,3,2-dioxaborolan-2-yl)naphthalen-2-yl pivalate in Step D to provide desired product. ES+APCI MS m/z 433.1 [M+H]⁺.

Example 7

Preparation of 4-((1-acryloylazetidin-3-yl)methyl)-6-chloro-7-(3-hydroxynaphthalen-1-yl)-2-((4-methylpiperazin-1-yl)methyl)-2H-benzo[b][1,4]oxazin-3(4H)-one bis(2,2,2-trifluoroacetate)

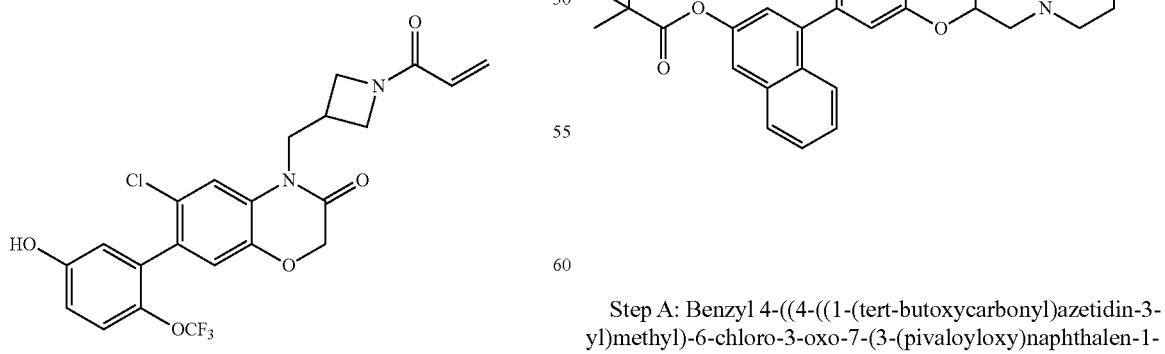

4-((1-acryloylazetidin-3-yl)methyl)-6-chloro-7-(5-hydroxy-2-(trifluoromethoxy)phenyl)-2H-benzo[b][1,4]oxazin-3(4H)-one, was prepared according to Example 1, Step A: Benzyl 4-((4-((1-(tert-butoxycarbonyl)azetidin-3-yl)methyl)-6-chloro-3-oxo-7-(3-(pivaloyloxy)naphthalen-1-yl)-3,4-dihydro-2H-benzo[b][1,4]oxazin-2-yl)methyl)piperazine-1-carboxylate, was prepared according to Example 4, Steps A-E, substituting benzyl piperazine-1-carboxylate for pyrrolidine in Step A.

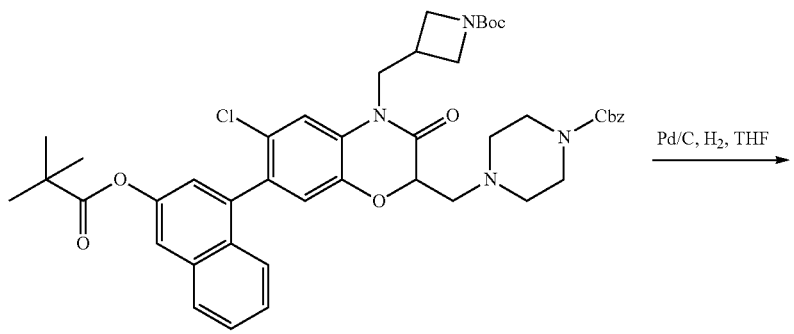

Step B: Tert-butyl 3-((6-chloro-3-oxo-2-(piperazin-1-yl-methyl)-7-(3-(pivaloyloxy)naphthalen-1-yl)-2,3-dihydro-4H-benzo[b][1,4]oxazin-4-yl)methyl)azetidine-1-carboxylate. To a solution of benzyl 4-((4-(((1-(tert-butoxycarbonyl)azetidin-3-yl)methyl)-6-chloro-3-oxo-7-(3-(pivaloyloxy)naphthalen-1-yl)-3,4-dihydro-2H-benzo[b][1,4]oxazin-2-yl)methyl)piperazine-1-carboxylate (409 mg, 0.504 mmol) in THF (5041 µl) was added Palladium (268 mg, 0.126 mmol, Degussa Type, 10 wt %, 50% H₂O) and then an atmosphere of H₂ was introduced via vacuum followed by balloon pressure. The mixture was stirred at ambient temperature for 5 hours. The mixture was diluted with MeOH and THF (1:1) and filtered. The filtrate was concentrated to provide the crude product which was used as is.

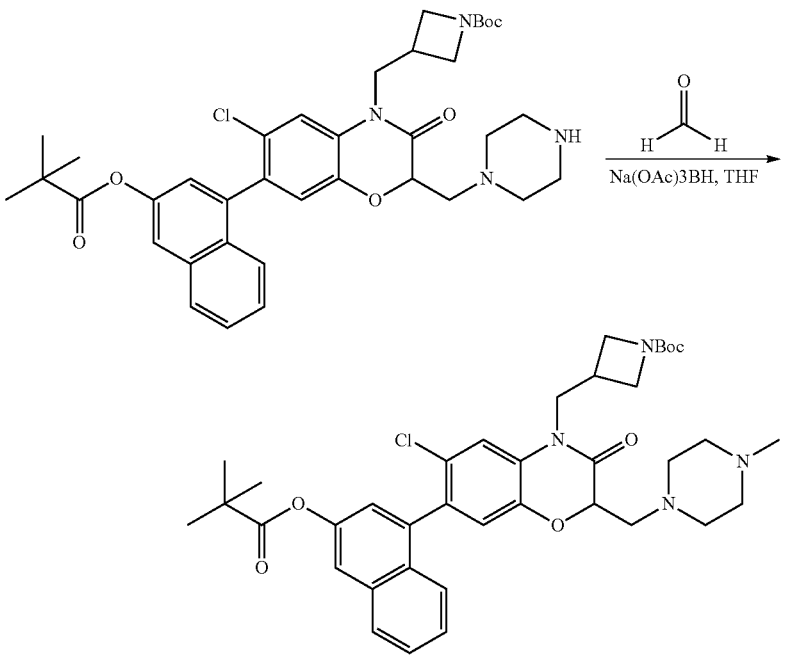

Step C: Tert-butyl 3-((6-chloro-2-((4-methylpiperazin-1-yl)methyl)-3-oxo-7-(3-(pivaloyloxy)naphthalen-1-yl)-2,3-dihydro-4H-benzo[b][1,4]oxazin-4-yl)methyl)azetidine-1-carboxylate. tert-butyl 3-((6-chloro-3-oxo-2-(piperazin-1-ylmethyl)-7-(3-(pivaloyloxy) naphthalen-1-yl)-2,3-dihydro-4H-benzo[b][1,4]oxazin-4-yl)methyl)azetidine-1- carboxylate (340 mg, 0.502 mmol), formaldehyde (204 mg, 2.51 mmol, 37% Aqueous) and Na(OAc)₃BH (213 mg, 1.00 mmol) and were placed in THF (10 mL) and stirred for 2 hours. Saturated aqueous bicarbonate was added and the mixture was extracted with 10% MeOH/DCM (3×15 mL). The organic layers were combined and concentrated and the resulting residue was purified by silica gel (0-10% MeOH in DCM w/0.2% NH₄OH) to provide the desired product (223 mg, 0.323 mmol, 64% yield).

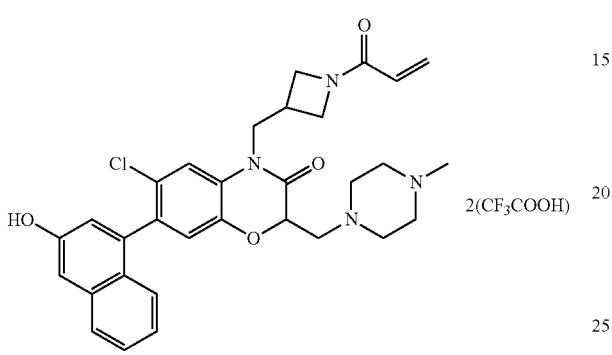

Step D: 4-((1-acryloylazetidin-3-yl)methyl)-6-chloro-7-(3-hydroxynaphthalen-1-yl)-2-((4-methylpiperazin-1-yl)methyl)-2H-benzo[b][1,4]oxazin-3(4H)-one bis(2,2,2-trifluoroacetate), was prepared according to Example 4 Steps F-H, substituting tert-butyl 3-((6-chloro-2-((4-methylpiperazin-1-yl)methyl)-3-oxo-7-(3-(pivaloyloxy)naphthalen-1-yl)-2,3-dihydro-4H-benzo[b][1,4]oxazin-4-yl)methyl)azetidine-1-carboxylate for tert-butyl 3-((6-chloro-3-oxo-7-(3-(pivaloyloxy)naphthalen-1-yl)-2-(pyrrolidin-1-ylmethyl)-2,3-dihydro-4H-benzo[b][1,4]oxazin-4-yl)methyl)azetidine-1-carboxylate in Step F to provide desired product. ES+APCI MS m/z 561.2 [M+H]⁺.

Example 9

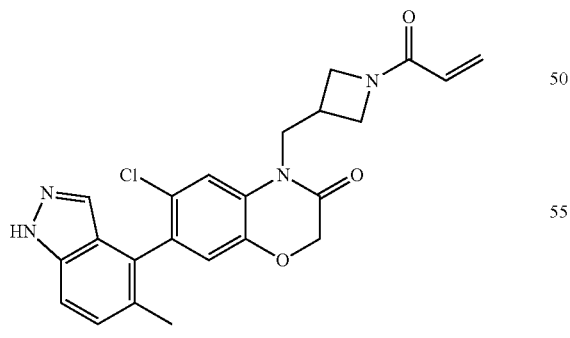

(R)-4-((1-acryloylpiperidin-3-yl)methyl)-6-chloro-7-(3-hydroxynaphthalen-1-yl)-2H-benzo[b][1,4]oxazin-3(4H)-one was prepared following Example 1 substituting 5-Methyl-1H-indazole-4-boronic acid for 4-(4,4,5,5-tetramethyl-1,3,2-dioxaborolan-2-yl)naphthalen-2-yl pivalate in Step D. ES+APCI MS m/z 437.1 [M+H]⁺.

Example 10

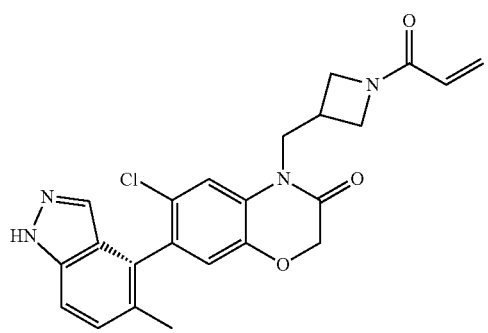

(S)-4-((1-acryloylazetidin-3-yl)methyl)-6-chloro-7-(5-methyl-1H-indazol-4-yl)-2H-benzo[b][1,4]oxazin-3(4H)-one was prepared by separation of atropisomeric mixture of Example 9 (SFC, ChiralTech 1A column, 5%-to-50% over 13 min, 80:20:1 methanol:isopropanol:diethylamine). Stereochemistry was arbitrarily assigned. ES+APCI MS m/z 437.1 [M+H]⁺.

Example 11

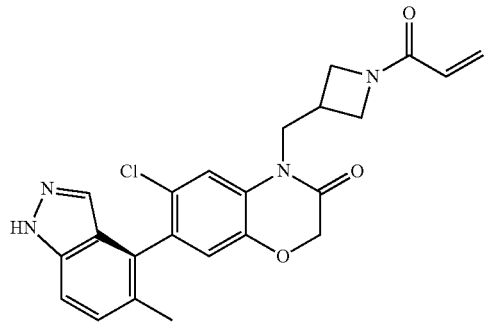

(R)-4-((1-acryloylazetidin-3-yl)methyl)-6-chloro-7-(5-methyl-1H-indazol-4-yl)-2H-benzo[b][1,4]oxazin-3(4H)-one was prepared by separation of atropisomeric mixture of Example 9 (SFC, ChiralTech 1A column, 5%-to-50% over 13 min, 80:20:1 methanol:isopropanol:diethylamine). Stereochemistry arbitrarily assigned. ES+APCI MS m/z 437.1 [M+H]+.

Example 12

Preparation of 4-((1-acryloylazetidin-3-yl)methyl)-7-(3-hydroxynaphthalen-1-yl)-2H-benzo[b][1,4]oxazin-3(4H)-one

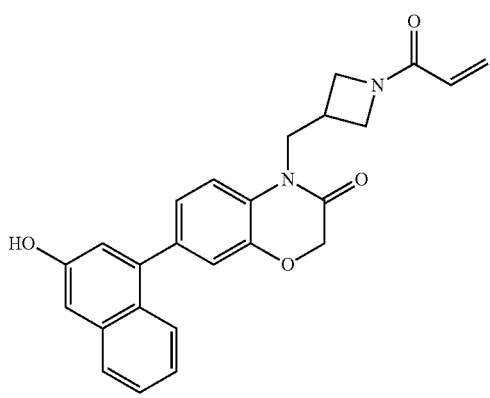 [SMILES: C=CC(=O)N1CC(CN2C(=O)COc3cc(-c4cc(O)cc5ccccc45)ccc32)C1]

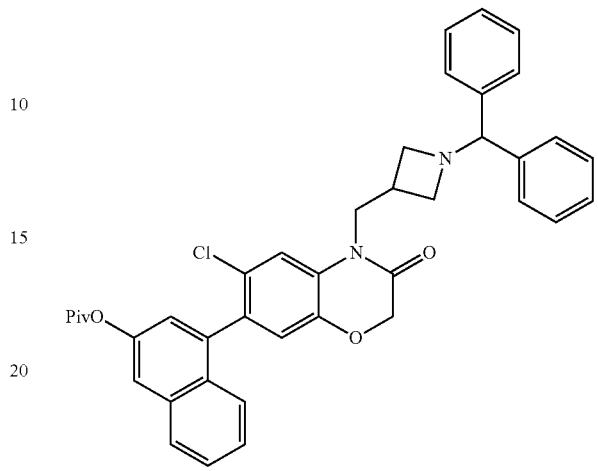

Step A: 4-(4-((1-benzhydrylazetidin-3-yl)methyl)-6-chloro-3-oxo-3,4-dihydro-2H-benzo[b][1,4]oxazin-7-yl)naphthalen-2-yl pivalate was prepared following Example 1, Steps A-D substituting 1-benzhydrylazetidine-3-carbaldehyde for 1-Boc-3-azetidinecarboxaldehyde in Step A. ES+APCI MS m/z 645.2 [M+H]+.

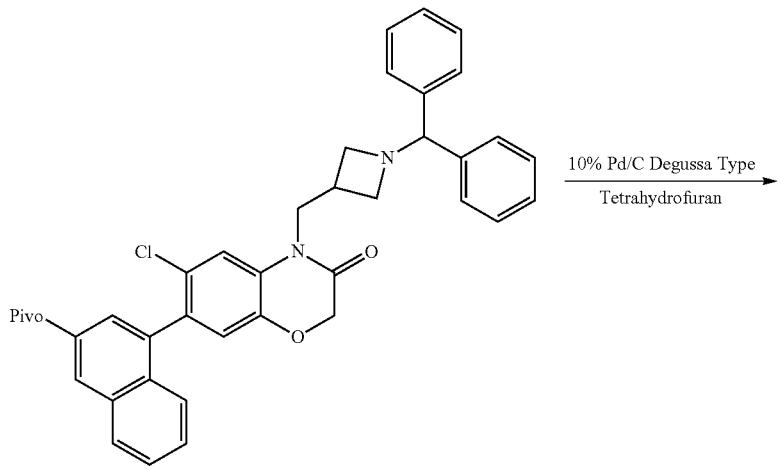

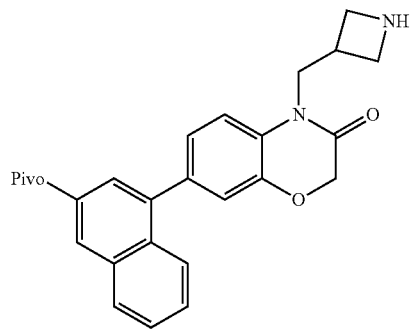

Step B: 4-(4-(azetidin-3-ylmethyl)-3-oxo-3,4-dihydro-2H-benzo[b][1,4]oxazin-7-yl)naphthalen-2-yl pivalate. To a solution of 4-(4-((1-benzhydrylazetidin-3-yl)methyl)-6-chloro-3-oxo-3,4-dihydro-2H-benzo[b][1,4]oxazin-7-yl)naphthalen-2-yl pivalate (350 mg, 0.542 mmol) in tetrahydrofuran (5.45 mL) was added palladium on carbon (289 mg, 0.136 mmol, Degussa Type, 10 wt %, 50% H$_2$O). An atmosphere of H$_2$ was introduced via vacuum followed by balloon pressure. This process was repeated three times. The mixture was stirred at ambient temperature for 7 days. The mixture was diluted with MeOH and filtered through GF/F paper. The colorless filtrate was concentrated and purified via column chromatography (0→20% MeOH:DCM) to provide desired product (44 mg, 0.0990 mmol, 18.2% yield). ES+APCI MS m/z 445.2 [M+H]+.

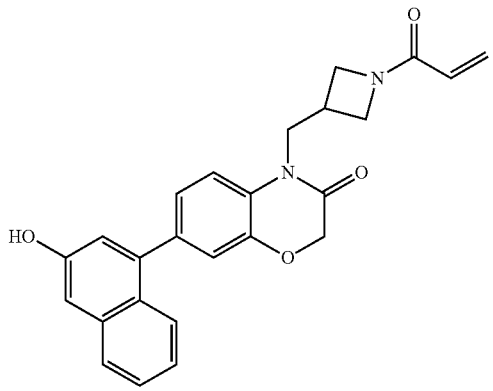 [SMILES: C=CC(=O)N1CC(CN2C(=O)COc3cc(-c4cc(O)cc5ccccc45)ccc32)C1]

Step C: 4-((1-acryloylazetidin-3-yl)methyl)-7-(3-hydroxynaphthalen-1-yl)-2H-benzo[b][1,4]oxazin-3(4H)-one was prepared following the procedure of Example 1, substituting 4-(4-(azetidin-3-ylmethyl)-3-oxo-3,4-dihydro-2H-benzo[b][1,4]oxazin-7-yl)naphthalen-2-yl pivalate for 4-(4-(azetidin-3-ylmethyl)-6-chloro-3-oxo-3,4-dihydro-2H-benzo[b][1,4]oxazin-7-yl)naphthalen-2-yl pivalate in Step F. ES+APCI MS m/z 415.2 [M+H]$^+$.

Example 13

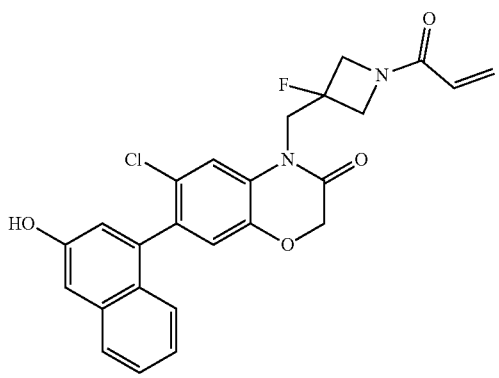 [SMILES: C=CC(=O)N1CC(F)(CN2C(=O)COc3cc(-c4cc(O)cc5ccccc45)c(Cl)cc32)C1]

Preparation of 4-((1-acryloyl-3-fluoroazetidin-3-yl)methyl)-6-chloro-7-(3-hydroxynaphthalen-1-yl)-2H-benzo[b][1,4]oxazin-3(4H)-one

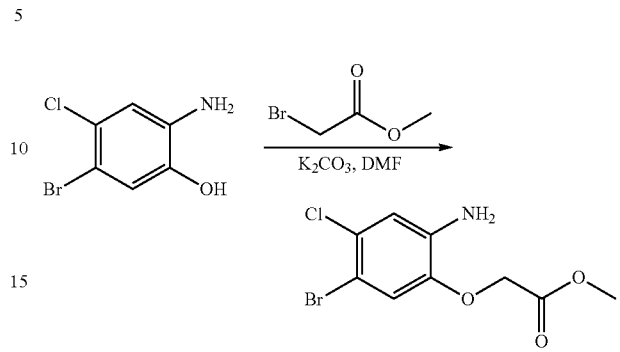

Step A: Methyl 2-(2-amino-5-bromo-4-chlorophenoxy)acetate. To a solution of 2-amino-5-bromo-4-chlorophenol (1.020 g, 4.59 mmol) in DMF (18.34 mL, 4.59 mmol) was added K$_2$CO$_3$ (1.90 g, 13.8 mmol) followed by methyl 2-bromoacetate (1.27 mL, 13.8 mmol). The mixture was stirred at ambient temperature for 1 hr. The mixture was diluted with H$_2$O (20 mL) and the mixture was extracted with EtOAc (2×20 mL). The extracts were combined and washed with water (2×10 mL), dried over sodium sulfate, filtered and concentrated to provide the crude product which was used as is.

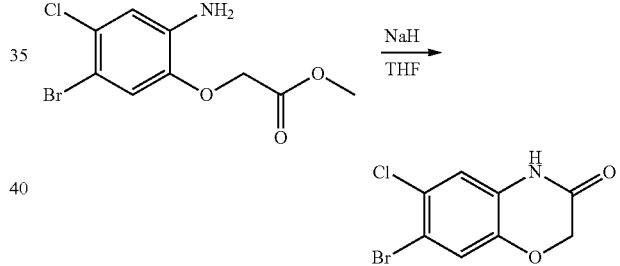

Step B: 7-bromo-6-chloro-2H-benzo[b][1,4]oxazin-3(4H)-one. Methyl 2-(2-amino-5-bromo-4-chlorophenoxy)acetate (1.35 g, 4.58 mmol) was placed in THF (5 mL). NaH (0.275 g, 6.88 mmol, 60% dispersion in mineral oil) was added and the reaction was stirred at ambient temperature for 3 hours. Water was added and the mixture was extracted with 10% MeOH in EtOAc (3×25 mL). The organic layers were concentrated and the resulting solids were triturated with EtOH to provide the desired product (943 mg, 3.59 mmol, 78.4% yield).

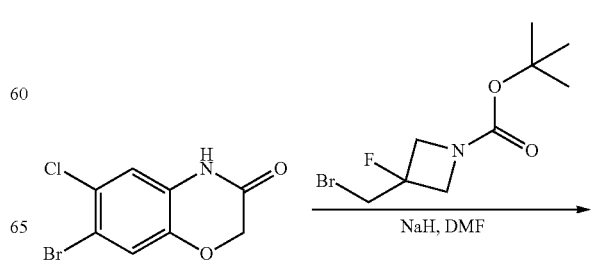

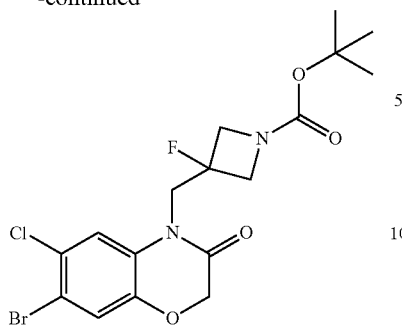

Step C: tert-butyl 3-((7-bromo-6-chloro-3-oxo-2,3-dihydro-4H-benzo[b][1,4]oxazin-4-yl)methyl)-3-fluoroazetidine-1-carboxylate. 7-bromo-6-chloro-2H-benzo[b][1,4]oxazin-3(4H)-one (65 mg) was placed in DMF and cooled to 0° C. NaH (12.9 mg, 60% dispersion in mineral oil) was added and the reaction was stirred for 5 minutes. Tert-butyl 3-(bromomethyl)-3-fluoroazetidine-1-carboxylate (199 mg) was added and the reaction was heated to 50° C. for 18 hours. The reaction was cooled and water was added slowly and the mixture was extracted with EtOAc (2×20 mL). The organic layers were combined and washed with water (2×10 mL) then concentrated. The resulting residue was purified by silica gel chromatography (0-30% EtOAc/hexanes) to provide the desired product (93 mg, 0.207 mmol, 83% yield).

Step D: 4-((1-acryloyl-3-fluoroazetidin-3-yl)methyl)-6-chloro-7-(3-hydroxynaphthalen-1-yl)-2H-benzo[b][1,4]oxazin-3(4H)-one was prepared following the procedure of Example 1, substituting t tert-butyl 3-((7-bromo-6-chloro-3-oxo-2,3-dihydro-4H-benzo[b][1,4]oxazin-4-yl)methyl)-3-fluoroazetidine-1-carboxylate in place of tert-butyl 3-((7-bromo-6-chloro-3-oxo-2,3-dihydro-4H-benzo[b][1,4]oxazin-4-yl)methyl)azetidine-1-carboxylate in Step D. ES+APCI MS m/z 467.2 [M+H]+.

Example 14

Preparation of 4-((1-acryloylazetidin-3-yl)methyl)-7-(3-hydroxynaphthalen-1-yl)-2H-benzo[b][1,4]thiazin-3(4H)-one

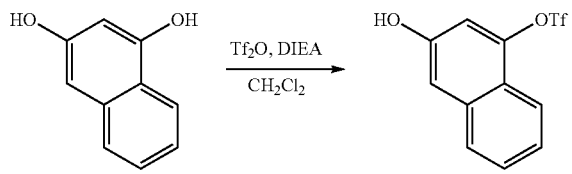

Step A: 3-hydroxynaphthalen-1-yl trifluoromethanesulfonate. A solution of naphthalene-1,3-diol (25.0 g, 156 mmol) in CH$_2$Cl$_2$ (700 mL) in a 3-necked flask at 10° C. (water bath+ice) was equipped with two addition funnels, separately charged with N-ethyl-N-isopropylpropan-2-amine (27.3 mL, 156 mmol) and trifluoromethanesulfonic anhydride (26.3 mL, 156 mmol). The two addition funnels were adjusted to equivalently slow dropwise rates of addition. After complete addition the reaction was stirred at 10° C. for 2 hours. The reaction mixture was transferred to a separatory funnel washing with CH$_2$Cl$_2$. The combined organic extracts were washed with water (2×) and brine (2×). The organic layer was dried over MgSO$_4$, filtered, and concentrated in vacuo. The residue was purified via column chromatography (0-15% EtOAc/hexanes) to afford the title compound (20.3 g, 69.3 mmol, 44.4%);

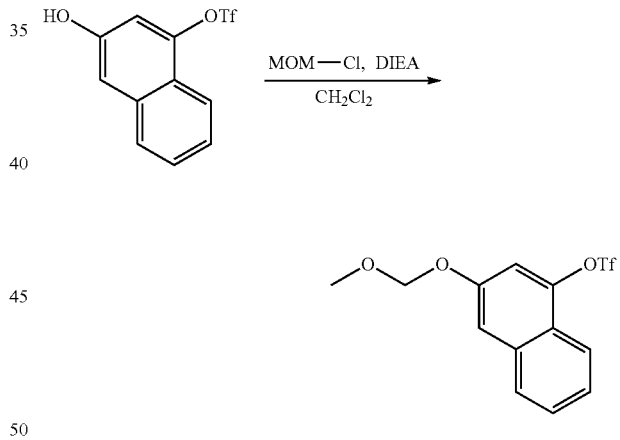

Step B: 3-(methoxymethoxy)naphthalen-1-yl trifluoromethanesulfonate. To a solution of 3-hydroxynaphthalen-1-yl trifluoromethanesulfonate (20.3 g, 69.3 mmol) and N-ethyl-N-isopropylpropan-2-amine (18.2 mL, 103 mmol) in CH$_2$Cl$_2$ (693 mL, 69.3 mmol) at 0° C. was added chloromethyl methyl ether (5.79 mL, 76.2 mmol) and the reaction was stirred at 0° C. for 1 hour. TLC (10% EtOAc: Hexane) showed that the reaction was complete. The reaction mixture was transferred into a separatory funnel and washed with water and brine. The organic layer was dried over MgSO$_4$, filtered, and concentrated in vacuo. The residue was purified by flash chromatography (2%-12% EtOAc/hexanes) to afford the title compound (20.0 g, 59.4 mmol, 85.7%).

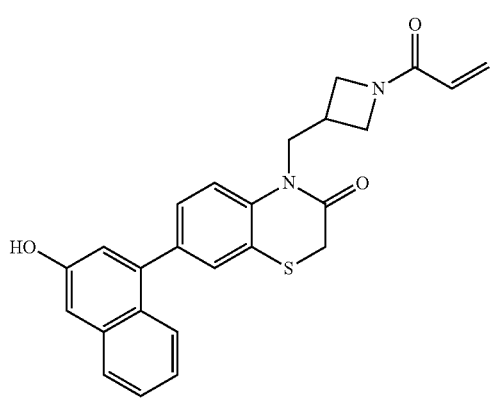

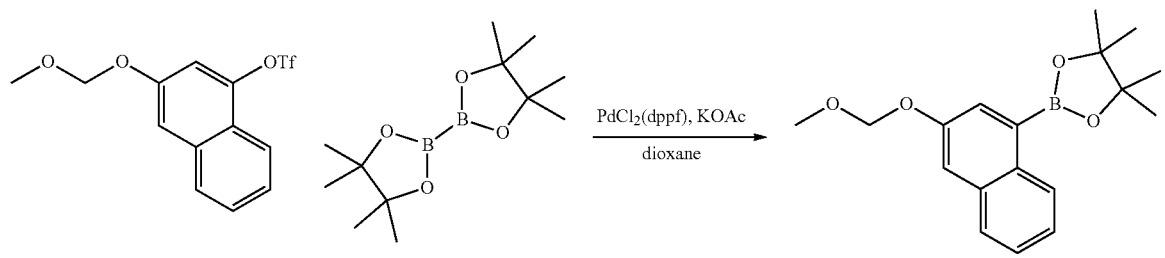

Step C: 2-(3-(methoxymethoxy)naphthalen-1-yl)-4,4,5,5-tetramethyl-1,3,2-dioxaborolane. To a solution of 3-(methoxymethoxy)naphthalen-1-yl trifluoromethanesulfonate (3.0 g, 8.9 mmol) in dioxane was added potassium acetate (4.4 g, 45 mmol) and 3-(methoxymethoxy)naphthalen-1-yl trifluoromethanesulfonate (3.0 g, 8.9 mmol) and the reaction sparged with nitrogen for 15 minutes, followed by addition of PdCl$_2$(dppf) (0.65 g, 0.89 mmol) and the reaction was heated to 85° C. for 8 hours. The reaction was concentrated in vacuo and reconstituted in CH$_2$Cl$_2$. The slurry was filtered through GF/F filter paper and the filtrate was concentrated in vacuo. The residue was purified via flash chromatography (10-100% CH$_2$Cl$_2$/hexanes) to afford the title compound (2.0 g, 6.4 mmol, 71%).

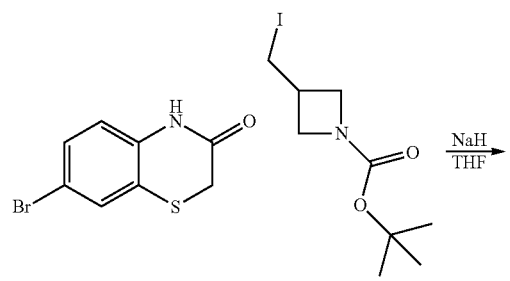

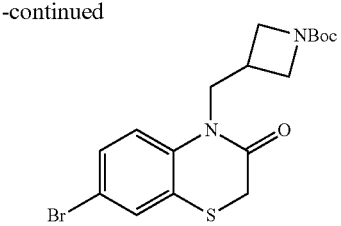

Step D: tert-butyl 3-((7-bromo-3-oxo-2,3-dihydro-4H-benzo[b][1,4]thiazin-4-yl)methyl)azetidine-1-carboxylate. To a solution of 7-bromo 2H[1,4]benzothiazin-3(4H)-one (388 mg, 1.59 mmol) in THF (7.95 mL) was added NaH (95.4 mg, 2.38 mmol, 60% dispersion in mineral oil) and the resulting mixture was stirred at ambient temperature for 1 hour. The reaction mixture was diluted with DMF (5 mL) then heated to 70° C. for 1 hour. LCMS (5-95% CH$_3$CN/H$_2$O+0.01% TFA) showed complete conversion. The reaction mixture was partitioned between EtOAc and water. The aqueous layer was discarded, and the organic layer was further extracted with EtOAc (3×). The combined organic layers were washed with brine, dried over Na$_2$SO$_4$, filtered and concentrated in vacuo. The residue was purified by flash chromatography (0-100 EtOAc/CH$_2$Cl$_2$) to afford the title compound (403 mg, 0.975 mmol, 61.3%). ES+APCI m/z 413 (30%), 415 (30%), 416 (10%) [M−H]$^+$.

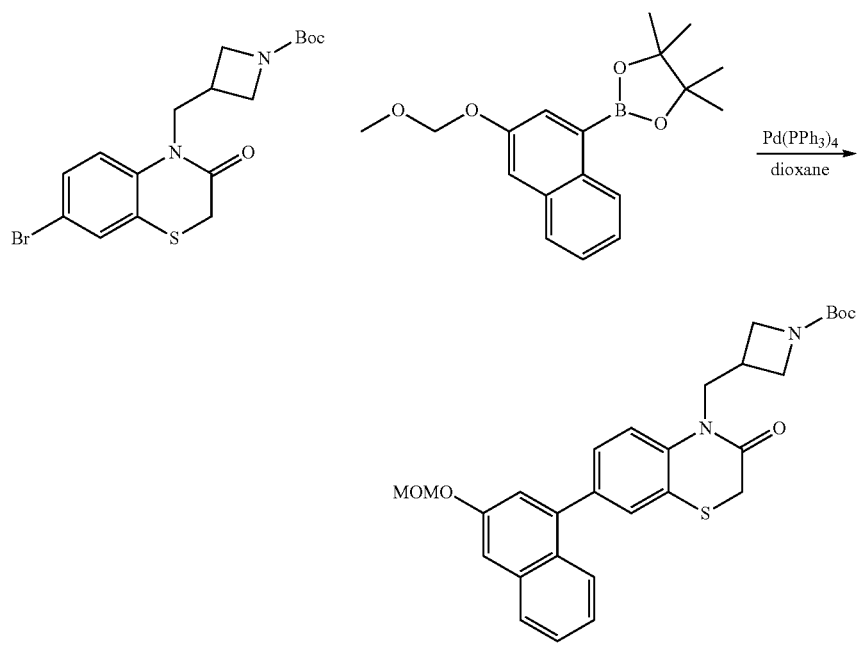

Step E: tert-butyl 3-((7-(3-(methoxymethoxy)naphthalen-1-yl)-3-oxo-2,3-dihydro-4H-benzo[b][1,4]thiazin-4-yl)methyl)azetidine-1-carboxylate. A solution of tert-butyl 3-((7-bromo-3-oxo-2,3-dihydro-4H-benzo[b][1,4]thiazin-4-yl)methyl)azetidine-1-carboxylate (125 mg, 0.302 mmol), 2-(3-(methoxymethoxy)naphthalen-1-yl)-4,4,5,5-tetramethyl-1,3,2-dioxaborolane (105 mg, 0.333 mmol), Pd(PPh$_3$)$_4$ (34.9 mg, 0.030 mmol), K$_2$CO$_3$ (454 µL, 0.907 mmol) in dioxane (1.51 mL)/water (3:1) was sparged with nitrogen for 1 min. The vial was sealed and heated at 100° C. for 1 day. The reaction mixture was partitioned between EtOAc/water. The aqueous layer was extracted with EtOAc (1×). The combined organic layers were dried (Na$_2$SO$_4$) and concentrated in vacuo. The residue was purified by flash chromatography (0-100% EtOAc/hexanes) to afford the title compound (150 mg, 0.288 mmol, 95.5%), ES+APCI m/z 521.2 (100%) [M−H]$^+$.

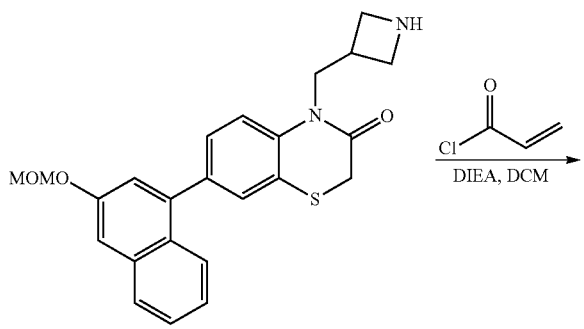

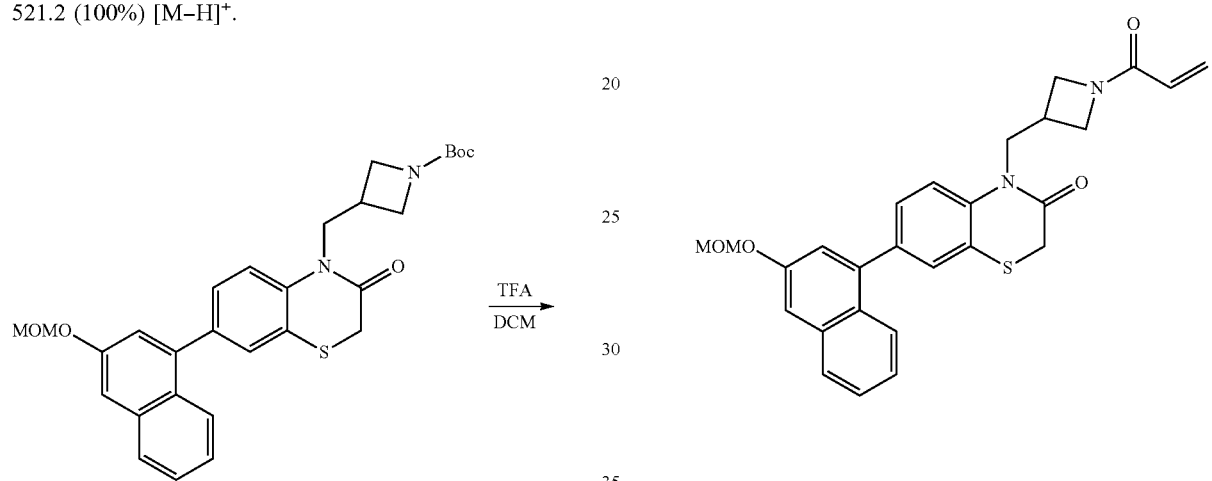

Step F: 4-(azetidin-3-ylmethyl)-7-(3-(methoxymethoxy)naphthalen-1-yl)-2H-benzo[b][1,4]thiazin-3(4H)-one. To a solution of tert-butyl 3-((7-(3-(methoxymethoxy)naphthalen-1-yl)-3-oxo-2,3-dihydro-4H-benzo[b][1,4]thiazin-4-yl)methyl)azetidine-1-carboxylate (30.0 mg, 0.058 mmol) in CH$_2$Cl$_2$ (0.115 mL) at 0° C. was added TFA (111 µL) and the ice-bath was immediately removed and the reaction mixture was stirred for 2 hours, while warming to ambient temperature. The reaction mixture was diluted with CH$_2$Cl$_2$ and poured into a separatory funnel containing 2.0 N K$_2$CO$_3$. The organic layer was separated, dried (MgSO$_4$) and concentrated in vacuo to give the title compound: (20.0 mg, 0.048 mmol, 83.0%) ES+APCI m/z 421.2 (100%) [M−H]$^+$.

Step G: 4-((1-acryloylazetidin-3-yl)methyl)-7-(3-(methoxymethoxy)naphthalen-1-yl)-2H-benzo[b][1,4]thiazin-3(4H)-one. A solution of crude 4-(azetidin-3-ylmethyl)-7-(3-(methoxymethoxy)naphthalen-1-yl)-2H-benzo[b][1,4]thiazin-3(4H)-one (20.0 mg, 0.048 mmol) and DIEA (24 µL, 0.15 mmol) in CH$_2$Cl$_2$ (951 µL) was treated with portions of acryloyl chloride (97 µL, 0.012 mmol) until the reaction was complete as determined by LCMS (1.0 equiv needed). The reaction mixture was quenched with NaHCO$_3$ (saturated aqueous), then partitioned between water/CH$_2$Cl$_2$. The organic layer was separated, dried and concentrated in vacuo. The residue was dissolved in methanol and purified by semi-preparative C18, 5-95% ACN/water+0.1% TFA gradient to afford the title compound (13.0 mg, 0.027 mmol, 58%), ES+APCI m/z 475.1 (100%) [M−H]$^+$.

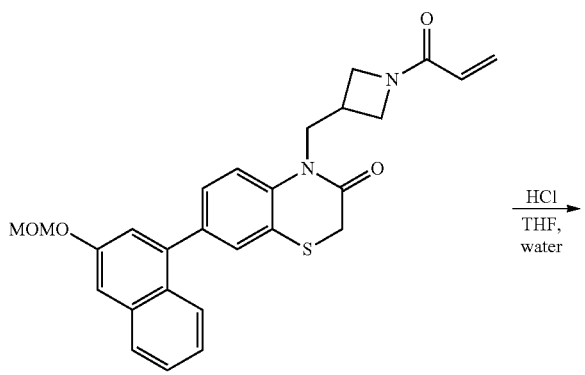

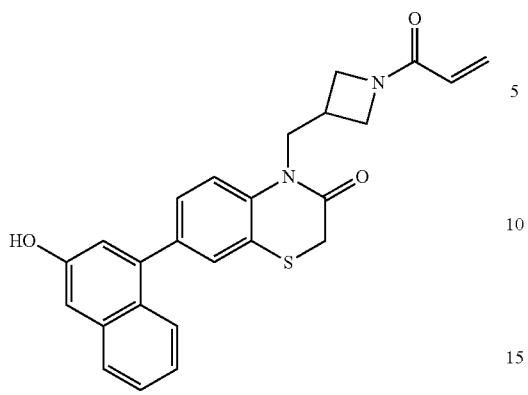

Step H: 4-((1-acryloylazetidin-3-yl)methyl)-7-(3-hydroxynaphthalen-1-yl)-2H-benzo[b][1,4]thiazin-3(4H)-one. To a solution of 4-((1-acryloylazetidin-3-yl)methyl)-7-(3-(methoxymethoxy)naphthalen-1-yl)-2H-benzo[b][1,4]thiazin-3(4H)-one (13 mg, 0.027 mmol) in THF (274 μL) and water (274 μL) was added concentrated aqueous HCl (1.00 mg, 0.027 mmol) and the resulting solution was stirred at 60° C. for 2 hours. The reaction mixture was concentrated. The residue was dissolved in MeOH and purified by semi-preparative C18 eluting with 5-95 ACN/water+0.1% TFA to afford the title compound: 5.0 mg, 0.012 mmol, 42%), ES+APCI m/z 431.1 (100%) [M−H]+.

Example 15

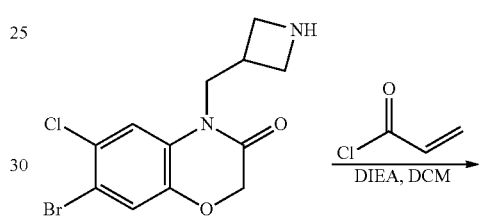

Preparation of 4-((1-acryloylazetidin-3-yl)methyl)-6-chloro-7-(5-methyl-1H-benzo[d]imidazol-4-yl)-2H-benzo[b][1,4]oxazin-3(4H)-one trifluoroacetate

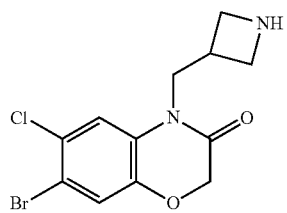

Step A: 4-(azetidin-3-ylmethyl)-7-bromo-6-chloro-2H-benzo[b][1,4]oxazin-3(4H)-one. Prepared according to procedure from Example 14, Step F, substituting tert-butyl 3-((7-bromo-6-chloro-3-oxo-2,3-dihydro-4H-benzo[b][1,4]oxazin-4-yl)methyl)azetidine-1-carboxylate for tert-butyl 3-((7-(3-(methoxymethoxy)naphthalen-1-yl)-3-oxo-2,3-dihydro-4H-benzo[b][1,4]thiazin-4-yl)methyl)azetidine-1-carboxylate to afford the title compound, ES+APCI m/z 331.0 (80%), 333.0 (100%) [M−H]+.

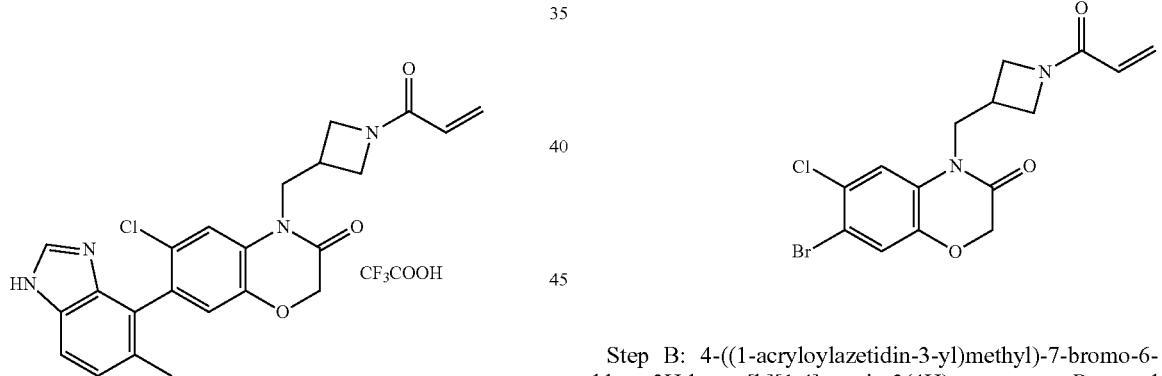

Step B: 4-((1-acryloylazetidin-3-yl)methyl)-7-bromo-6-chloro-2H-benzo[b][1,4]oxazin-3(4H)-one. Prepared according to procedure from Example 14, Step G, substituting 4-(azetidin-3-ylmethyl)-7-bromo-6-chloro-2H-benzo[b][1,4]oxazin-3(4H)-one for 4-(azetidin-3-ylmethyl)-7-(3-(methoxymethoxy)naphthalen-1-yl)-2H-benzo[b][1,4]thiazin-3(4H)-one to afford the title compound (35 mg), ES+APCI m/z 385.0 (80%), 387.0 (100%) [M−H]+.

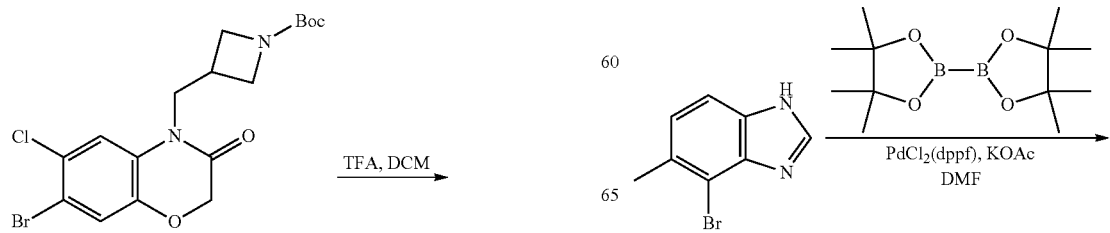

-continued

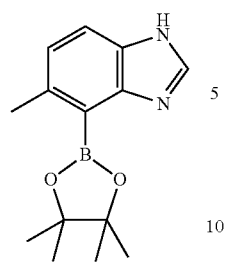

Step C: 5-methyl-4-(4,4,5,5-tetramethyl-1,3,2-dioxaborolan-2-yl)-1H-benzo[d]imidazole. A solution of 4-bromo-5-methyl-1H-benzo[d]imidazole (250 mg, 1.18 mmol), potassium acetate (232 mg, 2.37 mmol), bis(pinacolato)diboron (602 mg, 2.37 mmol), $PdCl_2(dppf)\text{-}CH_2Cl_2$ adduct (96.7 mg, 0.118 mmol), DMF (5.92 mL) was heated at 120° C. overnight. The reaction mixture was cooled to ambient temperature and partitioned between EtOAc/water. The layers were separated and the aqueous layer was extracted with EtOAc (1×). The organic layers were combined, dried ($Na_2SO_4$) and concentrated to give a dark residue that was used without further purification. ES+APCI m/z 259.1 (100%) [M−H]+.

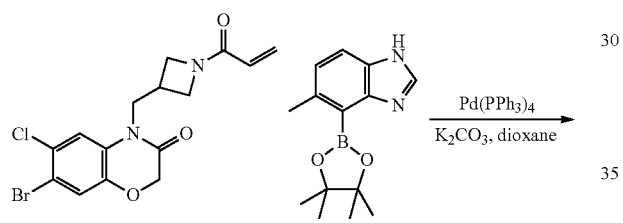

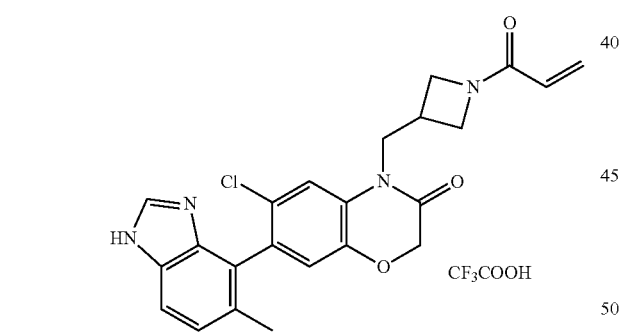

Step D. 4-((1-acryloylazetidin-3-yl)methyl)-6-chloro-7-(5-methyl-1H-benzo[d]imidazol-4-yl)-2H-benzo[b][1,4]oxazin-3(4H)-one trifluoroacetate salt. A mixture of 4-((1-acryloylazetidin-3-yl)methyl)-7-bromo-6-chloro-2H-benzo[b][1,4]oxazin-3(4H)-one (35.0 mg, 0.091 mmol), 5-methyl-4-(4,4,5,5-tetramethyl-1,3,2-dioxaborolan-2-yl)-1H-benzo[d]imidazole (59.0 mg, 0.230 mmol), $Pd(PPh_3)_4$ (10.0 mg, 0.009 mmol), and 2.0 N $K_2CO_3$ (136 µl, 0.27 mmol) in dioxane (1.00 mL) in a conical vial was sparged with nitrogen and heated at 90° C. for 1 day. The reaction mixture was diluted with methanol and filtered, purified by semi-preparative C18 to afford the title compound (2.60 mg, 0.005 mmol, 5.2% yield), ES+APCI m/z 437.1 (100%), 439.1 (50%) [M−H]+.

Example 16

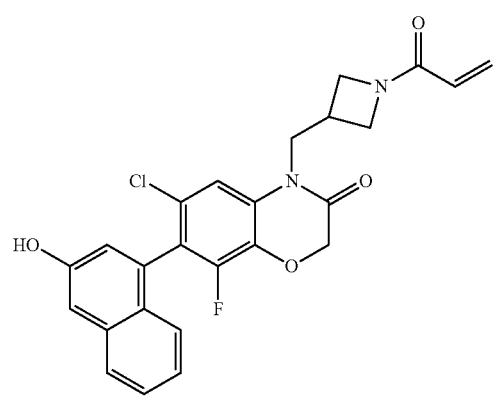 [SMILES: C=CC(=O)N1CC(CN2C(=O)COc3c2cc(Cl)c(-c2cc(O)cc4ccccc24)c3F)C1]

Preparation of 4-((1-acryloylazetidin-3-yl)methyl)-6-chloro-8-fluoro-7-(3-hydroxynaphthalen-1-yl)-2H-benzo[b][1,4]oxazin-3(4H)-one

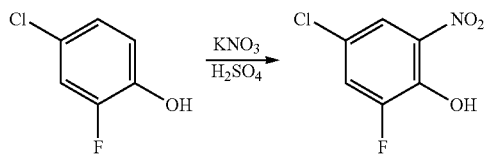

Step A: 4-chloro-2-fluoro-6-nitrophenol. To a solution of potassium nitrate (9.60 g, 95.0 mmol) in sulfuric acid (127 mL, 2375 mmol) at 0° C. was added dropwise 4-Chloro-2-fluorophenol (8.42 mL, 79.2 mmol) over 10 min. The reaction mixture was carefully partitioned between EtOAc/water. The organic layer was subsequently washed with water (5×), then the organic layer was concentrated in vacuo to give a dark solid product, 15 g, 78.3 mmol, 98%.

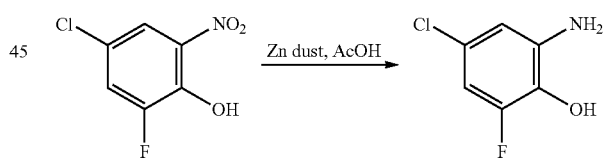

Step B: 2-amino-4-chloro-6-fluorophenol. A suspension of 4-chloro-2-fluoro-6-nitrophenol (15 g, 78.3 mmol) and Zn dust (10.2 g, 157 mmol) in glacial acetic acid (157 mL, 78.3 mmol) was heated at 75° C. for 1 hour. The reaction mixture was filtered, and the solid was washed with ethyl acetate. The filtrate was concentrated to a glassy black solid corresponding to the title compound (11.5 g, 71.2 mmol).

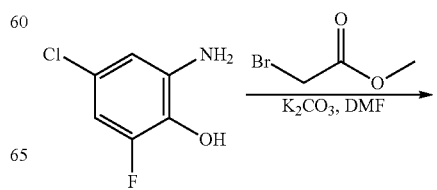

-continued

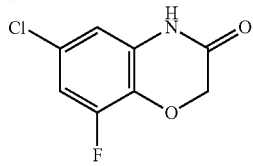

Step C: 6-chloro-8-fluoro-2H-benzo[b][1,4]oxazin-3(4H)-one. A mixture of 2-amino-4-chloro-6-fluorophenol (11.5 g, 71.2 mmol), methyl bromoacetate (6.54 mL, 71.2 mmol), $K_2CO_3$ (29.5 g, 214 mmol) in DMF (356 mL) was stirred at ambient temperature. Once the starting material was consumed the reaction mixture was partitioned between EtOAc and 0.5 N aqueous HCl. The organic layer was separated and dried over $Na_2SO_4$, filtered and concentrated in vacuo. The residue was purified by flash chromatography ($CH_2Cl_2$/EtOAc 0-70%). The solid was triturated using 25% MTBE/hexanes and washed with 50% MTBE/hexanes to give an off-white solid that corresponds to the title compound (4.00 g, 19.8 mmol, 27.9%).

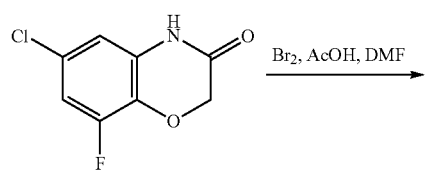

Step D: 7-bromo-6-chloro-8-fluoro-2H-benzo[b][1,4]oxazin-3(4H)-one. To a mixture of 6-chloro-8-fluoro-2H-benzo[b][1,4]oxazin-3(4H)-one (1.0 g, 4.96 mmol) in acetic acid (24.8 mL, 4.96 mmol) and DMF (24.8 mL) was added bromine (0.258 mL, 5.01 mmol). The reaction mixture was stirred at ambient temperature for 1 day. An additional 0.5 equivalents of bromine (0.124 mL, 2.50 mmol) was added and the reaction was stirred for another 6 hours. To the reaction mixture was added water (20 mL) and the resulting solid was collected by vacuum filtration and the solid washed with water. The tan cake was dried in the filter for 1 hour, transferred to a vial and further dried in vacuo to afford the title compound (1.20 g, 4.28 mmol, 86.2%).

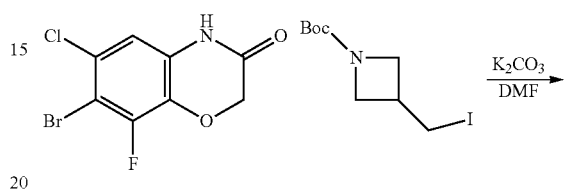

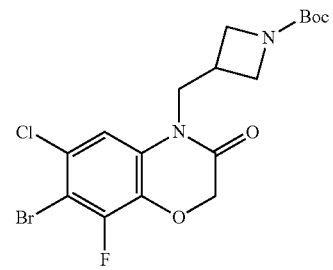

Step E: tert-butyl 3-((7-bromo-6-chloro-8-fluoro-3-oxo-2,3-dihydro-4H-benzo[b][1,4]oxazin-4-yl)methyl)azetidine-1-carboxylate. A suspension of 7-bromo-6-chloro-8-fluoro-2H-benzo[b][1,4]oxazin-3(4H)-one (408 mg, 1.45 mmol), tert-butyl 3-(iodomethyl)azetidine-1-carboxylate (475 mg, 1.60 mmol) and $K_2CO_3$ (603 mg, 4.36 mmol) in DMF (5.82 mL) was heated to 65° C. for 1 hour. The reaction mixture was partitioned between EtOAc and water and the organic layer washed with water (2×). The organic layer was dried ($Na_2SO_4$) and concentrated in vacuo. The residue was purified by flash chromatography (0-100% EtOAc/hexanes) to afford the title compound (450 mg, 1.00 mmol, 68.8 mg).

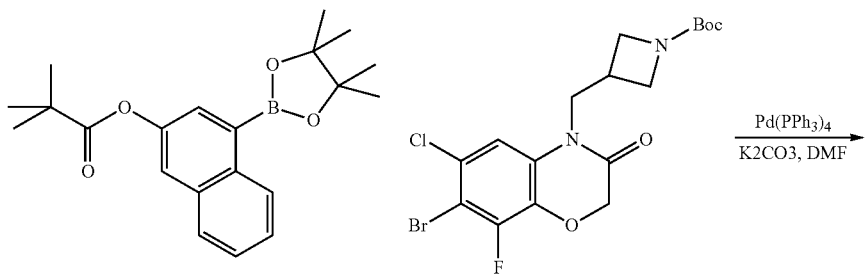

-continued

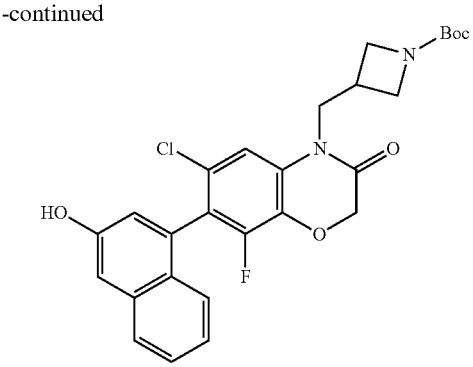

Step F: tert-butyl 3-((6-chloro-8-fluoro-7-(3-hydroxynaphthalen-1-yl)-3-oxo-2,3-dihydro-4H-benzo[b][1,4]oxazin-4-yl)methyl)azetidine-1-carboxylate. Prepared according to procedure from Example 2, Step D, substituting 4-(4,4,5,5-tetramethyl-1,3,2-dioxaborolan-2-yl)naphthalen-2-yl pivalate (187 mg, 0.529 mmol), tert-butyl 3-((7-bromo-6-chloro-8-fluoro-3-oxo-2,3-dihydro-4H-benzo[b][1,4]oxazin-4-yl)methyl)azetidine-1-carboxylate (170 mg, 0.378 mmol), and DMF (190 mL µl, 0.378 mmol), to afford the title compound (105 mg, 0.205 mmol, 54.1%), ES+APCI m/z 513.1 (15%) [M−H]⁺. Note: Piv ester is removed under these conditions.

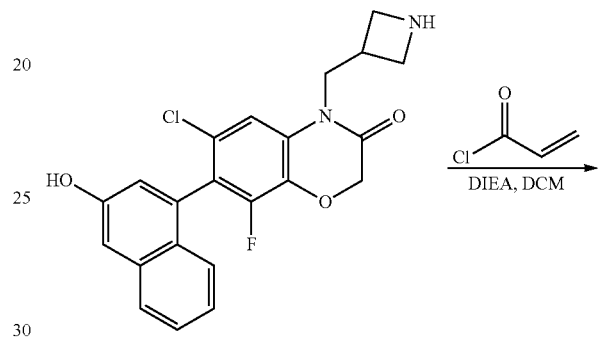

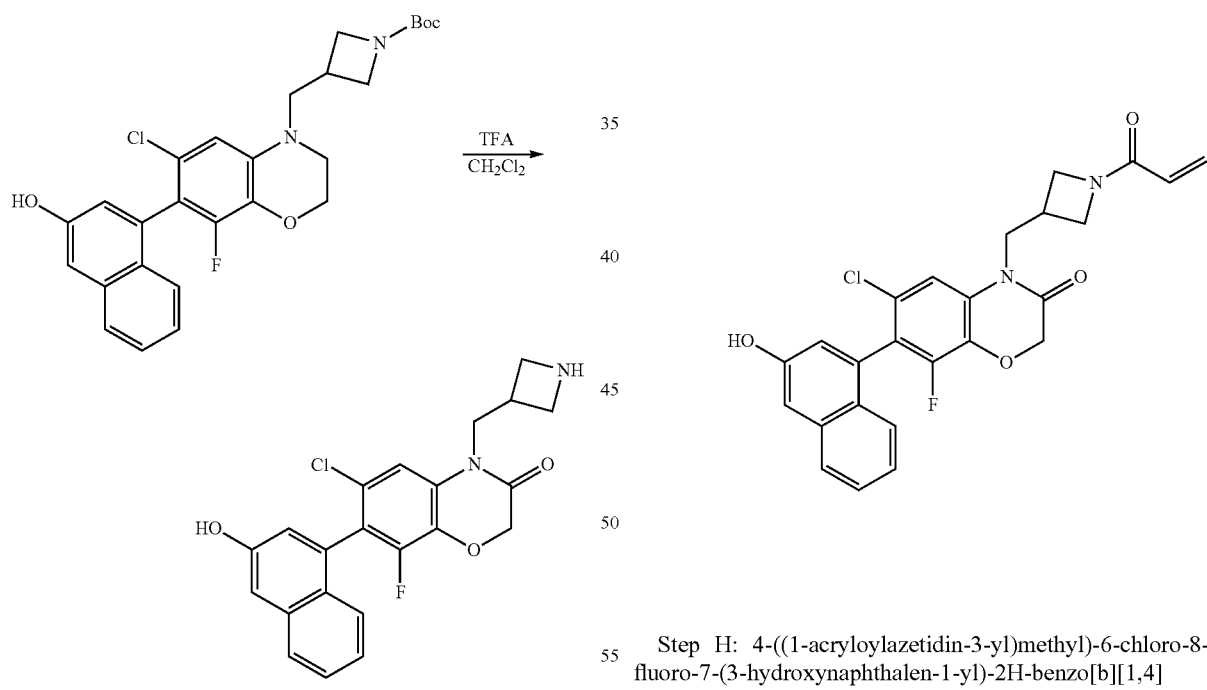

Step G: 4-(azetidin-3-ylmethyl)-6-chloro-8-fluoro-7-(3-hydroxynaphthalen-1-yl)-2H-benzo[b][1,4]oxazin-3(4H)-one. Prepared according to procedure from Example 14, Step F, substituting tert-butyl 3-((6-chloro-8-fluoro-7-(3-hydroxynaphthalen-1-yl)-3-oxo-2,3-dihydro-4H-benzo[b][1,4]oxazin-4-yl)methyl)azetidine-1-carboxylate for tert-butyl 3-((7-(3-(methoxymethoxy)naphthalen-1-yl)-3-oxo-2,3-dihydro-4H-benzo[b][1,4]thiazin-4-yl)methyl)azetidine-1-carboxylate to afford the title compound (84 mg), ES+APCI m/z 413.1 (100%), 415.1 (40%) [M−H]⁺.

Step H: 4-((1-acryloylazetidin-3-yl)methyl)-6-chloro-8-fluoro-7-(3-hydroxynaphthalen-1-yl)-2H-benzo[b][1,4]oxazin-3(4H)-one. To a solution of 4-(azetidin-3-ylmethyl)-6-chloro-8-fluoro-7-(3-hydroxynaphthalen-1-yl)-2H-benzo[b][1,4]oxazin-3(4H)-one (25.0 mg, 0.061 mmol) and DIEA (21.0 µL, 0.120 mmol) in CH₂Cl₂ (303 µL) at 0° C. was portion wise added a 10% solution of acryloyl chloride (49 µL, 0.061 mmol) in CH₂Cl₂. The reaction mixture was warmed to ambient temperature over 5 min. The reaction mixture was concentrated and diluted with MeOH and purified by semi-preparative C18 HPLC (5-95% CH₃CN/H₂O+0.1% TFA) to afford the title compound (2.9 mg, 0.006 mmol, 10.0%). ES+APCI m/z 467.1 (100%) [M−H]⁺.

Example 17

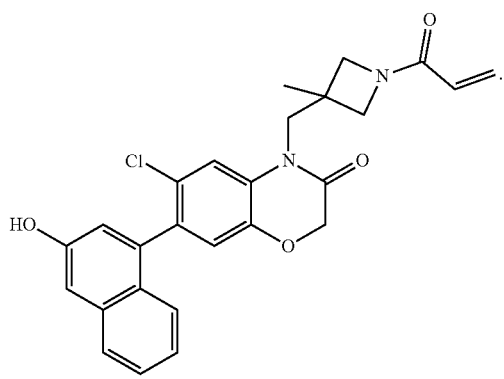 [SMILES: C=CC(=O)N1CC(C)(CN2C(=O)COc3cc(-c4cc(O)cc5ccccc45)c(Cl)cc32)C1]

4-((1-acryloyl-3-methylazetidin-3-yl)methyl)-6-chloro-7-(3-hydroxynaphthalen-1-yl)-2H-benzo[b][1,4]oxazin-3(4H)-one was prepared following Example 1 substituting tert-butyl 3-formyl-3-methylazetidine-1-carboxylate for 1-Boc-3-azetidinecarboxaldehyde in Step A. ES+APCI MS m/z 463.1 [M+H]+.

Example 18

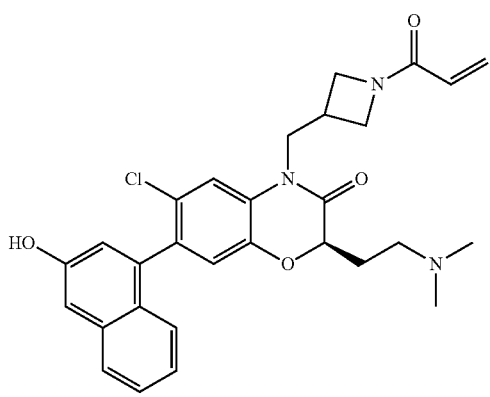 [SMILES: C=CC(=O)N1CC(CN2C(=O)[C@@H](CCN(C)C)Oc3cc(-c4cc(O)cc5ccccc45)c(Cl)cc32)C1]

Preparation of (R)-4-((1-acryloylazetidin-3-yl)methyl)-6-chloro-2-(2-(dimethylamino)ethyl)-7-(3-hydroxynaphthalen-1-yl)-2H-benzo[b][1,4]oxazin-3(4H)-one

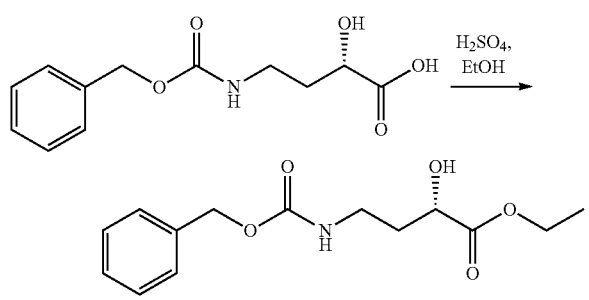

Step A: ethyl (S)-4-(((benzyloxy)carbonyl)amino)-2-hydroxybutanoate. To a solution of (S)-(+)-Z-4-Amino-2-hydroxybutyric acid (1.21 g, 4.78 mmol) and EtOH (4.78 mL) was added concentrated sulfuric acid (0.051 mL, 0.956 mmol). The flask was equipped with a reflux condenser and the mixture was warmed to 80° C. where it stirred overnight. The mixture was cooled to ambient temperature and poured into a saturated aqueous NaHCO$_3$ solution. The mixture was extracted with EtOAc and the organic layer was washed with brine, dried over Na$_2$SO$_4$, filtered and concentrated to afford the desired product as a pale yellow oil which was used directly in the subsequent step.

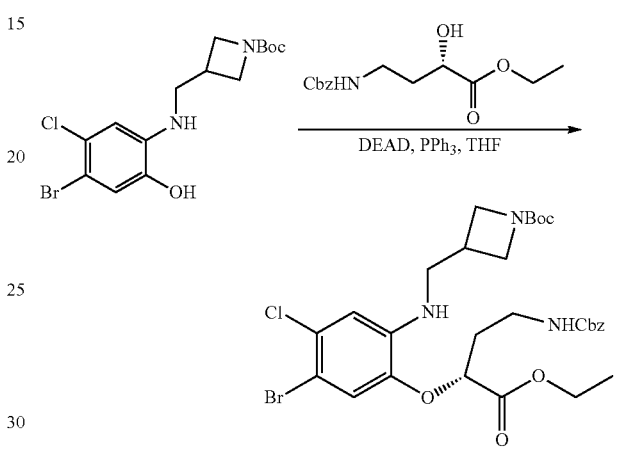

Step B: tert-butyl (R)-3-(((2-((4-(((benzyloxy)carbonyl)amino)-1-ethoxy-1-oxobutan-2-yl)oxy)-4-bromo-5-chlorophenyl)amino)methyl)azetidine-1-carboxylate. To a vial was added tert-butyl 3-(((4-bromo-5-chloro-2-hydroxyphenyl)amino)methyl)azetidine-1-carboxylate (0.250 g, 0.638 mmol), ethyl (S)-4-(((benzyloxy)carbonyl)amino)-2-hydroxybutanoate (0.269 g, 0.957 mmol) and THF (2.13 mL). Then triphenylphosphine (0.251 g, 0.957 mmol) was added followed by diethyl azodicarboxylate (0.151 mL, 0.957 mmol). The mixture was stirred at ambient temperature for 24 hours. The crude product was purified via column chromatography (10-50% EtOAc/hexanes) to afford the title compound as a pale yellow solid that became a red solid overnight under vacuum.

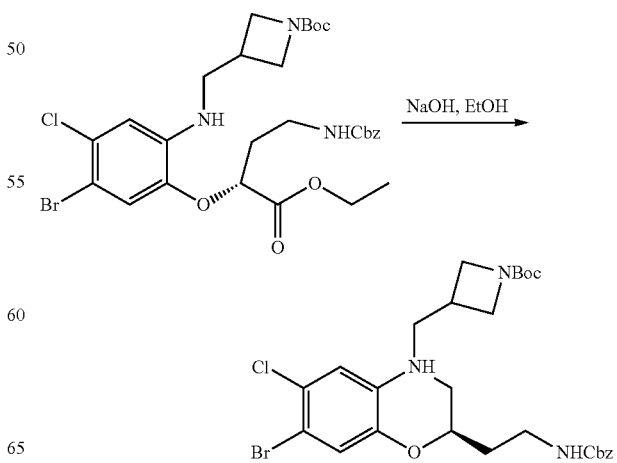

Step C: tert-butyl (R)-3-((2-(2-(((benzyloxy)carbonyl)amino)ethyl)-7-bromo-6-chloro-3-oxo-2,3-dihydro-4H-benzo[b][1,4]oxazin-4-yl)methyl)azetidine-1-carboxylate. To a suspension of tert-butyl (R)-3-(((2-((4-(((benzyloxy)carbonyl)amino)-1-ethoxy-1-oxobutan-2-yl)oxy)-4-bromo-5-chlorophenyl)amino)methyl)azetidine-1-carboxylate (0.418 g, 0.638 mmol) in EtOH (6.38 mL) was added NaOH (1.91 mL, 1.0M Aq). The mixture was stirred at ambient temperature overnight. The mixture was cooled to 0° C. and was treated with KHSO₄ (2.0 mL, 1.0M Aq) where it stirred for 10 minutes. The mixture was extracted with CHCl₃ (3×10 mL) and the combined organic layers were dried over Na₂SO₄, filtered and concentrated at 35° C. at which point the cyclization occurred. The crude yellow product was purified via column chromatography (20-40% EtOAc/hexanes loading with DCM) to afford the title compound as a pink solid.

Step D: tert-butyl (R)-3-((2-(2-(((benzyloxy)carbonyl)amino)ethyl)-6-chloro-3-oxo-7-(3-(pivaloyloxy)naphthalen-1-yl)-2,3-dihydro-4H-benzol[b][1,4]oxazin-4-yl)methyl)azetidine-1-carboxylate. To a vial was added tert-butyl (R)-3-((2-(2-(((benzyloxy)carbonyl)amino)ethyl)-7-bromo-6-chloro-3-oxo-2,3-dihydro-4H-benzo[b][1,4]oxazin-4-yl)methyl)azetidine-1-carboxylate (0.389 g, 0.639 mmol), 4-(4,4,5,5-tetramethyl-1,3,2-dioxaborolan-2-yl)naphthalen-2-yl pivalate (0.339 g, 0.958 mmol) and dioxane (6.39 mL). To this was added Tetrakis(triphenylphosphine) palladium (0) (0.074 g, 0.064 mmol) and Na₂CO₃ (0.958 mL, 1.92 mmol, 2.0M Aq). The mixture was purged with Ar then heated to 80° C. under an Ar atmosphere where it stirred for 16 hours. The mixture was cooled to ambient temperature diluted with CH₂Cl₂ and was filtered. The filtrate was dried over Na₂SO₄, filtered again and concentrated. The crude product was purified via column chromatography (30-50% EtOAc/hexanes loading with DCM) to afford the product (0.415 g, 85%) as a pale yellow foam.

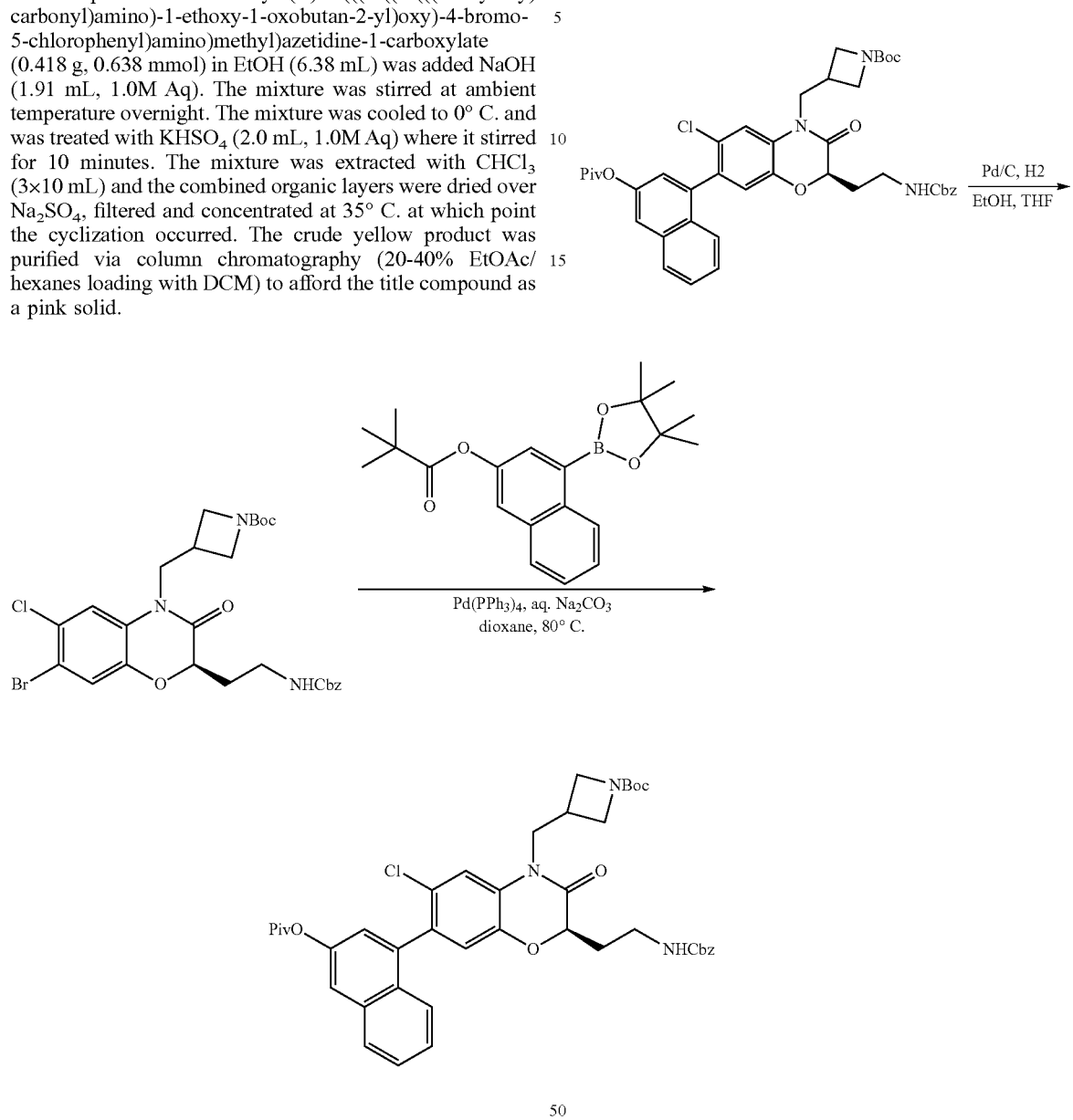

50

-continued

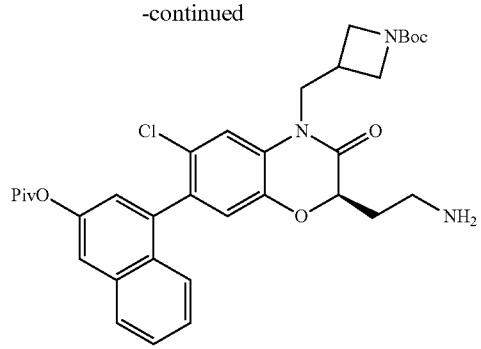

Step E: tert-butyl (R)-3-((2-(2-aminoethyl)-6-chloro-3-oxo-7-(3-(pivaloyloxy)naphthalen-1-yl)-2,3-dihydro-4H- benzo[b][1,4]oxazin-4-yl)methyl)azetidine-1-carboxylate. To a solution of tert-butyl (R)-3-((2-(2-(((benzyloxy)carbonyl)amino)ethyl)-6-chloro-3-oxo-7-(3-(pivaloyloxy)naphthalen-1-yl)-2,3-dihydro-4H-benzo[b][1,4]oxazin-4-yl)methyl)azetidine-1-carboxylate (0.200 g, 0.264 mmol) in EtOH (1.32 mL) and THF (1.32 mL) was added Palladium (0.113 g, 0.053 mmol, Degussa Type, 10 wt %, 50% H$_2$O) and then an atmosphere of H$_2$ was introduced via vacuum followed by balloon pressure. The mixture was stirred at ambient temperature for 2 hours. The mixture was diluted with MeOH and filtered through a nylon filter. The filtrate was concentrated in vacuo providing a light orange solid (0.161 g, 97%) that was used directly in the subsequent step.

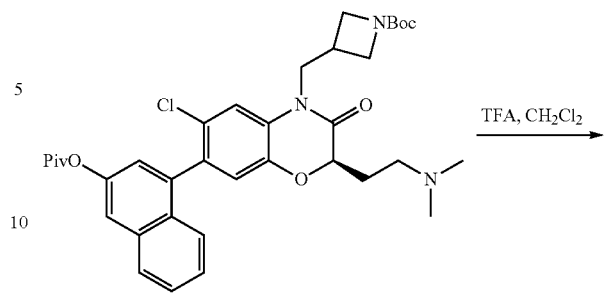

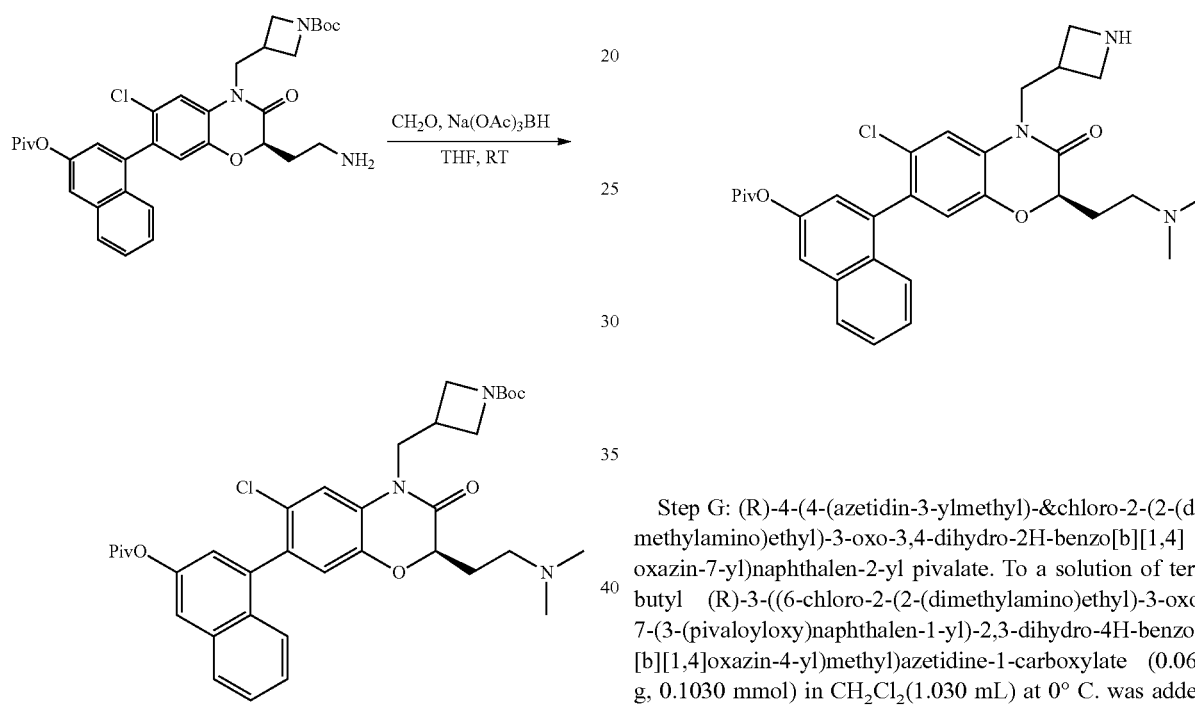

Step F: tert-butyl (R)-3-(((6-chloro-2-(2-(dimethylamino)ethyl)-3-oxo-7-(3-(pivaloyloxy)naphthalen-1-yl)-2,3-dihydro-4H-benzo[b][1,4]oxazin-4-yl)methyl)azetidine-1-carboxylate. To a round bottom flask was added tert-butyl (R)-3-((2-(2-aminoethyl)-6-chloro-3-oxo-7-(3-(pivaloyloxy)naphthalen-1-yl)-2,3-dihydro-4H-benzo[b][1,4]oxazin-4-yl)methyl)azetidine-1-carboxylate (0.161 g, 0.259 mmol) and THF (2.59 mL). The solution was treated with Formaldehyde (0.117 mL, 1.55 mmol, 37% Aq) followed by Na(OAc)$_3$BH (0.165 g, 0.776 mmol). The mixture was stirred at ambient temperature for 2 hours. The mixture was diluted with a saturated aqueous NH$_4$Cl solution and the mixture was extracted with CHCl$_3$ (3×10 mL). The combined organic extracts were then dried over Na$_2$SO$_4$, filtered and concentrated. The crude product was purified by column chromatography (2-8% MeOH/DCM) to afford the product (0.067 g, 39%) as an off-white solid foam.

Step G: (R)-4-(4-(azetidin-3-ylmethyl)-&chloro-2-(2-(dimethylamino)ethyl)-3-oxo-3,4-dihydro-2H-benzo[b][1,4]oxazin-7-yl)naphthalen-2-yl pivalate. To a solution of tert-butyl (R)-3-((6-chloro-2-(2-(dimethylamino)ethyl)-3-oxo-7-(3-(pivaloyloxy)naphthalen-1-yl)-2,3-dihydro-4H-benzo[b][1,4]oxazin-4-yl)methyl)azetidine-1-carboxylate (0.067 g, 0.1030 mmol) in CH$_2$Cl$_2$(1.030 mL) at 0° C. was added trifluoroacetic acid (0.158 mL, 2.06 mmol) and the mixture was stirred at 0° C. for 2 hours. The mixture was carefully added to a solution of saturated aqueous NaHCO$_3$. The mixture was extracted with 10% IPA/CHCl$_3$ (3×10 mL). The combined organic extracts were dried over Na$_2$SO$_4$, filtered and concentrated to afford an orange foam. The crude product was used directly in the subsequent step.

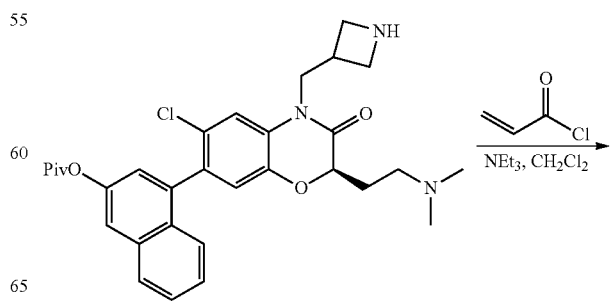

-continued

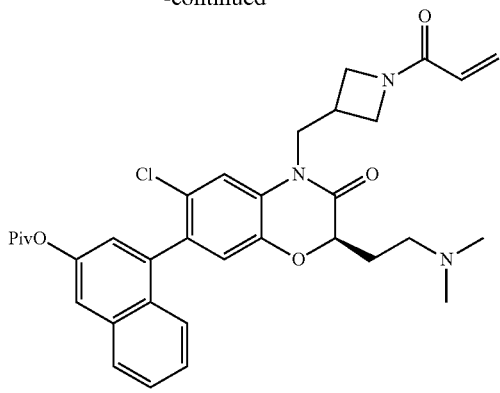

Step H: (R)-4-(4-((1-acryloylazetidin-3-yl)methyl)-6-chloro-2-(2-(dimethylamino)ethyl)-3-oxo-3,4-dihydro-2H-benzo[b][1,4]oxazin-7-yl)naphthalen-2-yl pivalate. To a solution of (R)-4-(4-(azetidin-3-ylmethyl)-6-chloro-2-(2-(dimethylamino)ethyl)-3-oxo-3,4-dihydro-2H-benzo[b][1,4]oxazin-7-yl)naphthalen-2-yl pivalate (0.057 g, 0.104 mmol) in CH₂Cl₂ (1.04 mL) at −78° C. was added Triethylamine (0.022 mL, 0.155 mmol). Acryloyl chloride (0.0093 mL, 0.114 mmol) was added and the reaction was stirred for 0.5 hours. The mixture was diluted with CHCl₃ and a saturated aqueous NH₄Cl solution. The layers were separated and the aqueous layer was extracted with CHCl₃ (2×10 mL). The combined extracts were dried over Na₂SO₄, filtered and concentrated. The crude product was purified via column chromatography (5-8% MeOH/DCM) to afford the product (0.023 g, 36%) as an off-white foam.

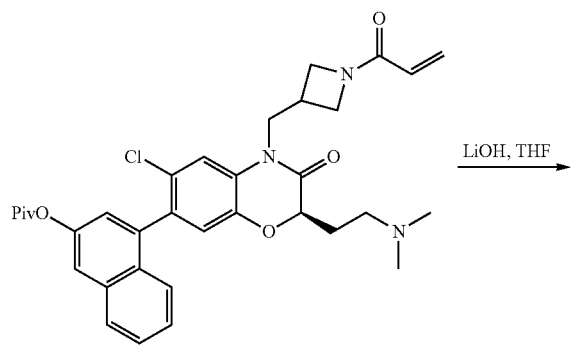

Step I: (R)-4-((1-acryloylazetidin-3-yl)methyl)-6-chloro-2-(2-(dimethylamino)ethyl)-7-(3-hydroxynaphthalen-1-yl)-2H-benzo[b][1,4]oxazin-3(4H)-one. (R)-4-(4-((1-acryloylazetidin-3-yl)methyl)-6-chloro-2-(2-(dimethylamino)ethyl)-3-oxo-3,4-dihydro-2H-benzo[b][1,4]oxazin-7-yl)naphthalen-2-yl pivalate (0.023 g, 0.038 mmol) was dissolved in THF (0.38 mL) and the solution was treated with LiOH (0.190 mL, 0.381 mmol, 2M aq) and the mixture was stirred vigorously at ambient temperature for 6 hours. The reaction mixture was purified directly via column chromatography (5% MeOH/DCM with 0.5% NH₄OH, loading with THF) to afford the title compound (0.012 g, 54%) as a white solid. ES+APCI MS m/z 520.2 [M+H]⁺.

Example 19

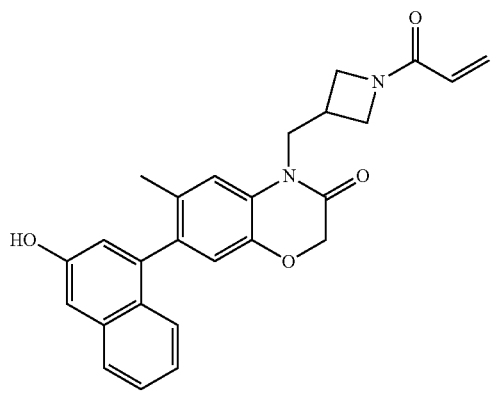 [SMILES: C=CC(=O)N1CC(CN2C(=O)COc3cc(-c4cc(O)cc5ccccc45)c(C)cc32)C1]

4-((1-acryloylazetidin-3-yl)methyl)-7-(3-hydroxynaphthalen-1-yl)-6-methyl-2H-benzo[b][1,4]oxazin-3(4H)-one was prepared following Example 16 substituting 6-methyl-2H-benzo[b][1,4]oxazin-3(4H)-one for 6-chloro-8-fluoro-2H-benzo[b][1,4]oxazin-3(4H)-one in Step D. ES+APCI MS m/z 429.2 [M+H]+.

Example 20

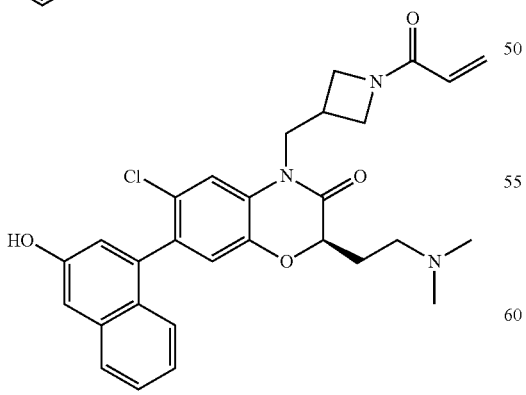

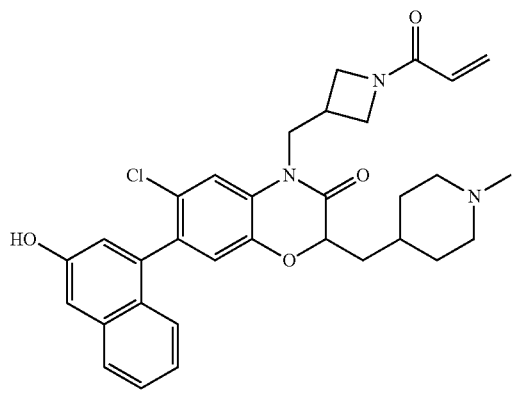 [SMILES: C=CC(=O)N1CC(CN2C(=O)C(CC3CCN(C)CC3)Oc3cc(-c4cc(O)cc5ccccc45)c(Cl)cc32)C1]

Preparation of 4-((1-acryloylazetidin-3-yl)methyl)-6-chloro-7-(3-hydroxynaphthalen-1-yl)-2-((1-methylpiperidin-4-yl)methyl)-2H-benzo[b][1,4]oxazin-3(4H)-one

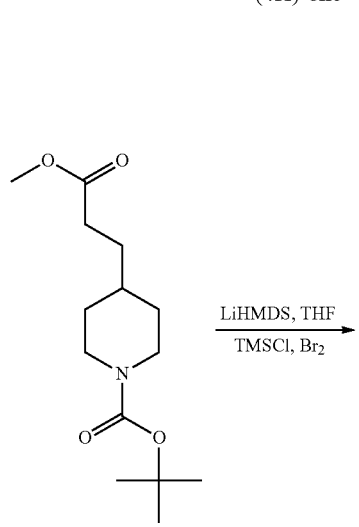

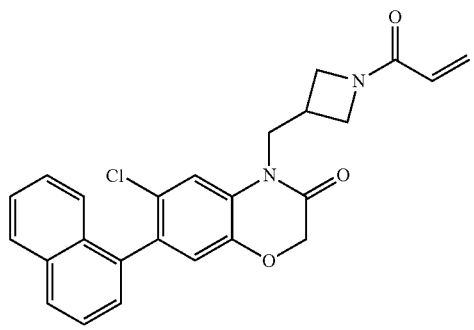 [SMILES: C=CC(=O)N1CC(CN2C(=O)COc3cc(-c4cccc5ccccc45)c(Cl)cc32)C1]

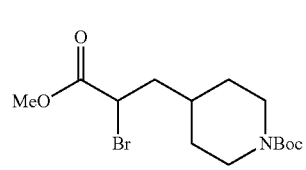

Step A: tert-butyl 4-(2-bromo-3-methoxy-3-oxopropyl)piperidine-1-carboxylate. To a dry 25 mL RBF was added methyl n-boc-4-piperidinepropionate (1.0 g, 3.69 mmol) and THF (4.61 ml, 3.69 mmol). The solution was cooled to −78° C. under N2 and then Lithium bis(trimethylsilyl)amide (6.63 ml, 6.63 mmol) (1.0M THF) was added dropwise. The mixture was stirred at −78° C. for 3 hours. Chlorotrimethylsilane (0.842 ml, 6.63 mmol) was added dropwise and the mixture was allowed to stir at −78° C. for another 1 hour at which time bromine (0.227 ml, 4.42 mmol) was added dropwise. The mixture stirred at −78° C. for another 2 hours at which point the mixture was warmed to 0° C., stirred for an additional 30 minutes. The mixture was diluted with EtOAc and the mixture was washed with a saturated aqueous NaHCO3 solution followed by distilled water. The organic layer was dried over Na2SO4, filtered and concentrated in vacuo. The crude product was purified via column chromatography (Biotage Isolera, 24 G Isco RediSep Gold, 5-25% EtOAc/hexanes) to afford the product as a colorless oil.

Step B: 4-((1-acryloylazetidin-3-yl)methyl)-6-chloro-7-(3-hydroxynaphthalen-1-yl)-2-((1-methylpiperidin-4-yl)methyl)-2H-benzo[b][1,4]oxazin-3(4H)-one was prepared following Example 5 substituting tert-butyl 4-(2-bromo-3-methoxy-3-oxopropyl)piperidine-1-carboxylate for methyl 2-bromo-3-(4-(((tert-butoxycarbonyl)(methyl)amino)piperidin-1-yl)propanoate in Step B. ES+APCI MS m/z 560.2 [M+H]+.

Example 21

Preparation of 4-((1-acryloylazetidin-3-yl)methyl)-6-chloro-7-(naphthalen-1-yl)-2H-benzo[b][1,4]oxazin-3(4H)-one 4-((1-benzhydrylazetidin-3-yl)methyl)-6-chloro-7-(naphthalen-1-yl)-2H-benzo[b][1,4]oxazin-3(4H)-one was prepared following Example 1, Steps A-D substituting 1-benzhydrylazetidine-3-carbaldehyde for 1-Boc-3-azetidinecarboxaldehyde in Step A. Also substituting 4-(4,4,5,5-tetramethyl-1,3,2-dioxaborolan-2-yl)naphthalen for 4-(4,4,5,5-tetramethyl-1,3,2-dioxaborolan-2-yl)naphthalen-2-yl pivalate in Step D. ES+APCI MS m/z 545.2 [M+H]+.

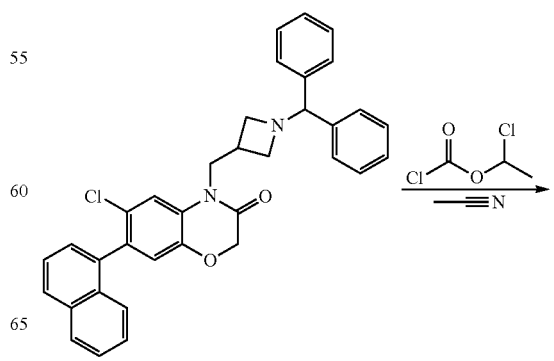

-continued

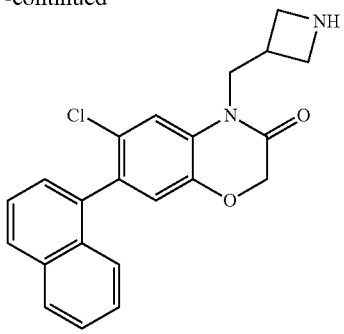

Step A: 4-(azetidin-3-ylmethyl)-6-chloro-7-(naphthalen-1-yl)-2H-benzo[b][1,4]oxazin-3(4H)-one: 1-Chloroethyl carbonochloridate (43.81 μl, 0.4183 mmol) was added to a solution of 4-((1-benzhydrylazetidin-3-yl)methyl)-6-chloro-7-(naphthalen-1-yl)-2H-benzo[b][1,4]oxazin-3(4H)-one (114 mg, 0.2091 mmol) in dry acetonitrile (4183 μl, 0.2091 mmol) and the mixture was refluxed for 2 h after which the mixture was concentrated. The residue was dissolved in MeOH (6.75 mL) and the mixture was refluxed for another 1 h. The solvent was evaporated to give the crude material that was used in the next step without further purification.

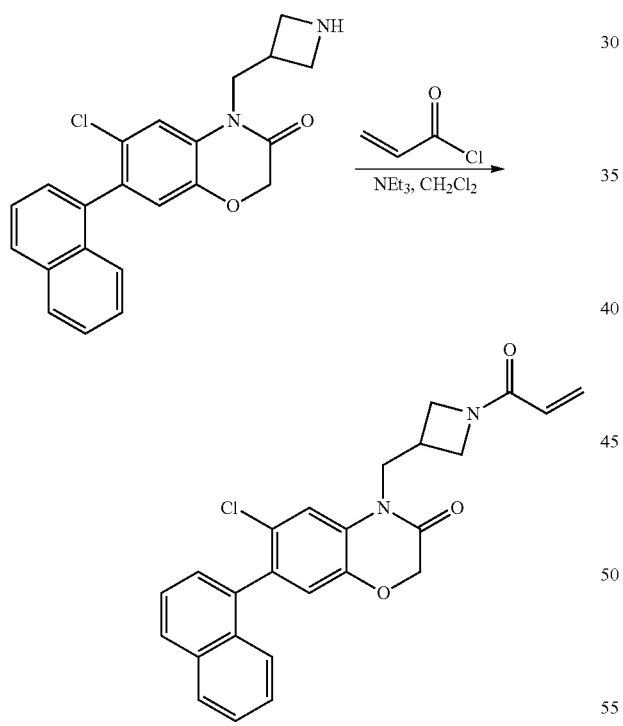

Step B: 4-((1-acryloylazetidin-3-yl)methyl)-6-chloro-7-(naphthalen-1-yl)-2H-benzo[b][1,4]oxazin-3(4H)-one: To a suspension of 4-(azetidin-3-ylmethyl)-6-chloro-7-(naphthalen-1-yl)-2H-benzo[b][1,4]oxazin-3(4H)-one (45.1 mg, 0.119 mmol) in CH$_2$Cl$_2$ (1190 μl, 0.119 mmol) at −78° C. was added acryloyl chloride (1190 μl, 0.119 mmol) (freshly prepared 0.1M solution in DCM) followed by Triethylamine (33.2 μl, 0.238 mmol). The reaction was stirred at −78° C. for 30 minutes. LC-MS indicated product formation. The reaction mixture was concentrated and purified by silica chromatography (100% EtOAc) to provide 4-((1-acryloylazetidin-3-yl)methyl)-6-chloro-7-(naphthalen-1-yl)-2H-benzo[b][1,4]oxazin-3(4H)-one (19.9 mg, 0.0460 mmol, 38.6% yield) ES+APCI MS m/z 433.1 [M+H]+.

Example 22

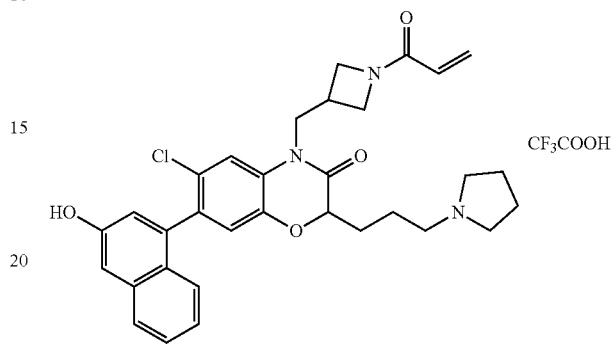

Preparation of 4-((1-acryloylazetidin-3-yl)methyl)-6-chloro-7-(3-hydroxynaphthalen-1-yl)-2-(3-(pyrrolidin-1-yl)propyl)-2H-benzo[b][1,4]oxazin-3(4H)-one 2,2,2-trifluoroacetate

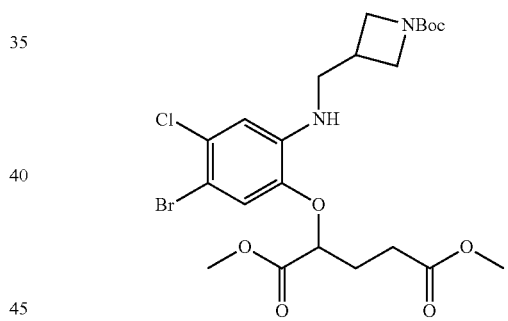

Steps A-C: Dimethyl 2-(5-bromo-2-(((1-(tert-butoxycarbonyl)azetidin-3-yl)methyl)amino)-4-chlorophenoxy)pentanedioate, was prepared following Example 1 substituting dimethyl 2-bromopentanedioate for methyl bromoacetate in Step B.

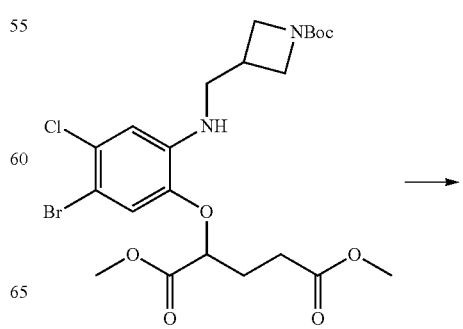

-continued

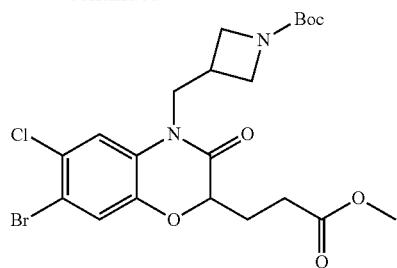

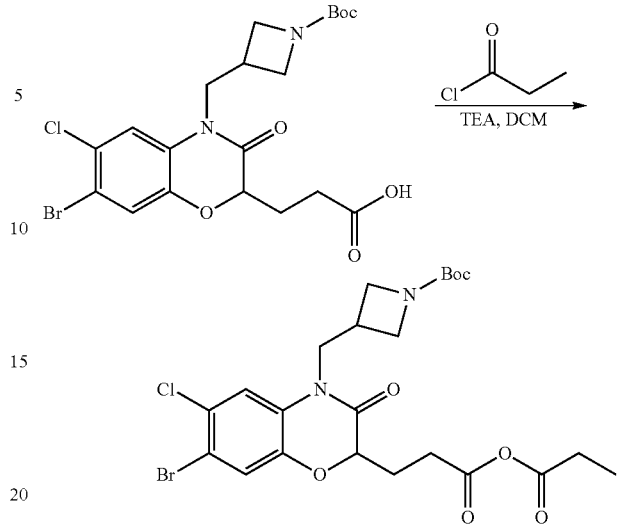

Step D: tert-butyl 3-((7-bromo-6-chloro-2-(3-methoxy-3-oxopropyl)-3-oxo-2,3-dihydro-4H-benzo[b][1,4]oxazin-4-yl)methyl)azetidine-1-carboxylate:Dimethyl 2-(5-bromo-2-(((1-(tert-butoxycarbonyl)azetidin-3-yl)methyl)amino)-4-chlorophenoxy)pentanedioate (702 mg, 1.28 mmol) was placed in THF (25 mL) and NaH (76.6 mg, 1.92 mmol) was added and the reaction stirred at room temperature for 1 hour. Water was added and the mixture was extracted with 10% MeOH in EtOAc. The organic layers were combined and concentrated. The resulting residue was purified by silica gel (0-5% MeOH in DCM) to provide tert-butyl 3-((7-bromo-6-chloro-2-(3-methoxy-3-oxopropyl)-3-oxo-2,3-dihydro-4H-benzo[b][1,4]oxazin-4-yl)methyl)azetidine-1-carboxylate (592 mg, 1.14 mmol, 89.5% yield).

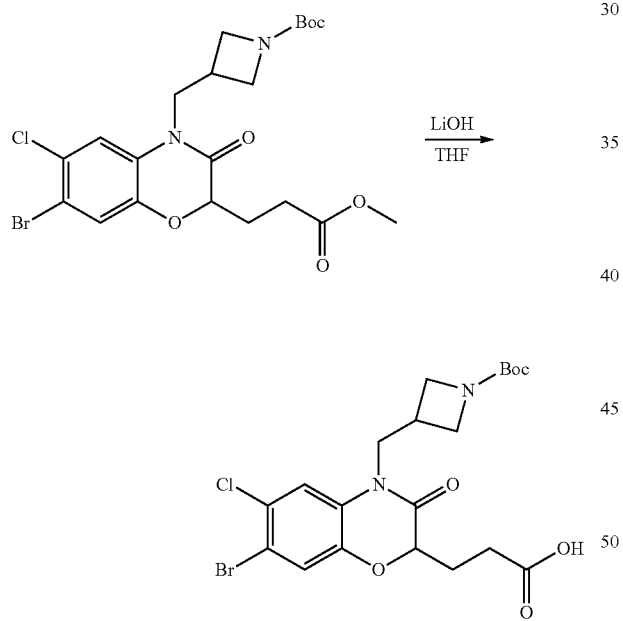

Step E: 3-(7-bromo-4-((1-(tert-butoxycarbonyl)azetidin-3-yl)methyl)-6-chloro-3-oxo-3,4-dihydro-2H-benzo[b][1,4]oxazin-2-yl)propanoic acid, tert-butyl 3-((7-bromo-6-chloro-2-(3-methoxy-3-oxopropyl)-3-oxo-2,3-dihydro-4H-benzo[b][1,4]oxazin-4-yl)methyl)azetidine-1-carboxylate (440 mg, 0.850 mmol) was placed in THF (3 mL) and LiOH (2124 µl, 4.25 mmol) was added and the reaction was stirred at rt for 3 hr. 1M KHSO₄ was added to bring the pH to ~3 and the mixture was extracted with 10% MeOH in DCM (3×20 mL). The extracts were combined, dried with sodium sulfate and concentrated to provide the desired product which was used as is.

Step F: 3-(7-bromo-4-((1-(tert-butoxycarbonyl)azetidin-3-yl)methyl)-6-chloro-3-oxo-3,4-dihydro-2H-benzo[b][1,4]oxazin-2-yl)propanoic propionic anhydride, 3-(7-bromo-4-((1-(tert-butoxycarbonyl)azetidin-3-yl)methyl)-6-chloro-3-oxo-3,4-dihydro-2H-benzo[b][1,4]oxazin-2-yl)propanoic acid (428 mg, 0.850 mmol) and TEA (177.6 µl, 1.27 mmol) were placed in DCM (10 mL). Propionyl chloride (89.1 µl, 1.02 mmol) was added and the reaction was stirred for 15 min. Water was added and the reaction was extracted with DCM (3×15 mL). The extracts were combined, washed with water, dried with sodium sulfate, filtered and concentrated to provide the desired product which was used as is.

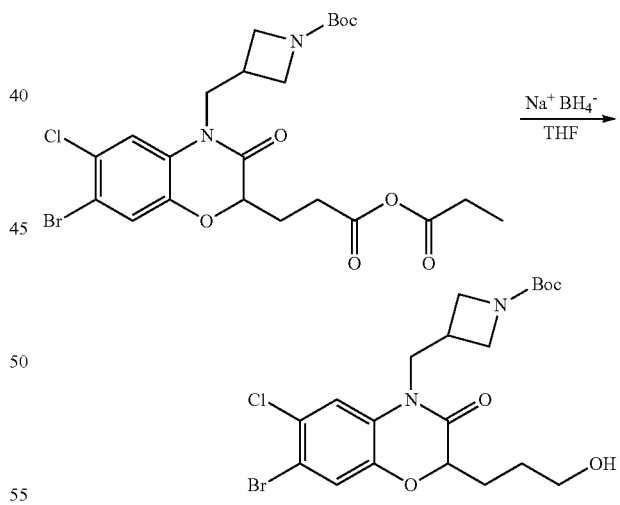

Step G: tert-butyl 3-((7-bromo-6-chloro-2-(3-hydroxypropyl)-3-oxo-2,3-dihydro-4H-benzo[b][1,4]oxazin-4-yl)methyl)azetidine-1-carboxylate, 3-(7-bromo-4-((1-(tert-butoxycarbonyl)azetidin-3-yl)methyl)-6-chloro-3-oxo-3,4-dihydro-2H-benzo[b][1,4]oxazin-2-yl)propanoic propionic anhydride (540 mg, 0.965 mmol) was placed in THF and cooled to 0C. NaBH₄ (109 mg, 2.89 mmol) was added and the reaction was stirred at 0° C. for 10 min. Saturated bicarbonate was added and the mixture was extracted with ether (3×10 mL). The organic layers were combined, dried with sodium sulfate and filtered to provide crude tert-butyl 3-((7-bromo-6-chloro-2-(3-hydroxypropyl)-3-oxo-2,3-dihydro-4H-benzo[b][1,4]oxazin-4-yl)methyl)azetidine-1-carboxylate (267 mg, 0.545 mmol, 56.5% yield).

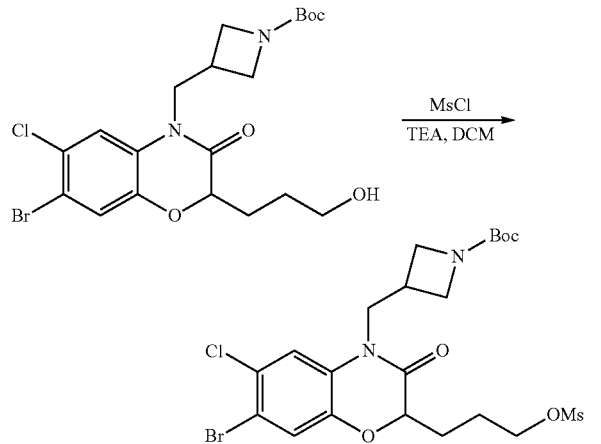

Step H: tert-butyl 3-((7-bromo-6-chloro-2-(3-((methylsulfonyl)oxy)propyl)-3-oxo-2,3-dihydro-4H-benzo[b][1,4]oxazin-4-yl)methyl)azetidine-1-carboxylate, tert-butyl 3-((7-bromo-6-chloro-2-(3-hydroxypropyl)-3-oxo-2,3-dihydro-4H-benzo[b][1,4]oxazin-4-yl)methyl)azetidine-1-carboxylate (267 mg, 0.545 mmol) and TEA (228 µl, 1.64 mmol) was placed in dry DCM (5 mL) and was cooled to 0° C. MsCl (63.3 µl, 0.818 mmol) was added and the reaction was stirred at rt for 20 min. Water was added and the mixture was extracted with DCM (2×20 mL), combined, dried with sodium sulfate, filtered and concentrated to provide the desired product which was used as is.

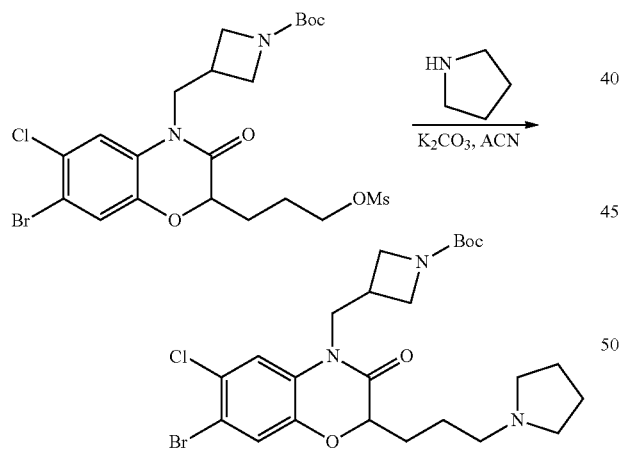

Step I: tert-butyl 3-((7-bromo-6-chloro-3-oxo-2-(3-(pyrrolidin-1-yl)propyl)-2,3-dihydro-4H-benzo[b][1,4]oxazin-4-yl)methyl)azetidine-1-carboxylate, Crude tert-butyl 3-((7-bromo-6-chloro-2-(3-((methylsulfonyl)oxy)propyl)-3-oxo-2,3-dihydro-4H-benzo[b][1,4]oxazin-4-yl)methyl)azetidine-1-carboxylate (80 mg, 0.14 mmol), pyrrolidine (24 µl, 0.28 mmol) and K₂CO₃ (58 mg, 0.42 mmol) were placed in dry ACN (2 mL) and the reaction was heated to 45° C. for 2 hr. Water was added and the mixture was extracted with DCM (3×10 mL). The organic layers were combined and concentrated. The residue was purified by silica gel (0-11% MeOH in DCM with NH₄OH) to provide tert-butyl 3-((7-bromo-6-chloro-3-oxo-2-(3-(pyrrolidin-1-yl)propyl)-2,3-dihydro-4H-benzo[b][1,4]oxazin-4-yl)methyl)azetidine-1-carboxylate (32 mg, 0.059 mmol, 42% yield).

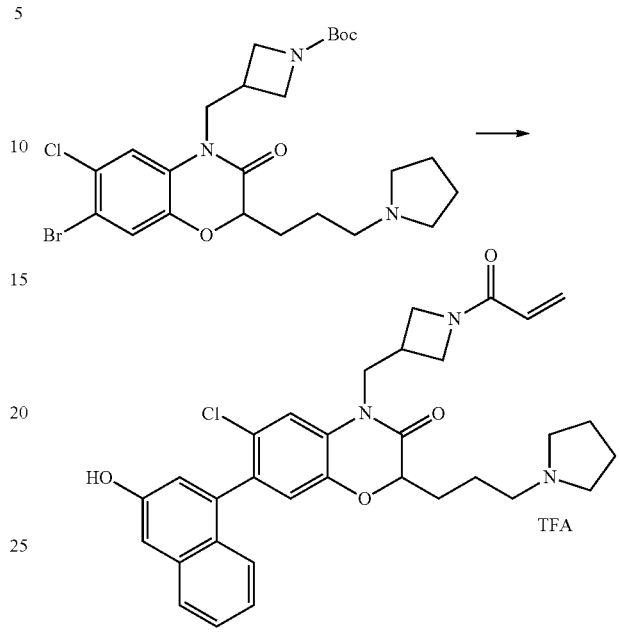

Step J: 4-((1-acryloylazetidin-3-yl)methyl)-6-chloro-7-(3-hydroxynaphthalen-1-yl)-2-(3-(pyrrolidin-1-yl)propyl)-2H-benzo[b][1,4]oxazin-3(4H)-one 2,2,2-trifluoroacetate was prepared according Example 3, Step D-F, substituting tert-butyl 3-((7-bromo-6-chloro-3-oxo-2-(3-(pyrrolidin-1-yl)propyl)-2,3-dihydro-4H-benzo[b][1,4]oxazin-4-yl)methyl)azetidine-1-carboxylate and 4-(4,4,5,5-tetramethyl-1,3,2-dioxaborolan-2-yl)naphthalen-2-ol for tert-butyl 3-((7-bromo-6-chloro-3-oxo-2,3-dihydro-4H-benzo[b][1,4]oxazin-4-yl)methyl)azetidine-1-carboxylate and 4-(4,4,5,5-tetramethyl-1,3,2-dioxaborolan-2-yl)naphthalen-2-yl pivalate in Example 1, Step D. ES+APCI MS m/z 561.2 [M+H]⁺.

Example 23

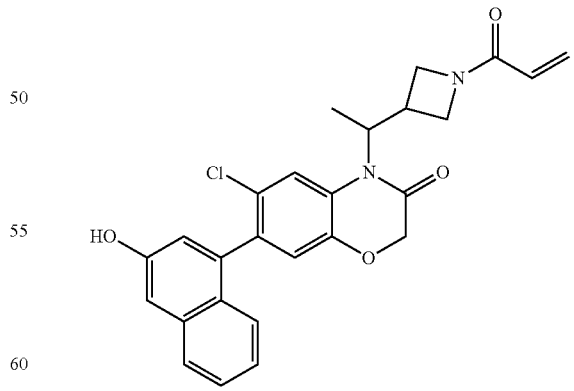

4-(1-(1-acryloylazetidin-3-yl)ethyl)-6-chloro-7-(3-hydroxynaphthalen-1-yl)-2H-benzo[b][1,4]oxazin-3(4H)-one was prepared following Example 1, substituting Tert-butyl 3-acetylaziridine-1-carboxylate for 1-Boc-3-azetidinecarboxaldehyde in Step A. ES+APCI MS m/z 463.1 [M+H]+.

Example 24

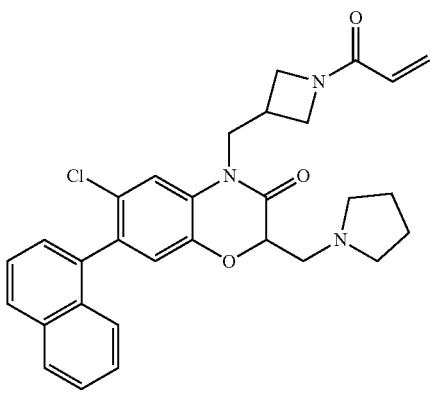 [SMILES: C=CC(=O)N1CC(CN2C(=O)C(CN3CCCC3)Oc3cc(-c4cccc5ccccc45)c(Cl)cc32)C1]

4-((1-acryloylazetidin-3-yl)methyl)-6-chloro-7-(naphthalen-1-yl)-2-(pyrrolidin-1-ylmethyl)-2H-benzo[b][1,4]oxazin-3(4H)-one 2,2,2-trifluoroacetate was prepared following Example 7, Steps A-G, substituting naphthalen-1-ylboronic acid for 4-(4,4,5,5-tetramethyl-1,3,2-dioxaborolan-2-yl)naphthalen-2-yl pivalate in Step E. ES+APCI MS m/z 516.2 [M+H]⁺.

Example 25

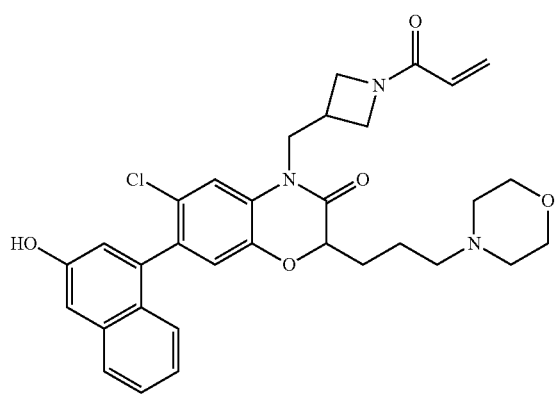 [SMILES: C=CC(=O)N1CC(CN2C(=O)C(CCCN3CCOCC3)Oc3cc(-c4cc(O)cc5ccccc45)c(Cl)cc32)C1]

4-((1-acryloylazetidin-3-yl)methyl)-6-chloro-7-(3-hydroxynaphthalen-1-yl)-2-(3-morpholinopropyl)-2H-benzo[b][1,4]oxazin-3(4H)-one 2,2,2-trifluoroacetate was prepared following Example 32, Step H, substituting morpholine for pyrrolidine, then Example 3, Step D-G substituting tert-butyl 3-((7-bromo-6-chloro-2-(3-morpholinopropyl)-3-oxo-2,3-dihydro-4H-benzo[b][1,4]oxazin-4-yl)methyl)azetidine-1-carboxylate for tert-butyl 3-((7-bromo-6-chloro-3-oxo-2,3-dihydro-4H-benzo[b][1,4]oxazin-4-yl)methyl)azetidine-1-carboxylate. ES+APCI MS m/z 576.1 [M+H]⁺.

Example 26

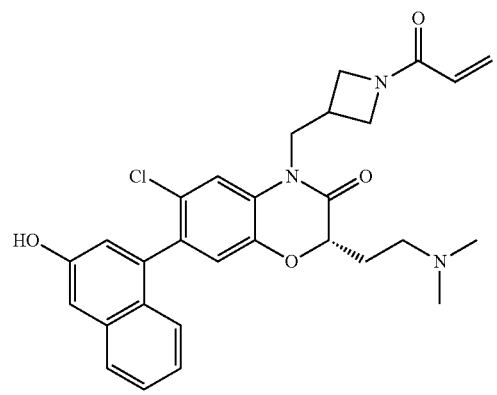 [SMILES: C=CC(=O)N1CC(CN2C(=O)[C@H](CCN(C)C)Oc3cc(-c4cc(O)cc5ccccc45)c(Cl)cc32)C1]

(S)-4-((1-acryloylazetidin-3-yl)methyl)-6-chloro-2-(2-(dimethylamino)ethyl)-7-(3-hydroxynaphthalen-1-yl)-2H-benzo[b][1,4]oxazin-3(4H)-one was prepared following the procedure outlined in Example 28 substituting ethyl (R)-4-(((benzyloxy)carbonyl)amino)-2-hydroxybutanoate for ethyl (S)-4-(((benzyloxy)carbonyl)amino)-2-hydroxybutanoate in Step B. ES+APCI MS m/z 520.1 [M+H]+.

Example 27

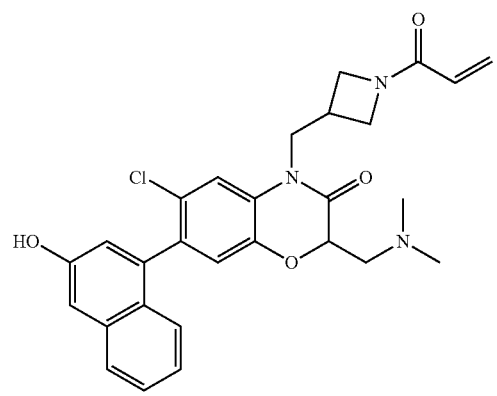

4-((1-acryloylazetidin-3-yl)methyl)-6-chloro-2-((dimethylamino)methyl)-7-(3-hydroxynaphthalen-1-yl)-2H-benzo[b][1,4]oxazin-3(4H)-one

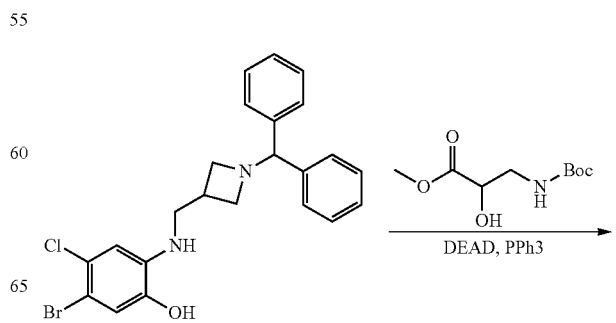

-continued

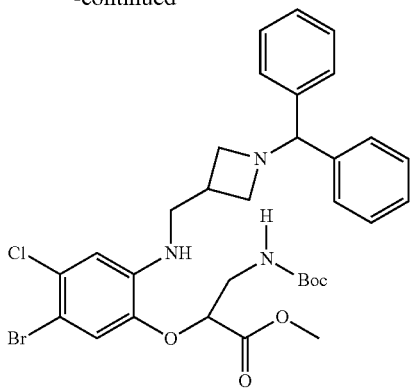

Step A: methyl 2-(2-(((1-benzhydrylazetidin-3-yl)methyl)amino)-5-bromo-4-chlorophenoxy)-3-((tert-butoxycarbonyl)amino)propanoate. 2-(((1-benzhydrylazetidin-3-yl)methyl)amino)-5-bromo-4-chlorophenol (400 mg, 0.87 mmol), PPh3 (344 mg, 1.3 mmol) and methyl 3-((tert-butoxycarbonyl)amino)-2-hydroxypropanoate (211 mg, 0.961 mmol) were placed in THF (5 mL) and was cooled to 0° C. DEAD (208 µl, 1.3 mmol) was added and the reaction was stirred at rt for 18 hr. Water was added and the mixture was extracted with DCM. The extracts were combined and concentrated. The resulting residue was purified by silica gel (0-4% MeOH in DCM with 0.25% NH4OH) to provide methyl 2-(2-(((1-benzhydrylazetidin-3-yl)methyl)amino)-5-bromo-4-chlorophenoxy)-3-((tert-butoxycarbonyl)amino)propanoate (400 mg, 0.607 mmol, 70% yield).

4-((1-acryloylazetidin-3-yl)methyl)-6-chloro-2-((dimethylamino)methyl)-7-(3-hydroxynaphthalen-1-yl)-2H-benzo[b][1,4]oxazin-3(4H)-one. was prepared following Example 6, Substituting Step A above and Step C-I substituting methyl 2-(2-(((1-benzhydrylazetidin-3-yl)methyl)amino)-5-bromo-4-chlorophenoxy)-3-((tert-butoxycarbonyl)amino)propanoate for tert-butyl 4-(1-(2-(((1-benzhydrylazetidin-3-yl)methyl)amino)-5-bromo-4-chlorophenoxy)-2-methoxy-2-oxoethyl)piperidine-1-carboxylate in Step C. ES+APCI MS m/z 506.1 [M+H]+.

Example 28

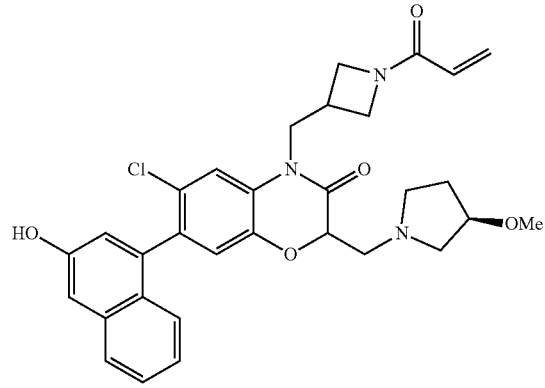 [SMILES: C=CC(=O)N1CC(CN2C(=O)C(CN3CC[C@@H](OC)C3)Oc3cc(-c4cc(O)cc5ccccc45)c(Cl)cc32)C1]

4-((1-acryloylazetidin-3-yl)methyl)-6-chloro-7-(3-hydroxynaphthalen-1-yl)-2-(((R)-3-methoxypyrrolidin-1-yl)methyl)-2H-benzo[b][1,4]oxazin-3(4H)-one was prepared following the procedure outlined in Example 7 substituting (R)-3-Methoxy-pyrrolidine for pyrrolidine in Step A. ES+APCI MS m/z 562.1 [M+H]+.

Example 29

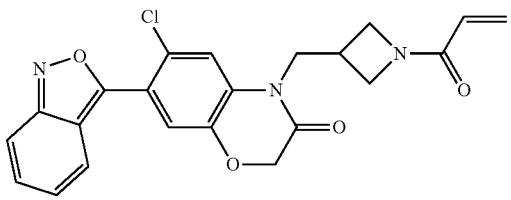

4-((1-acryloylazetidin-3-yl)methyl)-7-(benzo[c]isoxazol-3-yl)-6-chloro-2H-benzo[b][1,4]oxazin-3(4H)-one

Step A: tert-butyl 3-(methylsulfonyloxymethyl)azetidine-1-carboxylate: To a mixture of tert-butyl 3-(hydroxymethyl)azetidine-1-carboxylate: To a mixture of tert-butyl 3-(hydroxymethyl)azetidine-1-carboxylate (0.7 g, 3.74 mmol), Et3N (1.13 g, 11.22 mmol, 1.56 mL), DMAP (45.6 mg, 374 µmol) in DCM (20 mL) was added dropwise methanesulfonyl chloride (7.45 g, 65.04 mmol, 5.03 mL) at 0° C. The reaction mixture was warmed to 20° C. and stirred for 12 hours. The reaction was quenched by addition of water (100 mL) and the mixture extracted with ethyl acetate. The organic layer was dried with Na2SO4 and filtrated. The solvent was then removed under vacuum. The residue was purified by chromatography eluting with 2:1 to 1:1 Petroleum ether/Ethyl acetate to give tert-butyl 3-(methylsulfonyloxymethyl)azetidine-1-carboxylate (800 mg, 80.1%). ESI MS m/z 288.1 [M+H]+.

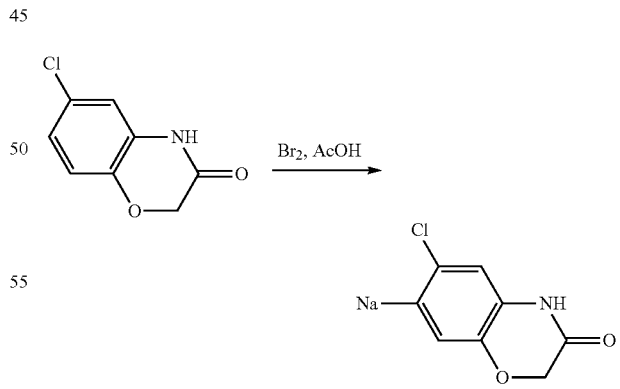

Step B: 7-bromo-6-chloro-4H-1,4-benzoxazin-3-one: To a solution of 6-chloro-4H-1,4-benzoxazin-3-one (5.0 g, 27.23 mmol) in acetic acid (50 mL) was dropwise added Br2 (7.83 g, 49.0 mmol, 2.53 mL). The mixture was stirred at 20° C. for 4 hr. The reaction was quenched by addition of a solution of Na2SO3 (500 mL) and the mixture extracted with ethyl acetate (1000 mL). The organic layer was dried by Na₂SO₄. The solvent was removed under vacuum to give a solid residue. The solid residue was washed with methanol (300 mL) and Petroleum ether (500 mL) and dried under vacuum to give 7-bromo-6-chloro-4H-1,4-benzoxazin-3-one (5.13 g, 14.0 mmol, 51.4%). ESI MS m/z 264.0 [M+H]⁺.

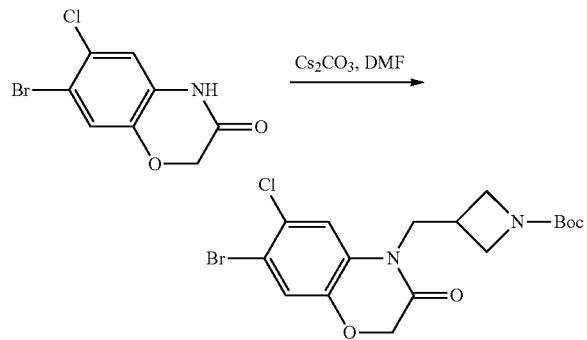

Step C: tert-butyl 3-[(7-bromo-6-chloro-3-oxo-1,4-benzoxazin-4-yl)methyl]azetidine-1-carboxylate: To a solution of 7-bromo-6-chloro-4H-1,4-benzoxazin-3-one (1.0 g, 3.81 mmol) in DMF (20 mL) was added Cs₂CO₃ (3.72 g, 11.43 mmol) at 0° C. The mixture was stirred at 0° C. for 1 hour followed by addition of tert-butyl 3-(methylsulfonyloxymethyl)azetidine-1-carboxylate (2.02 g, 7.62 mmol) in DMF (5 mL) dropwise at 0° C. The resulting mixture was stirred for 3 hours at 90° C. The reaction was quenched by addition of water (400 mL) and the mixture was extracted with ethyl acetate (3×300 mL). The combined organics were dried over Na₂SO₄ and the solvent was then removed under vacuum. The residue was purified by chromatography using 10/1 Petroleum ether/Ethyl acetate as eluent to give tert-butyl 3-[(7-bromo-6-chloro-3-oxo-1,4-benzoxazin-4-yl)methyl]azetidine-1-carboxylate (1.4 g, 76%). ESI MS m/z 431.1 [M+H]⁺.

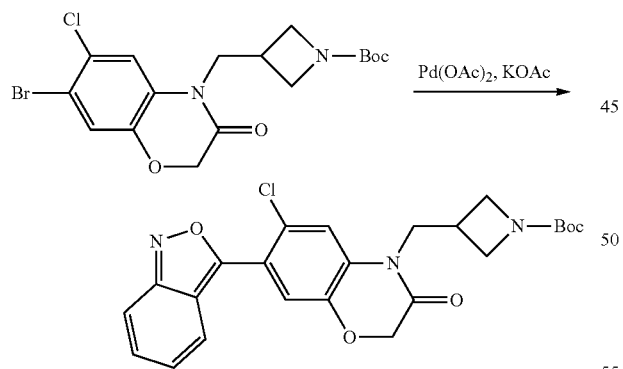

Step D: tert-butyl 3-[[7-(2,1-benzoxazol-3-yl)-6-chloro-3-oxo-1,4-benzoxazin-4-yl]methyl]azetidine-1-carboxylate; A mixture of tert-butyl 3-[(7-bromo-6-chloro-3-oxo-1,4-benzoxazin-4-yl)methyl]azetidine-1-carboxylate (250 mg, 579 μmol), 2,1-benzoxazole (120 mg, 1.01 mmol), Pd(OAc)₂ (14.95 mg, 66.6 μmol), and KOAc (115 mg, 1.17 mmol) in DMAc (4 mL) was degassed and purged with N₂ 3 times and the mixture heated to 150° C. for 20 hr under N₂ atmosphere. The reaction was quenched by addition of water (50 mL) and the mixture extracted with ethyl acetate (3×50 mL). The combined organics were dried over Na₂SO₄, filtered and concentrated in vacuo. The residue was purified by prep-HPLC (column: Phenomenex Synergi C18 150*25*10 um; mobile phase: [water (0.225% TFA)-ACN]; B %: 60%-84%, 10 min) to give tert-butyl 3-[[7-(2,1-benzoxazol-3-yl)-6-chloro-3-oxo-1,4-benzoxazin-4-yl]methyl]azetidine-1-carboxylate (50 mg, 98.95 μmol, 17.1). ESI MS m/z 492.2 [M+H]⁺.

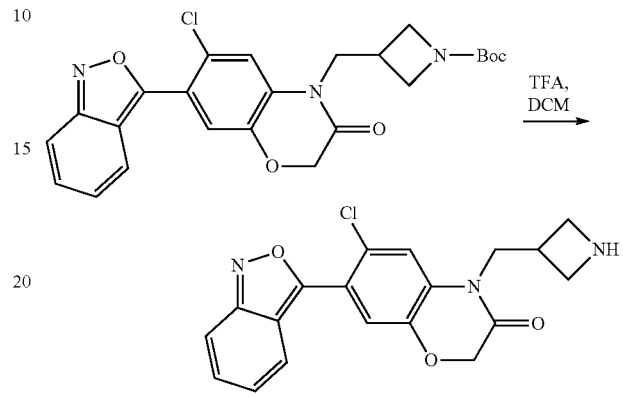

Step E: 4-(azetidin-3-ylmethyl)-7-(2,1-benzoxazol-3-yl)-6-chloro-1,4-benzoxazin-3-one: To a solution of tert-butyl 3-[[7-(2,1-benzoxazol-3-yl)-6-chloro-3-oxo-1,4-benzoxazin-4-yl]methyl]azetidine-1-carboxylate (50 mg, 106 μmol) in DCM (3.0 mL) was added TFA (3.08 g, 27.0 mmol) and the mixture stirred at 20° C. for 1 hr. The organic solvent was removed under vacuum to give 4-(azetidin-3-ylmethyl)-7-(2,1-benzoxazol-3-yl)-6-chloro-1,4-benzoxazin-3-one (60 mg, 100%). ESI MS m/z 370.2 [M+H]⁺.

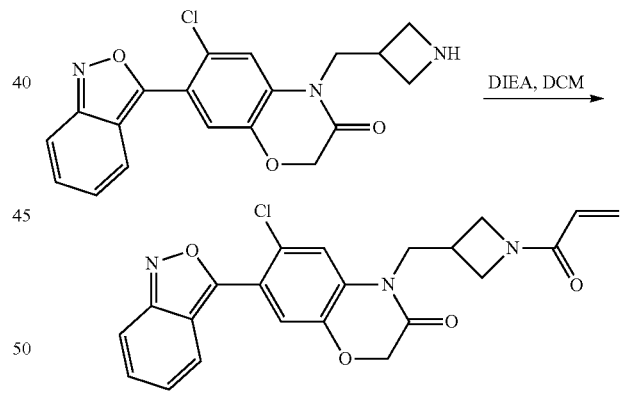

Step F: 7-(2,1-benzoxazol-3-yl)-6-chloro-4-[(1-prop-2-enoylazetidin-3-yl)methyl]-1,4-benzoxazin-3-one: To a solution of 4-(azetidin-3-ylmethyl)-7-(2,1-benzoxazol-3-yl)-6-chloro-1,4-benzoxazin-3-one (60.0 mg, 124.01 μmol) and DIEA (42 mg, 325 μmol) in DCM (3.0 mL) at −70° C. was added acrylic anhydride (13 μmol mg, 103 μmol) under N₂ atmosphere and the reaction stirred at −70° C. for 15 minutes. The reaction was quenched by addition of water (20.0 mL) and the mixture extracted with ethyl acetate (3×20 mL). The combined organics were dried over Na₂SO₄ and concentrated in vacuo. The residue was purified by prep-HPLC (column: Boston Green ODS 150*30 5 u; mobile phase: [water (0.225% TFA)-ACN]; B %: 45%-72%, 10 min) to give 4-((1-acryloylazetidin-3-yl)methyl)-7-(benzo

[c]isoxazol-3-yl)-6-chloro-2H-benzo[b][1,4]oxazin-3(4H)-one (11.2 mg, 25%). ESI MS m/z 423.8 [M+H]+.
¹H NMR (400 MHz, CDCl₃) δ 7.65 (d, J=8.8 Hz, 1H), 7.62 (d, J=8.8 Hz, 1H), 7.37 (s, 1H), 7.36-7.34 (m, 1H), 7.16 (s, 1H), 7.10-7.06 (m, 1H), 6.39-6.35 (m, 1H), 6.22-6.15 (m, 1H), 5.72-5.69 (m, 1H), 4.71 (s, 2H), 4.62-4.52 (m, 1H), 4.33 (t, J=8.4 HZ, 1H), 4.25 (t, J=9.2 Hz, 1H), 4.17-4.10 (m, 2H), 3.97-3.93 (m, 1H), 3.15-3.11 (m, 1H).

Example 30

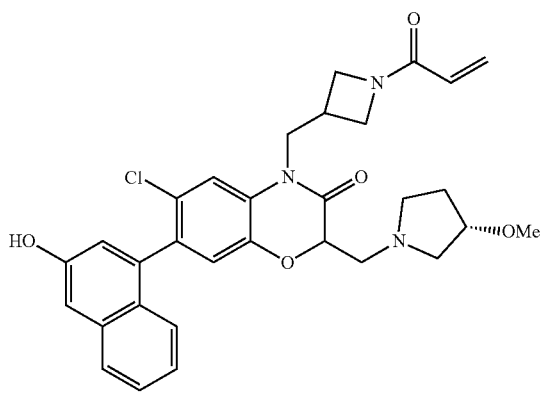 [SMILES: C=CC(=O)N1CC(CN2C(=O)C(CN3CC[C@H](OC)C3)Oc3cc(-c4cc(O)cc5ccccc45)c(Cl)cc32)C1]

4-((1-acryloylazetidin-3-yl)methyl)-6-chloro-7-(3-hydroxynaphthalen-1-yl)-2-(((S)-3-methoxypyrrolidin-1-yl)methyl)-2H-benzo[b][1,4]oxazin-3(4H)-one was prepared following the procedure outlined in Example 7 substituting (S)-3-Methoxy-pyrrolidine for pyrrolidine in Step A. ES+APCI MS m/z 562.2 [M+H]+.

Example 31

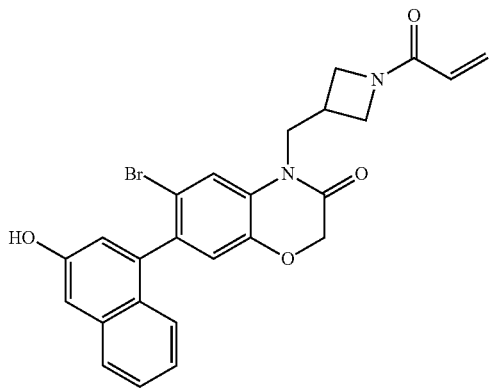

4-((1-acryloylazetidin-3-yl)methyl)-6-bromo-7-(3-hydroxynaphthalen-1-yl)-2H-benzo[b][1,4]oxazin-3(4H)-one

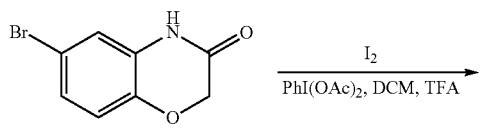

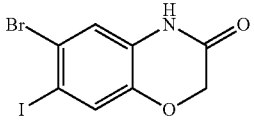

Step A: 6-bromo-7-iodo-2H-benzo[b][1,4]oxazin-3(4H)-one. A mixture of 6-bromo-2H-benzo[b][1,4]oxazin-3(4H)-one (400 mg, 1.75 mmol), diiodine (245 mg, 0.965 mmol), iodobenzene diacetate (169 mg, 0.526 mmol) and DCM (2 mL) was stirred at r.t. for 1.5 hours, followed by dropwise addition of 2,2,2-trifluoroacetic acid (0.5 ml, 6.53 mmol). Another portion of iodobenzene diacetate (169 mg, 0.526 mmol) was added and the reaction mixture stirred 30 minutes at r.t. The reaction was next filtered and the solid washed with DCM (2*2 mL). The filtrate was evaporated in vacuo and dried under vacuum. The solid was next washed with DCM (2*2 mL) and dried under air to give 230 mg of product. The filtrate was concentrated in vacuo and the solid recrystallized from boiling iPrOH (15 mL) to obtain additional 80 mg of product. (310 mg, 50%).

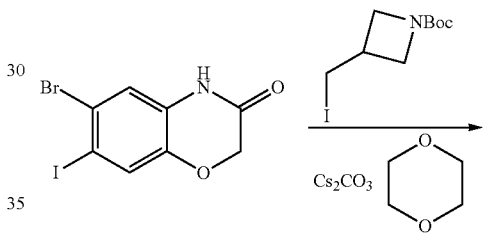

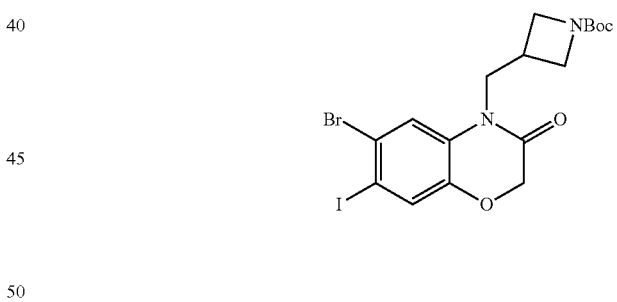

Step B: tert-butyl 3-(((6-bromo-7-iodo-3-oxo-2,3-dihydro-4H-benzo[b][1,4]oxazin-4-yl)methyl)azetidine-1-carboxylate. A mixture of 6-bromo-7-iodo-2H-benzo[b][1,4]oxazin-3(4H)-one (200 mg, 0.565 mmol), tert-butyl 3-(iodomethyl)azetidine-1-carboxylate (252 mg, 0.848 mmol), Cs₂CO₃ (552 mg, 1.70 mmol) and dioxane (3 mL) was purged with nitrogen and stirred at 100° C. overnight. The reaction mixture was cooled, partitioned between water (10 mL) and EtOAc (20 mL) and the layers separated. The organic layer was next washed with water (10 mL), brine (10 ml), dried over Na₂SO₄ and concentrated in vacuo. The residue was recrystallized from EtOAc (4 mL). The solids were filtered, washed with EtOAc-hex 1:1 (2*1 mL) and dried on air to obtain 158 mg of colorless crystals. The filtrate was evaporated and chromatographed using 20% EtOAc/hexane as eluent to give additional product (272 mg, 92%).

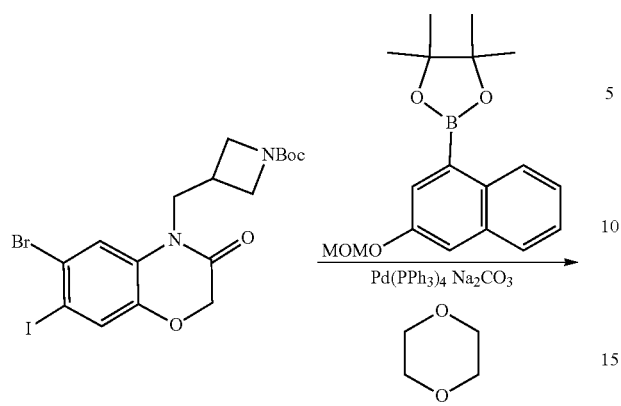

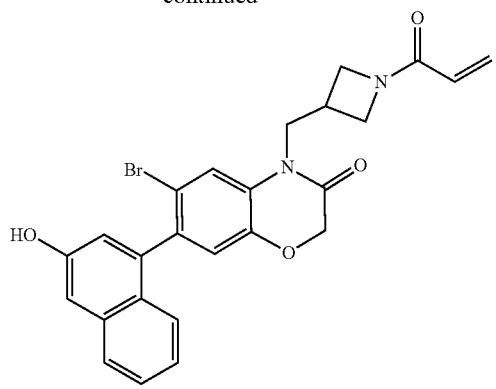

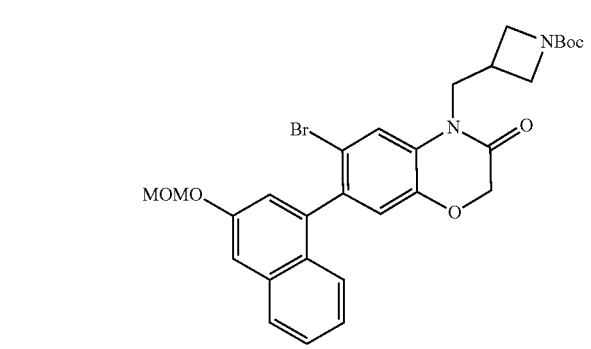

Step C: tert-butyl 3-((6-bromo-7-(3-(methoxymethoxy)naphthalen-1-yl)-3-oxo-2,3-dihydro-4H-benzo[b][1,4]oxazin-4-yl)methyl)azetidine-1-carboxylate. A mixture of tert-butyl 3-((6-bromo-7-iodo-3-oxo-2,3-dihydro-4H-benzo[b][1,4]oxazin-4-yl)methyl)azetidine-1-carboxylate (212 mg, 0.405 mmol), 2-(3-(methoxymethoxy)naphthalen-1-yl)-4,4,5,5-tetramethyl-1,3,2-dioxaborolane (134 mg, 0.425 mmol), Pd(PPh$_3$)$_4$ (23.4 mg, 0.0203 mmol), 2M Na$_2$CO$_3$ (0.608 ml, 1.22 mmol) and dioxane (4 mL) was purged with nitrogen, the vial was capped and the reaction stirred at 80° C. overnight, then at 100° C. for 24 h. The reaction was cooled, partitioned between EtOAc (20 mL) and water (10 mL) and the layers separated. The organics were next washed with water (5 mL), brine (5 mL), dried over Na$_2$SO$_4$ and concentrated in vacuo. The residue was chromatographed on silica gel using 20 to 40% EtOAc/hexanes as eluent to give product (157 mg, 66%).

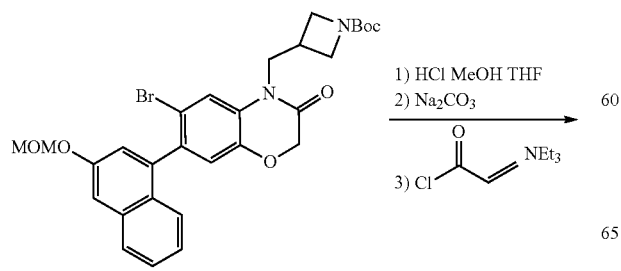

Step D: 4-((1-acryloylazetidin-3-yl)methyl)-6-bromo-7-(3-hydroxynaphthalen-1-yl)-2H-benzo[b][1,4]oxazin-3(4H)-one. A solution of tert-butyl 3-((6-bromo-7-(3-(methoxymethoxy)naphthalen-1-yl)-3-oxo-2,3-dihydro-4H-benzo[b][1,4]oxazin-4-yl)methyl)azetidine-1-carboxylate (25 mg, 0.04285 mmol) in a mixture of methanol (1.2 mL), tetrahydrofuran (1.2 ml) and 6M aq. hydrogen chloride (0.4 ml, 2.400 mmol) was heated with stirring to 50° C. for 1.5 h. The reaction mixture was cooled and poured into a stirred mixture of 2M Na$_2$CO$_3$ (1.5 mL, 3 mmol) and DCM (10 mL) and the layers were separated. The organic layer was cooled to −30° C. with stirring and triethylamine (0.03 ml, 0.2 mmol) added at once followed by addition of acryloyl chloride (0.006962 ml, 0.08569 mmol) and the mixture stirred 1 min at −30° C. temperature and then quenched by addition of NH$_4$OH (30 µL). The mixture was warmed to r.t. and evaporated in vacuo. The solid was chromatographed on silica gel using 4% MeOH/DCM as eluent to give product (10.2 mg, 48%). ESI+APCI MS m/z 493.3 [M+H]$^+$.

Example 32

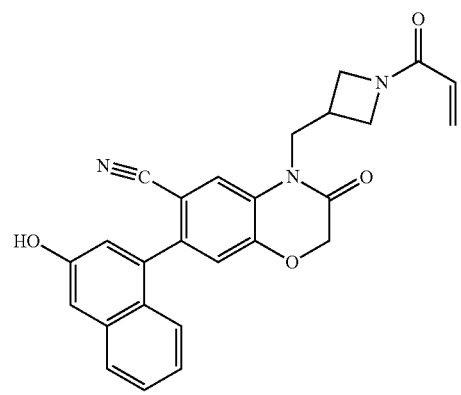 [SMILES: C=CC(=O)N1CC(CN2C(=O)COc3cc(-c4cc(O)cc5ccccc45)c(C#N)cc32)C1]

4-((1-acryloylazetidin-3-yl)methyl)-7-(3-hydroxynaphthalen-1-yl)-3-oxo-3,4-dihydro-2H-benzo[b][1,4]oxazine-6-carbonitrile

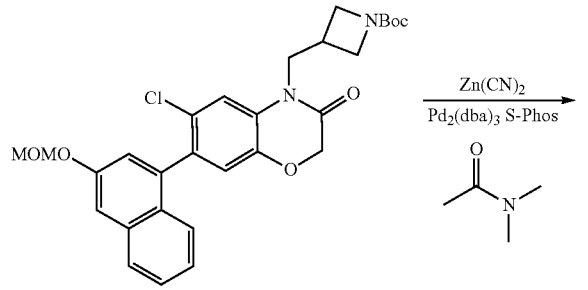

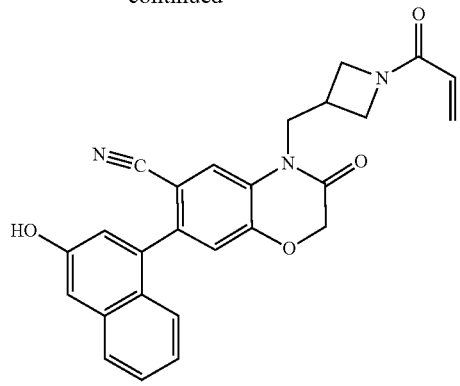

Step A: tert-butyl 3-((6-cyano-7-(3-(methoxymethoxy)naphthalen-1-yl)-3-oxo-2,3-dihydro-4H-benzo[b][1,4]oxazin-4-yl)methyl)azetidine-1-carboxylate. A mixture of tert-butyl 3-((6-chloro-7-(3-(methoxymethoxy)naphthalen-1-yl)-3-oxo-2,3-dihydro-4H-benzo[b][1,4]oxazin-4-yl)methyl)azetidine-1-carboxylate (30 mg, 0.056 mmol), dicyanozine (13 mg, 0.11 mmol), 2-Dicyclohexylphosphino-2',6'-dimethoxy-1,1'-biphenyl (11 mg, 0.028 mmol), tris(dibenzylideneacetone)dipalladium (0) (13 mg, 0.014 mmol) and N,N-dimethylacetamide (0.3 ml, 0.056 mmol) in a 0.5 mL vial was purged with nitrogen. The vial was capped and stirred under microwave at 150° C. (30 W) for 30 min. The mixture was cooled and partitioned between EtOAc (15 mL) and 0.5M NaOH and the layers separated. The organic layer was washed with water (5 mL), brine (5 mL), dried over Na$_2$SO$_4$ and evaporated in vacuo. The residue was chromatographed on silica gel using 30 to 40% EtOAc/hexane as eluent to give product (5 mg, 17%).

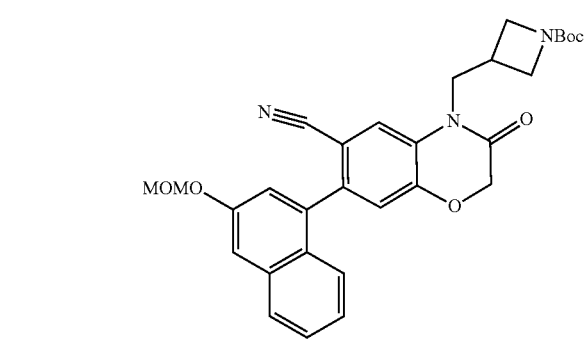

Step B: 4-((1-acryloylazetidin-3-yl)methyl)-7-(3-hydroxynaphthalen-1-yl)-3-oxo-3,4-dihydro-2H-benzo[b][1,4]oxazine-6-carbonitrile. A solution of tert-butyl 3-((6-cyano-7-(3-(methoxymethoxy)naphthalen-1-yl)-3-oxo-2,3-dihydro-4H-benzo[b][1,4]oxazin-4-yl)methyl)azetidine-1-carboxylate (5 mg, 0.009441 mmol) in a mixture of methanol (0.6 ml), tetrahydrofuran (0.6 ml) and 6M hydrogen chloride (0.2000 ml, 1.2 mmol) was heated to 50° C. with stirring for 1.5 h. The solution was cooled, neutralized with 2M Na$_2$CO$_3$ (1 mL) and the organics extracted with DCM (2*3 mL). The combined organics were cooled to −30° C. with stirring and triethylamine (0.01316 ml, 0.09441 mmol) added at once followed by addition of acryloyl chloride (0.003835 ml, 0.04721 mmol). The reaction mixture was stirred at −30° C. for 1 minute and then quenched by addition of NH$_4$OH (50 μL). The mixture was warmed up to r.t., and concentrated in vacuo. The residue was purified by reverse phase chromatographed, Gilson, C18, using 5 to 95% MeCN/water+0.1% TFA as eluent to give product (0.55 mg, 13%). ESI MS m/z 439.9 [M+H]$^+$.

Example 33

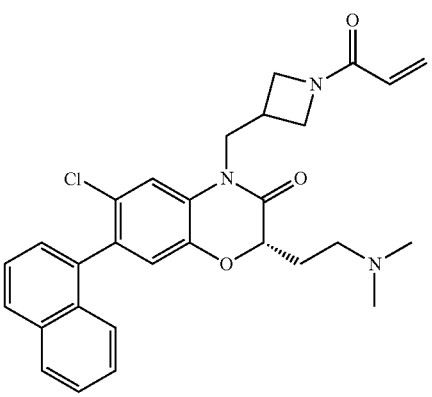 [SMILES: C=CC(=O)N1CC(CN2C(=O)[C@H](CCN(C)C)Oc3cc(-c4cccc5ccccc45)c(Cl)cc32)C1]

(S)-4-((1-acryloylazetidin-3-yl)methyl)-6-chloro-2-(2-(dimethylamino)ethyl)-7-(naphthalen-1-yl)-2H-benzo[b][1,4]oxazin-3(4H)-one was prepared following the procedure outlined in EXAMPLE 26 substituting 1-naphthaleneboronic acid for 4-(4,4,5,5-tetramethyl-1,3,2-dioxaborolan-2-yl)naphthalen-2-yl pivalate in Step D. ES+APCI MS m/z 504.2 [M+H]+.

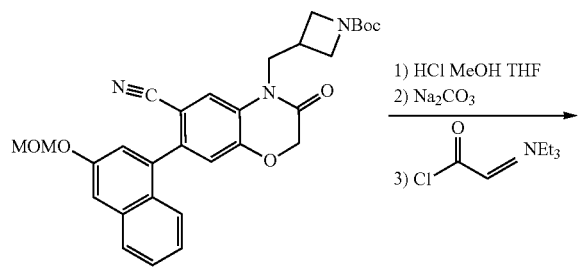

Example 34

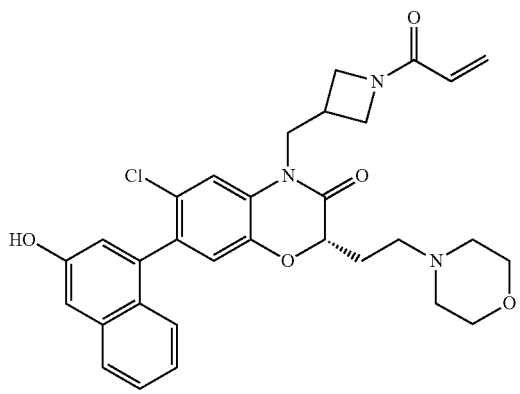 [SMILES: C=CC(=O)N1CC(CN2C(=O)[C@H](CCN3CCOCC3)Oc3cc(-c4cc(O)cc5ccccc45)c(Cl)cc32)C1]

(S)-4-((1-acryloylazetidin-3-yl)methyl)-6-chloro-7-(3-hydroxynaphthalen-1-yl)-2-(2-morpholinoethyl)-2H-benzo[b][1,4]oxazin-3(4H)-one was prepared following the procedure outlined in EXAMPLE 26 substituting the following reaction for Step E. ES+APCI MS m/z 562.2.

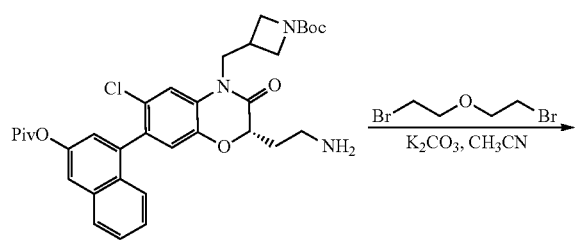

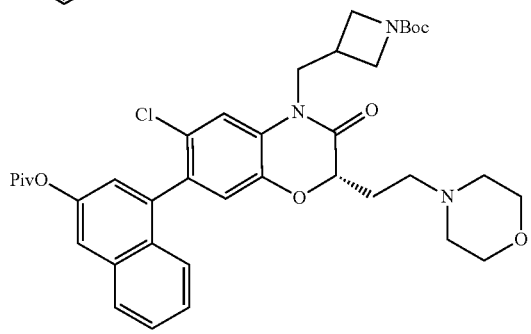

tert-butyl (S)-3-((6-chloro-2-(2-morpholinoethyl)-3-oxo-7-(3-(pivaloyloxy)naphthalen-1-yl)-2,3-dihydro-4H-benzo[b][1,4]oxazin-4-yl)methyl)azetidine-1-carboxylate. To a solution of tert-butyl (S)-3-((2-(2-aminoethyl)-6-chloro-3-oxo-7-(3-(pivaloyloxy)naphthalen-1-yl)-2,3-dihydro-4H-benzo[b][1,4]oxazin-4-yl)methyl)azetidine-1-carboxylate (0.150 g, 0.241 mmol) in dry acetonitrile (2.4 mL) was added K$_2$CO$_3$ (0.067 g, 0.482 mmol) and 2-bromoethyl ether (0.046 mL, 0.362 mmol). The mixture was then warmed to 60° C. where it stirred for 24 hours. The mixture was then diluted with a saturated aqueous NH$_4$Cl solution and was extracted with CHCl$_3$ (3×10 mL). The combined organic extracts were then dried over Na$_2$SO$_4$, filtered and concentrated. The crude product was purified by column chromatography (2-4% MeOH/DCM) to afford the desired product (0.047 g, 28%) as a yellow film.

Examples 35 & 36

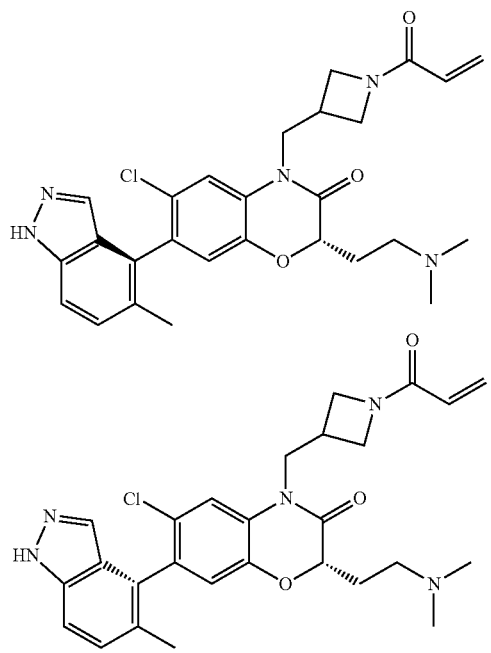

(2S,7R)-4-((1-acryloylazetidin-3-yl)methyl)-6-chloro-2-(2-(dimethylamino)ethyl)-7-(5-methyl-1H-indazol-4-yl)-2H-benzo[b][1,4]oxazin-3(4H)-one (2S,7S)-4-((1-acryloylazetidin-3-yl)methyl)-6-chloro-2-(2-(dimethylamino)ethyl)-7-(5-methyl-1H-indazol-4-yl)-2H-benzo[b][1,4]oxazin-3(4H)-one, 0.007 g, 16%, ES+APCI MS m/z 508.2 [M+H]+.

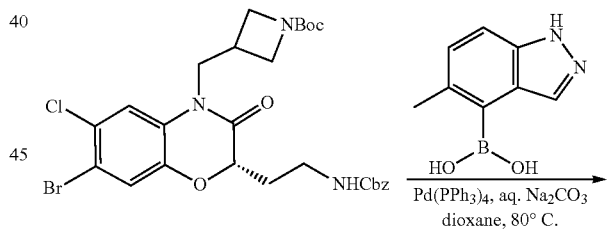

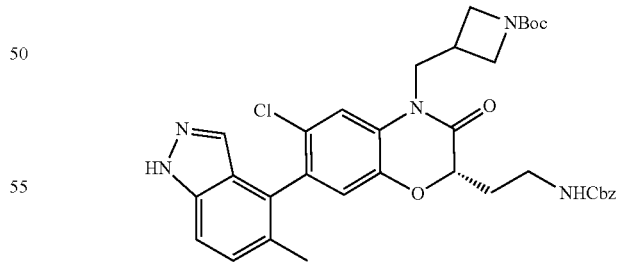

tert-butyl 3-(((2S)-2-(2-(((benzyloxy)carbonyl)amino)ethyl)-6-chloro-7-(5-methyl-1H-indazol-4-yl)-3-oxo-2,3-dihydro-4H-benzo[b][1,4]oxazin-4-yl)methyl)azetidine-1-carboxylate. To a vial was added tert-butyl (S)-3-((2-(2-(((benzyloxy)carbonyl)amino)ethyl)-7-bromo-6-chloro-3-oxo-2,3-dihydro-4H-benzo[b][1,4]oxazin-4-yl)methyl)azetidine-1-carboxylate (0.159 g, 0.261 mmol) [was prepared following the procedure outlined in EXAMPLE 26

Steps A-C], 5-Methyl-1H-indazole-4-boronic acid (0.092 g, 0.522 mmol) and dioxane (2.61 mL). To this was added Tetrakis(triphenylphosphine)palladium (0) (0.060 g, 0.052 mmol) and Na$_2$CO$_3$ (0.392 mL, 0.783 mmol, 2.0M Aq). The mixture was purged with Ar then heated to 80° C. under an Ar atmosphere where it stirred for 16 hours. The mixture was then cooled to ambient temperature diluted with CH$_2$Cl$_2$ and filtered through filter paper. The filtrate was then dried over Na$_2$SO$_4$, filtered and concentrated. The crude product was then purified via column chromatography (25-75% EtOAc/hexanes) to afford the title compound (0.113 g, 65%) as a yellow foam.

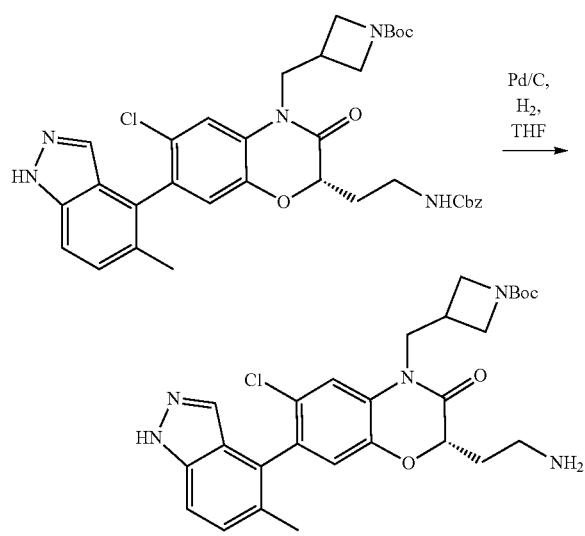

tert-butyl 3-(((2S)-2-(2-aminoethyl)-6-chloro-7-(5-methyl-1H-indazol-4-yl)-3-oxo-2,3-dihydro-4H-benzo[b][1,4]oxazin-4-yl)methyl)azetidine-1-carboxylate. To a solution of tert-butyl 3-(((2S)-2-(2-(((benzyloxy)carbonyl)amino)ethyl)-6-chloro-7-(5-methyl-11H-indazol-4-yl)-3-oxo-2,3-dihydro-4H-benzo[b][1,4]oxazin-4-yl)methyl)azetidine-1-carboxylate (0.107 g, 0.162 mmol) in THF (1.62 mL) was added Palladium on carbon (0.035 g, 0.0162 mmol, Degussa Type, 10 wt %, 50% H$_2$O) and then an atmosphere of H$_2$ was introduced via vacuum followed by balloon pressure. The mixture was then stirred at ambient temperature for 24 hours at which point additional Palladium on carbon (0.035 g, 0.0162 mmol, Degussa Type, 10 wt %, 50% H$_2$O) was added. The reaction was stirred for another 8 hours. The mixture was diluted with MeOH/EtOAc and filtered through a nylon filter. The filtrate was then concentrated in vacuo providing a grey solid (0.079 g, 92%) that was used directly in the subsequent step.

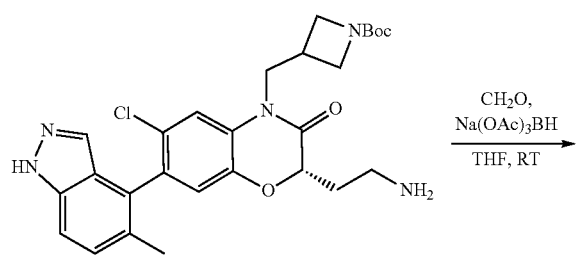

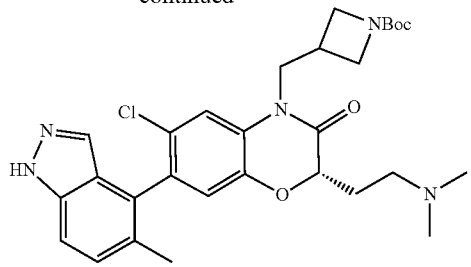

ethyl (R)-4-(((benzyloxy)carbonyl)amino)-2-hydroxybutanoate tert-butyl 3-(((2S)-6-chloro-2-(2-(dimethylamino)ethyl)-7-(5-methyl-1H-indazol-4-yl)-3-oxo-2,3-dihydro-4H-benzo[b][1,4]oxazin-4-yl)methyl)azetidine-1-carboxylate. To a vial was added tert-butyl 3-(((2S)-2-(2-aminoethyl)-6-chloro-7-(5-methyl-1H-indazol-4-yl)-3-oxo-2,3-dihydro-4H-benzo[b][1,4]oxazin-4-yl)methyl)azetidine-1-carboxylate (0.079 g, 0.150 mmol) and THF (1.50 mL). The solution was then treated with Formaldehyde (0.068 mL, 0.90 mmol, 37% Aqueous) followed by Sodium triacetoxyborohydride (0.095 g, 0.450 mmol). The mixture was then stirred at ambient temperature for 3 hours. The mixture was then diluted with a saturated aqueous NH$_4$Cl solution and was extracted with EtOAc (3×10 mL). The combined organic extracts were then dried over Na$_2$SO$_4$, filtered and concentrated. The crude product was then treated with 7N NH$_3$ in MeOH and then stirred at ambient temperature for 1.5 hours. The mixture was then concentrated in vacuo, dissolved in DCM and purified by column chromatography (5-10% MeOH/DCM with 0.25% NH$_4$OH) to afford the product (0.040 g, 48%) as an off-white solid foam.

(2S)-4-(azetidin-3-ylmethyl)-6-chloro-2-(2-(dimethylamino)ethyl)-7-(5-methyl-1H-indazol-4-yl)-2H-benzo[b][1,4]oxazin-3(4H)-one. To a solution of tert-butyl 3-(((2S)-6-chloro-2-(2-(dimethylamino)ethyl)-7-(5-methyl-1H-indazol-4-yl)-3-oxo-2,3-dihydro-4H-benzo[b][1,4]oxazin-4-yl)methyl)azetidine-1-carboxylate (0.040 g, 0.072 mmol) in CH$_2$Cl$_2$ (0.72 mL) at 0° C. was added trifluoroacetic acid (0.110 mL, 1.44 mmol) and the mixture was stirred at 0° C. for 2 hours. The mixture was then carefully added to a solution of saturated aqueous NaHCO₃. The mixture was then extracted with 10% IPA/CHCl₃ (3×10 mL). The combined organic extracts were then washed with brine, dried over Na₂SO₄, filtered and concentrated to afford an off-white foam (0.032 g, 98%). The crude product was used directly in the subsequent step.

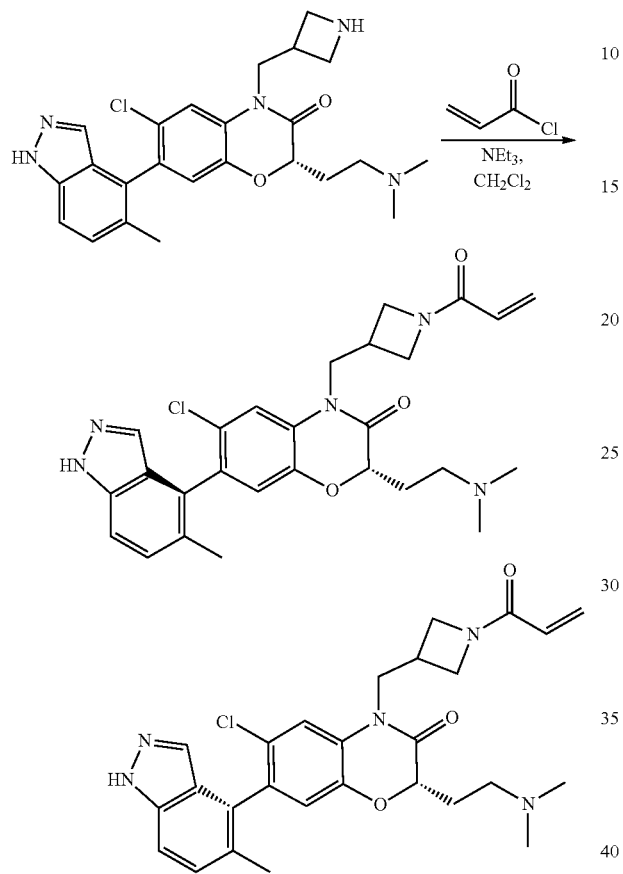

2S,7R)-4-((1-acryloylazetidin-3-yl)methyl)-6-chloro-2-(2-(dimethylamino)ethyl)-7-(5-methyl-1H-indazol-4-yl)-2H-benzo[b][1,4]oxazin-3(4H)-one & (2S,7S)-4-((1-acryloylazetidin-3-yl)methyl)-6-chloro-2-(2-(dimethylamino) ethyl)-7-(5-methyl-1H-indazol-4-yl)-2H-benzo[b][1,4] oxazin-3(4H)-one. To a solution of (2S)-4-(azetidin-3-ylmethyl)-6-chloro-2-(2-(dimethylamino)ethyl)-7-(5-methyl-1H-indazol-4-yl)-2H-benzo[b][1,4]oxazin-3(4H)-one (0.032 g, 0.070 mmol) in CH₂Cl₂ (0.70 mL) at −78° C. was added NEt₃ (0.015 mL, 0.11 mmol). Then acryloyl chloride (0.235 mL, 0.070 mmol, 0.3M in CH₂Cl₂) was added and the reaction was stirred for 30 minutes, then additional acryloyl chloride (0.235 mL, 0.070 mmol, 0.3M in CH₂Cl₂) was added and the mixture was stirred for another 30 minutes. The mixture was diluted with CHCl₃ and a saturated aqueous NH₄Cl solution. The layers were separated and the aqueous layer was extracted with CHCl₃ (2×10 mL). The combined extracts were dried over Na₂SO₄, filtered and concentrated. The crude atropisomers were then purified and separated via RP chromatography (0 to 50% ACN/H₂O with 0.1% TFA) to afford the disasteromerically pure products as their TFA salts. The relative stereochemistry was ambiguously assigned.

First eluting peak=(2S,7R)-4-((1-acryloylazetidin-3-yl) methyl)-6-chloro-2-(2-(dimethylamino)ethyl)-7-(5-methyl-1H-indazol-4-yl)-2H-benzo[b][1,4]oxazin-3(4H)-one, 0.005 g, 11%, ES+APCI MS m/z 508.1 [M+H]+.

Second eluting peak=(2S,7S)-4-((1-acryloylazetidin-3-yl) methyl)-6-chloro-2-(2-(dimethylamino)ethyl)-7-(5-methyl-1H-indazol-4-yl)-2H-benzo[b][1,4]oxazin-3(4H)-one, 0.007 g, 16%, ES+APCI MS m/z 508.2 [M+H]+.

Example 37

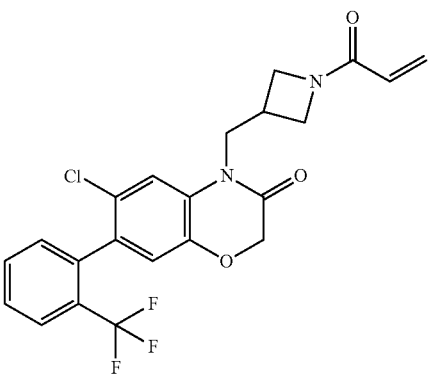 [SMILES: C=CC(=O)N1CC(CN2C(=O)COc3cc(-c4ccccc4C(F)(F)F)c(Cl)cc32)C1]

4-((1-acryloylazetidin-3-yl)methyl)-6-chloro-7-(2-(trifluoromethyl)phenyl)-2H-benzo[b][1,4]oxazin-3 (4H)-one

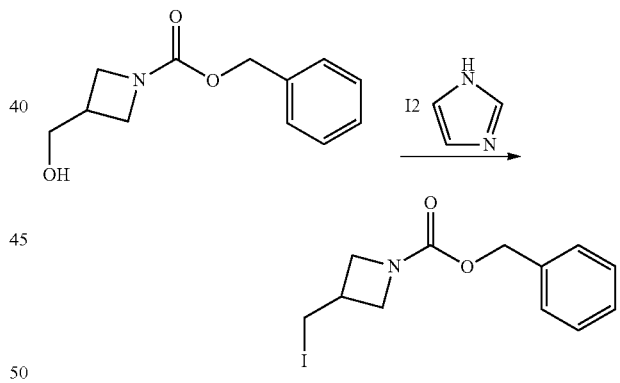

Step A: benzyl 3-(iodomethyl)azetidine-1-carboxylate. PS-PPh3 (5.54 g, 11.3 mmol) was suspended in 9:1 THF: ACN and treated with I2 (2.87 g, 11.3 mmol) followed by stirring for 15 minutes. Imidazole (0.769 g, 11.3 mmol) was added followed by a solution of benzyl 3-(hydroxymethyl) azetidine-1-carboxylate (1.0 g, 4.52 mmol) in THF. The mixture was stirred at room temperature over night. The reaction mixture was then filtered through Celite® and the filtrate concentrated. The residue was dissolved in CHCl3 and washed with NaS₂O₃, water and brine. The solution was dried over MgSO4 and concentrated in vacuo. The concentrate was next chromatographed on the CombiFlash with a 0%-25% EtOAc:Hexanes gradient. All fractions containing clean desired product were combined and concentrated to afford title compound (0.859 g, 2.59 mmol, 57.4% yield).

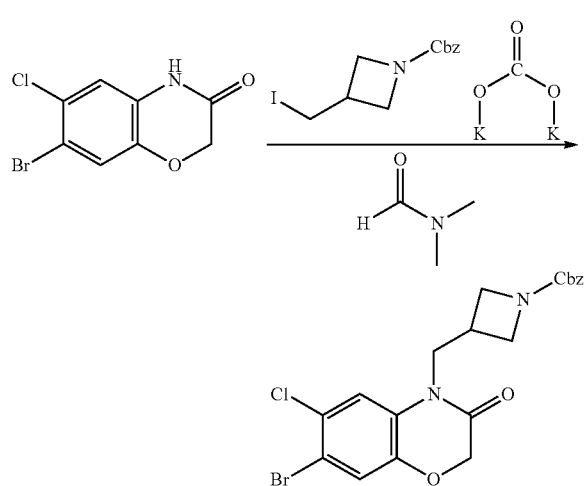

Step B: benzyl 3-((7-bromo-6-chloro-3-oxo-2,3-dihydro-4H-benzo[b][1,4]oxazin-4-yl)methyl)azetidine-1-carboxylate. A mixture of 7-bromo-6-chloro-2H-benzo[b][1,4]oxazin-3(4H)-one (450 mg, 1.71 mmol), benzyl 3-(iodomethyl)azetidine-1-carboxylate (681 mg, 2.06 mmol), K$_2$CO$_3$ (711 mg, 5.14 mmol) in DMF (8572 µl, 1.71 mmol) was heated at 60° C. for 4 hours. TLC (25% EtOAc:Hex, UV vis) showed reaction completion. The reaction mixture was partitioned between EtOAc and water. The organics were combined and dried over MgSO4. The organics were concentrated in vacuo and purified by flash chromatography eluting with 0-100% EtOAc:Hexanes. All fractions containing clean product were combined and concentrated in vacuo to afford tittle compound (658 mg, 1.41 mmol, 82.4% yield). ES+APCI MS m/z 465.0 [M+H]$^+$.

Step C: benzyl 3-((6-chloro-3-oxo-7-(2-(trifluoromethyl)phenyl)-2,3-dihydro-4H-benzo[b][1,4]oxazin-4-yl)methyl)azetidine-1-carboxylate. benzyl 3-((7-bromo-6-chloro-3-oxo-2,3-dihydro-4H-benzo[b][1,4]oxazin-4-yl)methyl)azetidine-1-carboxylate (658 mg, 1.41 mmol) and 2-(Trifluoromethyl)phenylboronic acid (403 mg, 2.12 mmol) were dissolved in 1,4-dioxane (14128 µl, 1.41 mmol) and treated with potassium carbonate (3532 µl, 7.06 mmol). The mixture stirred under N2 for 15 minutes at room temperature. Tetrakis (triphenylphosphine) palladium (0) (81.6 mg, 0.0706 mmol) was added to the reaction mixture and immediately capped and stirred at 90° C. over night. The reaction mixture was cooled to room temperature and diluted with EtOAc. The product was washed with water and brine. The organics were combined and dried over MgSO4. The concentrate was purified using the CombiFlash (0%-15% DCM:MeOH). All fractions containing clean product were combined and concentrated to afford title compound (477 mg, 0.898 mmol, 63.6% yield). ES+APCI MS m/z 531.1[M+H]$^+$.

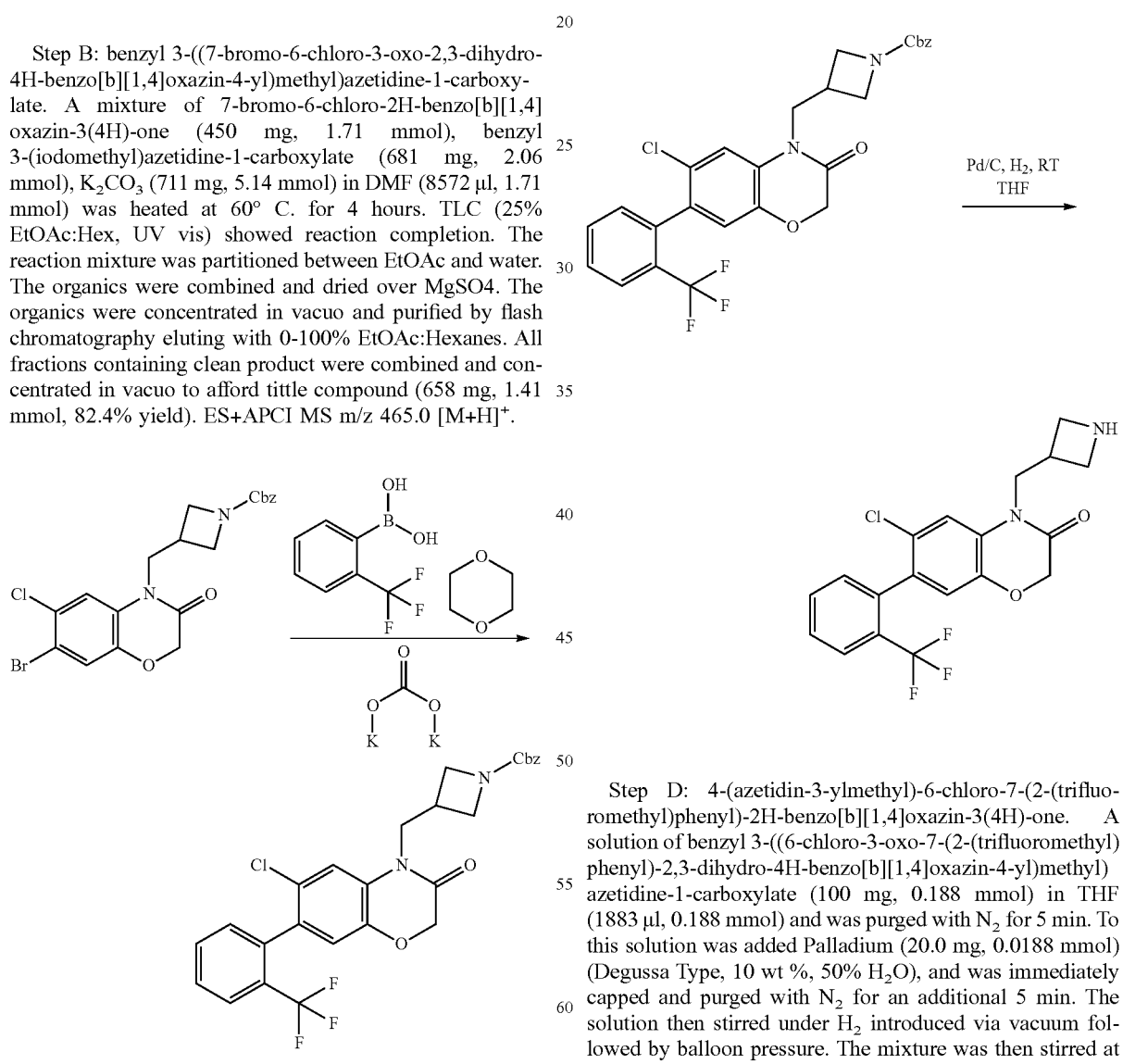

Step D: 4-(azetidin-3-ylmethyl)-6-chloro-7-(2-(trifluoromethyl)phenyl)-2H-benzo[b][1,4]oxazin-3(4H)-one. A solution of benzyl 3-((6-chloro-3-oxo-7-(2-(trifluoromethyl)phenyl)-2,3-dihydro-4H-benzo[b][1,4]oxazin-4-yl)methyl)azetidine-1-carboxylate (100 mg, 0.188 mmol) in THF (1883 µl, 0.188 mmol) and was purged with N$_2$ for 5 min. To this solution was added Palladium (20.0 mg, 0.0188 mmol) (Degussa Type, 10 wt %, 50% H$_2$O), and was immediately capped and purged with N$_2$ for an additional 5 min. The solution then stirred under H$_2$ introduced via vacuum followed by balloon pressure. The mixture was then stirred at ambient temperature for 5 hours. The mixture was diluted with MeOH and filtered through packed Celite®. The filtrate was then concentrated in vacuo and the reaction taken forward as crude title compound (75 mg, 0.189 mmol, 100% yield). ES+APCI MS m/z 397.0[M+H]$^+$.

127

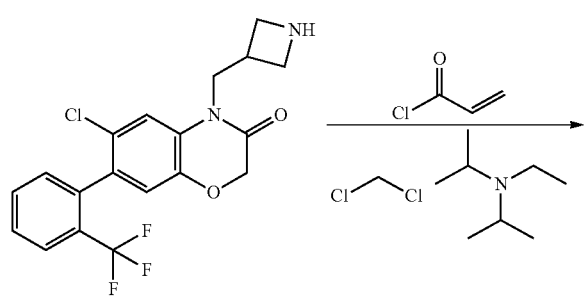

128

6-chloro-7-(3,4-dimethyl-1H-pyrazol-5-yl)-4-[(1-prop-2-enoylazetidin-3-yl)methyl]-1,4-benzoxazin-3-one

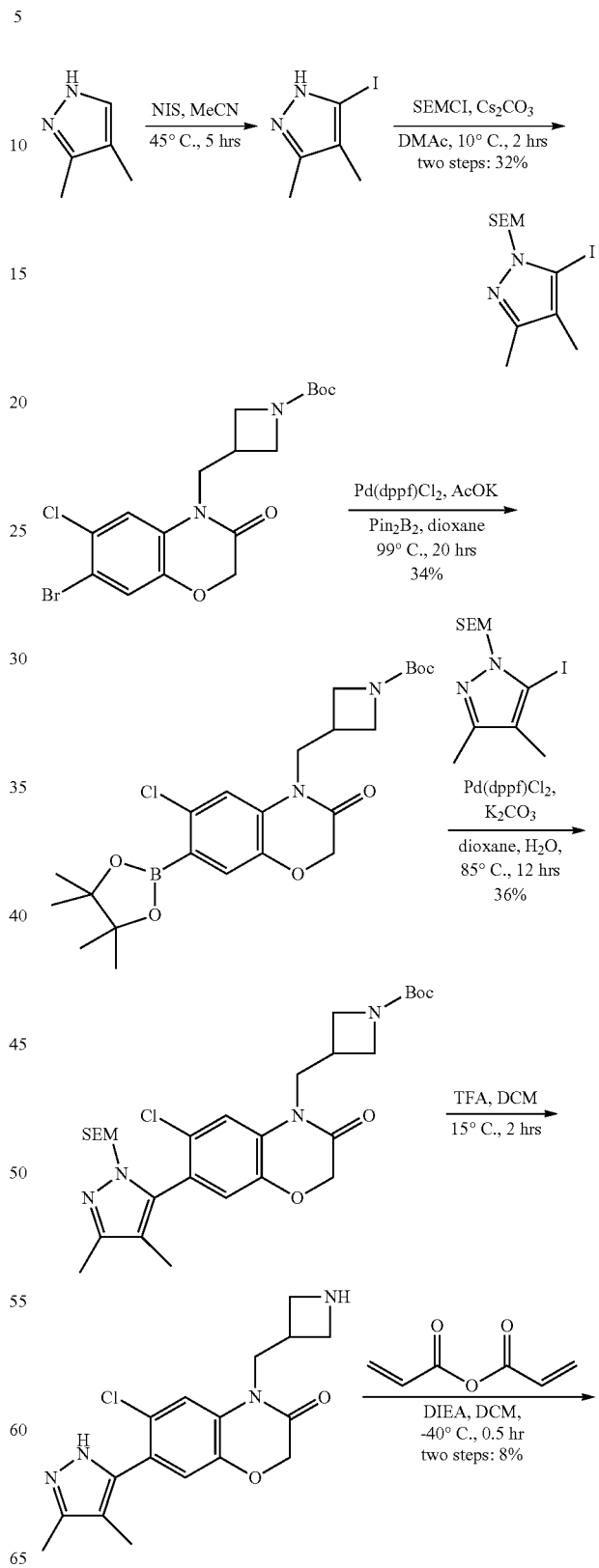

Step E: 4-((1-acryloylazetidin-3-yl)methyl)-6-chloro-7-(2-(trifluoromethyl)phenyl)-2H-benzo[b][1,4]oxazin-3(4H)-one. To a suspension of 4-(azetidin-3-ylmethyl)-6-chloro-7-(2-(trifluoromethyl)phenyl)-2H-benzo[b][1,4]oxazin-3(4H)-one (75 mg, 0.1890 mmol) in dichloromethane (1890 μl, 0.1890 mmol) at 0° C. was added N-ethyl-N-isopropylpropan-2-amine (66.03 μl, 0.3780 mmol) followed by acryloyl chloride (15.36 μl, 0.1890 mmol). The reaction was then stirred at 0° C. for 1 hour (white precipitate was formed). The reaction was then concentrated in vacuo and purified by flash chromatography eluting with 0-20% DCM/MeOH+2% NH4OH. Fractions containing product were combined and concentrated to give title compound (33.8 mg, 0.07197 mmol, 38.08% yield). ES+APCI MS m/z 451.1[M+H]$^+$.

Example 38

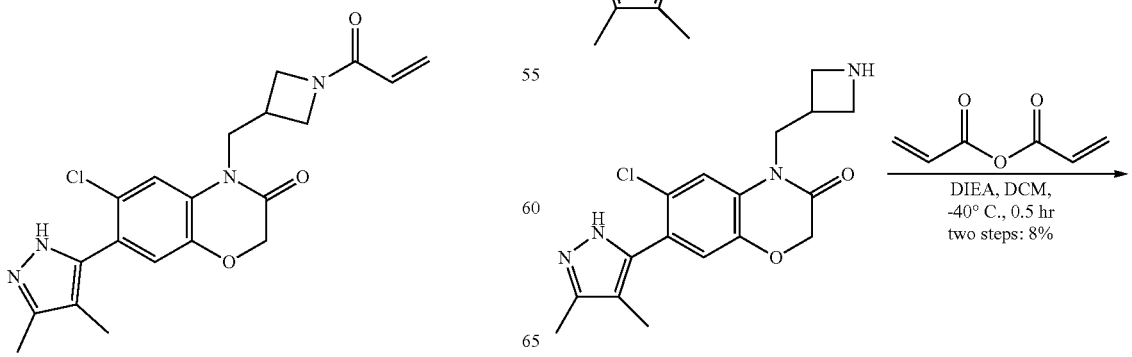

-continued

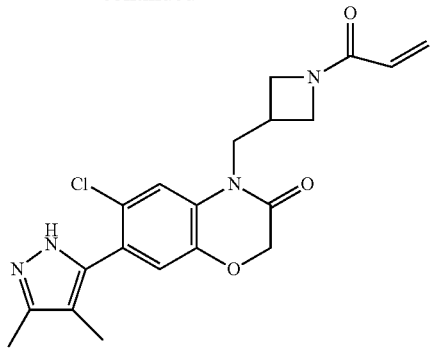 [SMILES: C=CC(=O)N1CC(CN2C(=O)COc3cc(-c4[nH]nc(C)c4C)c(Cl)cc32)C1]

Step A: 5-iodo-3,4-dimethyl-1H-pyrazole. To a solution of 3,4-dimethyl-1H-pyrazole (3 g, 15.6 mmol, 1 eq) in MeCN (90 mL) was added portionwise NIS (14.0 g, 62.4 mmol, 4 eq) 10° C. The reaction was stirred at 45° C. for 5 hours. The reaction mixture was filtered and concentrated to dryness. The residue was dissolved in water (100 mL) and extracted with EtOAc (2×50 mL), the combined organic phase was dried over $Na_2SO_4$ and concentrated to dryness to give 5-iodo-3,4-dimethyl-1H-pyrazole (7 g, crude) was obtained as a red solid which was used to next step directly.

Step B: 2-[(5-iodo-3,4-dimethyl-pyrazol-1-yl)methoxy]ethyl-trimethyl-silane. To a solution of 5-iodo-3,4-dimethyl-1H-pyrazole (2 g, 9.01 mmol, 1 eq) and $Cs_2CO_3$ (5.87 g, 18.0 mmol, 2 eq) in DMAc (15 mL) was added dropwise 2-(chloromethoxy)ethyl-trimethyl-silane (2.25 g, 13.5 mmol, 2.39 mL, 1.5 eq) at 6-8° C., the reaction was stirred at this temperature for 2 hours. The reaction mixture was diluted with water (30 mL) and extracted with EtOAc (2×50 mL). The organic solvent was concentrated under vacuum. The residue was purified by silica gel column eluted with PE/EtOAc (100/1 to 60/1) to give 2-[(5-iodo-3,4-dimethyl-pyrazol-1-yl)methoxy]ethyl-trimethyl-silane (1 g, 2.51 mmol, two steps: 32% yield, 88.4% purity) as colorless oil. LCMS [ESI, M+1]: 352.

Step C: tert-butyl 3-[[6-chloro-3-oxo-7-(4,4,5,5-tetramethyl-1,3,2-dioxaborolan-2-yl)-1,4-benzoxazin-4-yl]methyl]azetidine-1-carboxylate. To a mixture of tert-butyl3-[(7-bromo-6-chloro-3-oxo-1,4-benzoxazin-4-yl)methyl]azetidine-1-carboxylate (1 g, 2.32 mmol, 1 eq) and $Pin_2B_2$ (2.35 g, 9.27 mmol, 4 eq) in dioxane (20 mL) was added $Pd(dppf)Cl_2$ (169 mg, 232 µmol, 0.1 eq) and KOAc (909 mg, 9.27 mmol, 4 eq), the reaction system was degassed under vacuum, and purged with $N_2$. The reaction mixture was stirred at 99° C. for 20 hours. The reaction mixture was filtered and poured into brine (6 mL), then extracted with EtOAc (2×6 mL). The combined organic solvent was dried and concentrated to dryness. The residue was purified by silica gel column eluted with petroleum ether/EtOAc (10/1 to 4/1) to give tert-butyl 3-[[6-chloro-3-oxo-7-(4,4,5,5-tetramethyl-1,3,2-dioxaborolan-2-yl)-1,4-benzoxazin-4-yl]methyl]azetidine-1-carboxylate (1.4 g, 789 µmol, 34% yield, 27% purity) as a white solid.

Step D: tert-butyl 3-[[6-chloro-7-[4,5-dimethyl-2-(2-trimethylsilylethoxymethyl)pyrazol-3-yl]-3-oxo-1,4-benzoxazin-4-yl]methyl]azetidine-1-carboxylate. To a solution of 2-[(5-iodo-3,4-dimethyl-pyrazol-1-yl)methoxy]ethyl-trimethyl-silane (530 mg. 1.50 mmol, 1 eq) and tert-butyl3-[[6-chloro-3-oxo-7-(4,4,5,5-tetramethyl-1,3,2-dioxaborolan-2-yl)-1,4-benzoxazin-4-yl]methyl]azetidine-1-carboxylate (1.3 g, 1.25 mmol, 0.83 eq) in dioxane (16 mL) and $H_2O$ (4 mL) was added $K_2CO_3$ (520 mg, 3.76 mmol, 2.5 eq) and $Pd(dppf)Cl_2$ (110 mg, 150 µmol, 0.1 eq). The reaction mixture was stirred at 85° C. for 12 hours under $N_2$. The reaction mixture was poured into 15 mL brine and 20 mL EtOAc, and the layers were separated. The aqueous phase was extracted with EtOAc (15 mL). The combined organic phase was dried over $Na_2SO_4$, then concentrated under vacuum. The residue was purified with silica gel column eluted with petroleum ether/EtOAc (8/1 to 5/1) to give tert-butyl 3-[[6-chloro-7-[4,5-dimethyl-2-(2-trimethylsilylethoxymethyl)pyrazol-3-yl]-3-oxo-1,4-benzoxazin-4-yl]methyl]azetidine-1-carboxylate (459 mg, 549 µmol, 36% yield, 69% purity) as a yellow oil. LCMS [ESI, M+1]: 577.

$^1$H NMR (400 MHz, chloroform-d) δ=7.02 (s, 2H), 5.43 (s, 2H), 4.61 (s, 2H), 4.22 (br s, 1H), 4.07-3.98 (m, 3H), 3.78 (dd, J=5.6, 8.8 Hz, 2H), 3.61-3.56 (m, 2H), 3.02-2.90 (m, 1H), 2.32 (s, 3H), 1.93 (s, 3H), 1.45 (s, 9H), 0.93-0.88 (m, 2H), −0.01--0.04 (m, 9H).

Step E: 4-(azetidin-3-ylmethyl)-6-chloro-7-(3,4-dimethyl-1H-pyrazol-5-yl)-1,4-benzoxazin-3-one. The mixture of tert-butyl 3-[[6-chloro-7-[4,5-dimethyl-2-(2-trimethylsilylethoxymethyl)pyrazol-3-yl]-3-oxo-1,4-benzoxazin-4-yl]methyl]azetidine-1-carboxylate (200 mg, 346 µmol, 1 eq) and TFA (395 mg, 3.47 mmol, 256 uL, 10 eq) was stirred at 15° C. for 2 hours. The reaction mixture was concentrated under vacuum to give 4-(azetidin-3-ylmethyl)-6-chloro-7-(3,4-dimethyl-1H-pyrazol-5-yl)-1,4-benzoxazin-3-one (150 mg, crude, TFA) as a brown oil which was used for next step without further purification.

Step F: 6-chloro-7-(3,4-dimethyl-1H-pyrazol-5-yl)-4-[(1-prop-2-enoylazetidin-3-yl)methyl]-1,4-benzoxazin-3-one. To the solution of 4-(azetidin-3-ylmethyl)-6-chloro-7-(3,4-dimethyl-1H-pyrazol-5-yl)-1,4-benzoxazin-3-one (130 mg, crude, TFA) and DIEA (547 mg, 4.23 mmol, 737 uL) in DCM (2.5 mL) was added prop-2-enoyl prop-2-enoate (28.5 mg, 226 µmol) at −40° C., the mixture was stirred at −40° C. for 0.5 hour. The reaction mixture was quenched with water (2 mL). The mixture was diluted with DCM (5 mL) and extracted with DCM (3×5 mL). The combined organic layers were dried over anhydrous $Na_2SO_4$, filtered and concentrated under vacuum. The residue was purified by prep-HPLC (column: Waters Xbridge 150*25 5 u; mobile phase: [water (0.05% ammonia hydroxide v/v)-ACN]; B %: 18%-48%, 10 min) to give title compound 6-chloro-7-(3,4-dimethyl-1H-pyrazol-5-yl)-4-[(1-prop-2-enoylazetidin-3-yl)methyl]-1,4-benzoxazin-3-one (9.82 mg, 23.6 µmol, two steps 8% yield, 96.2% purity) as a white solid. LCMS [ESI, M+1]: 401.

$^1$H NMR (400 MHz, chloroform-d) δ=7.07-7.02 (m, 2H), 6.42-6.30 (m, 11H), 6.24-6.11 (m, 11H), 5.69 (dd, J=1.6, 10.2 Hz, 1H), 4.64 (d, J=2.4 Hz, 2H), 4.45 (dd, J=8.8, 14.4 Hz, 1H), 4.34-4.19 (m, 2H), 4.17-4.01 (m, 2H), 3.93 (dd, J=5.6, 10.4 Hz, 1H), 3.17-3.03 (m, 1H), 2.29 (s, 3H), 1.96 (s, 3H).

Example A

KRas G12C Modification Assay

This Example illustrates that exemplary compounds of the present invention covalently bind to KRas G12C using a LCMS assay to detect a covalent adduct of the exemplary compound and KRAS G12C.

The protein concentration of GDP-loaded K-Ras (1-169) G12C, C51S, C80L, C118S and GTP-loaded K-Ras (1-169) G12C, C51S, C80L, C118S, Q61H was adjusted to 2 µM in K-Ras Assay Buffer (25 mM HEPES, 150 mM NaCl, 5 mM $MgCl_2$, and 10 mM Octyl β-glucopyranoside at pH 7.5). A 10 µL aliquot of each protein solution was transferred to a 384 well microtiter plate. Initial compound stocks were generated at fifty times their desired final assay concentration in DMSO.

Exemplary compounds of formula (I) were diluted 25-fold into K-Ras Assay Buffer to a final of two times their final concentration. A 10 µL aliquot of each diluted compound solution was added to each of the protein solutions in the microtiter plate to initiate reaction. Typical final compound concentrations were 3.0, 5.0 and 25.0 µM. At each time point, the reactions were quenched with 20 µL of a 25 mM acetic acid solution. Usual assay endpoints were 15, 180 and 1440 minutes. Once all reactions were quenched, the plates were heat sealed and the samples were injected into a LC/MS system for data acquisition.

Data collection took place on an Agilent 6520 Q-TOF Accurate Mass Spectrometer. Samples were injected in their liquid phase onto a C-3 reverse phase column to remove assay buffer and prepare the samples for mass spectrometer. The proteins were eluted from the column using an acetonitrile gradient and fed directly into the mass analyzer. Initial raw data analysis took place in Agilent MassHunter software immediately post data acquisition.

Raw data analysis of the intact protein was exclusively a deconvolution of the multiple charge states of each protein in solution using a maximum entropy deconvolution provided in Mass Hunter. To minimize complexity, only the data over limited mass ranges were considered for analysis, with a minimum of one Dalton mass step intervals. The heights of all masses identified during raw data analysis were exported to be further analyzed in Spotfire® data analysis software.

Final data analysis was a multistep process in the Spotfire® data analysis software package. Briefly, each protein mass was calculated as a percent of the total signal of that sample, that percentage was normalized to the percentage of signal of the protein in the absence of reactive compounds. Those normalized signals were reported as normalized percent of control (POC). An increased POC value indicates a compound that displays a higher degree of modification at a given condition compared to other compounds under the same conditions. The results for exemplary compounds of Formula I tested at 5 µM concentration for 3 hours are shown in Table 1. Key: N.D. is not determined.

TABLE 1

Inhibition of KRas G12C Activity by
Exemplary Compounds of Formula I

| Example No. | POC |
|---|---|
| 1 | 104 |
| 2 | 94 |
| 3 | 91 |
| 4 | 104 |
| 5 | 95 |
| 6 | 86 |
| 7 | 96 |
| 8 | 87 |
| 9 | N.D. |
| 10 | 53 |
| 11 | 96 |
| 12 | 94 |
| 13 | 93 |
| 14 | 102 |
| 15 | 97 |
| 16 | 100 |
| 17 | 85 |
| 18 | 91 |
| 19 | 99 |

TABLE 1-continued

Inhibition of KRas G12C Activity by
Exemplary Compounds of Formula I

| Example No. | POC |
|---|---|
| 20 | 99 |
| 21 | 90 |
| 22 | 97 |
| 23 | 34 |
| 24 | 86 |
| 25 | 93 |
| 26 | 90 |
| 27 | 94 |
| 28 | 93 |
| 29 | 25 |
| 30 | 93 |
| 31 | 88 |
| 32 | 81 |
| 33 | 32 |
| 34 | 93 |
| 35 | 86 |
| 36 | 27 |
| 37 | 66 |
| 38 | 72 |

Example B

Inhibition of KRas G12C-Dependent Cell Growth

This Example illustrates that exemplary compounds of the present invention inhibit the growth of tumor cell lines that express KRas G12C.

The cellular inhibition of KRAs G12C by exemplary compounds of the present invention was determined by measuring the amount of a downstream marker of KRas activity, phosphorylated ERK ("Phospho-ERK").

NCI-11358 cells (ATCC CRL-5807) express KRas G12C and were grown in RPMI medium supplemented with 10% fetal bovine serum, penicillin/streptomycin and 10 mM HEPES. Cells were plated in poly-D-Lysine coated 96-well plates at a concentration of 50,000 cells/well and allowed to attach for 8-12 hours. Diluted compounds were then added at a final concentration of 0.5% DMSO. After 3 hours, the medium was removed, 150 µL of 4% formaldehyde was added and the plates were incubated for 20 minutes. The plates were washed with PBS, and permeabilized using 150 µL of ice cold 100% methanol for 10 minutes. Non-specific antibody binding to the plates was blocked using 100 µL Licor Blocking Buffer (Li-Cor Biotechnology, Lincoln NE) for 1 hour at room temperature. Positive control samples and samples lacking cells were parallel processed with test samples as standards.

The amount Phospho-ERK was determined using an antibody specific for the phosphorylated form of ERK and compared to the amount of GAPDH. Primary antibodies used for detection were added as follows: Phospho-ERK (Cell Signaling cs9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 in Licor Block+0.05% Tween 20 and incubated for 1 hour at room temperature. The plates were washed with PBS+0.05% Tween 20. A 100 µL aliquot of PBS was added to each well and the plates were read on a LICOR AERIUS plate reader.

The pERK (Thr202/Tyr204) signal was normalized with the GAPDH signal and percent of DMSO control values were calculated. IC$_{50}$ values were generated using a 4 parameter fit of the dose response curve. The results for exemplary compounds of Formula I are shown in Table 2. Key: "A": ≤1 µM, "B">1 µM and N.D.=not determined.

TABLE 2

Inhibition of KRas G12C-mediated Cell Proliferation by Exemplary Compounds

| Example No. | Inhibition |
|---|---|
| 1 | A |
| 2 | B |
| 3 | A |
| 4 | A |
| 5 | A |
| 6 | B |
| 7 | B |
| 8 | A |
| 9 | N.D. |
| 10 | B |
| 11 | B |
| 12 | B |
| 13 | A |
| 14 | B |
| 15 | B |
| 16 | B |
| 17 | B |
| 18 | A |
| 19 | B |
| 20 | A |
| 21 | B |
| 22 | A |
| 23 | B |
| 24 | B |
| 25 | A |
| 26 | A |
| 27 | A |
| 28 | A |
| 29 | B |
| 30 | A |
| 31 | A |
| 32 | B |
| 33 | B |
| 34 | A |
| 35 | A |
| 36 | B |
| 37 | B |
| 38 | B |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound of formula I:

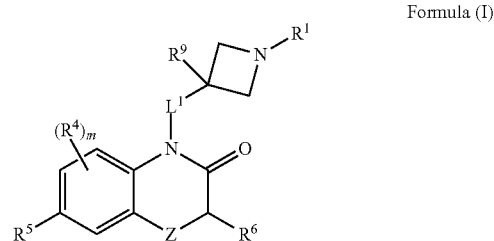

Formula (I)

or a pharmaceutically acceptable salt or solvate thereof, wherein:

$R^1$ is —C(O)C($R^A$)═══C($R^B$)$_p$ or —SO$_2$C($R^A$)═══C($^R$B)$_p$;

$L^1$ is a bond or (CH$_2$)$_q$CR$^2$R$^3$(CH$_2$)$_t$—, wherein q and t are each independently 0, 1, 2, or 3 and q+t is equal to or less than 3;

$R^2$ and $R^3$ are each independently hydrogen, cyano, C3-C4 cycloalkyl, or C1-C3 alkyl, wherein the C1-C3 alkyl may be optionally substituted with cyano or —OR$^{10}$; or $R^2$ and $R^3$ together with the carbon atom to which they are attached form a C3-C4 cycloalkyl;

each $R^4$ is independently cyano, C1-C3 alkyl, C1-C3 alkoxy, halogen, haloalkyl, aryl, or heteroaryl, wherein the aryl and heteroaryl may be optionally substituted with one or more $R^7$;

$R^5$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^7$;

Z is O or S;

$R^6$ is hydrogen, alkyl, hydroxyalkyl, dihydroxyalkyl, alkylaminylalkyl, dialkylaminylalkyl, —W—NR$^{10}$R$^{11}$, —W—C(═O)NR$^{10}$R$^{11}$, heterocyclyl, heterocyclylalkyl, aryl, heteroaryl, or heteroarylalkyl, wherein each of the heterocyclyl, heterocyclylalkyl, aryl, heteroaryl, and heteroarylalkyl may be optionally substituted with one or more $R^8$;

W is C1-C5 alkylene;

each $R^7$ is independently halogen, hydroxyl, alkyl, cycloalkyl, alkoxy, haloalkyl, haloalkyloxy, amino, alkylaminyl, cyano or hydroxyalkyl;

each $R^8$ is independently acyl, hydroxyl, hydroxyalkyl, cyano, halogen, alkyl, cycloalkyl, alkoxy, heteroalkyl, or dialkylaminyl;

$R^9$ is hydrogen, hydroxyl, cyano, halogen, haloalkyl, or alkyl;

each $R^{10}$ is independently hydrogen or C1-C3 alkyl;

each $R^{11}$ is independently hydrogen, acyl, alkyl, heteroalkyl or hydroxyalkyl;

m is 0, 1, 2, or 3;

$R^A$ is absent, hydrogen, or C1-C3 alkyl;

each $R^B$ is independently hydrogen, C1-C3 alkyl, alkylaminylalkyl or dialkylaminylalkyl;

p is one or two; and wherein, when ═══ is a triple bond then $R^A$ is absent, $R^B$ is present and p equals one, or when ═══ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

2. The compound of claim 1, wherein $R^1$ is —C(O)CH=CH$_2$.

3. The compound of claim 1, wherein $L^1$ is (CH$_2$)$_q$CR$^2$R$^3$(CH$_2$)$_t$—, and wherein q and t are each zero.

4. The compound according to claim 1, wherein Z is O.

5. The compound according to claim 1, wherein m is one.

6. The compound according to claim 1, wherein each $R^4$ is independently C1-C3 alkyl, cyano or halogen.

7. The compound of claim 6, wherein the halogen is chlorine or fluorine.

8. The compound of claim 1, wherein the compound is of Formula I-A:

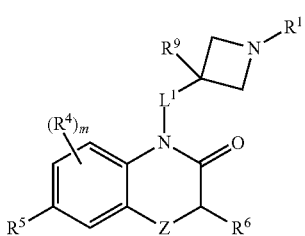

Formula I-A wherein $R^1$, $R^4$, $R^5$, $R^6$, $R^9$, Z, $L^1$ and m are as defined in claim 1.

9. The compound of claim 8, wherein $R^1$ is —C(O)CH=CH$_2$.

10. The compound of claim 8, wherein $L^1$ is (CH$_2$)$_q$R$^2$R$^3$(CH$_2$)$_t$—, and wherein q and t are each zero.

11. The compound according to claim 8, wherein Z is O.

12. The compound according to claim 8, wherein $R^4$ is C1-C3 alkyl, cyano or halogen.

13. The compound of claim 12, wherein the halogen is chlorine or fluorine.

14. The compound according to claim 1, wherein $R^5$ is aryl optionally substituted with one or more independently selected $R^7$.

15. The compound of claim 14, wherein the aryl is phenyl or naphthyl, each optionally substituted with one or more independently selected $R^7$.

16. The compound of claim 15, wherein the phenyl and the naphthyl are each optionally substituted with one or more substituents independently selected from hydroxyl, halogen or haloalkyl.

17. The compound of claim 15, wherein each $R^7$ is independently selected from the group consisting of halogen, hydroxyl, C1-C3 alkyl, haloalkyloxy, and alkoxy.

18. The compound according to claim 1, wherein $R^5$ is heteroaryl optionally substituted with one or more $R^7$.

19. The compound of claim 18, wherein the heteroaryl is pyrazolyl, indazolyl, benzisoxazolyl or benzimidazolyl, each optionally substituted with one or more $R^7$.

20. The compound of claim 19, wherein the pyrazolyl, the indazolyl or the benzimidazolyl are each substituted with one or more independently selected C1-C6 alkyl.

21. The compound according to claim 1, wherein $R^6$ is independently hydrogen, C1-C4 alkyl, hydroxyalkyl, dialkylaminylalkyl, —W—NR$^{10}$R$^{11}$, heterocyclyl or heterocyclylalkyl, wherein each of the heterocyclyl or heterocyclylalkyl are independently optionally substituted with $R^8$.

22. The compound of claim 21, wherein $R^6$ is hydrogen.

23. The compound of claim 21, wherein $R^6$ is C1-C4 alkyl.

24. The compound of claim 21, wherein $R^6$ is dialkylaminylalkyl.

25. The compound of claim 21, wherein $R^6$ is heterocyclyl or heterocyclylalkyl, wherein each of the heterocyclyl or heterocyclylalkyl are independently optionally substituted with one or more $R^8$.

26. The compound of claim 25, wherein the heterocyclyl or the heterocyclyl portion of the heterocylcylalkyl is independently pyrrolidinyl, 1-methyl-pyrrolinidinyl, 3-methoxy-pyrrolidinyl, piperdinyl, 1-methyl-piperdinyl, 4-dimethyl-aminyl-piperdinyl, piperazinyl, 1-methyl-piperazinyl or morpholinyl.

27. The compound according to claim 1, wherein $R^9$ is hydrogen.

28. The compound according to claim 1, wherein $R^9$ is C1-C3 alkyl or halogen.

29. The compound of claim 28, wherein the halogen is fluorine.

30. The compound according to claim 1, wherein $R^2$ is methyl.

31. The compound according to claim 1, wherein $R^2$ is hydrogen.

32. The compound of claim 1, wherein the compound is:

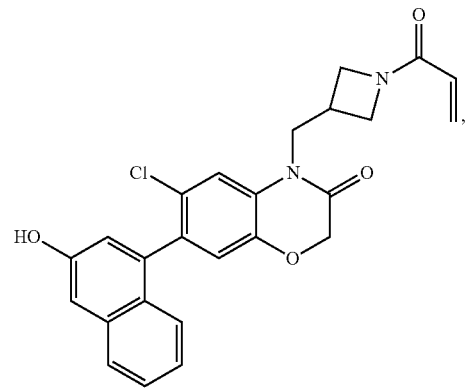

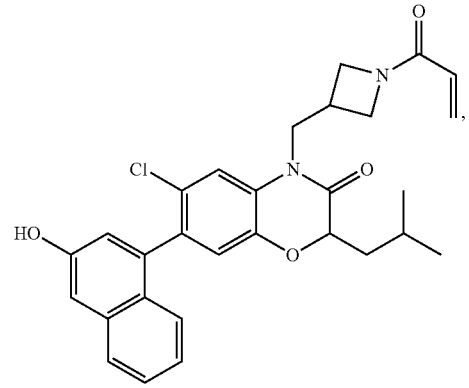

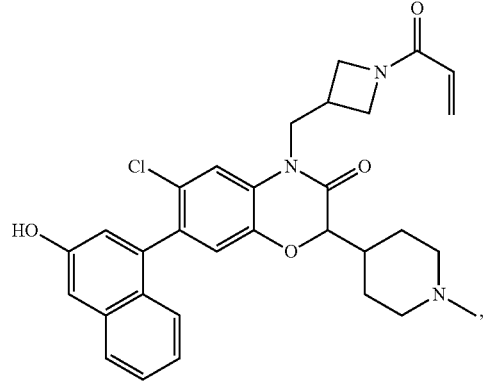

-continued
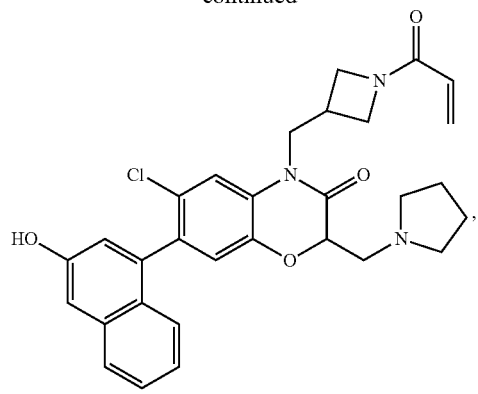
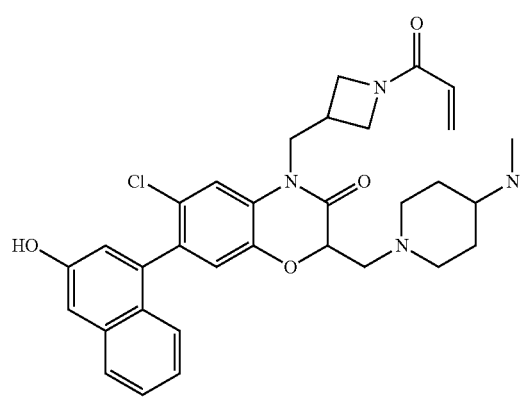
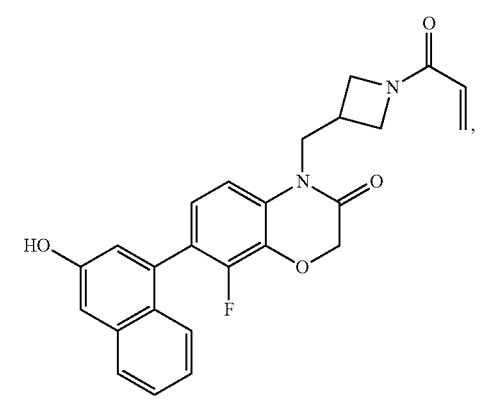
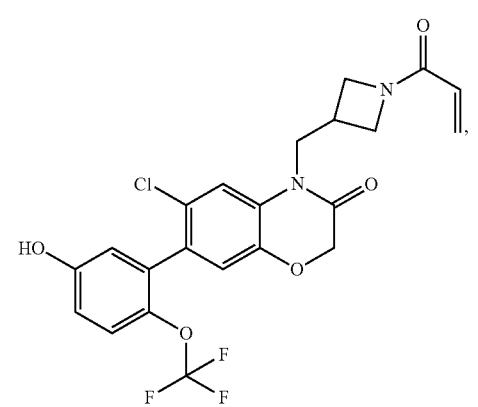
-continued
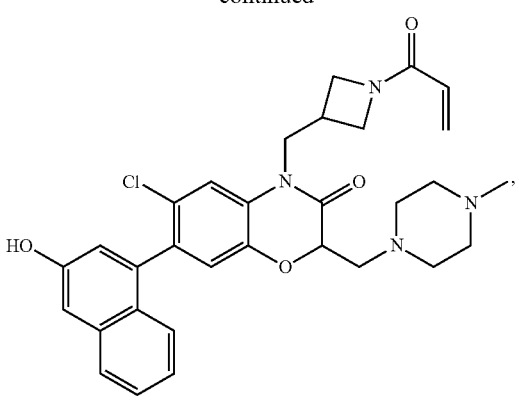
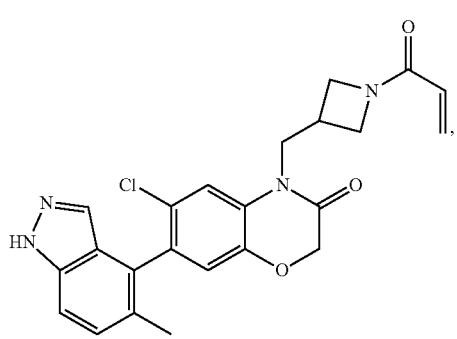
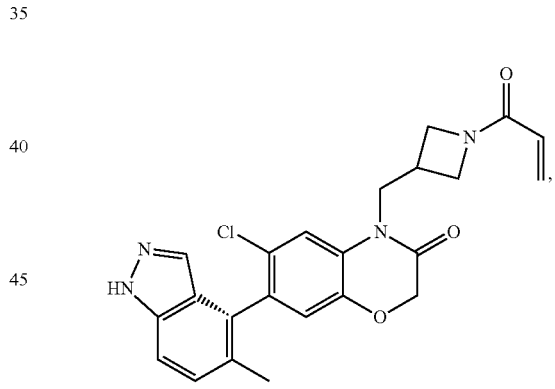
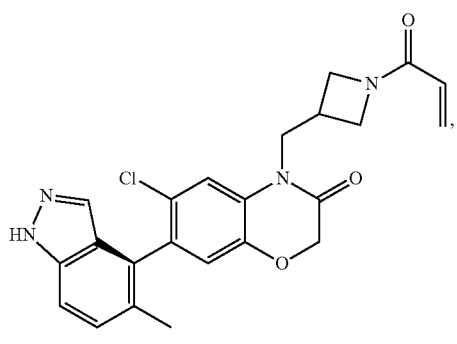

139
-continued
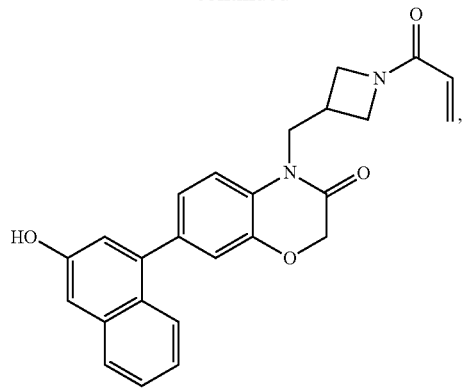
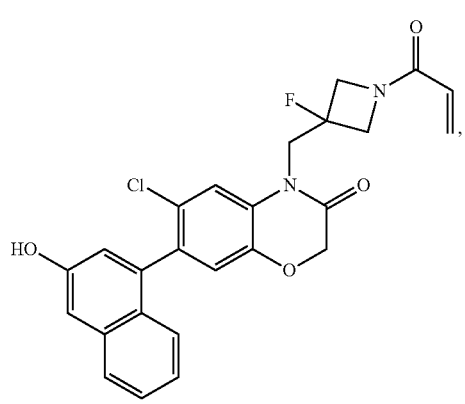
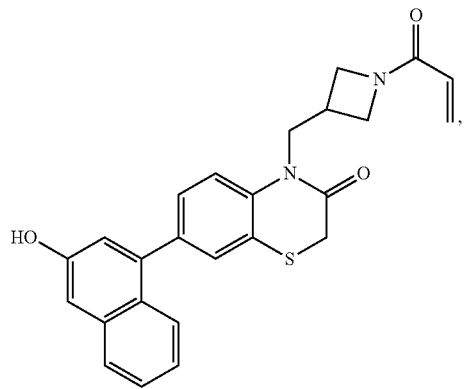
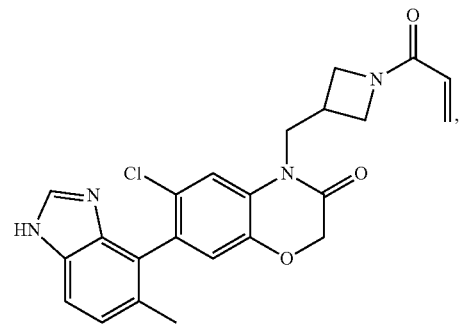
140
-continued
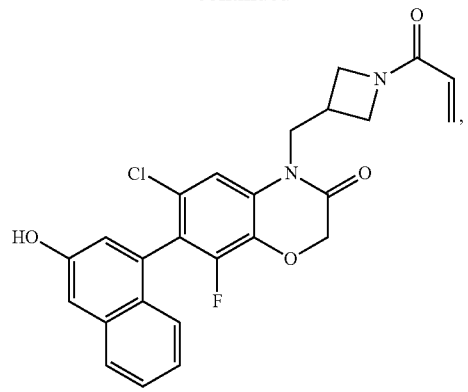
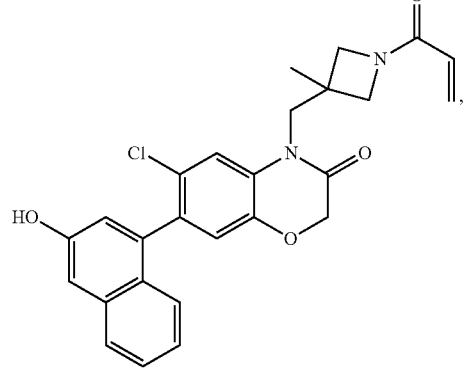
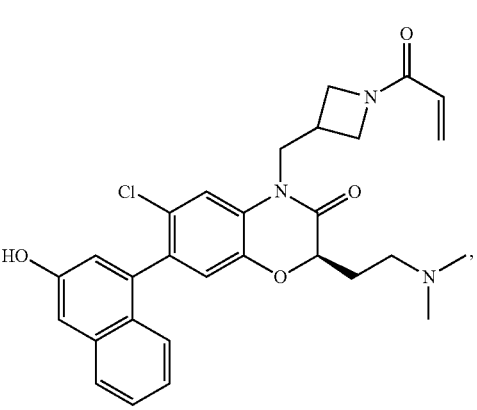
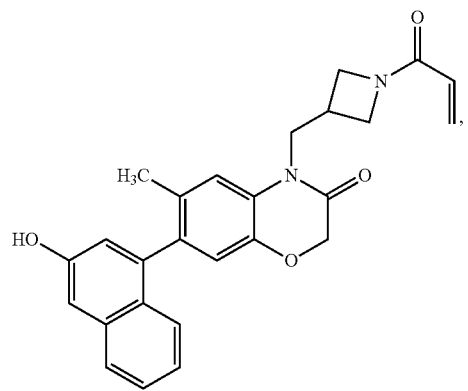

141
-continued
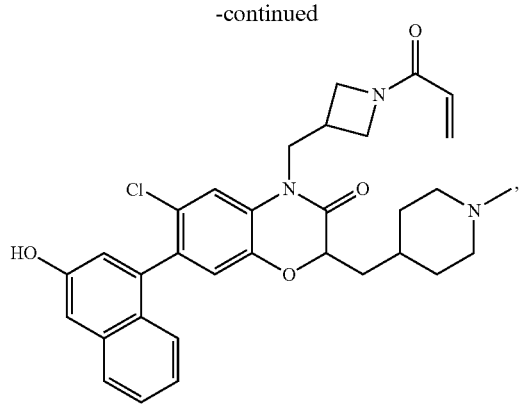
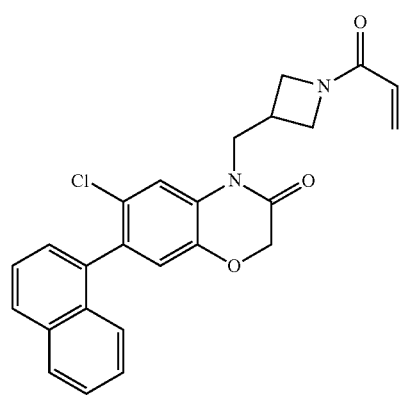
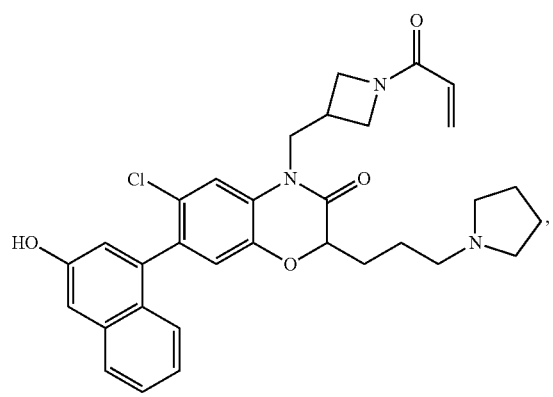
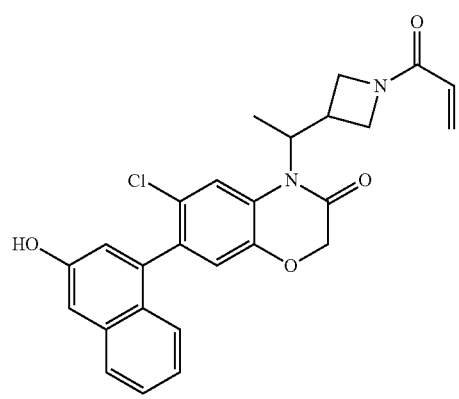
142
-continued
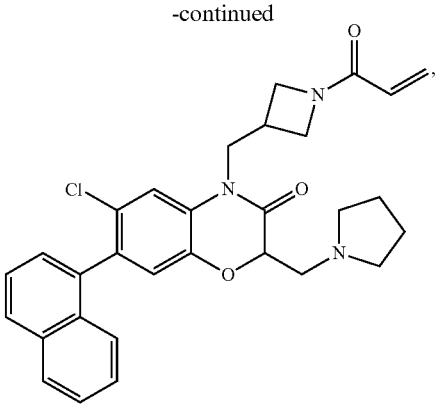
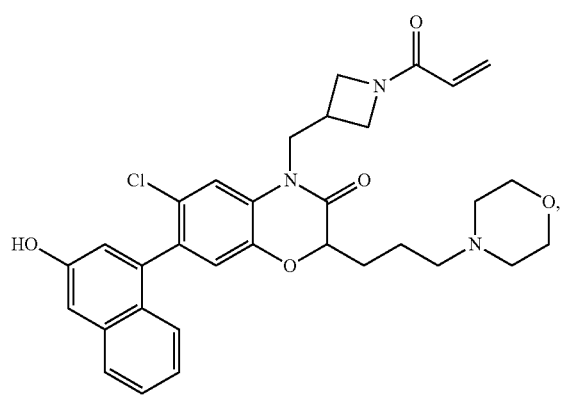
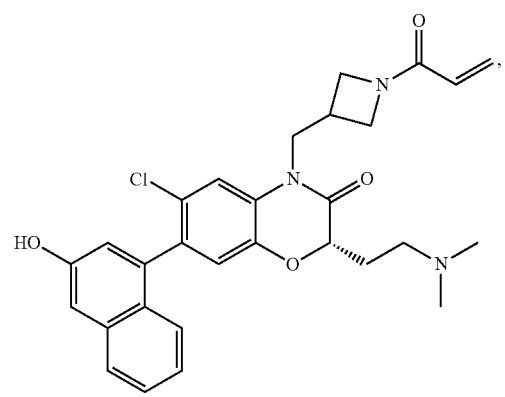
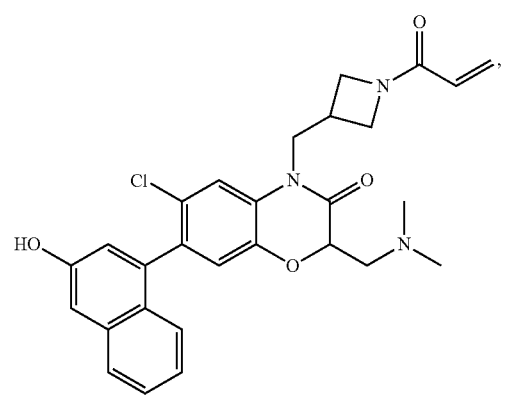

143
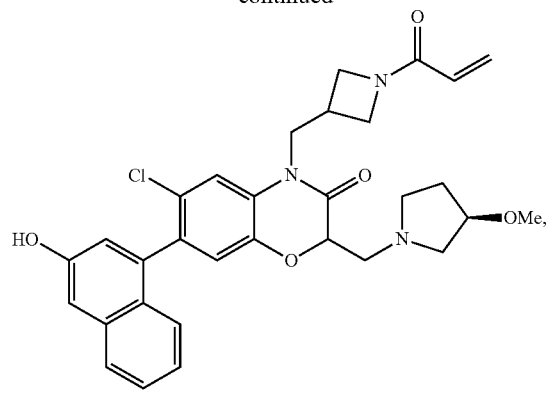
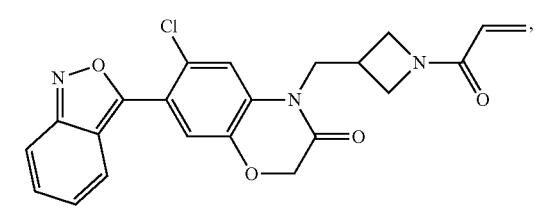
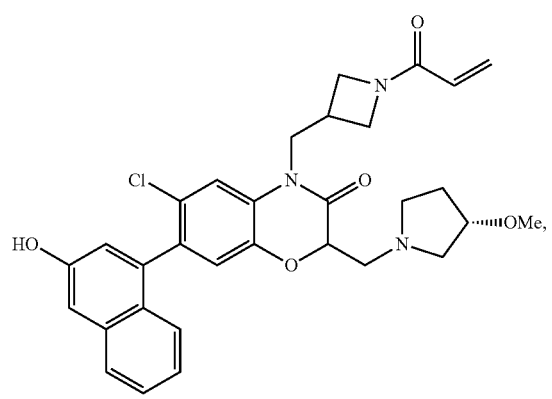
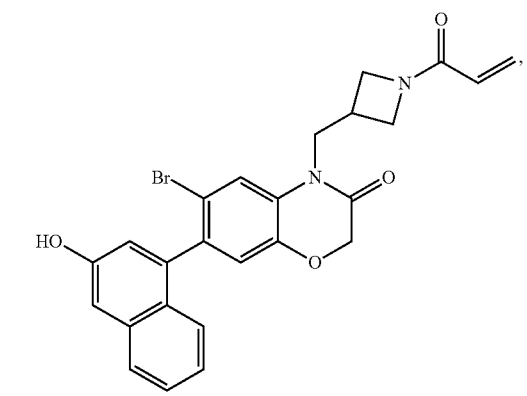
144
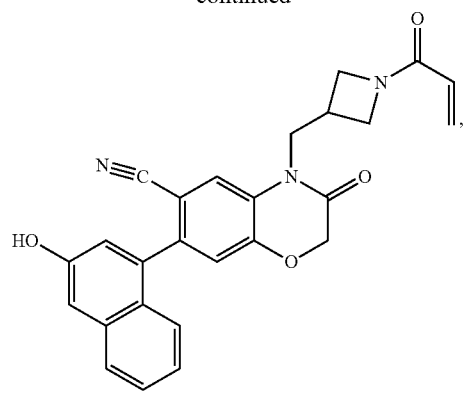
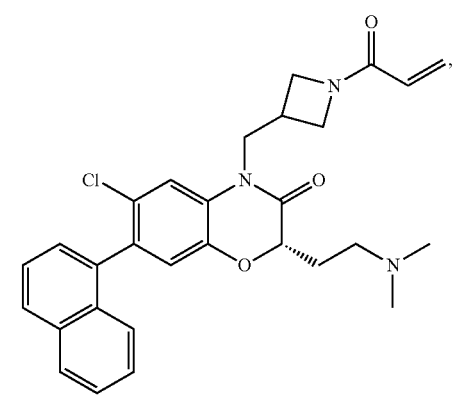
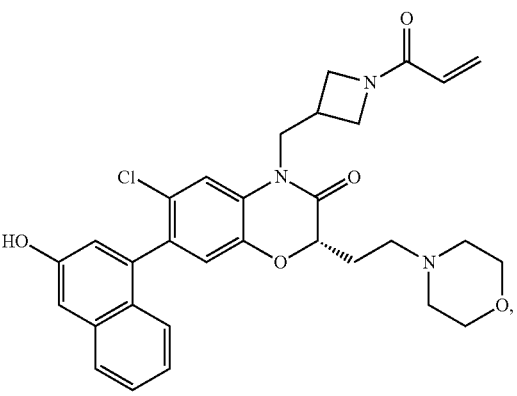
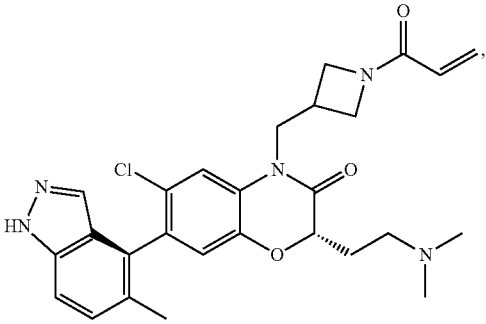

-continued

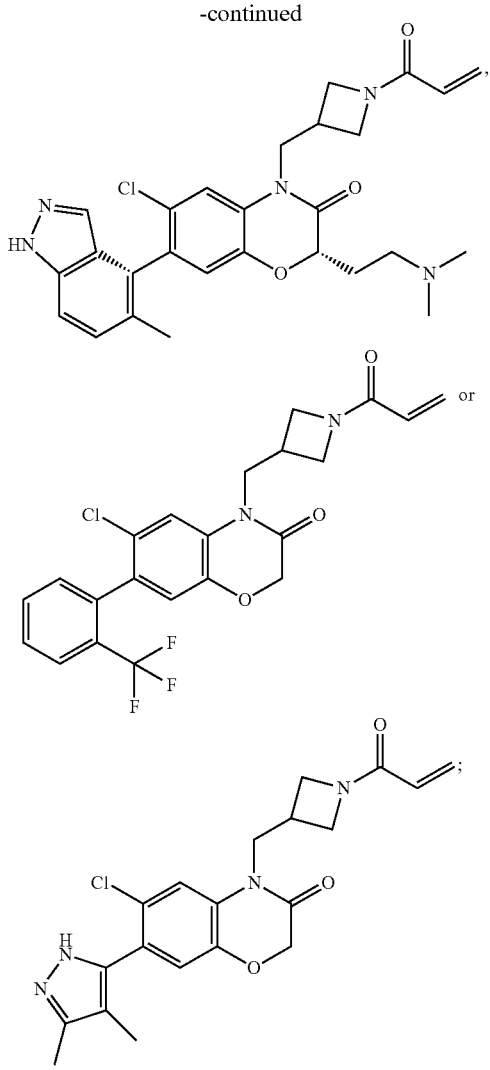

and pharmaceutical acceptable salts thereof.

33. A pharmaceutical composition, comprising a therapeutically effective amount of a compound of formula I according to claim 1 or a pharmaceutically acceptable salt or solvate thereof, and a pharmaceutically acceptable excipient.

34. A method for inhibiting KRas G12C activity in a cell, comprising contacting the cell in which inhibition of KRas G12C activity is desired with an effective amount of a compound of formula I or formula I-A according to claim 1 or claim 8, or a pharmaceutically acceptable salt or solvate thereof, or a pharmaceutical composition according to claim 33.

35. A method for treating a KRas G12C-associated cancer comprising administering to a patient having cancer a therapeutically effective amount of a compound of formula I or formula I-A according to claim 1 or claim 8, or a pharmaceutically acceptable salt or solvate thereof, or a pharmaceutically acceptable salt or solvate thereof, alone or combined with a pharmaceutically acceptable carrier, excipient or diluents.

36. The method of claim 35, wherein the therapeutically effective amount of the compound is between about 0.01 to 300 mg/kg per day.

37. The method of claim 36, wherein the therapeutically effective amount of the compound is between about 0.1 to 100 mg/kg per day.

38. The method according to claim 35, wherein the cancer is selected from the group consisting of Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial wearcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

39. The method of claim 35, wherein the cancer is non-small cell lung cancer.

40. A method for treating cancer in a patient in need thereof, the method comprising:
(a) determining if the cancer is associated with a KRas G12C mutation; and (b) if the cancer is determined to be associated with a KRas G12C mutation, administering to the patient a therapeutically effective amount of a compound of formula I or formula I-A or a pharmaceutically acceptable salt or solvate thereof according to claim 32, or a pharmaceutical composition thereof according to claim 33.

41. A process for preparing a compound of formula I according to claim 1, comprising:
  (a) reacting a compound of formula 5

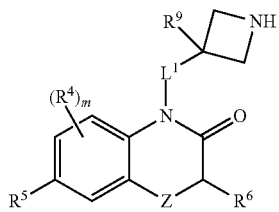

Formula 5 where $L^1$, Z, m, $R^4$, $R^5$, $R^6$ and $R^9$ are as defined for Formula I according to claim 1, with an acrolyl chloride in the presence of a base; and optionally forming a salt thereof.

* * * * *